US010557114B2

(12) United States Patent
Rudenko et al.

(10) Patent No.: US 10,557,114 B2
(45) Date of Patent: Feb. 11, 2020

(54) THIOESTERASES AND CELLS FOR PRODUCTION OF TAILORED OILS

(71) Applicant: Corbion Biotech, Inc., South San Francisco, CA (US)

(72) Inventors: George N. Rudenko, South San Francisco, CA (US); Jason Casolari, South San Francisco, CA (US); Scott Franklin, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 10 days.

(21) Appl. No.: 15/727,624

(22) Filed: Oct. 8, 2017

(65) Prior Publication Data

US 2018/0208953 A1 Jul. 26, 2018

Related U.S. Application Data

(63) Continuation of application No. 14/209,931, filed on Mar. 13, 2014, now Pat. No. 9,783,836, which is a continuation-in-part of application No. 13/837,996, filed on Mar. 15, 2013, now Pat. No. 9,290,749.

(60) Provisional application No. 61/917,217, filed on Dec. 17, 2013, provisional application No. 61/791,861, filed on Mar. 15, 2013.

(51) Int. Cl.

| | |
|---|---|
| ***C12N 15/82*** | (2006.01) |
| ***C12N 9/16*** | (2006.01) |
| ***C12N 1/12*** | (2006.01) |
| ***C12P 7/64*** | (2006.01) |

(52) U.S. Cl.

CPC ................ *C12N 1/12* (2013.01); *C12N 9/16* (2013.01); *C12N 15/8247* (2013.01); *C12P 7/6463* (2013.01)

(58) Field of Classification Search

None

See application file for complete search history.

(56) References Cited

U.S. PATENT DOCUMENTS

| | | | |
|---|---|---|---|
| 4,049,724 | A | 9/1977 | Sheng et al. |
| 4,288,378 | A | 9/1981 | Japikse et al. |
| 4,335,156 | A | 6/1982 | Kogan et al. |
| 4,584,139 | A | 4/1986 | Gray et al. |
| 4,603,188 | A | 7/1986 | Kusakawa et al. |
| 4,683,202 | A | 7/1987 | Mullis |
| 4,798,793 | A | 1/1989 | Eigtved |
| 4,940,835 | A | 7/1990 | Shah et al. |
| 4,940,845 | A | 7/1990 | Hirota et al. |
| 4,945,050 | A | 7/1990 | Sanford et al. |
| 4,992,189 | A | 2/1991 | Chen et al. |
| 5,080,848 | A | 1/1992 | Strauss et al. |
| 5,091,116 | A | 2/1992 | Krishnamurthy et al. |
| 5,156,963 | A | 10/1992 | Eigtved |
| 5,233,099 | A | 8/1993 | Tabata |
| 5,233,100 | A | 8/1993 | Tabata et al. |
| 5,258,197 | A | 11/1993 | Wheeler et al. |
| 5,268,192 | A | 12/1993 | Zook et al. |
| 5,298,421 | A | 3/1994 | Davies et al. |
| 5,298,637 | A | 3/1994 | Cooper |
| 5,304,481 | A | 4/1994 | Davies et al. |
| 5,304,664 | A | 4/1994 | Peppmoller et al. |
| 5,342,768 | A | 8/1994 | Pedersen et al. |
| 5,344,771 | A | 9/1994 | Davies et al. |
| 5,346,724 | A | 9/1994 | Ohgake et al. |
| 5,380,894 | A | 1/1995 | Burg et al. |
| 5,391,383 | A | 2/1995 | Sullivan et al. |
| 5,427,704 | A | 6/1995 | Lawate |
| 5,434,278 | A | 7/1995 | Pelloso et al. |
| 5,451,332 | A | 9/1995 | Lawate |
| 5,455,167 | A | 10/1995 | Voelker et al. |
| 5,458,795 | A | 10/1995 | Lawate |
| 5,475,160 | A | 12/1995 | Singleton et al. |
| 5,506,201 | A | 4/1996 | McDermott et al. |
| 5,512,482 | A | 4/1996 | Voelker et al. |
| 5,567,359 | A | 10/1996 | Cassidy et al. |
| 5,576,027 | A | 11/1996 | Friedman et al. |
| 5,639,790 | A | 6/1997 | Voelker et al. |
| 5,654,495 | A | 8/1997 | Voelker et al. |
| 5,667,997 | A * | 9/1997 | Voelker .................... A23D 9/00 435/134 |
| 5,674,385 | A | 10/1997 | Ivaschenko et al. |
| 5,686,131 | A | 11/1997 | Sato et al. |
| 5,693,507 | A | 12/1997 | Daniell et al. |

(Continued)

FOREIGN PATENT DOCUMENTS

| | | |
|---|---|---|
| CN | 102 066 569 A | 5/2011 |
| CN | 102 300 996 A | 12/2011 |

(Continued)

OTHER PUBLICATIONS

Tjellstrom et al 2013 (FEBS Letters 587:7 p. 936-942).*

U.S. Notice of Allowance, dated Nov. 15, 2018, issued in U.S. Appl. No. 15/684,941.

Australian Examination Report No. 1, dated Feb. 15, 2019, issued in Application No. AU 2014212439.

European Third Office Action dated Apr. 4, 2019 issued in EP 14 706 996.7.

Mexican Second Office Action dated Jun. 28, 2018 issued in MX/a/2015/009730.

Malaysia Modified Substantive Examination Clear Report dated Sep. 28, 2018 issued in MY PI2015001876.

(Continued)

*Primary Examiner* — Matthew R Keogh

(74) *Attorney, Agent, or Firm* — Leydig, Voit & Mayer, Ltd.

(57) ABSTRACT

The invention features plant acyl-ACP thioesterase genes of the FatB class and proteins encoded by these genes. The genes are useful for constructing recombinant host cells having altered fatty acid profiles. Oleaginous microalga host cells with the new genes or previously identified FatB genes are disclosed. The microalgae cells produce triglycerides with useful fatty acid profiles.

9 Claims, No Drawings

Specification includes a Sequence Listing.

(56) References Cited

U.S. PATENT DOCUMENTS

| | | | |
|---|---|---|---|
| 5,723,761 | A | 3/1998 | Voelker et al. |
| 5,776,741 | A | 7/1998 | Pedersen et al. |
| 5,807,893 | A | 9/1998 | Voelker et al. |
| 5,833,999 | A | 11/1998 | Trinh et al. |
| 5,850,022 | A | 12/1998 | Dehesh et al. |
| 5,885,440 | A | 3/1999 | Hoehn et al. |
| 5,888,947 | A | 3/1999 | Lambert et al. |
| 5,900,370 | A | 5/1999 | Running |
| 5,910,631 | A | 6/1999 | Topfer et al. |
| 5,928,696 | A | 7/1999 | Best et al. |
| 5,942,479 | A | 8/1999 | Frankenbach et al. |
| 5,945,585 | A | 8/1999 | Hitz et al. |
| 6,020,509 | A | 2/2000 | Weerasooriya et al. |
| 6,022,577 | A | 2/2000 | Chrysam et al. |
| 6,027,900 | A | 2/2000 | Allnutt et al. |
| 6,051,539 | A | 4/2000 | Kodali et al. |
| 6,057,375 | A | 5/2000 | Wollenweber et al. |
| 6,080,853 | A | 6/2000 | Corrigan et al. |
| 6,086,903 | A | 7/2000 | Trinh et al. |
| 6,113,971 | A | 9/2000 | Elmaleh |
| 6,140,302 | A | 10/2000 | Lueder et al. |
| 6,150,512 | A | 11/2000 | Yuan |
| 6,217,746 | B1 | 4/2001 | Thakkar et al. |
| 6,268,517 | B1 | 7/2001 | Filler et al. |
| 6,278,006 | B1 | 8/2001 | Kodali et al. |
| 6,320,101 | B1 | 11/2001 | Kaplan et al. |
| 6,331,664 | B1 | 12/2001 | Rubin-Wilson et al. |
| 6,342,208 | B1 | 1/2002 | Hyldgaard et al. |
| 6,380,410 | B1 | 4/2002 | Oftring et al. |
| 6,391,815 | B1 | 5/2002 | Weston et al. |
| 6,395,965 | B1 | 5/2002 | Xia |
| 6,398,707 | B1 | 6/2002 | Wu et al. |
| 6,407,044 | B2 | 6/2002 | Dixon |
| 6,465,642 | B1 | 10/2002 | Kenneally et al. |
| 6,468,955 | B1 | 10/2002 | Smets et al. |
| 6,538,169 | B1 | 3/2003 | Pittman et al. |
| 6,590,113 | B1 | 7/2003 | Sleeter |
| 6,596,155 | B1 | 7/2003 | Gates et al. |
| 6,596,768 | B2 | 7/2003 | Block et al. |
| 6,630,066 | B2 | 10/2003 | Cash et al. |
| 6,680,426 | B2 | 1/2004 | Daniell et al. |
| 6,692,730 | B2 | 2/2004 | Perron et al. |
| 6,750,048 | B2 | 6/2004 | Ruecker et al. |
| 6,770,104 | B2 | 8/2004 | Murphy |
| 6,808,737 | B2 | 10/2004 | Ullanoormadam |
| 6,869,597 | B2 | 3/2005 | Arnaud |
| 6,881,873 | B2 | 4/2005 | Gillespie et al. |
| 6,924,333 | B2 | 8/2005 | Bloom et al. |
| 6,946,430 | B2 | 9/2005 | Sakai et al. |
| 6,977,322 | B2 | 12/2005 | Gillespie |
| 7,041,866 | B1 | 5/2006 | Gillespie |
| 7,053,267 | B2 | 5/2006 | Knauf et al. |
| 7,081,567 | B2 | 7/2006 | Xue et al. |
| 7,115,173 | B2 | 10/2006 | Caswell et al. |
| 7,115,760 | B2 | 10/2006 | Sparso et al. |
| 7,118,773 | B2 | 10/2006 | Floeter et al. |
| 7,135,290 | B2 | 11/2006 | Dillon |
| 7,135,620 | B2 | 11/2006 | Daniell et al. |
| 7,196,124 | B2 | 3/2007 | Parker et al. |
| 7,232,935 | B2 | 6/2007 | Jakkula et al. |
| 7,238,277 | B2 | 7/2007 | Dahlberg et al. |
| 7,262,158 | B1 | 8/2007 | Lukenbach et al. |
| 7,264,886 | B2 | 9/2007 | Cui et al. |
| 7,268,276 | B2 | 9/2007 | Ruezinksy et al. |
| 7,288,278 | B2 | 10/2007 | Mellerup et al. |
| 7,288,685 | B2 | 10/2007 | Marker |
| 7,588,931 | B2 | 9/2009 | Damude et al. |
| 7,622,570 | B2 | 11/2009 | Oswald et al. |
| 8,029,579 | B2 | 10/2011 | Knuth et al. |
| 8,530,207 | B2 | 9/2013 | Watts et al. |
| 8,956,834 | B2 | 2/2015 | Roessler et al. |
| 9,290,749 | B2 | 3/2016 | Rudenko et al. |
| 9,567,615 | B2 | 2/2017 | Davis |
| 9,765,368 | B2 | 9/2017 | Davis et al. |
| 9,783,836 | B2 | 10/2017 | Rudenko et al. |
| 9,816,079 | B2 | 11/2017 | Davis |
| 10,125,382 | B2 | 11/2018 | Casolari et al. |
| 10,246,728 | B2 | 4/2019 | Davis et al. |
| 2002/0178467 | A1 | 11/2002 | Dehesh |
| 2003/0097686 | A1 | 5/2003 | Knauf et al. |
| 2003/0145350 | A1 | 7/2003 | Spener et al. |
| 2005/0005333 | A1 | 1/2005 | Ruezinsky et al. |
| 2005/0102716 | A1 | 5/2005 | Venkatramesh et al. |
| 2005/0262588 | A1 | 11/2005 | Dehesh et al. |
| 2007/0175091 | A1 | 8/2007 | Danzer et al. |
| 2007/0261138 | A1 | 11/2007 | Graham et al. |
| 2009/0176272 | A1 | 7/2009 | Champagne et al. |
| 2009/0317878 | A1 | 12/2009 | Champagne et al. |
| 2010/0058651 | A1 | 3/2010 | Knuth et al. |
| 2010/0105955 | A1 | 4/2010 | Alibhai et al. |
| 2010/0151538 | A1 | 6/2010 | Franklin et al. |
| 2010/0154293 | A1 | 6/2010 | Hom et al. |
| 2011/0072714 | A1 | 3/2011 | Gaertner et al. |
| 2011/0145944 | A1 | 6/2011 | Laga et al. |
| 2011/0250659 | A1 | 10/2011 | Roberts et al. |
| 2011/0293785 | A1 | 12/2011 | Franklin et al. |
| 2012/0009636 | A1 | 1/2012 | Berry et al. |
| 2012/0283460 | A1 | 11/2012 | Franklin et al. |
| 2012/0288930 | A1 | 11/2012 | Trimbur et al. |
| 2013/0029387 | A1 | 1/2013 | Nikolau et al. |
| 2013/0031678 | A1 | 1/2013 | Zheng et al. |
| 2013/0034887 | A1 | 2/2013 | Franklin et al. |
| 2013/0219557 | A1 | 8/2013 | Tojo et al. |
| 2014/0215654 | A1 | 7/2014 | Davis |
| 2014/0234920 | A1 | 8/2014 | Davis |
| 2014/0275586 | A1 | 9/2014 | Rudenko et al. |
| 2014/0288320 | A1 | 9/2014 | Rudenko et al. |
| 2016/0032332 | A1 | 2/2016 | Davis et al. |
| 2016/0083758 | A1 | 3/2016 | Casolari et al. |
| 2016/0251685 | A1 | 9/2016 | Rudenko et al. |
| 2018/0148747 | A1 | 5/2018 | Davis et al. |
| 2018/0171312 | A1 | 6/2018 | Davis |

FOREIGN PATENT DOCUMENTS

| | | | |
|---|---|---|---|
| CN | 102 459569 | A | 5/2012 |
| CN | 102 559 727 | A | 7/2012 |
| CN | 102 586 350 | A | 7/2012 |
| EP | 1 605 048 | A1 | 12/2005 |
| EP | 1 640 437 | A1 | 3/2006 |
| EP | 1 681 337 | A1 | 7/2006 |
| EP | 1 741 767 | A1 | 1/2007 |
| EP | 1 741 768 | A1 | 1/2007 |
| EP | 1 795 576 | A1 | 6/2007 |
| EP | 1 682 466 | B1 | 11/2008 |
| JP | 11-505115 | A | 5/1999 |
| JP | 2012-510275 | A | 5/2012 |
| WO | WO 89/01032 | A1 | 2/1989 |
| WO | WO 92/11373 | A1 | 7/1992 |
| WO | WO 92/020236 | | 11/1992 |
| WO | WO 92/20636 | A1 | 11/1992 |
| WO | WO 94/10288 | A2 | 5/1994 |
| WO | WO 95/06740 | | 3/1995 |
| WO | WO 95/13390 | A2 | 5/1995 |
| WO | WO 96/23892 | A2 | 8/1996 |
| WO | WO 96/36719 | A1 | 11/1996 |
| WO | WO 98/55633 | A1 | 12/1998 |
| WO | WO 00/61740 | A1 | 10/2000 |
| WO | WO 00/66750 | A2 | 11/2000 |
| WO | WO 02/08403 | A2 | 1/2002 |
| WO | WO 2005/047216 | A1 | 5/2005 |
| WO | WO 2006/055322 | A2 | 5/2006 |
| WO | WO 2007/106903 | A2 | 9/2007 |
| WO | WO 2008/002643 | A2 | 1/2008 |
| WO | WO 2008/151149 | A2 | 12/2008 |
| WO | WO 2010/019813 | A2 | 2/2010 |
| WO | WO 2010/063031 | A2 | 6/2010 |
| WO | WO 2010/063032 | A2 | 6/2010 |
| WO | WO 2010/120939 | A2 | 10/2010 |
| WO | WO 2011/003034 | A2 | 1/2011 |
| WO | WO 2011/008565 | A1 | 1/2011 |
| WO | WO 2011/127069 | A1 | 10/2011 |
| WO | WO 2011/150410 | A2 | 12/2011 |
| WO | WO 2011/150411 | A1 | 12/2011 |

(56) References Cited

FOREIGN PATENT DOCUMENTS

| | | | |
|---|---|---|---|
| WO | WO 2012/061647 | A2 | 5/2012 |
| WO | WO 2012/106560 | A1 | 8/2012 |
| WO | WO 2012/154626 | A1 | 11/2012 |
| WO | WO 2013/158938 | A1 | 10/2013 |
| WO | WO 2014/120829 | A1 | 8/2014 |
| WO | WO 2014/151904 | A1 | 9/2014 |
| WO | WO 2015/051319 | A2 | 4/2015 |
| WO | WO 2016/014968 | A1 | 1/2016 |
| WO | WO 2016/044779 | A2 | 3/2016 |

OTHER PUBLICATIONS

Australian Third Office Action dated Aug. 1, 2018 issued in AU 2014236763.

European Second Office Action [Examiner's Report] dated Mar. 5, 2018 issued in EP 14769502.7.

European Third Office Action [Examiner's Report] dated Jan. 14, 2019 issued in EP 14769502.7.

Chinese Second Office Action dated Mar. 7, 2019 issued in CN 201480020002.5.

U.S. Appl. No. 16/283,373, filed Feb. 22, 2019, Davis et al.

U.S. Appl. No. 16/185,705, filed Nov. 9, 2018, Casolari et al.

U.S. Office Action, dated Jul. 16, 2015, issued in U.S. Appl. No. 13/797,733.

U.S. Final Office Action, dated Dec. 14, 2015, issued in U.S. Appl. No. 13/797,733.

U.S. Office Action, dated Jul. 26, 2016, issued in U.S. Appl. No. 13/797,733.

U.S. Notice of Allowance, dated Sep. 21, 2016, issued in U.S. Appl. No. 13/797,733.

U.S. Office Action (Requirement for Restriction/Election), dated Jul. 12, 2016, issued in U.S. Appl. No. 14/167,908.

U.S. Office Action, dated Apr. 3, 2017, issued in U.S. Appl. No. 14/167,908.

U.S. Notice of Allowance, dated Jul. 10, 2017, issued in U.S. Appl. No. 14/167,908.

U.S. Notice of Allowance, dated Aug. 4, 2017 issued in U.S. Appl. No. 14/167,908.

U.S. Office Action, dated Jul. 22, 2015, issued in U.S. Appl. No. 13/837,996.

U.S. Notice of Allowance, dated Nov. 17, 2015, issued in U.S. Appl. No. 13/837,996.

U.S. Office Action (Requirement for Restriction/Election), dated Jul. 12, 2016, issued in U.S. Appl. No. 14/209,931.

U.S. Office Action, dated Jan. 26, 2017, issued in U.S. Appl. No. 14/209,931.

U.S. Notice of Allowance, dated May 15, 2017, issued in U.S. Appl. No. 14/209,931.

U.S. Notice of Allowance, dated Jun. 14, 2017, issued in U.S. Appl. No. 14/209,931.

U.S. Office Action, dated May 25, 2018, issued in U.S. Appl. No. 15/062,045.

U.S. Office Action, dated Jan. 19, 2017, issued in U.S. Appl. No. 14/808,361.

U.S. Notice of Allowance, dated Apr. 28, 2017, issued in U.S. Appl. No. 14/808,361.

U.S. Office Action, dated May 31, 2018, issued in U.S. Appl. No. 15/684,941.

U.S. Office Action (Requirement for Restriction/Election), dated Jun. 8, 2017, issued in U.S. Appl. No. 14/858,527.

U.S. Office Action dated Oct. 18, 2017 issued in U.S. Appl. No. 14/858,527.

U.S. Notice of Allowance dated Apr. 6, 2018 issued in U.S. Appl. No. 14/858,527.

U.S. Notice of Allowance dated Jun. 29, 2018 issued in U.S. Appl. No. 14/858,527.

Chinese Second Office Action dated Mar. 22, 2016 issued in CN 201280068060.6.

PCT International Search Report and Written Opinion dated Jun. 24, 2014 issued in PCT/US2014/013676.

PCT International Preliminary Report on Patentability and Written Opinion dated Aug. 13, 2015 issued in PCT/US2014/013676.

Database Geneseq [Online] (Jun. 6, 2000) "Bay C18:1 preferring acyl-ACP thioesterase protein from clone 3A-17.", retrieved from EBI accession No. GSP:AAY80558 Database accession No. AAY80558; and Database Geneseq [Online] (Jun. 6, 2000) "Bay C18:1 preferring acyl-ACP thioesterase protein.", retrieved from EBI accession No. GSP:AAY80559 Database accession No. AAY80559.

Database Geneseq [Online] (Nov. 2, 1995) "Camphor thioesterase.", retrieved from EBI accession No. GSP:AAR74148 Database accession No. AAR74148.

Database Geneseq [Online] (Oct. 26, 1996) "Cuphea C14:0-ACP thioesterase.", retrieved from EBI accession No. GSP:AAW02081 Database accession No. AAW02081.

Database Geneseq [Online] (Aug. 5, 2010) "U. californica fatty acyl-ACP thioesterase protein (without PTS), Seq:139.", retrieved from EBI accession No. GSP:AYC84249 Database accession No. AYC84249.

Database Geneseq [Online] Jun. 15, 2007 (Jun. 15, 2007), "Medium chain-specific acyl-(ACP)-thioesterase CITEG1.", retrieved from EBI accession No. GSP:AAW06703 Database accession No. AAW06703.

Brazilian First Office Action dated Mar. 7, 2018 issued in Application No. BR 1120150179207.

Chinese First Office Action dated Jun. 13, 2017 issued in CN 201480018889.4.

Chinese Second Office Action dated Mar. 5, 2018 issued in CN 201480018889.4.

European Examination Report dated Oct. 25, 2016 issued in EP 14 706 996.7.

European Second Office Action dated Jan. 4, 2018 issued in EP 14 706 996.7.

Japanese First Office Action dated Mar. 29, 2018 issued in JP 2015-555436.

Mexican Office Action [no translation] dated Sep. 21, 2015 issued in MX/a/2015/009730.

Australian First Office Action dated Aug. 14, 2017 issued in AU 2014236763.

Australian Second Office Action dated Jun. 12, 2018 issued in AU 2014236763.

PCT Invitation to Pay Additional Fees and, Where Applicable, Protest Fee dated Jun. 18, 2014 issued in PCT/US2014/026644.

PCT International Search Report and Written Opinion dated Aug. 29, 2014 issued in PCT/US2014/026644.

PCT International Preliminary Report on Patentability dated Sep. 24, 2015 issued in PCT/US2014/026644.

Genbank Accession No. U17097, Umbellularia californica UC FatB2 (FatB) mRNA, complete cds., Jun. 1, 1995, 2pp.

Genbank: Accession No. U39834.1, Cuphea hookeriana 8:0- and 10:0-ACP specific thioesterase (FatB2) mRNA, complete cds, May 21, 2014, 2pp.

Genbank Accession No. AAC49001, UC FatB2 (FatB) Umbellularica californica, May 30, 1995, 2pp.

GenBank Accession No. AAC49001.1, UC FatB2, May 1995, [Retrieved from the Internet Oct. 14, 2014: <URL: http://www.ncbi.nlrrtnih.gov/protein/595955?sat=13&satkey=6522409>], 1page.

European Partial Supplementary Search Report (Communication pursuant to Rule 164(1)EPC) dated Jul. 6, 2016 issued in EP 14 76 9502.7.

European Extended Search Report dated Oct. 13, 2016 issued in EP 14 76 9502.7.

European First Office Action dated Jul. 11, 2017 issued in EP 14769502.7.

European First Office Action dated Jan. 4, 2018 issued in EP 15747911.4.

Mexican First Office Action dated Jan. 26, 2018 issued in MX MX/a/2015/011507.

Mexican Second Office Action dated Jun. 15, 2018 issued in MX MX/a/2015/011507.

Chinese First Office Action dated Apr. 23, 2018 issued in CN 201480020002.5.

(56) References Cited

OTHER PUBLICATIONS

PCT International Search Report and Written Opinion dated Dec. 22, 2015 issued in PCT/US2015/042044.
PCT International Preliminary Report on Patentability dated Feb. 2, 2017 issued in PCT/US2015/042044.
Database UniProt [Online] (Jul. 24, 2013) "SubName: Full =FatB type acyl-ACP thioesterase-3 {EC0:0000313:EMBL:AGG79285.1}," retrieved on Nov. 10, 2015 from EBI accession No. Uniprot:R4J2L6, Database accession No. R4J2L6 sequence, 1 page.
Database UniProt [Online] (Jul. 9, 2014) "SubName: Full= Uncharacterized protein {EC0:0000313:EMBL:KCW58039.1}," retrieved on Nov. 16, 2015 from EBI accession No. Uniprot:A0A059AWB4, Database accession No. A0A059AWB4 sequence, 1 page.
PCT Invitation to Pay Additional Fees and, Where Applicable, Protest Fee dated Jan. 13, 2016 issued in PCT/US2015/051042.
PCT International Search Report and Written Opinion dated Mar. 31, 2016 issued in PCT/US2015/051042.
PCT International Preliminary Report on Patentability dated Mar. 30, 2017 issued in PCT/US2015/051042.
European First Office Action dated Jun. 8, 2018 issued in EP 15775855.8.
Apt et al., (1996) "Stable nuclear transformation of the diatom *Phaeodactylum tricomutum,*" *Molecular and General Genetics*, 252:572-579.
Barnes et al., (2005) "Contribution of 5'- and 3'-untranslated regions of plastid mRNAs to the expression of *Chlamydomonas reinhardtii* chloroplast genes," *Mol Gen Genomics*274:625-636.
Blatti et al., (Sep. 2012) "Manipulating Fatty Acid Biosynthesis in Microalgae for Biofuel through Protein-Protein Interactions," *PLoS One* 7(9):e42949, 12pp.
Blowers et al., (Jan. 1989) "Studies on *Chlamydomonas* Chloroplast Transformation: Foreign DNA Can Be Stably Maintained in the Chromosome," *The Plant Cell*, 1:123-132.
Bonaventure et al., (Apr. 2003) "Disruption of the FATB Gene in *Arabidopsis* Dethonstrates an Essential Role of Saturated Fatty Acids in Plant Growth," *The Plant Cell* 15:1020-1033.
Boynton et al.,(1988) "Chloroplast Transformation in *Chlamydomonas* with High Velocity Microprojectiles," *Science*, 240(4858):1534-1538.
Brandt, et al. (1993) "Gametic Selection at Fatty Acid and Allozyme Marker Loci and Meiosis within Cuphea *viscosissima* x Cuphea *lanceolata* Populations," Crop Science, vol. 33, pp. 1138-1143.
Chasan, (Mar. 1995) "Engineering Fatty Acids—The Long and Short of It," *Plant Cell*, 7:235-237.
Chen et al., (1988) "Recognition of prokaryotic transcription terminators by spinach chloroplast RNA polymerase," *Nucleic Acids Research*, 16(17):8411-8431.
Chen et al., (2001) "Highly efficient expression of rabbit neutrophil peptide-1 gene in *Chlorella ellipsoidea* cells," *Current Genetics*, 39(5):365-370.
Chow et al., (1999) "Electrotransformation of *Chlorella vulgaris,*" *Plant Cell Reports*, 18:778-780.
Cobley et al., (Sep. 1993) "Construction of Shuttle Plasmids Which Can Be Efficiently Mobilzed from *Escherichia coli* into the Chromatically Adapting Cyanobacterium, *Fremyella diplosiphon*," *Plasmid*, 30(2):90-105.
Cobley et al., (2002) "CpeR is an activator required for expression of the phycoerythrin operon (cpeBA) in the cyanobacterium Fremyella diplosiphon and is encoded in the phycoerythrin linker-polypeptide operon (cpeCDESTR)," *Molecular Microbiololgy*,44(6):1517-1531.
Comai et al., (Oct. 15, 1988) "Chloroplast Transport of a Ribulose Bisphosphate Carboxylase Small Subunit-5-Enolpyruvyl 3-Phosphoshikimate Synthase Chimeric Protein Requires Part of the Mature Small Subunit in Addition to the Transit Peptide," *The Journal of Biological Chemistry*, 263(29):15104-15109.
Courchesne, Noémie Manuelle Dorval el al., (2009) "Enhancement of lipid production using biochemical, genetic and transcription factor engineering approaches," *Journal of Biotechnology*, 141(1):31-41.
Davies et al., (1992) "Expression of the arylsulfatase gene from the $\beta_2$-tubulin promoter in *Chlamydomonas reinhardtii,*" *Nucleic Acids Res.*, 20(12):2959-2965.
Dawson et al., (1997) "Stable Transformation of *Chlorella*: Rescue of Nitrate Reductase-Deficient Mutants with the Nitrate Reductase Gene," *Current Microbiol.*, 35(6):356-362.
Debuchy et al., (1989) "The argininosuccinate lyase gene of *Chlamydomonas reinhardtii*: an important tool for nuclear transformation and for correlating the genetic and molecular maps of the ARG7 locus," *EMBO Journal*, 8(10):2803-2809.
Dehesh et al. (1996) "Production of high levels of 8:0 and 10:0 fatty acids in transgenic canola by overexpression of Ch FatB2, a thioesterase cDNA from *Cuphea hookeriana,*" *The Plant Journal*, 9(2):167-172.
Dehesh et al., (1998) "KAS IV: a 3-ketoacyl-ACP synthase from Cuphea sp. is a medium chain specific condensing enzyme," *The Plant Journal*, 15:383-390.
Deshnium et al., (1995) "Transformation of *Synechococcus* with a gene for choline oxidase enhances tolerance to salt stress," *Plant Mol. Biol.*,29(5):897-907.
Dörmann et al., (Jan. 1995) "Cloning and Expression in *Escherichia coli* of a Novel Thioesterase from *Arabidopsis thaliana* Specific for Long-Chain Acyl-Acyl Carrier Proteins," *Archives of Biochemistry and Biophysics*, 316(1):612-618.
Dubois et al., (2007) "Fatty acid profiles of 80 vegetable oils with regard to their nutritional potential," *Eur. J. Lipid Sci. Technol.*, 109:710-732.
Eccleston et al., (1996) "Medium-chain fatty Acid biosynthesis and utilization in *Brassica napus* plants expressing lauroyl-acyl carrier protein thioesterase," *Planta*, 198:46-53.
El-Sheekh et al., (1999) "Stable transformation of the intact cells of *Chlorella kessleri* with high velocity microprojectiles," *Biologia Plantarium*, 42:(2):209-216.
Facciotti et al., (1998) "Molecular dissection of the plant acyl-acyl carrier protein thioesterases," *Fett/Lipid*, 100(4-5, S.):167-172.
Facciotti et al., (Jun. 1, 1999) "Improved stearate phenotype in transgenic canola expressing a modified acyl-acyl carrier protein thioesterase," *Nat Biotechnol.*, 17(6):593-597.
Falciatore et al., (May 1999) "Transformation of Nonselectable Reporter Genes in Marine Diatoms," *Mar. Biotechnol.*, 1(3):239-251.
Frenz et al., (1989) "Hydrocarbon recovery by extraction with a biocompatible solvent from free and immobilized cultures of *Botryococcus braunii,*" *Enzyme Microb. Technol.*, 11:717-724.
Fromm et al., (Sep. 1985) "Expression of genes transferred into monocot and dicot plant cells by electroporation," *Proc. Natl. Acad. Sci. USA*, 82:5824 5828.
Ginalski et al., (2003) "Detection of reliable and unexpected protein fold predictions using 3D-Jury," *Nucleic Acids Research*,31(13):3291-3292.
Giuffrida et al., (2004) "Formation and Hydrolysis of Triacylglycerol and Sterol Epoxides: Role of Unsaturated Triacylglycerol Peroxyl Radicals," *Free Radical Biology and & Medicine*, 37(1):104-114.
Gruber et al., (1991) "*Escherichia coli-Anacystis nidulans* Plasmid Shuttle Vectors Containing the $P_L$ Promoter from Bacteriophage Lambda," *Current Micro.* 22:15-19.
Gruber et al., (1996) "Expression of the *Volvox* gene encoding nitrate reductase: Mutation-dependent activation of cryptic splice sites and intron-enhanced gene expression from a cDNA," *Plant Molecular Biology*, 31(1):1-12.
Guo et al. (Jun. 22, 2004) "Protein tolerance to random amino acid change," *Proc. Natl. Acad. Sci. USA*, 101(25):9205-9210.
Hall et al., (1993) "Expression of a foreign gene *Chlamydomonas reinhardtii*," Gene, 124:75-81.
Hallmann et al., (Nov. 1994) "Reporter genes and highly regulated promoters as tools for transformation experiments in *Volvox carteri,*" *Proc. Natl. Acad. Sci. USA*, 91:11562-11566.
Hanley-Bowdoin et al., (Feb. 1987) "Chloroplast promoters," *TIBS*, 12:67-70.

(56) References Cited

OTHER PUBLICATIONS

Hawkins et al., (1999) "Expression of Human Growth Hormone by the Eukaryotic Alga, *Chlorella," Current Microbiology*, 38:335-341.
Heise et al., (1994) "Factors Controlling Medium-Chain Fatty Acid Synthesis in Plastids From *Cuphea* Embryos," *Prog. Lipid Res.*, 33(1/2):87-95.
Hejazi et al., (Apr. 2004) "Milking of microalgae," *TRENDS in Biotechnology*, 22(4):189-194.
Hill et al., (1998) "Functional Analysis of Conserved Histidines in ADP-Glucose Pyrophosphorylase from *Escherichia coli," Biochem. Biophys. Res. Comm.*, 244(2):573-577.
Hillen et al., (1982) "Hydrocracking of the Oils of *Botryococcus braunii* to Transport Fuels," *Biotechnology and Bioengineering*, XXIV:193-205.
Hitz et al., (1994) "Cloning of a Higher-Plant Plastid ω-6 Fatty Acid Desaturase cDNA and Its Expression in a *Cyanobacterium," Plant Physiol.*, 105(2):635-641.
Huang et al. (2006) "Expression of mercuric reductase from *Bacillus megaterium* MB1 in eukaryotic microalga *Chlorella* sp. DT: an approach for mercury phytoremediation," *Appl. Microbiol. Biotechnol.* 72:197-205.
Inoue et al., (1994) "Analysis of Oil Derived From Liquefaction of *Botryococcus braunii," Biomass Bioenergy*, 6(4):269-274).
Isbell et al., (Feb. 1994) "Acid-Catalyzed Condensation of Oleic Acid into Estolides and Polyestolides," *JAOCS*, 71(2):169-174.
Jakobiak et al. (Dec. 2004) "The Bacterial Paromomycin Resistance Gene, *aphH*, as a Dominant Selectable Marker in *Volvox carteri," Protist*,155(4):381-393.
Jarvis et al. (1991) "Transient expression of firefly luciferase in protoplasts of the green alga *Chlorella ellipsoidea," Current Genetics*, 19:317-321.
Jha et al., (2006) "Cloning and functional expression of an acyl-ACP thioesterase FatB type from *Diploknema* (*Madhuca*) *butyracea seeds in Escherichia coli," Plant Physiology and Biochemistry*, 44:645-655.
Jiang et al., (Apr. 2005) "The Actin Gene Promoter-driven bar as a Dominant Selectable Marker for Nuclear Transformation of Dunaliella salina," *Acta Genetica Sinica*, 32(4):424-433.
Jing et al., (2011) "Phylogenetic and experimental characterization of an acyl-ACP thioesterase family reveals significant diverstiy in enzymatic specificity and activity," BMC Biochemistry, 2011, vol. 12.1, No. 44, pp. 1-16.
Jones et al., (Mar. 1995) "Palmitoyl-Acyl Carrier Protein (ACP) Thioesterase and the Evolutionary Origin of Plant Acyl-ACP Thioesterases," *The Plant Cell*, 7:359-371.
Kalscheuer et al., (1999) "Establishment of a gene transfer system for *Rhodococcus opacus* PD630 based on electroporation and its application for recombinant biosynthesis of poly(3-hydroxyalkanoic acids)," *Applied and Environmental Microbiology*, 52:508-515.
Kang et al., (Jul. 2000) "The Regulation Activity of Chlorella Virus Gene 5' Upstream Sequence in *Escherichia coli* and Eucaryotic Algae," [English Abstract] *Chinese Journal of Biotechnology*, 16(4):6 pages.
Kang et al., (2004) "Genetic diversity in chlorella viruses flanking *kcv*, a gene that encodes a potassium ion channel protein," *Virology*, 326(1):150-159.
Kawasaki et al., (2004) "Immediate early genes expressed in chlorovirus infections," *Virology*,318(1):214-223.
Kim et al., (2002) Stable Integration and Functional Expression of Flounder Growth Hormone Gene in Transformed Microalga, *Chlorella ellipsoidea, Mar. Biotechnol.*, 4(1):63-73.
Kindle, (Feb. 1990) "High-frequency nuclear transformation of *Chlamydomonas reinhardtii," Proc. Natl. Acad. Sci. USA*, 87(3):1228-1232.
Klein et al., (1987) "High-velocity microprojectiles for delivering nucleic acids into living cells," *Nature* London 327(7):70-73.
Knauf, (Feb. 1987) "The application of genetic engineering to oilseed crops," *TIBTECH*, 5:40-47.
Knutzon et al., (Jul. 1999) "Lysophosphatidic Acid Acyltransferase from Coconut Endosperm Mediates the Insertion of Laurate at the sn-2 Position of Triacylglycerols in Lauric Rapeseed Oil and Can Increase Total Laurate Levels," *Plant Physiology*, 120:739-746.
Kojima et al., (1999) "Growth and Hydrocarbon Production of Microalga *Botryococcus braunii* in Bubble Column Photobioreactors," *Journal of Bioscience and Bioengineering*, 87(6):811-815.
Koksharova et al., (Feb. 2002) "Genetic tools for cyanobacteria," *Appl Microbiol Biotechnol* 58(2):123-137.
Krebbers et al., (1982) "The maize chloroplast genes for the β and ϵ subunits of the photosynthetic coupling factor $CF_1$ are fused," *Nucleic Acids Research*, 10(16):4985-5002.
La Scala et al., (Jan. 2002) "The Effect of Fatty Acid Composition on the Acrylation Kinetics of Epoxidized Triacylglycerols", *Journal of the American Oil Chemists' Society*, 79(1):59-63.
Lapidot et al., (May 2002) "Stable Chloroplast Transformation of the Unicellular Red Alga *Porphyridium* Species," *Plant Physiol.*, 129(1):7-12.
Larson et al., (2002) "Acyl CoA profilesof transgenic plants that accumulate medium-chain fatty acids indicate inefficient storage lipid synthesis in developing oilseeds," *The Plant Journal*, 32(4):519-527.
Leonard et al., (1997) "Cuphea wrightii thioesterases have unexpected broad specificities on saturated fatty acids," Plant Molecular Biology, vol. 34, pp. 669-679.
Lumbreras et al., (1998) "Efficient foreign gene expression in *Chlamydomonas reinhardtii* mediated by an endogenous intron," *Plant Journal*, 14(4):441-447.
Manuell et al., (2007) "Robust expression of a bioactive mammalian protein in *Chlamydomonas* chloroplast," *Plant Biotechnol Journal*, 5:402-412.
Mayer et al., (Feb. 4, 2005) "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," *The Journal of Biological Chemistry*, 280(5):3621-3627.
Mayer et al., (Jan. 3, 2007) "Identification of amino acid residues involved in substrate specificity of plant acyl-ACP thioesterases using a bioinformatics-guided approach," *BMC Plant Biology*, 7(1):1-11 pages.
Mayfield et al., (Jan. 21, 2003) "Expression and assembly of a fully active antibody in algae," *Proc. Natl. Acad. Sci. USA*, 100(2):438-442.
Mekhedov et al., (Feb. 2000) "Toward a Functional Catalog of the Plant Genome. A Survey of Genes for Lipid Biosynthesis," *Plant Physiology*, 122:389-401.
Mendes et al. (2003) "Supercritical carbon dioxide extraction of compounds with pharmaceutical importance from microalgae," *Inorganica Chimica Acta*, 356:328-334.
Metzger et al., (Jun. 2003) "Lycopanerols I-L, Four New Tetraterpenoid Ethers from *Botryococcus braunii," J Nat. Prod.*66(6):772-778.
Metzger et al., (2005) "*Botryococcus braunii*: a rich source for hydrocarbons and related ether lipids," *Appl Microbiol Biotechnol* 66:486-496.
Miao et al., (2004) "High yield bio-oil production from fast pyrolysis by metabolic controlling of *Chlorella protothecoides," Journal of Biotechnology*, 110:85-93.
Miao et al., (2006) "Biodiesel production from heterotrophic microalgal oil," *Biosource Technology*, 97:841-846.
Minowa et al., (1995) "Oil production from algal cells of *Dunaliella tertiolecta* by direct thermochemical liquefaction," *Fuel*, 74(12):1735-1738.
Mitra et al., (Oct. 14, 1994) "A Chlorella Virus Gene Promoter Functions As a Strong Promoter Both in Plants and Bacteria," *Biochemical Biophysical Research Communication*, 204(1):187-194.
Mitra et al., (Oct. 1994) "The Chlorella virus adenine methyltransferase gene promoter is a strong promoter in plants," *Plant Mol. Biol.*, 26(1):85-93.
Mittendorf et al., (1999) "Polyhydroxyalkanoate synthesis in transgenic plants as a new tool to study carbon flow through β-oxidation," *The Plant Journal*, 20(1):45-55.

(56) References Cited

OTHER PUBLICATIONS

Moreno-Pérez et al., (2012) "Reduced expression of FatA thioesterases in *Arabidopsis* affects the oil content and fatty acid composition of the seeds," *Planta*, 235:629-639.
Mullet et al., (1985) "Multiple transcripts for higher plant rbcL and atpB genes and localization of the transcription initiation site of the rbcL gene," *Plant Molecular Biology*, 4:39-54.
Oda et al., (2000) "Degradation of Polylactide by Commercial Proteases," *Journal of Polymers and the Environment*, 8(1):29-32.
Onai et al., (2004) "Natural transformation of the thermophilic cyanobacterium *Thermosynechococcus elongatus* BP-1: a simple and efficient method for gene transfer," *Mol Genet Genomics*, 271(1):50-59.
Park et al., (2005) "ICORBtion and Characterization of Chlorella Virus from Fresh Water in Korea and Application in Chlorella Transformation System," The Plant Patholology Journal, 21(1):13-20.
Pröschold et al., (Aug. 2005) "Portrait of a species: *Chlamydomonas reinhardtii,*" *Genetics*,170:1601-1610.
Radakovits et al., (Apr. 2010) "Genetic Engineering of Algae for Enhanced Biofuel Production," *Eukaryotic Cell*, 9(4):486-501.
Rao et al., (2006) "Antioxidant Activity of *Botryococcus braunii* Extract Elucidated in Vitro Models," *J. Agric. Food Chem.*, 54(13):4593-4599.
Rehm et al., (2001)"Heterologous expression of the acyl—acyl carrier protein thioesterase gene from the plant *Umbellularia californica* mediates polyhydroxyalkanoate biosynthesis in recombinant *Escherichia coli,*" *Appl Microbiol Biotechnol*, 55:205-209.
Rismani-Yazdi et al., (2011) "Transcriptome sequencing and annotation of the microalgae *Dunaliella tertiolecta*: Pathway description and gene discovery for production of next-generation biofuels," *BMC Genomics*, 12:148, 17 pages; doi:10.1186/1471-2164-12-148.
Rosenberg, Julian N. et al., (2008) "A green light for engineered algae: redirecting metabolism to fuel a biotechnology revolution," *Current Opinion in Biotechnology*, 19(5):430-436.
Salas et al., (Jul. 1, 2002) "Characterization of substrate specificity of plant FatA and FatB acyl-ACP thioesterases," *Archives of Biochemistry and Biophysics*, 403(1):25-34.
Sanford, (Dec. 1988) "The biolistic process," *Trends in Biotech.* 6:299-302.
Sawayama et al. (1999) Possibility of renewable energy production and $CO_2$ mitigation by thermochemical liquefaction of microalgae *Biomass and Bioenergy*, 17:33-39.
Schreier et al., (1985) "The use of nuclear-encoded sequences to direct the light-regulated synthesis and transport of a foreign protein into plant chloroplasts," *EMBO J.* 4(1):25-32.
Schultz et al., (Apr. 2005) "A common core of secondary structure of the internal transcribed spacer 2 (ITS2) throughout the Eukaryota," *RNA*, 11(4):361-364.
Schütt et al., (1998) "The role of acyl carrier protein isoforms from *Cuphea lanceolata* seeds in the de-novo biosynthesis of medium-chain fatty acids," *Publication, Planta*, 205:263-268.
Shao et al., (2002) "Cloning and expression of metallothionein mutant α-KKS-α in *Anabaena* sp. PCC 7120," *Marine Pollution Bulletin*,45(1-12):163-167.
Sheehan, John; Dunahay, Terri; Benemann, John; Roessler, Paul; (Jul. 1998) "A Look Back at the U.S. Department of Energy's Aquatic Species Program: Biodiesel from Algae," Prepared for U.S. Department of Energy's Office of Fuels Development, Prepared by *National Renewable Energy Laboratory*, NREL/TP-580-24190, 328 pages.
Stemmer et al., (1995) "Single-step assembly of a gene and entire plasmid from large numbers of oligodeoxyribonucleotides," *Gene*, 164(1):49-53.
Tan et al., (Aug. 2005) "Establishment of a Micro-Particle Bombardment Transformation System for *Dunaliella salina,*" *The Journal of Microbiology*, 43(4):361-365.
Tang et al., (Aug. 1995) "Insertion Mutagenesis of *Chlamydomonas reinhardtii* by Electroporation and Heterologous DNA," *Biochemistry and Molecular Biology International*, 36(5):1025-1035.
Tjellström et al., (Feb. 20, 2013) "Disruption of plastid acyl:acyl carrier protein synthetases increases medium chain fatty acid accumulation in seeds of transgenic *Arabidopsis*," *FEBS Letters*, 587(7):936-942.
Tyystjärvi et al., (2005) "Mathematical modelling of the light response curve of photoinhibition of Photosystem II," *Photosynthesis Research*, 84(1-3):21-27.
Vázquez-Bermúdez et al., (Jan. 2000) "Uptake of 2-Oxoglutarate in *Synechococcus* Strains Transformed with the *Escherichia coli kgtP* Gene," *Journal of Bacteriology*, 182(1):211-215.
Vázquez-Bermúdez et al., (2003) "Carbon supply and 2-oxoglutarate ejects on expression of nitrate reductase and nitrogen-regulated genes in *Synechococcus* sp. strain PCC 7942," *FEMS Microbiology Letters*, 221(2):155-159.
Voelker, (1996) "Plant Acyl-ACP Thioesterases: Chain-Length Determining Enzymes in Plant Fatty Acid Biosynthesis," *Genetic Engineering*, Edited by: Setlow JK. Plenum Pres, New York, 18:111-133.
Voelker et al., (Dec. 1994) "Alteration of the Specificity and Regulation of Fatty Acid Synthesis of *Escherichia coli* by Expression of a Plant Medium Chain Acyl-Acyl Carrier Protein Thioesterase," *Journal of Bacteriology*, 176(23):7320-7327.
Voelker et al., (1997) "Broad-Range and Binary-Range Acyl-Acyl-Carrier-Protein Thioesterases Suggest an Alternative Mechanism for Medium-Chain Production in Seeds," *Plant Physiol.*, 114:669-677.
Voetz et al., (1994) "Three Different cDNAs Encoding Acyl Carrier Proteins from *Cuphea lanceolata,*" *Plant Physiol.*, 106:785-786.
Walker et al., (2005) "Characterisation of the *Dunaliella tertiolecta RbcS* genes and their promoter activity in *Chlamydomonas reinhardtii,*" *Plant Cell Rep.* 23(10-11):727-735.
Westphal et al., (Mar. 27, 2001) "*Vippl* deletion mutant of *Synechocystis*: A connection between bacterial phage shock and thylakoid biogenesis?" *Proc. Natl. Acad. Sci. USA*, 98(7):4243-4248.
Wiberg et al., (2000) "The distribution of caprylate, caprate and laurate in lipids from developing and mature seeds of transgenic *Brassica napus* L.," *Planta*, 212:33-40.
Wirth et al., (1989) "Transformation of various species of gram-negative bacteria belonging to 11 different genera by electroporation," *Mol Gen Genet.* 216(1):175-177.
Wolk et al., (Mar. 1984) "Construction of shuttle vectors capable of conjugative transfer from *Escherichia coli* to nitrogen-fixing filamentous cyanobacteria," *Proc. Natl. Acad. Sci. USA*, 81(5):1561-1565.
Wong et al., (1992) "*Arabidopsis thaliana* small subunit leader and transit peptide enhance the expression of *Bacillus thuringiensis* proteins in transgenic plants," *Plant Molecular Biology*, 20:81-93.
Wu et al., (2001) "Identification of Chlorella spp. iCORBtes using ribosomal DNA sequences," Bot. Bull. Acad. Sin.42:115-121.
Yu et al., (2011) "Modifications of the metabolic pathways of lipid and triacylglycerol production in microalgae," *Microbial Cell Factories*, 10:91 [Retrieved from the Internet Jul. 24, 2012: <URL:http://www.microbialcellfactories.com/content/10/1/91>], 11 pages.
Yuan et al., (Nov. 1995) "Modification of the substrate specificity of an acyl-acyl carrier protein thioesterase by protein engineering," *Proc. Natl. Acad. Sci. USA*, 92:10639-10643.
Yuan et al., (Feb. 16, 1996) "The Catalytic Cysteine and Histidine in the Plant Acyl-Acyl Carrier Protein Thioesterases," *The Journal of Biological Chemistry*, 271(7):3417-3419.
Zurawski et al., (1981) "The structure of the gene for the large subunit of ribulose 1,5-bisphosphate carboxylase from spinach chloroplast DNA," *Nucleic Acids Res.* 9(14):3251-3270.
Zurawski et al., (Dec. 1982) "Nucleotide sequence of the gene for the $M_{r\ 32,000}$ *thylakoid membrane protein from Spinacia oleracea* and *Nicotiana debneyi* predicts a totally conserved primary translation product of $M_{r\ 38,950}$," *Proc. Natl. Acad. Sci. USA*, 79:7699-7703.

* cited by examiner

SEQUENCE LISTING

<160> NUMBER OF SEQ ID NOS: 193

<210> SEQ ID NO 1
<211> LENGTH: 380
<212> TYPE: PRT
<213> ORGANISM: Cinnamomum camphora
<220> FEATURE:
<223> OTHER INFORMATION: Cinnamomum camphora (Cc) FATB1b variant M25L, M322R, deltaT367-D368 amino acid sequence

<400> SEQUENCE: 1

```
Met Ala Thr Thr Ser Leu Ala Ser Ala Phe Cys Ser Met Lys Ala Val
1               5                   10                  15

Met Leu Ala Arg Asp Gly Arg Gly Leu Lys Pro Arg Ser Ser Asp Leu
            20                  25                  30

Gln Leu Arg Ala Gly Asn Ala Gln Thr Ser Leu Lys Met Ile Asn Gly
        35                  40                  45

Thr Lys Phe Ser Tyr Thr Glu Ser Leu Lys Lys Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Asn Pro Pro Gln Leu Leu
                85                  90                  95

Asp Asp His Phe Gly Pro His Gly Leu Val Phe Arg Arg Thr Phe Ala
            100                 105                 110

Ile Arg Ser Tyr Glu Val Gly Pro Asp Arg Ser Thr Ser Ile Val Ala
        115                 120                 125

Val Met Asn His Leu Gln Glu Ala Ala Leu Asn His Ala Lys Ser Val
    130                 135                 140

Gly Ile Leu Gly Asp Gly Phe Gly Thr Thr Leu Glu Met Ser Lys Arg
145                 150                 155                 160

Asp Leu Ile Trp Val Val Lys Arg Thr His Val Ala Val Glu Arg Tyr
                165                 170                 175

Pro Ala Trp Gly Asp Thr Val Glu Val Glu Cys Trp Val Gly Ala Ser
            180                 185                 190

Gly Asn Asn Gly Arg Arg His Asp Phe Leu Val Arg Asp Cys Lys Thr
        195                 200                 205

Gly Glu Ile Leu Thr Arg Cys Thr Ser Leu Ser Val Met Met Asn Thr
    210                 215                 220

Arg Thr Arg Arg Leu Ser Lys Ile Pro Glu Glu Val Arg Gly Glu Ile
225                 230                 235                 240

Gly Pro Ala Phe Ile Asp Asn Val Ala Val Lys Asp Glu Glu Ile Lys
                245                 250                 255

Lys Pro Gln Lys Leu Asn Asp Ser Thr Ala Asp Tyr Ile Gln Gly Gly
```

```
            260                 265                 270

Leu Thr Pro Arg Trp Asn Asp Leu Asp Ile Asn Gln His Val Asn Asn
        275                 280                 285

Ile Lys Tyr Val Asp Trp Ile Leu Glu Thr Val Pro Asp Ser Ile Phe
    290                 295                 300

Glu Ser His His Ile Ser Ser Phe Thr Ile Glu Tyr Arg Arg Glu Cys
305                 310                 315                 320

Thr Arg Asp Ser Val Leu Gln Ser Leu Thr Thr Val Ser Gly Gly Ser
                325                 330                 335

Ser Glu Ala Gly Leu Val Cys Glu His Leu Leu Gln Leu Glu Gly Gly
            340                 345                 350

Ser Glu Val Leu Arg Ala Lys Thr Glu Trp Arg Pro Lys Leu Ser Phe
        355                 360                 365

Arg Gly Ile Ser Val Ile Pro Ala Glu Ser Ser Val
    370                 375                 380


<210> SEQ ID NO 2
<211> LENGTH: 1128
<212> TYPE: DNA
<213> ORGANISM: Cinnamomum camphora
<220> FEATURE:
<223> OTHER INFORMATION: Cinnamomum camphora (Cc) FATB1b variant M25L,
      M322R, deltaT367-D368 coding DNA sequence

<400> SEQUENCE: 2

ttagcttctg ctttctgctc gatgaaagct gtaatgttgg ctcgtgatgg caggggcttg     60

aaacccagga gcagtgattt gcagctgagg gcgggaaatg cacaaacctc tttgaagatg    120

atcaatggga ccaagttcag ttacacagag agcttgaaaa agttgcctga ctggagcatg    180

ctctttgcag tgatcacgac catcttttcg gctgctgaga agcagtggac caatctagag    240

tggaagccga agccgaatcc accccagttg cttgatgacc attttgggcc gcatgggtta    300

gttttcaggc gcacctttgc catcagatcg tatgaggtgg gacctgaccg ctccacatct    360

atagtggctg ttatgaatca cttgcaggag gctgcactta atcatgcgaa gagtgtggga    420

attctaggag atggattcgg tacgacgcta gagatgagta agagagatct gatatgggtt    480

gtgaaacgca cgcatgttgc tgtggaacgg taccctgctt ggggtgatac tgttgaagta    540

gagtgctggg ttggtgcatc gggaaataat ggcaggcgcc atgatttcct tgtccgggac    600

tgcaaaacag gcgaaattct tacaagatgt accagtcttt cggtgatgat gaatacaagg    660

acaaggaggt tgtccaaaat ccctgaagaa gttagagggg agatagggcc tgcattcatt    720

gataatgtgg ctgtcaagga cgaggaaatt aagaaaccac agaagctcaa tgacagcact    780

gcagattaca tccaaggagg attgactcct cgatggaatg atttggatat caatcagcac    840

gttaacaaca tcaaatacgt tgactggatt cttgagactg tcccagactc aatctttgag    900

agtcatcata tttccagctt cactattgaa tacaggagag agtgcacgag ggatagcgtg    960

ctgcagtccc tgaccactgt ctccggtggc tcgtcggaag ctgggttagt gtgcgagcac   1020

ttgctccagc ttgaaggtgg gtctgaggta ttgagggcaa aaacagagtg gaggcctaag   1080

cttagtttca gagggattag tgtgataccc gcagaatcga gtgtctaa                1128


<210> SEQ ID NO 3
<211> LENGTH: 1128
<212> TYPE: DNA
<213> ORGANISM: Artificial Sequence
<220> FEATURE:
<223> OTHER INFORMATION: Description of Artificial Sequence: Synthetic
```

polynucleotide
<220> FEATURE:
<223> OTHER INFORMATION: Cinnamomum camphora (Cc) FATB1b variant M25L, M322R, deltaT367-D368 coding DNA sequence codon optimized for Prototheca moriformis

<400> SEQUENCE: 3
ttagcttctg ctttctgctc gatgaaagct gtaatgttgg ctcgtgatgg caggggcttg 60
aaacccagga gcagtgattt gcagctgagg gcgggaaatg cacaaacctc tttgaagatg 120
atcaatggga ccaagttcag ttacacagag agcttgaaaa agttgcctga ctggagcatg 180
ctctttgcag tgatcacgac catcttttcg gctgctgaga agcagtggac caatctagag 240
tggaagccga agccgaatcc accccagttg cttgatgacc attttgggcc gcatgggtta 300
gttttcaggc gcacctttgc catcagatcg tatgaggtgg gacctgaccg ctccacatct 360
atagtggctg ttatgaatca cttgcaggag gctgcactta atcatgcgaa gagtgtggga 420
attctaggag atggattcgg tacgacgcta gagatgagta agagagatct gatatgggtt 480
gtgaaacgca cgcatgttgc tgtggaacgg taccctgctt ggggtgatac tgttgaagta 540
gagtgctggg ttggtgcatc gggaaataat ggcaggcgcc atgatttcct tgtccgggac 600
tgcaaaacag gcgaaattct tacaagatgt accagtcttt cggtgatgat gaatacaagg 660
acaaggaggt tgtccaaaat ccctgaagaa gttagagggg agatagggcc tgcattcatt 720
gataatgtgg ctgtcaagga cgaggaaatt aagaaaccac agaagctcaa tgacagcact 780
gcagattaca tccaaggagg attgactcct cgatggaatg atttggatat caatcagcac 840
gttaacaaca tcaaatacgt tgactggatt cttgagactg tcccagactc aatctttgag 900
agtcatcata tttccagctt cactattgaa tacaggagag agtgcacgag ggatagcgtg 960
ctgcagtccc tgaccactgt ctccggtggc tcgtcggaag ctgggttagt gtgcgagcac 1020
ttgctccagc ttgaaggtgg gtctgaggta ttgagggcaa aaacagagtg gaggcctaag 1080
cttagtttca gagggattag tgtgataccc gcagaatcga gtgtctaa 1128

<210> SEQ ID NO 4
<211> LENGTH: 357
<212> TYPE: PRT
<213> ORGANISM: Cinnamomum camphora
<220> FEATURE:
<223> OTHER INFORMATION: Cinnamomum camphora (Cc) FATB4 amino acid sequence

<400> SEQUENCE: 4

Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu

-continued

```
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Thr Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
        355


<210> SEQ ID NO 5
<211> LENGTH: 1074
<212> TYPE: DNA
<213> ORGANISM: Cinnamomum camphora
<220> FEATURE:
<223> OTHER INFORMATION: Cinnamomum camphora (Cc) FATB4 coding DNA
      sequence

<400> SEQUENCE: 5

atggtcacca cctctttagc ttccgcttac ttctcgatga aagctgtaat gttggctcct     60

gacggcaggg gcataaagcc caggagcagt ggtttgcagg tgagggcggg aaatgaacga    120

aactcttgca aggtgatcaa tgggaccaag gtcaaagaca cggagggctt gaaagggtgc    180

agcacgttgc aaggccagag catgcttgat gaccattttg gtctgcatgg gctagttttc    240

aggcgcacct ttgcaatcag atgctatgag gttggacctg accgctccac atccataatg    300

gctgttatga atcacttgca ggaagctgca cgtaatcatg cggagagtct gggacttcta    360

ggagatggat tcggtgagac actggagatg agtaagagag atctgatatg ggttgtgaga    420

cgcacgcatg ttgctgtgga acggtaccct gcttggggcg atactgttga agtcgaggcc    480

tgggtgggtg catcaggtaa cactggcatg cgccgcgatt tccttgtccg cgactgcaaa    540

actggccaca ttcttacaag atgtaccagt gtttcagtga tgatgaatat gaggacaagg    600

agattgtcca aaattcccca agaagttaga gcggagattg accctctttt cattgaaaag    660
```

```
gttgctgtca aggaagggga aattaaaaaa ttacagaagt tgaatgatag cactgcagat    720

tacattcaag gggttggac tcctcgatgg aatgatttgg atgtcaatca gcacgtgaac    780

aatatcatat acgttggctg gatttttaag agcgtcccag actctatctc tgagaatcat    840

catctttcta gcatcactct cgaatacagg agagagtgca caaggggcaa caagctgcag    900

tccctgacca ctgtttgtgg tggctcgtcg gaagctggga tcatatgtga gcacctactc    960

cagcttgagg atgggtctga ggttttgagg gcaagaacag agtggaggcc caagcacacc   1020

gatagtttcc aaggcattag tgagagattc ccgcagcaag aaccgcataa gtaa         1074
```

```
<210> SEQ ID NO 6
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cinnamomum camphora (Cc) FATB4 coding DNA
      sequence codon optimized for Prototheca moriformis

<400> SEQUENCE: 6
```

```
atggtgacca cctccctggc ctccgcctac ttctccatga aggccgtgat gctggccccc     60

gacggccgcg gcatcaagcc ccgctcctcc ggcctgcagg tgcgcgccgg caacgagcgc    120

aactcctgca aggtgatcaa cggcaccaag gtgaaggaca ccgagggcct gaagggctgc    180

tccaccctgc agggccagtc catgctggac gaccacttcg gcctgcacgg cctggtgttc    240

cgccgcacct tcgccatccg ctgctacgag gtgggccccg accgctccac ctccatcatg    300

gccgtgatga accacctgca ggaggccgcc cgcaaccacg ccgagtccct gggcctgctg    360

ggcgacggct tcggcgagac cctggagatg tccaagcgcg acctgatctg ggtggtgcgc    420

cgcacccacg tggccgtgga gcgctacccc gcctggggcg acaccgtgga ggtggaggcc    480

tgggtgggcg cctccggcaa caccggcatg cgccgcgact tcctggtgcg cgactgcaag    540

accggccaca tcctgacccg ctgcacctcc gtgtccgtga tgatgaacat gcgcacccgc    600

cgcctgtcca agatccccca ggaggtgcgc gccgagatcg acccccctgtt catcgagaag    660

gtggccgtga aggagggcga gatcaagaag ctgcagaagc tgaacgactc caccgccgac    720

tacatccagg gcggctggac cccccgctgg aacgacctgg acgtgaacca gcacgtgaac    780

aacatcatct acgtgggctg gatcttcaag tccgtgcccg actccatctc cgagaaccac    840

cacctgtcct ccatcaccct ggagtaccgc cgcgagtgca cccgcggcaa caagctgcag    900

tccctgacca ccgtgtgcgg cggctcctcc gaggccggca tcatctgcga gcacctgctg    960

cagctggagg acggctccga ggtgctgcgc gcccgcaccg agtggcgccc caagcacacc   1020

gactccttcc agggcatctc cgagcgcttc cccagcagg agccccacaa gtga          1074
```

```
<210> SEQ ID NO 7
<211> LENGTH: 419
<212> TYPE: PRT
<213> ORGANISM: Cinnamomum camphora
<220> FEATURE:
<223> OTHER INFORMATION: Cinnamomum camphora (Cc) FATB3 amino acid
      sequence

<400> SEQUENCE: 7

Met Val Ala Thr Ala Ala Ala Ser Ala Phe Phe Pro Val Gly Ala Pro
1               5                   10                  15
```

-continued

```
Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu
```

<210> SEQ ID NO 8

<211> LENGTH: 1254
<212> TYPE: DNA
<213> ORGANISM: Cinnamomum camphora
<220> FEATURE:
<223> OTHER INFORMATION: Cinnamomum camphora (Cc) FATB3 coding DNA
sequence

<400> SEQUENCE: 8
atggttgcca ccgctgctgc ttctgctttc ttcccggtcg gtgctccggc tacgtcatct 60
gcaacttcag ccaaagcgtc gatgatgcct gataatttgg atgccagagg catcaaaccg 120
aagccggctt cgtccagcgg cttgcaggtt aaggcaaatg cccatgcctc tcccaagatt 180
aatggttcca aggtgagcac ggataccttg aagggggaag acaccttaac ttcctcgccc 240
gccccacgga cctttatcaa ccaattgcct gactggagca tgttccttgc tgccatcaca 300
actattttct tggctgccga gaagcagtgg acgaatctcg actggaagcc cagaagaccc 360
gacatgcttg ctgacccgtt tggcatcggg aggtttatgc aggatgggct gattttcagg 420
cagcactttg caatcagatc ttatgagatt ggggctgata gaacggcgtc tatagagact 480
ttaatgaatc acttgcagga gactgcactt aatcatgtga ggagtgctgg actcctaggt 540
gatggatttg gtgcgacacc tgagatgagt agaagagatc tgatatgggt tgtaacacgt 600
atgcaggttc ttgtggaccg ctaccctgct tggggtgata ttgttgaagt agagacctgg 660
gttggtgcat ctggaaaaaa tggtatgcgc cgtgattggc ttgttcggga cagccaaact 720
ggtgaaattc tcacacgagc taccagtgtt tgggtgatga tgaataaacg gacaaggcga 780
ttgtccaaac ttcctgaaga agttagaggg gaaatagggc cttattttat agaagatgtt 840
gctatcatag aggaggacaa caggaaacta cagaagctca atgaaaacac tgctgataat 900
gttcgaaggg gtttgactcc tcgctggagt gatctggatg ttaatcagca tgtgaacaat 960
gtcaaataca ttggttggat tcttgagagt gcaccaggat ccatcttgga gagtcatgag 1020
ctttcctgca tgacccttga atacaggaga gaatgtggga aggacagtgt gctgcagtca 1080
atgactgctg tctctggtgg aggcagtgca gcaggtggct caccagaatc tagcgttgag 1140
tgtgaccact tgctccagct agagagtggg cctgaagttg tgaggggaag aaccgagtgg 1200
aggcccaaga gtgctaataa ctcgaggagc atcctggaga tgccggccga gagc 1254

<210> SEQ ID NO 9
<211> LENGTH: 1260
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cinnamomum camphora (Cc) FATB4 coding DNA
sequence codon optimized for Prototheca moriformis

<400> SEQUENCE: 9
atggtggcca ccgccgccgc ctccgccttc ttccccgtgg gcgcccccgc cacctcctcc 60
gccacctccg ccaaggcctc catgatgccc gacaacctgg acgcccgcgg catcaagccc 120
aagcccgcct cctcctccgg cctgcaggtg aaggccaacg cccacgcctc ccccaagatc 180
aacggctcca aggtgtccac cgacaccctg aagggcgagg acaccctgac ctcctccccc 240
gccccccgca ccttcatcaa ccagctgccc gactggtcca tgttcctggc cgccatcacc 300
accatcttcc tggccgccga gaagcagtgg accaacctgg actggaagcc ccgccgcccc 360
gacatgctgg ccgacccctt cggcatcggc cgcttcatgc aggacggcct gatcttccgc 420

```
cagcacttcg ccatccgctc ctacgagatc ggcgccgacc gcaccgcctc catcgagacc    480

ctgatgaacc acctgcagga gaccgccctg aaccacgtgc gctccgccgg cctgctgggc    540

gacggcttcg gcgccacccc cgagatgtcc cgccgcgacc tgatctgggt ggtgacccgc    600

atgcaggtgc tggtggaccg ctaccccgcc tggggcgaca tcgtggaggt ggagacctgg    660

gtgggcgcct ccggcaagaa cggcatgcgc cgcgactggc tggtgcgcga ctcccagacc    720

ggcgagatcc tgacccgcgc cacctccgtg tgggtgatga tgaacaagcg cacccgccgc    780

ctgtccaagc tgcccgagga ggtgcgcggc gagatcggcc cctacttcat cgaggacgtg    840

gccatcatcg aggaggacaa ccgcaagctg cagaagctga acgagaacac cgccgacaac    900

gtgcgccgcg gcctgacccc ccgctggtcc gacctggacg tgaaccagca cgtgaacaac    960

gtgaagtaca tcggctggat cctggagtcc gcccccggct ccatcctgga gtcccacgag   1020

ctgtcctgca tgaccctgga gtaccgccgc gagtgcggca aggactccgt gctgcagtcc   1080

atgaccgccg tgtccggcgg cggctccgcc gccggcggct cccccgagtc ctccgtggag   1140

tgcgaccacc tgctgcagct ggagtccggc cccgaggtgg tgcgcggccg caccgagtgg   1200

cgccccaagt ccgccaacaa ctcccgctcc atcctggaga tgcccgccga gtccctgtga   1260
```

```
<210> SEQ ID NO 10
<211> LENGTH: 361
<212> TYPE: PRT
<213> ORGANISM: Cuphea hyssopifolia
<220> FEATURE:
<223> OTHER INFORMATION: Cuphea hyssopifolia (Chs) FATB1 amino acid
      sequence

<400> SEQUENCE: 10

Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60

Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125

Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160

Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
```

```
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360


<210> SEQ ID NO 11
<211> LENGTH: 1086
<212> TYPE: DNA
<213> ORGANISM: Cuphea hyssopifolia
<220> FEATURE:
<223> OTHER INFORMATION: Cuphea hyssopifolia (Chs) FATB1 coding DNA
      sequence

<400> SEQUENCE: 11

atggttgcca ctaatgctgc tgccttttct gcttatactt tcttccttac ttcaccaact     60

catggttact cttccaaacg tctcgccgat actcaaaatg gttatccggg tacctccttg    120

aaatcgaaat ccactcctcc accagctgct gctgctgctc gtaacggtgc attgccactg    180

ctggcctcca tctgcaaatg ccccaaaaag gctgatggga gtatgcaact agacagctcc    240

ttggtcttcg ggtttcaatt ttacattaga tcatatgaag tgggtgcgga tcaaaccgtg    300

tcaatacaga cagtactcaa ttacttacag gaggcagcca tcaatcatgt tcagagtgct    360

ggctattttg gtgatagttt tggcgccacc ccggaaatga ccaagaggaa cctcatctgg    420

gttatcacta agatgcaggt tttggtggat cgctatcccg cttggggcga tgttgttcaa    480

gttgatacat ggacctgtag ttctggtaaa aacagcatgc agcgtgattg gttcgtacgg    540

gatctcaaaa ctggagatat tataacaaga gcctcgagcg tgtgggtgct gatgaataga    600

ctcaccagaa aattatcaaa aattcctgaa gcagttctgg aagaagcaaa actttttgtg    660

atgaacactg cccccaccgt agatgacaac aggaagctac caaagctgga tggcagcagt    720

gctgattatg tcctctctgg cttaactcct agatggagcg acttagatat gaaccagcat    780

gtcaacaatg tgaagtacat agcctggatc cttgagagtg tccctcagag cataccggag    840

acacacaagc tgtcagcgat aaccgtggag tacaggagag aatgtggcaa gaacagcgtc    900

ctccagtctc tgaccaacgt ctccggggat ggaatcacat gtggaaacag tattatcgag    960

tgccaccatt tgcttcaact tgagactggc ccagagattc tactagcgcg gacggagtgg   1020

atatccaagg aacctgggtt caggggagct ccaatccagg cagagaaagt ctacaacaac   1080

aaataa                                                              1086
```

<210> SEQ ID NO 12
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB1 coding DNA
      sequence codon optimized for Prototheca moriformis

<400> SEQUENCE: 12
atggtggcca ccaacgccgc cgccttctcc gcctacacct tcttcctgac ctcccccacc 60
cacggctact cctccaagcg cctggccgac acccagaacg gctaccccgg cacctccctg 120
aagtccaagt ccaccccccc ccccgccgcc gccgccgccc gcaacggcgc cctgcccctg 180
ctggcctcca tctgcaagtg ccccaagaag gccgacggct ccatgcagct ggactcctcc 240
ctggtgttcg gcttccagtt ctacatccgc tcctacgagg tgggcgccga ccagaccgtg 300
tccatccaga ccgtgctgaa ctacctgcag gaggccgcca tcaaccacgt gcagtccgcc 360
ggctacttcg gcgactcctt cggcgccacc cccgagatga ccaagcgcaa cctgatctgg 420
gtgatcacca agatgcaggt gctggtggac cgctaccccg cctggggcga cgtggtgcag 480
gtggacacct ggacctgctc ctccggcaag aactccatgc agcgcgactg gttcgtgcgc 540
gacctgaaga ccggcgacat catcacccgc gcctcctccg tgtgggtgct gatgaaccgc 600
ctgacccgca agctgtccaa gatccccgag gccgtgctgg aggaggccaa gctgttcgtg 660
atgaacaccg cccccaccgt ggacgacaac cgcaagctgc ccaagctgga cggctcctcc 720
gccgactacg tgctgtccgg cctgaccccc cgctggtccg acctggacat gaaccagcac 780
gtgaacaacg tgaagtacat cgcctggatc ctggagtccg tgccccagtc catccccgag 840
acccacaagc tgtccgccat caccgtggag taccgccgcg agtgcggcaa gaactccgtg 900
ctgcagtccc tgaccaacgt gtccggcgac ggcatcacct gcggcaactc catcatcgag 960
tgccaccacc tgctgcagct ggagaccggc cccgagatcc tgctggcccg caccgagtgg 1020
atctccaagg agcccggctt ccgcggcgcc cccatccagg ccgagaaggt gtacaacaac 1080
aagtga 1086

<210> SEQ ID NO 13
<211> LENGTH: 415
<212> TYPE: PRT
<213> ORGANISM: Cuphea hyssopifolia
<220> FEATURE:
<223> OTHER INFORMATION: Cuphea hyssopifolia (Chs) FATB2 amino acid
      sequence

<400> SEQUENCE: 13

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

```
Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415
```

<210> SEQ ID NO 14
<211> LENGTH: 1248
<212> TYPE: DNA
<213> ORGANISM: Cuphea hyssopifolia
<220> FEATURE:
<223> OTHER INFORMATION: Cuphea hyssopifolia (Chs) FATB2 coding DNA sequence

<400> SEQUENCE: 14

```
atggtggcta ccgctgcaag ttcagcattc ttccctgtgc cgtcccccga cgcctcctct     60

agacctggaa agctcggcaa tgggtcatcg agcttgagcc ccctcaagcc caaattgatg    120

gccaatggcg ggttgcaggt taaggcaaac gccagtgccc ctcctaagat caatggttct    180

tcggtcggtc taaagtccgg cagtctcaag actcaggaag acactccttc ggcgcctcct    240
```

```
ccccggactt ttattaacca gctgcctgat tggagtatgc ttcttgctgc aatcactact    300

gtcttcttgg cagcagagaa gcagtggatg atgcttgatt ggaaacccaa gaggcctgac    360

atgcttgtgg acccgttcgg attgggaagg attgttcaag atgggcttgt gttcaggcag    420

aatttttcga ttaggtccta tgaaataggc gctgatcgca ctgcgtctat agagacggtg    480

atgaaccact tgcaggaaac agctctcaat catgttaaga gtgctgggct tcttaatgac    540

ggctttggtc gtactcttga gatgtataaa agggacctta tttgggttgt tgcaaaaatg    600

caggtcatgg ttaaccgcta tcctacttgg ggcgacacgg ttgaagtgaa tacttgggtt    660

gccaagtcag ggaaaaatgg tatgcgtcgt gattggctca taagtgattg caatacagga    720

gaaattctta ctagagcatc aagtgtgtgg gtcatgatga atcaaaagac aagaagattg    780

tcaaaaattc cagatgaggt tcgacatgag atagagcctc atttcgtgga ctctgctccc    840

gtcattgaag atgatgaccg gaaacttccc aagctggatg agaagactgc tgactccatc    900

cgcaagggtc taactccgaa gtggaatgac ttggatgtca atcagcacgt caacaacgtg    960

aagtacattg ggtggattct tgagagtact ccaccagaag ttctggagac ccaggagtta   1020

tgttccctta ccctggaata taggcgggaa tgcggaaggg agagcgtgct ggagtccctc   1080

actgctgtgg acccctctgg aaagggctct gggtctcagt tccagcacct tctgcggctt   1140

gaggatggag gtgagattgt gaaggggaga actgagtggc gacccaagac tgcaggaatc   1200

aatgggccaa tagcatccgg ggagacctca cctggagact cttcttag                1248
```

```
<210> SEQ ID NO 15
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB2 coding DNA
      sequence codon optimized for Prototheca moriformis

<400> SEQUENCE: 15
```

```
atggtggcca ccgccgcctc ctccgccttc ttccccgtgc cctcccccga cgcctcctcc     60

cgccccggca agctgggcaa cggctcctcc tccctgtccc ccctgaagcc caagctgatg    120

gccaacggcg gcctgcaggt gaaggccaac gcctccgccc cccccaagat caacggctcc    180

tccgtgggcc tgaagtccgg ctccctgaag acccaggagg acacccccctc cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360

atgctggtgg accccttcgg cctgggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgaacgac    540

ggcttcggcc gcaccctgga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgccgcctg    780

tccaagatcc ccgacgaggt gcgccacgag atcgagcccc acttcgtgga ctccgccccc    840

gtgatcgagg acgacgaccg caagctgccc aagctggacg agaagaccgc cgactccatc    900
```

-continued

```
cgcaagggcc tgaccccCaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg acccctccgg caagggctcc ggctcccagt tccagcacct gctgcgcctg   1140

gaggacggcg gcgagatcgt gaagggccgc accgagtggc gccccaagac cgccggcatc   1200

aacggcccca tcgcctccgg cgagacctcc cccggcgact cctcctga                1248
```

```
<210> SEQ ID NO 16
<211> LENGTH: 427
<212> TYPE: PRT
<213> ORGANISM: Cuphea hyssopifolia
<220> FEATURE:
<223> OTHER INFORMATION: Cuphea hyssopifolia (Chs) FATB2b +a.a.248-259
      variant amino acid sequence

<400> SEQUENCE: 16

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Lys Ser Gln Ile Met Leu Pro Leu
                245                 250                 255

His Tyr Cys Ser Val Trp Val Met Met Asn Gln Lys Thr Arg Arg Leu
            260                 265                 270

Ser Lys Ile Pro Asp Glu Val Arg His Glu Ile Glu Pro His Phe Val
        275                 280                 285

Asp Ser Ala Pro Val Ile Glu Asp Asp Asp Arg Lys Leu Pro Lys Leu
    290                 295                 300
```

```
Asp Glu Lys Thr Ala Asp Ser Ile Arg Lys Gly Leu Thr Pro Lys Trp
305                 310                 315                 320

Asn Asp Leu Asp Val Asn Gln His Val Asn Asn Val Lys Tyr Ile Gly
                325                 330                 335

Trp Ile Leu Glu Ser Thr Pro Pro Glu Val Leu Glu Thr Gln Glu Leu
            340                 345                 350

Cys Ser Leu Thr Leu Glu Tyr Arg Arg Glu Cys Gly Arg Glu Ser Val
        355                 360                 365

Leu Glu Ser Leu Thr Ala Val Asp Pro Ser Gly Lys Gly Ser Gly Ser
    370                 375                 380

Gln Phe Gln His Leu Leu Arg Leu Glu Asp Gly Gly Glu Ile Val Lys
385                 390                 395                 400

Gly Arg Thr Glu Trp Arg Pro Lys Thr Ala Gly Ile Asn Gly Pro Ile
                405                 410                 415

Ala Ser Gly Glu Thr Ser Pro Gly Asp Ser Ser
            420                 425


<210> SEQ ID NO 17
<211> LENGTH: 1284
<212> TYPE: DNA
<213> ORGANISM: Cuphea hyssopifolia
<220> FEATURE:
<223> OTHER INFORMATION: Cuphea hyssopifolia (Chs) FATB2b+a.a.248-259
      variant coding DNA sequence

<400> SEQUENCE: 17

atggtggcta ccgctgcaag ttcagcattc ttccctgtgc cgtcccccga cgcctcctct     60

agacctggaa agctcggcaa tgggtcatcg agcttgagcc ccctcaagcc caaattgatg    120

gccaatggcg ggttgcaggt taaggcaaac gccagtgccc ctcctaagat caatggttct    180

tcggtcggtc taaagtccgg cagtctcaag actcaggaag acactccttc ggcgcctcct    240

ccccggactt ttattaacca gctgcctgat tggagtatgc ttcttgctgc aatcactact    300

gtcttcttgg cagcagagaa gcagtggatg atgcttgatt ggaaacccaa gaggcctgac    360

atgcttgtgg acccgttcgg attgggaagg attgttcaag atgggcttgt gttcaggcag    420

aatttttcga ttaggtccta tgaaataggc gctgatcgca ctgcgtctat agagacggtg    480

atgaaccact tgcaggaaac agctctcaat catgttaaga gtgctgggct tcttaatgac    540

ggctttggtc gtactcttga gatgtataaa agggacctta tttgggttgt tgcaaaaatg    600

caggtcatgg ttaaccgcta tcctacttgg ggcgacacgg ttgaagtgaa tacttgggtt    660

gccaagtcag ggaaaaatgg tatgcgtcgt gattggctca taagtgattg caatacagga    720

gaaattctta ctagagcatc aagtaaaagc caaattatgt tacccttaca ttattgcagt    780

gtgtgggtca tgatgaatca aaagacaaga agattgtcaa aaattccaga tgaggttcga    840

catgagatag agcctcattt cgtggactct gctcccgtca ttgaagatga tgaccggaaa    900

cttcccaagc tggatgagaa gactgctgac tccatccgca agggtctaac tccgaagtgg    960

aatgacttgg atgtcaatca gcacgtcaac aacgtgaagt acattgggtg gattcttgag   1020

agtactccac cagaagttct ggagacccag gagttatgtt cccttaccct ggaatatagg   1080

cgggaatgcg gaagggagag cgtgctggag tccctcactg ctgtggaccc ctctggaaag   1140

ggctctgggt ctcagttcca gcaccttctg cggcttgagg atggaggtga gattgtgaag   1200

gggagaactg agtggcgacc caagactgca ggaatcaatg ggccaatagc atccggggag   1260

acctcacctg gagactcttc ttag                                           1284
```

<210> SEQ ID NO 18
<211> LENGTH: 1284
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hyssopifolia (Chs) FATB2b +a.a.248-259 variant coding DNA sequence codon optimized for Prototheca moriformis

<400> SEQUENCE: 18

```
atggtggcca ccgccgcctc ctccgccttc ttccccgtgc cctcccccga cgcctcctcc     60
cgccccggca agctgggcaa cggctcctcc tccctgtccc ccctgaagcc caagctgatg    120
gccaacggcg gcctgcaggt gaaggccaac gcctccgccc cccccaagat caacggctcc    180
tccgtgggcc tgaagtccgg ctccctgaag acccaggagg acacccccctc cgcccccccc    240
ccccgcacct tcatcaacca gctgcccgac tggtccatgc tgctggccgc catcaccacc    300
gtgttcctgg ccgccgagaa gcagtggatg atgctggact ggaagcccaa gcgccccgac    360
atgctggtgg accccttcgg cctgggccgc atcgtgcagg acggcctggt gttccgccag    420
aacttctcca tccgctccta cgagatcggc gccgaccgca ccgcctccat cgagaccgtg    480
atgaaccacc tgcaggagac cgccctgaac cacgtgaagt ccgccggcct gctgaacgac    540
ggcttcggcc gcaccctgga gatgtacaag cgcgacctga tctgggtggt ggccaagatg    600
caggtgatgg tgaaccgcta ccccacctgg ggcgacaccg tggaggtgaa cacctgggtg    660
gccaagtccg gcaagaacgg catgcgccgc gactggctga tctccgactg caacaccggc    720
gagatcctga cccgcgcctc ctccaagtcc cagatcatgc tgcccctgca ctactgctcc    780
gtgtgggtga tgatgaacca gaagacccgc cgcctgtcca agatccccga cgaggtgcgc    840
cacgagatcg agccccactt cgtggactcc gcccccgtga tcgaggacga cgaccgcaag    900
ctgcccaagc tggacgagaa gaccgccgac tccatccgca agggcctgac ccccaagtgg    960
aacgacctgg acgtgaacca gcacgtgaac aacgtgaagt acatcggctg gatcctggag   1020
tccacccccc ccgaggtgct ggagacccag gagctgtgct ccctgaccct ggagtaccgc   1080
cgcgagtgcg gccgcgagtc cgtgctggag tccctgaccg ccgtggaccc ctccggcaag   1140
ggctccggct cccagttcca gcacctgctg cgcctggagg acggcggcga gatcgtgaag   1200
ggccgcaccg agtggcgccc caagaccgcc ggcatcaacg gccccatcgc ctccggcgag   1260
acctcccccg gcgactcctc ctga                                          1284
```

<210> SEQ ID NO 19
<211> LENGTH: 417
<212> TYPE: PRT
<213> ORGANISM: Cuphea hyssopifolia
<220> FEATURE:
<223> OTHER INFORMATION: Cuphea hyssopifolia (Chs) FATB3 amino acid sequence

<400> SEQUENCE: 19

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45
```

```
Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser
```

<210> SEQ ID NO 20
<211> LENGTH: 1254
<212> TYPE: DNA
<213> ORGANISM: Cuphea hyssopifolia
<220> FEATURE:
<223> OTHER INFORMATION: Cuphea hyssopifolia (Chs) FATB3 coding DNA sequence

<400> SEQUENCE: 20

```
atggtggctg ccgaagcaag ttctgcactc ttctccgttc gaaccccggg aacctcccct     60
aaacccggga agttcgggaa ttggccaacg agcttgagcg tccccttcaa gtccaaatca    120
aaccacaatg gcggctttca ggttaaggca aacgccagtg cccgtcctaa ggctaacggt    180
tctgcagtaa gtctaaagtc tggcagcctc gacactcagg aggacacttc atcgtcgtcc    240
tctcctcctc ggactttcat taaccagttg cccgactgga gtatgctgct gtccgcgatc    300
acgaccgtct tcgtggcggc tgagaagcag tggacgatgc ttgatcggaa atctaagagg    360
cccgacatgc tcatggaccc gtttggggtt gacagggttg ttcaggatgg ggctgtgttc    420
agacagagtt tttcgattag gtcttacgaa ataggcgctg atcgaacagc ctctatagag    480
acgctgatga acatcttcca ggaaacatct ctcaatcatt gtaagagtat cggtcttctc    540
aatgacggct ttggtcgtac tcctgagatg tgtaagaggg acctcatttg ggtggttaca    600
aaaatgcacg tcgaggttaa tcgctatcct acttggggtg atactatcga ggtcaatact    660
tgggtctccg agtcggggaa aaccggtatg ggtcgtgatt ggctgataag tgattgtcat    720
acaggagaaa ttctaataag agcaacgagc atgtgtgcta tgatgaatca aaagacgaga    780
agattctcaa aatttccata tgaggttcga caggagttgg cgcctcattt tgtggactct    840
gctcctgtca ttgaagacta tcaaaaattg cacaagcttg atgtgaagac gggtgattcc    900
atttgcaatg gcctaactcc aaggtggaat gacttggatg tcaatcagca cgttaacaat    960
gtgaagtaca ttgggtggat tctcgagagt gttccaacgg aagttttcga gacccaggag   1020
ctatgtggcc tcacccttga gtataggcgg gaatgcggaa gggacagtgt gctggagtcc   1080
gtgaccgcta tggatccatc aaaagaggga gacagatctc tgtaccagca ccttcttcgg   1140
cttgaggatg gggctgatat cgcgaagggc agaaccaagt ggcggccgaa gaatgcagga   1200
accaatgggg caatatcaac aggaaagact tcaaatggaa actcgatctc ttag         1254
```

<210> SEQ ID NO 21
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea hyssopifolia (Chs) FATB3 coding DNA
      sequence codon optimized for Prototheca moriformis

<400> SEQUENCE: 21

```
atggtggccg ccgaggcctc ctccgccctg ttctccgtgc gcacccccgg cacctccccc     60
aagcccggca agttcggcaa ctggcccacc tccctgtccg tgcccttcaa gtccaagtcc    120
aaccacaacg gcggcttcca ggtgaaggcc aacgcctccg cccgccccaa ggccaacggc    180
tccgccgtgt ccctgaagtc cggctccctg gacacccagg aggacacctc ctcctcctcc    240
tcccccccc gcaccttcat caaccagctg cccgactggt ccatgctgct gtccgccatc    300
accaccgtgt tcgtggccgc cgagaagcag tggaccatgc tggaccgcaa gtccaagcgc    360
cccgacatgc tgatggaccc cttcggcgtg gaccgcgtgg tgcaggacgg cgccgtgttc    420
cgccagtcct tctccatccg ctcctacgag atcggcgccg accgcaccgc ctccatcgag    480
accctgatga acatcttcca ggagacctcc ctgaaccact gcaagtccat cggcctgctg    540
aacgacggct tcggccgcac ccccgagatg tgcaagcgcg acctgatctg ggtggtgacc    600
```

```
aagatgcacg tggaggtgaa ccgctacccc acctggggcg acaccatcga ggtgaacacc    660

tgggtgtccg agtccggcaa gaccggcatg ggccgcgact ggctgatctc cgactgccac    720

accggcgaga tcctgatccg cgccacctcc atgtgcgcca tgatgaacca gaagacccgc    780

cgcttctcca agttccccta cgaggtgcgc caggagctgg ccccccactt cgtggactcc    840

gcccccgtga tcgaggacta ccagaagctg cacaagctgg acgtgaagac cggcgactcc    900

atctgcaacg gcctgacccc ccgctggaac gacctggacg tgaaccagca cgtgaacaac    960

gtgaagtaca tcggctggat cctggagtcc gtgcccaccg aggtgttcga gacccaggag   1020

ctgtgcggcc tgaccctgga gtaccgccgc gagtgcggcc gcgactccgt gctggagtcc   1080

gtgaccgcca tggacccctc caaggagggc gaccgctccc tgtaccagca cctgctgcgc   1140

ctggaggacg gcgccgacat cgccaagggc cgcaccaagt ggcgccccaa gaacgccggc   1200

accaacggcg ccatctccac cggcaagacc tccaacggca actccatctc ctga         1254
```

<210> SEQ ID NO 22
<211> LENGTH: 417
<212> TYPE: PRT
<213> ORGANISM: Cuphea hyssopifolia
<220> FEATURE:
<223> OTHER INFORMATION: Cuphea hyssopifolia (Chs) FATB3b (V204I,C239F, E243D, M251V variant) amino acid sequence

<400> SEQUENCE: 22

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240
```

-continued

```
Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 23
<211> LENGTH: 1254
<212> TYPE: DNA
<213> ORGANISM: Cuphea hyssopifolia
<220> FEATURE:
<223> OTHER INFORMATION: Cuphea hyssopifolia (Chs) FATB3b (V204I,C239F,
      E243D, M251V variant) coding DNA sequence

<400> SEQUENCE: 23

atggtggctg ccgaagcaag ttctgcactc ttctccgttc gaaccccggg aacctcccct     60

aaacccggga agttcgggaa ttggccaacg agcttgagcg tccccttcaa gtccaaatca    120

aaccacaatg gcggctttca ggttaaggca aacgccagtg cccgtcctaa ggctaacggt    180

tctgcagtaa gtctaaagtc tggcagcctc gacactcagg aggacacttc atcgtcgtcc    240

tctcctcctc ggactttcat taaccagttg cccgactgga gtatgctgct gtccgcgatc    300

acgaccgtct tcgtggcggc tgagaagcag tggacgatgc ttgatcggaa atctaagagg    360

cccgacatgc tcatggaccc gtttggggtt gacagggttg ttcaggatgg ggctgtgttc    420

agacagagtt tttcgattag gtcttacgaa ataggcgctg atcgaacagc ctctatagag    480

acgctgatga acatcttcca ggaaacatct ctcaatcatt gtaagagtat cggtcttctc    540

aatgacggct ttggtcgtac tcctgagatg tgtaagaggg acctcatttg ggtggttaca    600

aaaatgcaca tcgaggttaa tcgctatcct acttggggtg atactatcga ggtcaatact    660

tgggtctccg agtcggggaa aaccggtatg ggtcgtgatt ggctgataag tgattttcat    720

acaggagaca ttctaataag agcaacgagc gtgtgtgcta tgatgaatca aaagacgaga    780

agattctcaa aatttccata tgaggttcga caggagttag cgcctcattt tgtggactct    840

gctccagtca ttgaagacta tcaaaaattg cacaagcttg atgtgaagac gggtgattcc    900

atttgcaatg gcctaactcc aaggtggaat gacttggatg tcaatcagca cgttaacaat    960

gtgaagtaca ttgggtggat tctcgagagt gttccaacgg aagttttcga gacccaggag   1020
```

ctatgtggcc tcacccttga gtataggcgg gaatgcggaa gggacagtgt gctggagtcc 1080
gtgaccgcta tggatccctc aaaagaggga gacagatctc tgtaccagca ccttcttcgg 1140
cttgaggatg gggctgatat cgcgaagggc agaaccaagt ggcggccgaa gaatgcagga 1200
accaatgggg caatatcaac aggaaagact tcaaatggaa actcgatctc ttag 1254

<210> SEQ ID NO 24
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hyssopifolia (Chs) FATB3b (V204I,C239F, E243D, M251V variant) coding DNA sequence codon optimized for Prototheca moriformis

<400> SEQUENCE: 24
atggtggccg ccgaggcctc ctccgccctg ttctccgtgc gcacccccgg cacctccccc 60
aagcccggca agttcggcaa ctggcccacc tccctgtccg tgcccttcaa gtccaagtcc 120
aaccacaacg gcggcttcca ggtgaaggcc aacgcctccg cccgccccaa ggccaacggc 180
tccgccgtgt ccctgaagtc cggctccctg gacacccagg aggacacctc ctcctcctcc 240 tcccccccc gcaccttcat caaccagctg cccgactggt ccatgctgct gtccgccatc 300
accaccgtgt tcgtggccgc cgagaagcag tggaccatgc tggaccgcaa gtccaagcgc 360
cccgacatgc tgatggaccc cttcggcgtg gaccgcgtgg tgcaggacgg cgccgtgttc 420
cgccagtcct tctccatccg ctcctacgag atcggcgccg accgcaccgc ctccatcgag 480
accctgatga acatcttcca ggagacctcc ctgaaccact gcaagtccat cggcctgctg 540
aacgacggct tcggccgcac ccccgagatg tgcaagcgcg acctgatctg ggtggtgacc 600
aagatgcaca tcgaggtgaa ccgctacccc acctggggcg acaccatcga ggtgaacacc 660
tgggtgtccg agtccggcaa gaccggcatg ggccgcgact ggctgatctc cgacttccac 720
accggcgaca tcctgatccg cgccacctcc gtgtgcgcca tgatgaacca gaagacccgc 780
cgcttctcca agttccccta cgaggtgcgc caggagctgg ccccccactt cgtggactcc 840
gcccccgtga tcgaggacta ccagaagctg cacaagctgg acgtgaagac cggcgactcc 900
atctgcaacg gcctgacccc ccgctggaac gacctggacg tgaaccagca cgtgaacaac 960
gtgaagtaca tcggctggat cctggagtcc gtgcccaccg aggtgttcga gacccaggag 1020
ctgtgcggcc tgaccctgga gtaccgccgc gagtgcggcc gcgactccgt gctggagtcc 1080
gtgaccgcca tggacccctc caaggagggc gaccgctccc tgtaccagca cctgctgcgc 1140
ctggaggacg gcgccgacat cgccaagggc cgcaccaagt ggcgccccaa gaacgccggc 1200
accaacggcg ccatctccac cggcaagacc tccaacggca actccatctc ctga 1254

<210> SEQ ID NO 25
<211> LENGTH: 419
<212> TYPE: PRT
<213> ORGANISM: Cuphea sp.
<220> FEATURE:
<223> OTHER INFORMATION: Cuphea PSR23 (Cu) FATB3 amino acid sequence

<400> SEQUENCE: 25

Met Val Val Ala Ala Ala Thr Ser Ala Phe Phe Pro Val Pro Ala Pro
1 5 10 15

```
Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Cys Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser
```

<210> SEQ ID NO 26

<211> LENGTH: 1260
<212> TYPE: DNA
<213> ORGANISM: Cuphea sp.
<220> FEATURE:
<223> OTHER INFORMATION: Cuphea PSR23 (Cu) FATB3 coding DNA sequence

<400> SEQUENCE: 26
atggtggtgg ctgcagcaac ttctgcattc ttccccgttc cagccccggg aacctcccct 60
aaacccggga agtccggcaa ctggccatcg agcttgagcc ctaccttcaa gcccaagtca 120
atccccaatg ccggatttca ggttaaggca aatgccagtg cccatcctaa ggctaacggt 180
tctgcagtaa atctaaagtc tggcagcctc aacactcagg aggacacttc gtcgtcccct 240
cctccccggg ctttccttaa ccagttgcct gattggagta tgcttctgac tgcaatcacg 300
accgtcttcg tggcggcaga gaagcagtgg actatgcttg ataggaaatc taagaggcct 360
gacatgctcg tggactcggt tgggttgaag tgtattgttc gggatgggct cgtgtccaga 420
cagagttttt tgattagatc ttatgaaata ggcgctgatc gaacagcctc tatagagacg 480
ctgatgaacc acttgcagga aacatctatc aatcattgta agagtttggg tcttctcaat 540
gacggctttg gtcgtactcc tgggatgtgt aaaaacgacc tcatttgggt gcttacaaaa 600
atgcagatca tggtgaatcg ctacccaact tggggcgata ctgttgagat caatacctgg 660
ttctctcagt cggggaaaat cggtatggct agcgattggc taataagtga ttgcaacaca 720
ggagaaattc ttataagagc aacgagcgtg tgggctatga tgaatcaaaa gacgagaaga 780
ttctcaagac ttccatacga ggttcgccag gagttaacgc ctcattttgt ggactctcct 840
catgtcattg aagacaatga tcagaaattg cataagtttg atgtgaagac tggtgattcc 900
attcgcaagg gtctaactcc gaggtggaac gacttggatg tgaatcagca cgtaagcaac 960
gtgaagtaca ttgggtggat tctcgagagt atgccaatag aagttttgga gacacaggag 1020
ctatgctctc tcaccgtaga atataggcgg gaatgcggaa tggacagtgt gctggagtcc 1080
gtgactgctg tggatccctc agaaaatgga ggccggtctc agtacaagca ccttctgcgg 1140
cttgaggatg ggactgatat cgtgaagagc agaactgagt ggcgaccgaa gaatgcagga 1200
actaacgggg cgatatcaac atcaacagca aagacttcaa atggaaactc ggtctcttag 1260

<210> SEQ ID NO 27
<211> LENGTH: 1260
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea PSR23 (Cu) FATB3 coding DNA sequence
codon optimized for Prototheca moriformis

<400> SEQUENCE: 27
atggtggtgg ccgccgccac ctccgccttc ttccccgtgc ccgcccccgg cacctccccc 60
aagcccggca agtccggcaa ctggccctcc tccctgtccc ccaccttcaa gcccaagtcc 120
atccccaacg ccggcttcca ggtgaaggcc aacgcctccg cccaccccaa ggccaacggc 180
tccgccgtga acctgaagtc cggctccctg aacacccagg aggacacctc ctcctccccc 240 ccccccgcg ccttcctgaa ccagctgccc gactggtcca tgctgctgac cgccatcacc 300
accgtgttcg tggccgccga gaagcagtgg accatgctgg accgcaagtc caagcgcccc 360
gacatgctgg tggactccgt gggcctgaag tgcatcgtgc gcgacggcct ggtgtcccgc 420
cagtccttcc tgatccgctc ctacgagatc ggcgccgacc gcaccgcctc catcgagacc 480

```
ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatggcc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccagaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgccg tggacccctc cgagaacggc ggccgctccc agtacaagca cctgctgcgc   1140

ctggaggacg gcaccgacat cgtgaagtcc cgcaccgagt ggcgccccaa gaacgccggc   1200

accaacggcg ccatctccac ctccaccgcc aagacctcca acggcaactc cgtgtcctga   1260


<210> SEQ ID NO 28
<211> LENGTH: 408
<212> TYPE: PRT
<213> ORGANISM: Cuphea wrightii
<220> FEATURE:
<223> OTHER INFORMATION: Cuphea wrightii (Cw) FATB3 amino acid sequence

<400> SEQUENCE: 28

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220
```

-continued

```
Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405
```

<210> SEQ ID NO 29
<211> LENGTH: 1227
<212> TYPE: DNA
<213> ORGANISM: Cuphea wrightii
<220> FEATURE:
<223> OTHER INFORMATION: Cuphea wrightii (Cw) FATB3 coding DNA sequence

<400> SEQUENCE: 29

```
atggtggtgg ctgctgcagc aagttctgca ttcttccctg ttccagcacc tagaaccacg     60

cctaaacccg ggaagttcgg caattggcca tcgagcttga gcccgccctt caagcccaag    120

tcaaacccca atggtagatt tcaggttaag gcaaatgtca gtcctcatcc taaggctaac    180

ggttctgcag taagtctaaa gtctggcagc ctcaacactc tggaggaccc tccgtcgtcc    240

cctcctcctc ggactttcct taaccagttg cctgattgga gtaggcttcg gactgcaatc    300

acgaccgtct tcgtggcggc agagaagcag ttcactaggc tcgatcgaaa atctaagagg    360

cctgacatgc tagtggactg gtttgggtca gagactattg ttcaggatgg gctcgtgttc    420

agagagagat tttcgatcag gtcttacgaa ataggcgctg atcgaacagc ctctatagag    480

acgctgatga accacttgca ggacacatct ctgaatcatt gtaagagtgt gggtcttctc    540

aatgacggct ttggtcgtac ctcggagatg tgtacaagag acctcatttg ggtgcttaca    600

aaaatgcaga tcgtggtgaa tcgctatcca acttggggcg atactgtcga gatcaatagc    660

tggttctccc agtcggggaa aatcggtatg ggtcgcgatt ggctaataag tgattgcaac    720

acaggagaaa ttcttgtaag agcaacgagc gcttgggcca tgatgaatca aaagacgaga    780

agattctcaa aacttccatg cgaggttcgc caggagatag cgcctcattt tgtggacgct    840

cctcctgtca ttgaagacaa tgatcggaaa ttgcataagt ttgatgtgaa gactggtgat    900

tccatttgca agggtctaac tccggggtgg aatgacttgg atgtcaatca gcacgtaagc    960

aacgtgaagt acattgggtg gattctcgag agtatgccta cagaagtttt ggagacccag   1020
```

```
gagctatgct ctctcaccct tgaatatagg cgggaatgtg gaagggaaag tgtggtagag   1080

tccgtgacct ctatgaatcc ctcaaaagtt ggagaccggt ctcagtacca acaccttctg   1140

cggcttgagg atggggctga tatcatgaag ggcagaactg agtggagacc aaagaatgca   1200

ggaaccaacc gggcgatatc aacatga                                       1227
```

<210> SEQ ID NO 30
<211> LENGTH: 1227
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea wrightii (Cw) FATB3 coding DNA sequence codon optimized for Prototheca moriformis

<400> SEQUENCE: 30

```
atggtggtgg ccgccgccgc ctcctccgcc ttcttccccg tgcccgcccc ccgcaccacc     60

cccaagcccg gcaagttcgg caactggccc tcctccctgt cccccccctt caagcccaag    120

tccaacccca acggccgctt ccaggtgaag gccaacgtgt ccccccaccc caaggccaac    180

ggctccgccg tgtccctgaa gtccggctcc ctgaacaccc tggaggaccc cccctcctcc    240

cccccccccc gcaccttcct gaaccagctg cccgactggt cccgcctgcg caccgccatc    300

accaccgtgt tcgtggccgc cgagaagcag ttcacccgcc tggaccgcaa gtccaagcgc    360

cccgacatgc tggtggactg gttcggctcc gagaccatcg tgcaggacgg cctggtgttc    420

cgcgagcgct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ctccgagatg tgcacccgcg acctgatctg ggtgctgacc    600

aagatgcaga tcgtggtgaa ccgctacccc acctggggcg acaccgtgga gatcaactcc    660

tggttctccc agtccggcaa gatcggcatg ggccgcgact ggctgatctc cgactgcaac    720

accggcgaga tcctggtgcg cgccacctcc gcctgggcca tgatgaacca gaagacccgc    780

cgcttctcca agctgccctg cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtggtggag   1080

tccgtgacct ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacc gcgccatctc cacctga                                       1227
```

<210> SEQ ID NO 31
<211> LENGTH: 416
<212> TYPE: PRT
<213> ORGANISM: Cuphea wrightii
<220> FEATURE:
<223> OTHER INFORMATION: Cuphea wrightii (Cw) FATB4a amino acid sequence

<400> SEQUENCE: 31

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
```

```
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415
```

<210> SEQ ID NO 32
<211> LENGTH: 1251
<212> TYPE: DNA
<213> ORGANISM: Cuphea wrightii
<220> FEATURE:
<223> OTHER INFORMATION: Cuphea wrightii (Cw) FATB4a coding DNA sequence

<400> SEQUENCE: 32

```
ttggtggcta ccgctgcaag ttctgcattt ttccccgtgc catccgccga cacctcctcc     60

tcgagacccg gaaagctcgg cagtggacca tcgagcttga gccccctcaa gcccaaatcg    120

atccccaatg gcggcttgca ggttaaggca aacgccagtg cccctcctaa gatcaatggt    180

tcctcggtcg gtctaaagtc gggcggtttc aagactcagg aagactctcc ttcggcccct    240

cctccgcgga cttttatcaa ccagttgcct gattggagta tgcttcttgc tgcaatcact    300

actgtcttct tggctgcaga gaagcagtgg atgatgcttg attggaaacc taagaggcct    360

gacatgctcg tggacccgtt cggattggga agtattgttc aggatgggct tgtgttcagg    420

cagaattttt caattaggtc ctacgaaata ggcgccgatc gaactgcgtc tatagagacg    480

gtgatgaacc atttgcagga aacagctctc aatcatgtca agattgctgg gctttctaat    540

gacggctttg gtcgtactcc tgagatgtat aaaagagacc ttatttgggt tgttgcaaaa    600

atgcaggtca tggttaaccg ctatcctact tggggtgaca cggttgaagt gaatacttgg    660

gttgccaagt cagggaaaaa tggtatgcgt cgtgactggc tcataagtga ttgcaatact    720

ggagagattc ttacaagagc atcaagcgtg tgggtcatga tgaatcaaaa gacaagaaga    780

ttgtcaaaaa ttccagatga ggttcgaaat gagatagagc ctcattttgt ggactctgct    840

cccgtcgttg aagatgatga tcggaaactt cccaagctgg atgagaacac tgctgactcc    900

atccgcaagg gtctaactcc gaggtggaat gacttggatg tcaatcagca cgtcaacaac    960

gtgaagtaca tcggatggat tcttgagagt actccaccag aagttctgga gacccaggag   1020

ttatgctccc tgaccctgga atacaggcgg gaatgtggaa gggagagcgt gctggagtcc   1080

ctcactgctg tcgacccgtc tgcagagggc tatgcgtccc ggtttcagca ccttctgcgg   1140

cttgaggatg gaggtgagat cgtgaaggcg agaactgagt ggcgacccaa gaatgctgga   1200

atcaatgggg tggtaccatc cgaggagtcc tcacctggag acttctttta g             1251
```

<210> SEQ ID NO 33
<211> LENGTH: 1251
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea wrightii (Cw) FATB4a coding DNA sequence
      codon optimized for Prototheca moriformis

<400> SEQUENCE: 33

```
atggtggcca ccgccgcctc ctccgccttc ttccccgtgc cctccgccga cacctcctcc     60

tcccgccccg gcaagctggg ctccggcccc tcctccctgt ccccccctgaa gcccaagtcc    120

atccccaacg gcggcctgca ggtgaaggcc aacgcctccg cccccccccaa gatcaacggc    180

tcctccgtgg gcctgaagtc cggcggcttc aagacccagg aggactcccc ctccgccccc    240

cccccccgca ccttcatcaa ccagctgccc gactggtcca tgctgctggc cgccatcacc    300

accgtgttcc tggccgccga gaagcagtgg atgatgctgg actggaagcc caagcgcccc    360

gacatgctgg tggacccctt cggcctgggc tccatcgtgc aggacggcct ggtgttccgc    420

cagaacttct ccatccgctc ctacgagatc ggcgccgacc gcaccgcctc catcgagacc    480

gtgatgaacc acctgcagga gaccgccctg aaccacgtga agatcgccgg cctgtccaac    540
```

gacggcttcg gccgcacccc cgagatgtac aagcgcgacc tgatctgggt ggtggccaag 600
atgcaggtga tggtgaaccg ctaccccacc tggggcgaca ccgtggaggt gaacacctgg 660
gtggccaagt ccggcaagaa cggcatgcgc cgcgactggc tgatctccga ctgcaacacc 720
ggcgagatcc tgacccgcgc ctcctccgtg tgggtgatga tgaaccagaa gacccgccgc 780
ctgtccaaga tccccgacga ggtgcgcaac gagatcgagc cccacttcgt ggactccgcc 840
cccgtggtgg aggacgacga ccgcaagctg cccaagctgg acgagaacac cgccgactcc 900
atccgcaagg gcctgacccc ccgctggaac gacctggacg tgaaccagca cgtgaacaac 960
gtgaagtaca tcggctggat cctggagtcc acccccccg aggtgctgga gacccaggag 1020
ctgtgctccc tgaccctgga gtaccgccgc gagtgcggcc gcgagtccgt gctggagtcc 1080
ctgaccgccg tggacccctc cgccgagggc tacgcctccc gcttccagca cctgctgcgc 1140
ctggaggacg gcggcgagat cgtgaaggcc cgcaccgagt ggcgccccaa gaacgccggc 1200
atcaacggcg tggtgccctc cgaggagtcc tcccccggcg acttcttctg a 1251

<210> SEQ ID NO 34
<211> LENGTH: 417
<212> TYPE: PRT
<213> ORGANISM: Cuphea wrightii
<220> FEATURE:
<223> OTHER INFORMATION: Cuphea wrightii (Cw) FATB4b amino acid sequence

<400> SEQUENCE: 34

Met Val Ala Thr Ala Ala Ser Ser Ala Phe Phe Pro Val Pro Ser Ala
1 5 10 15

Asp Thr Ser Ser Ser Arg Pro Gly Lys Leu Gly Asn Gly Pro Ser Ser
20 25 30

Leu Ser Pro Leu Lys Pro Lys Ser Ile Pro Asn Gly Gly Leu Gln Val
35 40 45

Lys Ala Asn Ala Ser Ala Pro Pro Lys Ile Asn Gly Ser Ser Val Gly
50 55 60

Leu Lys Ser Gly Ser Phe Lys Thr Gln Glu Asp Ala Pro Ser Ala Pro
65 70 75 80

Pro Pro Arg Thr Phe Ile Asn Gln Leu Pro Asp Trp Ser Met Leu Leu
85 90 95

Ala Ala Ile Thr Thr Val Phe Leu Ala Ala Glu Lys Gln Trp Met Met
100 105 110

Leu Asp Trp Lys Pro Lys Arg Pro Asp Met Leu Val Asp Pro Phe Gly
115 120 125

Leu Gly Ser Ile Val Gln Asp Gly Leu Val Phe Arg Gln Asn Phe Ser
130 135 140

Ile Arg Ser Tyr Glu Ile Gly Ala Asp Arg Thr Ala Ser Ile Glu Thr
145 150 155 160

Val Met Asn His Leu Gln Glu Thr Ala Leu Asn His Val Lys Ile Ala
165 170 175

Gly Leu Ser Ser Asp Gly Phe Gly Arg Thr Pro Ala Met Ser Lys Arg
180 185 190

Asp Leu Ile Trp Val Val Ala Lys Met Gln Val Met Val Asn Arg Tyr
195 200 205

Pro Ala Trp Gly Asp Thr Val Glu Val Asn Thr Trp Val Ala Lys Ser
210 215 220

Gly Lys Asn Gly Met Arg Arg Asp Trp Leu Ile Ser Asp Cys Asn Thr
225 230 235 240

-continued

```
Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 35
<211> LENGTH: 1254
<212> TYPE: DNA
<213> ORGANISM: Cuphea wrightii
<220> FEATURE:
<223> OTHER INFORMATION: Cuphea wrightii (Cw) FATB4b coding DNA sequence

<400> SEQUENCE: 35

ttggtggcta ccgctgcaag ttctgcattt ttccccgtac catccgccga cacctcctca     60

tcgagacccg gaaagctcgg caatgggcca tcgagcttga gccccctcaa gccgaaatcg    120

atccccaatg gcgggttgca ggttaaggca aacgccagtg cccctcctaa gatcaatggt    180

tcctcggtcg gtctgaagtc gggcagtttc aagactcagg aagacgctcc ttcggcccct    240

cctcctcgga cttttatcaa ccagttgcct gattggagta tgcttcttgc tgcaatcact    300

actgtcttct tggctgcaga gaagcagtgg atgatgcttg attggaaacc taagaggcct    360

gacatgcttg tcgacccgtt cggattggga agtattgttc aggatgggct tgttttcagg    420

cagaatttct cgattaggtc ctacgaaata ggcgctgatc gcactgcgtc tatagagacg    480

gtgatgaacc atttgcagga aacagctctc aatcatgtta agattgctgg gctttctagt    540

gatggctttg gtcgtactcc tgcgatgtct aaacgggacc tcatttgggt tgttgcgaaa    600

atgcaggtca tggttaaccg ctaccctgct tggggtgaca cggttgaagt gaatacttgg    660

gttgccaagt cagggaaaaa tggtatgcgt cgtgactggc tcataagtga ttgcaacact    720

ggagagattc ttacaagagc atcaagcgtg tgggtcatga tgaatcaaaa gacaagaaga    780

ttgtcaaaaa ttccagatga ggttcgaaat gagatagagc ctcattttgt ggactctgcg    840

cccgtcgttg aagacgatga ccggaaactt cccaagctgg atgagaacac tgctgactcc    900

atccgcaagg gtctaactcc gaggtggaat gacttggatg tcaatcagca cgtcaacaac    960

gtgaagtaca ttgggtggat tcttgagagt actccagcag aagttctgga gacccaggaa   1020
```

ttatgttccc tgaccctgga atacaggcgg gaatgtggaa gggagagcgt gctggagtcc 1080
ctcactgctg tagatccgtc tggagagggc gatgggtcca agttccagca ccttctgcgg 1140
cttgaggatg gaggtgagat cgtgaaggcg agaactgagt ggcgaccaaa gaatgctgga 1200
atcaatgggg tggtaccatc cgaggagtcc tcacctggtg gagacttctt ttaa 1254

<210> SEQ ID NO 36
<211> LENGTH: 1254
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea wrightii (Cw) FATB4b coding DNA sequence
codon optimized for Prototheca moriformis

<400> SEQUENCE: 36
atggtggcca ccgccgcctc ctccgccttc ttccccgtgc cctccgccga cacctcctcc 60
tcccgccccg gcaagctggg caacggcccc tcctccctgt ccccccctgaa gcccaagtcc 120 atccccaacg gcggcctgca ggtgaaggcc aacgcctccg cccccccccaa gatcaacggc 180 tcctccgtgg gcctgaagtc cggctccttc aagacccagg aggacgcccc ctccgccccc 240
cccccccgca ccttcatcaa ccagctgccc gactggtcca tgctgctggc cgccatcacc 300
accgtgttcc tggccgccga gaagcagtgg atgatgctgg actggaagcc caagcgcccc 360
gacatgctgg tggacccctt cggcctgggc tccatcgtgc aggacggcct ggtgttccgc 420
cagaacttct ccatccgctc ctacgagatc ggcgccgacc gcaccgcctc catcgagacc 480
gtgatgaacc acctgcagga gaccgccctg aaccacgtga agatcgccgg cctgtcctcc 540
gacggcttcg gccgcacccc cgccatgtcc aagcgcgacc tgatctgggt ggtggccaag 600
atgcaggtga tggtgaaccg ctaccccgcc tggggcgaca ccgtggaggt gaacacctgg 660
gtggccaagt ccggcaagaa cggcatgcgc cgcgactggc tgatctccga ctgcaacacc 720
ggcgagatcc tgacccgcgc ctcctccgtg tgggtgatga tgaaccagaa gacccgccgc 780
ctgtccaaga tccccgacga ggtgcgcaac gagatcgagc cccacttcgt ggactccgcc 840
cccgtggtgg aggacgacga ccgcaagctg cccaagctgg acgagaacac cgccgactcc 900
atccgcaagg gcctgacccc ccgctggaac gacctggacg tgaaccagca cgtgaacaac 960
gtgaagtaca tcggctggat cctggagtcc acccccgccg aggtgctgga gacccaggag 1020
ctgtgctccc tgaccctgga gtaccgccgc gagtgcggcc gcgagtccgt gctggagtcc 1080
ctgaccgccg tggaccctc cggcgagggc gacggctcca agttccagca cctgctgcgc 1140
ctggaggacg gcggcgagat cgtgaaggcc cgcaccgagt ggcgccccaa gaacgccggc 1200
atcaacggcg tggtgccctc cgaggagtcc tcccccggcg gcgacttctt ctga 1254

<210> SEQ ID NO 37
<211> LENGTH: 413
<212> TYPE: PRT
<213> ORGANISM: Cuphea wrightii
<220> FEATURE:
<223> OTHER INFORMATION: Cuphea wrightii (Cw) FATB5 amino acid sequence

<400> SEQUENCE: 37

Met Val Ala Ala Ala Ala Ser Ser Ala Phe Phe Ser Val Pro Thr Pro
1 5 10 15

Gly Thr Pro Pro Lys Pro Gly Lys Phe Gly Asn Trp Pro Ser Ser Leu
20 25 30

```
Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410
```

<210> SEQ ID NO 38
<211> LENGTH: 1242
<212> TYPE: DNA
<213> ORGANISM: Cuphea wrightii
<220> FEATURE:

<223> OTHER INFORMATION: Cuphea wrightii (Cw) FATB5 coding DNA sequence

<400> SEQUENCE: 38
atggtggctg ccgcagcaag ttctgcattc ttctctgttc caaccccggg aacgcccccct 60 aaacccggga agttcggtaa ctggccatcg agcttgagcg tccccttcaa gcccgacaat 120
ggtggctttc atgtcaaggc aaacgccagt gcccatccta aggctaatgg ttctgcggta 180
aatctaaagt ctggcagcct cgagactcct cctcggagtt tcattaacca gctgccggac 240
ttgagtgtgc ttctgtccaa aatcacgact gtcttcgggg cggctgagaa gcagtggaag 300
aggcccggca tgctcgtgga accgtttggg gttgacagga tttttcagga tggtgttttt 360
ttcagacaga gtttttctat caggtcttac gaaataggcg ttgatcgaac agcctcgata 420
gagacactga tgaacatctt ccaggaaaca tctttgaatc attgcaagag tatcggtctt 480
ctcaacgatg gctttggtcg tactcctgag atgtgtaaga gggacctcat ttgggtggtt 540
acgaaaattc aggtcgaggt gaatcgctat cctacttggg gtgacactat cgaagtcaat 600
acttgggtct cggagtcggg gaaaaacggt atgggtcggg attggctgat aagtgattgc 660
cgtactggag agattcttat aagagcaacg agcgtgtggg cgatgatgaa tcaaaacacg 720
agaagattgt caaaatttcc atatgaggtt cgacaggaga tagcgcctca ttttgtggac 780
tctgctcctg tcattgaaga cgatcaaaag ttgcagaagc ttgatgtgaa gacaggtgat 840
tccattcgcg atggtctaac tccgagatgg aatgacttgg atgtcaatca acacgttaac 900
aatgtgaagt acattggatg gattctcaag agtgttccaa tagaagtttt cgagacacag 960
gagctatgcg gcgtcacact tgaatatagg cgggaatgcg gaagggacag tgtgctggag 1020
tcagtgaccg ctatggatcc agcaaaagag ggagaccggt gtgtgtacca gcaccttctt 1080
cggcttgagg atggagctga tatcactata ggcagaaccg agtggcggcc gaagaatgca 1140
ggagccaatg gtgcaatgtc atcaggaaag acttcaaatg gaaactgtct catagaagga 1200
aggggttggc aacctttccg agttgtgcgt ttaattttct ga 1242

<210> SEQ ID NO 39
<211> LENGTH: 1242
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea wrightii (Cw) FATB5 coding DNA sequence codon optimized for Prototheca moriformis

<400> SEQUENCE: 39
atggtggccg ccgccgcctc ctccgccttc ttctccgtgc ccacccccgg cacccccccc 60
aagcccggca agttcggcaa ctggccctcc tccctgtccg tgcccttcaa gcccgacaac 120
ggcggcttcc acgtgaaggc caacgcctcc gcccacccca aggccaacgg ctccgccgtg 180
aacctgaagt ccggctccct ggagaccccc ccccgctcct tcatcaacca gctgcccgac 240
ctgtccgtgc tgctgtccaa gatcaccacc gtgttcggcg ccgccgagaa gcagtggaag 300
cgccccggca tgctggtgga gcccttcggc gtggaccgca tcttccagga cggcgtgttc 360
ttccgccagt ccttctccat ccgctcctac gagatcggcg tggaccgcac cgcctccatc 420
gagaccctga tgaacatctt ccaggagacc tccctgaacc actgcaagtc catcggcctg 480
ctgaacgacg gcttcggccg cacccccgag atgtgcaagc gcgacctgat ctgggtggtg 540
accaagatcc aggtggaggt gaaccgctac cccacctggg gcgacaccat cgaggtgaac 600

```
acctgggtgt ccgagtccgg caagaacggc atgggccgcg actggctgat ctccgactgc    660

cgcaccggcg agatcctgat ccgcgccacc tccgtgtggg ccatgatgaa ccagaacacc    720

cgccgcctgt ccaagttccc ctacgaggtg cgccaggaga tcgcccccca cttcgtggac    780

tccgcccccg tgatcgagga cgaccagaag ctgcagaagc tggacgtgaa gaccggcgac    840

tccatccgcg acggcctgac cccccgctgg aacgacctgg acgtgaacca gcacgtgaac    900

aacgtgaagt acatcggctg gatcctgaag tccgtgccca tcgaggtgtt cgagacccag    960

gagctgtgcg gcgtgaccct ggagtaccgc cgcgagtgcg gccgcgactc cgtgctggag   1020

tccgtgaccg ccatggaccc cgccaaggag ggcgaccgct gcgtgtacca gcacctgctg   1080

cgcctggagg acggcgccga catcaccatc ggccgcaccg agtggcgccc caagaacgcc   1140

ggcgccaacg gcgccatgtc ctccggcaag acctccaacg gcaactgcct gatcgagggc   1200

cgcggctggc agcccttccg cgtggtgcgc ctgatcttct ga                      1242


<210> SEQ ID NO 40
<211> LENGTH: 410
<212> TYPE: PRT
<213> ORGANISM: Cuphea heterophylla
<220> FEATURE:
<223> OTHER INFORMATION: Cuphea heterophylla (Cht) FATB1a amino acid
      sequence

<400> SEQUENCE: 40

Met Val Ala Ala Ala Ala Ser Ser Ala Phe Phe Ser Val Pro Thr Pro
1               5                   10                  15

Gly Thr Ser Thr Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240
```

```
Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 41
<211> LENGTH: 1233
<212> TYPE: DNA
<213> ORGANISM: Cuphea heterophylla
<220> FEATURE:
<223> OTHER INFORMATION: Cuphea heterophylla (Cht) FATB1a coding DNA
      sequence

<400> SEQUENCE: 41

atggtggctg ccgcagcaag ttctgcattc ttctccgttc caaccccggg aacctccact     60

aaacccggga acttcggcaa ttggccatcg agcttgagcg tccccttcaa gcccgaatca    120

aaccacaatg gtggctttcg ggtcaaggca aacgccagtg ctcatcctaa ggctaacggt    180

tctgcagtaa atctaaagtc tggcagcctc gagactcagg aggacacttc atcgtcgtcc    240

cctcctcctc ggacttttat taagcagttg cccgactggg gtatgcttct gtccaaaatc    300

acgactgtct tcggggcggc tgagaggcag tggaagaggc ccggcatgct tgtggaaccg    360

tttggggttg acaggatttt tcaggatggg gttttttca gacagagttt ttcgatcagg     420

tcttacgaaa taggcgctga tcgaacagcc tcaatagaga cgctgatgaa catcttccag    480

gaaacatctc tgaatcattg taagagtatc ggtcttctca atgacggctt tggtcgtact    540

cctgagatgt gtaagaggga cctcatttgg gtggttacga aaattcaggt cgaggtgaat    600

cgctatccta cttggggtga tactattgag gtcaatactt gggtctcaga gtcggggaaa    660

aacggtatgg gtcgtgattg gctgataagc gattgccgta ccggagaaat tcttataaga    720

gcaacgagcg tgtgggctat gatgaatcga aagacgagaa gattgtcaaa atttccatat    780

gaggttcgac aggagatagc gcctcatttt gtggactctg ctcctgtcat tgaagacgat    840

aaaaaattgc acaagcttga tgttaagacg ggtgattcca ttcgcaaggg tctaactcca    900

aggtggaatg acttggatgt caatcagcac gttaacaatg tgaagtacat tgggtggatt    960

ctcaagagtg ttccagcaga agttttcgag acccaggagc tatgcggagt caccettgag   1020

tacaggcggg aatgtggaag ggacagtgtg ctggagtccg tgaccgctat ggataccgca   1080
```

aaagagggag accggtctct gtaccagcac cttcttcggc ttgaggatgg ggctgatatc 1140
accataggca gaaccgagtg gcggccgaag aatgcaggag ccaatggggc aatatcaaca 1200
ggaaagactt caaatgaaaa ctctgtctct tag 1233

<210> SEQ ID NO 42
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB1a coding DNA sequence codon optimized for Prototheca moriformis

<400> SEQUENCE: 42
atggtggccg ccgccgcctc ctccgccttc ttctccgtgc ccacccccgg cacctccacc 60
aagcccggca acttcggcaa ctggccctcc tccctgtccg tgcccttcaa gcccgagtcc 120
aaccacaacg gcggcttccg cgtgaaggcc aacgcctccg cccaccccaa ggccaacggc 180
tccgccgtga acctgaagtc cggctccctg gagacccagg aggacacctc ctcctcctcc 240
cccccccccc gcaccttcat caagcagctg cccgactggg gcatgctgct gtccaagatc 300
accaccgtgt tcggcgccgc cgagcgccag tggaagcgcc ccggcatgct ggtggagccc 360
ttcggcgtgg accgcatctt ccaggacggc gtgttcttcc gccagtcctt ctccatccgc 420
tcctacgaga tcggcgccga ccgcaccgcc tccatcgaga ccctgatgaa catcttccag 480
gagacctccc tgaaccactg caagtccatc ggcctgctga acgacggctt cggccgcacc 540
cccgagatgt gcaagcgcga cctgatctgg gtggtgacca agatccaggt ggaggtgaac 600
cgctacccca cctggggcga caccatcgag gtgaacacct gggtgtccga gtccggcaag 660
aacggcatgg gccgcgactg gctgatctcc gactgccgca ccggcgagat cctgatccgc 720
gccacctccg tgtgggccat gatgaaccgc aagacccgcc gcctgtccaa gttcccctac 780
gaggtgcgcc aggagatcgc cccccacttc gtggactccg cccccgtgat cgaggacgac 840
aagaagctgc acaagctgga cgtgaagacc ggcgactcca tccgcaaggg cctgaccccc 900
cgctggaacg acctggacgt gaaccagcac gtgaacaacg tgaagtacat cggctggatc 960
ctgaagtccg tgcccgccga ggtgttcgag acccaggagc tgtgcggcgt gaccctggag 1020
taccgccgcg agtgcggccg cgactccgtg ctggagtccg tgaccgccat ggacaccgcc 1080
aaggagggcg accgctccct gtaccagcac ctgctgcgcc tggaggacgg cgccgacatc 1140
accatcggcc gcaccgagtg gcgccccaag aacgccggcg ccaacggcgc catctccacc 1200
ggcaagacct ccaacgagaa ctccgtgtcc tga 1233

<210> SEQ ID NO 43
<211> LENGTH: 410
<212> TYPE: PRT
<213> ORGANISM: Cuphea heterophylla
<220> FEATURE:
<223> OTHER INFORMATION: Cuphea heterophylla (Cht) FATB1b (P16S, T20P, G94S, G105W, S293F, L305F variant) amino acid sequence

<400> SEQUENCE: 43

Met Val Ala Ala Ala Ala Ser Ser Ala Phe Phe Ser Val Pro Thr Ser
1 5 10 15

Gly Thr Ser Pro Lys Pro Gly Asn Phe Gly Asn Trp Pro Ser Ser Leu
20 25 30

```
Ser Val Pro Phe Lys Pro Glu Ser Ser His Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Trp Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Phe Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 44
<211> LENGTH: 1233
<212> TYPE: DNA
<213> ORGANISM: Cuphea heterophylla
<220> FEATURE:

-continued

<223> OTHER INFORMATION: Cuphea heterophylla (Cht) FATB1b(P16S, T20P, G94S, G105W, S293F, L305F variant) coding DNA sequence

<400> SEQUENCE: 44

```
atggtggctg ccgcagcaag ttctgcattc ttctccgttc caacctcggg aacctcccct     60
aaacccggga acttcggcaa ttggccatcg agcttgagcg tccccttcaa gcccgaatca    120
agccacaatg gtggctttca ggtcaaggca aacgccagtg cccatcctaa ggctaacggt    180
tctgcagtaa atctaaagtc tggcagcctc gagactcagg aggacacttc atcgtcgtcc    240
cctcctcctc ggacttttat taagcagttg cccgactgga gtatgcttct gtccaaaatc    300
acgactgtct tctgggcggc tgagaggcag tggaagaggc ccggcatgct tgtggaaccg    360
tttggggttg acaggatttt tcaggatggg gttttttca gacagagttt ttcgatcagg    420
tcttacgaaa taggcgctga tcgaacagcc tcaatagaga cgctgatgaa catcttccag    480
gaaacatctc tgaatcattg taagagtatc ggtcttctca atgacggctt tggtcgtact    540
cctgagatgt gtaagaggga cctcatttgg gtggttacga aaattcaggt cgaggtgaat    600
cgctatccta cttggggtga tactattgag gtcaatactt gggtctcaga gtcggggaaa    660
aacggtatgg gtcgtgattg gctgataagc gattgccgta ccggagaaat tcttataaga    720
gcaacgagcg tgtgggctat gatgaatcga aagacgagaa gattgtcaaa atttccatat    780
gaggttcgac aggagatagc gcctcatttt gtggactctg ctcctgtcat tgaagacgat    840
aaaaaattgc acaagcttga tgttaagacg ggtgatttca ttcgcaaggg tctaactcca    900
aggtggaatg actttgatgt caatcagcac gttaacaatg tgaagtacat tgggtggatt    960
ctcaagagtg ttccagcaga agttttcgag acccaggagc tatgcggagt caccccttgag   1020
tataggcggg aatgtggaag ggacagtgtg ctggagtccg tgaccgctat ggataccgca   1080
aaagagggag accggtctct gtaccagcac cttcttcggc ttgaggatgg ggctgatatc   1140
accataggca gaaccgagtg gcggccgaag aatgcaggag ccaatggggc aatatcaaca   1200
ggaaagactt caaatgaaaa ctctgtctct tag                                1233
```

<210> SEQ ID NO 45
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB1b (P16S, T20P, G94S, G105W, S293F, L305F variant) coding DNA sequence codon optimized for Prototheca moriformis

<400> SEQUENCE: 45

```
atggtggccg ccgccgcctc ctccgccttc ttctccgtgc ccacctccgg cacctccccc     60
aagcccggca acttcggcaa ctggccctcc tccctgtccg tgcccttcaa gcccgagtcc    120
tcccacaacg gcggcttcca ggtgaaggcc aacgcctccg cccaccccaa ggccaacggc    180
tccgccgtga acctgaagtc cggctccctg gagacccagg aggacacctc ctcctcctcc    240
cccccccccc gcaccttcat caagcagctg cccgactggt ccatgctgct gtccaagatc    300
accaccgtgt tctgggccgc cgagcgccag tggaagcgcc ccggcatgct ggtggagccc    360
ttcggcgtgg accgcatctt ccaggacggc gtgttcttcc gccagtcctt ctccatccgc    420
tcctacgaga tcggcgccga ccgcaccgcc tccatcgaga ccctgatgaa catcttccag    480
gagacctccc tgaaccactg caagtccatc ggcctgctga acgacggctt cggccgcacc    540
```

```
cccgagatgt gcaagcgcga cctgatctgg gtggtgacca agatccaggt ggaggtgaac    600

cgctacccca cctggggcga caccatcgag gtgaacacct gggtgtccga gtccggcaag    660

aacggcatgg gccgcgactg gctgatctcc gactgccgca ccggcgagat cctgatccgc    720

gccacctccg tgtgggccat gatgaaccgc aagacccgcc gcctgtccaa gttcccctac    780

gaggtgcgcc aggagatcgc cccccacttc gtggactccg cccccgtgat cgaggacgac    840

aagaagctgc acaagctgga cgtgaagacc ggcgacttca tccgcaaggg cctgaccccc    900

cgctggaacg acttcgacgt gaaccagcac gtgaacaacg tgaagtacat cggctggatc    960

ctgaagtccg tgcccgccga ggtgttcgag acccaggagc tgtgcggcgt gaccctggag   1020

taccgccgcg agtgcggccg cgactccgtg ctggagtccg tgaccgccat ggacaccgcc   1080

aaggagggcg accgctccct gtaccagcac ctgctgcgcc tggaggacgg cgccgacatc   1140

accatcggcc gcaccgagtg gcgccccaag aacgccggcg ccaacggcgc catctccacc   1200

ggcaagacct ccaacgagaa ctccgtgtcc tga                                1233


<210> SEQ ID NO 46
<211> LENGTH: 418
<212> TYPE: PRT
<213> ORGANISM: Cuphea heterophylla
<220> FEATURE:
<223> OTHER INFORMATION: Cuphea heterophylla (Cht) FATB2b amino acid
      sequence

<400> SEQUENCE: 46

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
```

-continued

```
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 47
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2b coding DNA sequence

<400> SEQUENCE: 47

```
atggtggtgg ctgctgcagc aagctctgca ttcttccctg ttccggcatc tggaacctcc     60

cctaaacccg ggaagttcgg gacttggcta tcgagctcga gcccttccta caagcccaag    120

tcaaacccca gtggtggatt tcaggttaag gcaaatgcca gtgctcatcc taaggctaac    180

ggttccgcag taagtctaaa gtctggcagc ctcaacactc aggagggcac ttcgtcgtcc    240

cctcctcctc ggactttcct taaccagttg cctgattgga gtaggcttcg gactgcaatc    300

acgaccgtct tcgtggcggc agagaagcag ttgactatgc tcgatcgaaa gtctaagaag    360

cctgacatgc acgtggactg gtttgggttg gagattattg ttcaggatgg gctcgtgttc    420

agagagagtt tttcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac ccccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960
```

```
aacgtgaagt acattgggtg gattctcgag agtatgccaa aagaagtttt ggacacccag   1020

gagctatgct ctctcaccct tgaatatagg cgggaatgcg gaagggatag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg gggctatatc aacaggaaag acttcaaatg gaaactcggt ctcttag      1257
```

<210> SEQ ID NO 48
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2b coding DNA sequence codon optimized for Prototheca moriformis

<400> SEQUENCE: 48

```
atggtggtgg ccgccgccgc ctcctccgcc ttcttccccg tgcccgcctc cggcacctcc     60

cccaagcccg gcaagttcgg cacctggctg tcctcctcct cccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggagggcac ctcctcctcc    240

cccccccccc gcaccttcct gaaccagctg cccgactggt cccgcctgcg caccgccatc    300

accaccgtgt tcgtggccgc cgagaagcag ctgaccatgc tggaccgcaa gtccaagaag    360

cccgacatgc acgtggactg gttcggcctg gagatcatcg tgcaggacgg cctggtgttc    420

cgcgagtcct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 49
<211> LENGTH: 418
<212> TYPE: PRT
<213> ORGANISM: Cuphea heterophylla
<220> FEATURE:
<223> OTHER INFORMATION: Cuphea heterophylla (Cht) FATB2a (S17P, P21S, T28N, L30P, S33L, G76D, S78P, G137W variant) amino acid sequence

<400> SEQUENCE: 49

-continued

```
Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Trp Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Leu Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 50
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2a (S17P, P21S, T28N, L30P, S33L, G76D, S78P, G137W variant) coding DNA sequence

<400> SEQUENCE: 50

```
atggtggtgg ctgctgcagc aagttctgca ttcttccctg ttccagcacc tggaaccacg     60

tctaaacccg ggaagttcgg caattggcca tcgagcttga gcccttcctt caagcccaag    120

tcaaacccca atggtggatt tcaggttaag gcaaatgcca gcgctcatcc taaggctaac    180

gggtctgcag taagtctaaa gtctggcagc ctcaacacta aggaggacac tccgtcgtcc    240

cctcctcctc ggactttcct taaccagttg cctgattgga gtaggcttcg gactgcaatc    300

acgaccgtct tcgtggcggc agagaagcag ttgactatgc tcgatcgaaa gtctaagaag    360

cctgacatgc acgtggactg gtttgggttg gagattattg ttcaggattg gctcgtgttc    420

agagagagtt tttcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac cccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa cgaggttcgc caggagatag ctcctcattt tgtggacgcc    840

cctcctctca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg ggcgatatc aacaggaaag acttcaaatg gaaactcggt ctcttag      1257
```

<210> SEQ ID NO 51
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2a (S17P, P21S, T28N, L30P, S33L, G76D, S78P, G137W variant) coding DNA sequence codon optimized for Prototheca moriformis

<400> SEQUENCE: 51

```
atggtggtgg ccgccgccgc ctcctccgcc ttcttccccg tgcccgcccc cggcaccacc     60

tccaagcccg gcaagttcgg caactggccc tcctccctgt ccccctcctt caagcccaag    120

tccaacccca acggcggctt ccaggtgaag gccaacgcct ccgcccaccc caaggccaac    180

ggctccgccg tgtccctgaa gtccggctcc ctgaacacca aggaggacac cccctcctcc    240

cccccccccc gcaccttcct gaaccagctg cccgactggt cccgcctgcg caccgccatc    300
```

```
accaccgtgt tcgtggccgc cgagaagcag ctgaccatgc tggaccgcaa gtccaagaag    360

cccgacatgc acgtggactg gttcggcctg gagatcatcg tgcaggactg gctggtgttc    420

cgcgagtcct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccctga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 52
<211> LENGTH: 418
<212> TYPE: PRT
<213> ORGANISM: Cuphea heterophylla
<220> FEATURE:
<223> OTHER INFORMATION: Cuphea heterophylla (Cht) FATB2c (G76D, S78P variant) amino acid sequence

<400> SEQUENCE: 52

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Asn Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190
```

```
Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 53
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2c (G76D, S78P
      variant) coding DNA sequence

<400> SEQUENCE: 53

atggtggtgg ctgctgcagc aagctctgca ttcttccctg ttccggcatc tggaacctcc     60

cctaaacccg ggaagttcgg gacttggcta tcgagctcga gcccttccta caagcccaag    120

tcaaacccca gtggtggatt tcaggttaag gcaaatgcca gtgctcatcc taaggctaac    180

ggttccgcag taagtctaaa gtctggcagc ctcaacacta aggaggacac tccgtcgtcc    240

cctcctcctc ggactttcct taaccagttg cctgattgga ataggcttcg gactgcaatc    300

acgaccgtct tcgtggcggc agagaagcag ttgactatgc tcgatcgaaa gtctaagaag    360

cctgacatgc acgtggactg gtttgggttg gagattattg ttcaggatgg gctcgtgttc    420

agagagagtt tttcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac ccccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720
```

```
acaggagaaa ttcttataag agcaacgagc atttgggcca tgatgaatca aaagacgaga    780

agattctcaa aacttccaaa cgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aatgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggggaccgat ctcagtacca gcaccttctg   1140

cggcttgaag atgggactga tatcatgaag ggcagaactg agtggcgacc aaagaatgca   1200

ggaaccaacg ggctatatc aacaggaaag acttcaaatg gaaactcggt ctcttag       1257
```

```
<210> SEQ ID NO 54
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea heterophylla (Cht) FATB2c (G76D, S78P
      variant) coding DNA sequence
      codon optimized for Prototheca moriformis

<400> SEQUENCE: 54

atggtggtgg ccgccgccgc ctcctccgcc ttcttccccg tgcccgcctc cggcacctcc     60

cccaagcccg gcaagttcgg cacctggctg tcctcctcct ccccctccta caagcccaag    120

tccaacccct ccggcggctt ccaggtgaag gccaacgcct ccgcccaccc caaggccaac    180

ggctccgccg tgtccctgaa gtccggctcc ctgaacacca aggaggacac cccctcctcc    240

cccccccccc gcaccttcct gaaccagctg cccgactgga accgcctgcg caccgccatc    300

accaccgtgt tcgtggccgc cgagaagcag ctgaccatgc tggaccgcaa gtccaagaag    360

cccgacatgc acgtggactg gttcggcctg gagatcatcg tgcaggacgg cctggtgttc    420

cgcgagtcct tctccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg gcaactccgt gtcctga      1257

<210> SEQ ID NO 55
<211> LENGTH: 418
```

<212> TYPE: PRT
<213> ORGANISM: Cuphea heterophylla
<220> FEATURE:
<223> OTHER INFORMATION: Cuphea heterophylla (Cht) FATB2d (S21P, T28N, L30P, S33L, G76D, R97L, H124L, W127L, I132S, K258N, C303R, E309G, K334T, T386A variant) amino acid sequence

<400> SEQUENCE: 55

```
Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Leu Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
```

```
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 56
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2d (S21P, T28N,
      L30P, S33L, G76D, R97L, H124L, W127L, I132S, K258N, C303R,
      E309G, K334T, T386A variant) coding DNA sequence

<400> SEQUENCE: 56

atggtggtgg ctgctgcagc aagttctgca ttcttccctg ttccagcacc tggaaccacg     60

tctaaacccg ggaagttcgg caattggcca tcgagcttga gcccttcctt caagcccaag    120

tcaaacccca atggtggatt tcaggttaag gcaaatgcca gtgctcatcc taaggctaac    180

ggttctgcgg taagtctaaa gtctggcagc ctcaacactc aggaggacac ttcgtcgtcc    240

cctcctcctc ggacattcct taaccagttg cctgattgga gtaggcttct gactgcaatc    300

tcgaccgtct tcgtggcggc agagaagcag ttgactatgc tcgatcgaaa atctaagagg    360

cctgacatgc tcgtggactt gtttgggttg gagagtattg ttcaggatgg gctcgtgttc    420

agagagagtt attcgatcag gtcttacgaa ataggcgctg atcgaacagc ctctatagaa    480

acgttgatga accatttgca ggacacatct ttgaaccatt gtaagagtgt gggtcttctc    540

aatgacggct ttggtcgtac cccggagatg tgtaaaaggg acctcatttg ggtgcttaca    600

aaaatgcaga tcatggtgaa tcgctatcca acttggggcg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaatacgaga    780

agattctcaa aacttccaaa cgaggttcgc caggagatag cgcctcattt tgttgacgct    840

cctcctgtca ttgaagacaa tgatcgaaaa ttgcataagt ttgatgtgaa gactggtgat    900

tccattcgca agggtctaac tccggggtgg aatgacttgg atgtcaatca gcacgtaagc    960

aacgtgaagt acattgggtg gattctcgag agtatgccaa cagaagtttt ggagacccag   1020

gagctatgct ctctcaccct tgaatatagg cgggaatgcg gaagggaaag tgtgctggag   1080

tccgtgaccg ctatgaatcc ctcaaaagtt ggagaccggt ctcagtacca gcaccttcta   1140

cggcttgagg atggggctga tatcatgaag ggcagaactg agtggcgacc aaagaatgca   1200

ggaaccaacg ggcgatatc aacaggaaag acttcaaatg gaaactcggt ctcttag       1257


<210> SEQ ID NO 57
<211> LENGTH: 1257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea heterophylla (Cht) FATB2d (S21P, T28N,
      L30P, S33L, G76D, R97L, H124L, W127L, I132S, K258N, C303R,
      E309G, K334T, T386A variant) coding DNA sequence
      codon optimized for Prototheca moriformis

<400> SEQUENCE: 57
```

```
atggtggtgg ccgccgccgc ctcctccgcc ttcttccccg tgcccgcccc cggcaccacc     60

tccaagcccg gcaagttcgg caactggccc tcctccctgt ccccctcctt caagcccaag    120

tccaacccca acggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc gcaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggacct gttcggcctg gagtccatcg tgcaggacgg cctggtgttc    420

cgcgagtcct actccatccg ctcctacgag atcggcgccg accgcaccgc ctccatcgag    480

accctgatga accacctgca ggacacctcc ctgaaccact gcaagtccgt gggcctgctg    540

aacgacggct tcggccgcac ccccgagatg tgcaagcgcg acctgatctg ggtgctgacc    600

aagatgcaga tcatggtgaa ccgctacccc acctggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaacacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatccgca agggcctgac ccccggctgg aacgacctgg acgtgaacca gcacgtgtcc    960

aacgtgaagt acatcggctg gatcctggag tccatgccca ccgaggtgct ggagacccag   1020

gagctgtgct ccctgaccct ggagtaccgc cgcgagtgcg gccgcgagtc cgtgctggag   1080

tccgtgaccg ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 58
<211> LENGTH: 418
<212> TYPE: PRT
<213> ORGANISM: Cuphea heterophylla
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) amino acid sequence

<400> SEQUENCE: 58

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Gln Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125
```

```
Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 59
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) coding DNA sequence

<400> SEQUENCE: 59

```
atggtggtgg ctgctgcagc aagctctgca ttcttccctg ttccggcatc tggaacctcc      60

cctaaacccg ggaagttcgg gacttggcta tcgagctcga gcccttccta caagcccaag     120

tcaaacccca gtggtggatt tcaggttaag gcaaatgcca gtgctcatcc taaggctaac     180

ggttctgcag taagtctaaa gtctggcagc ctcaacactc aggaggacac ttcgtcgtcc     240

cctcctcctc agacattcct taaccagttg cctgattgga gtaggcttct gacagcaatc     300

tcgaccgtct tcgtggcggc agagaagcag ttgactatgc tcgatcgaaa atctaaaagg     360
```

```
cctgacatgc tcgtggactg gtttgggttg gagagtattg ttcaggatgg gctcgtgttc    420

agagagagtt attcgatcag gtcttacgaa ataagcgctg atcgaacagc ctctatagag    480

acggtgatga acctcttgca ggaaacatct ctcaatcatt gtaagagtat gggtattctc    540

aatgacggct ttggtcgtac cccggagatg tgcaaaaggg acctcatttg ggtgcttaca    600

aaaatgcaga tcttggtgaa tcgctatcca aattggggtg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaatacgaga    780

agattctcaa aacttccaaa cgaggttcgc caggagatag cgcctcattt tgttgacgct    840

cctcctgtca ttgaagacaa tgatcgaaaa ttgcataagt ttgatgtgaa gactggtgat    900

tccattcgca agggtctaac tccggggtgg aatgacttgg atgtcaatca gcacgtaagc    960

aacgtgaagt acattgggtg gattctcgag agtatgccaa cagaagtttt ggagacccag   1020

gagctatgct ctctcaccct tgaatatagg cgggaatgcg gaagggacag tgtgctggag   1080

tccgtgaccg ctatgaatcc ctcaaaagtt ggagaccggt ctcagtacca gcaccttcta   1140

cggcttgagg atggggctga tatcatgaag ggcagaactg agtggcgacc aaagaatgca   1200

ggaaccaacg ggcgatatc aacaggaaag acttcaaatg gaaactcggt ctcttag       1257
```

<210> SEQ ID NO 60
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2e (G76D, R97L, H124L, I132S, G152S, H165L, T211N, K258N, C303R, E309G, K334T, T386A variant) coding DNA sequence codon optimized for Prototheca moriformis

<400> SEQUENCE: 60

```
atggtggtgg ccgccgccgc ctcctccgcc ttcttccccg tgcccgcctc cggcacctcc     60

cccaagcccg gcaagttcgg cacctggctg tcctcctcct ccccctccta caagcccaag    120

tccaacccct ccggcggctt ccaggtgaag gccaacgcct ccgcccaccc caaggccaac    180

ggctccgccg tgtccctgaa gtccggctcc ctgaacaccc aggaggacac ctcctcctcc    240

cccccccccc agaccttcct gaaccagctg cccgactggt cccgcctgct gaccgccatc    300

tccaccgtgt tcgtggccgc cgagaagcag ctgaccatgc tggaccgcaa gtccaagcgc    360

cccgacatgc tggtggactg gttcggcctg gagtccatcg tgcaggacgg cctggtgttc    420

cgcgagtcct actccatccg ctcctacgag atctccgccg accgcaccgc ctccatcgag    480

accgtgatga acctgctgca ggagacctcc ctgaaccact gcaagtccat gggcatcctg    540

aacgacggct tcggccgcac ccccgagatg tgcaagcgcg acctgatctg ggtgctgacc    600

aagatgcaga tcctggtgaa ccgctacccc aactggggcg acaccgtgga gatcaactcc    660

tggttctccc agtccggcaa gatcggcatg ggccgcaact ggctgatctc cgactgcaac    720

accggcgaga tcctgatccg cgccacctcc atctgggcca tgatgaacca gaacacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatccgca agggcctgac ccccggctgg aacgacctgg acgtgaacca gcacgtgtcc    960
```

-continued

```
aacgtgaagt acatcggctg gatcctggag tccatgccca ccgaggtgct ggagacccag   1020

gagctgtgct ccctgaccct ggagtaccgc cgcgagtgcg gccgcgactc cgtgctggag   1080

tccgtgaccg ccatgaaccc ctccaaggtg ggcgaccgct cccagtacca gcacctgctg   1140

cgcctggagg acggcgccga catcatgaag ggccgcaccg agtggcgccc caagaacgcc   1200

ggcaccaacg gcgccatctc caccggcaag acctccaacg gcaactccgt gtcctga      1257
```

<210> SEQ ID NO 61
<211> LENGTH: 418
<212> TYPE: PRT
<213> ORGANISM: Cuphea heterophylla
<220> FEATURE:
<223> OTHER INFORMATION: Cuphea heterophylla (Cht) FATB2f (R97L, H124L, I132S, G152S, H165L, T211N variant) amino acid sequence

<400> SEQUENCE: 61

```
Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
```

-continued

```
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 62
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2f (R97L, H124L, I132S, G152S, H165L, T211N variant) coding DNA sequence

<400> SEQUENCE: 62

```
atggtggtgg ctgctgcagc aagctctgca ttcttccctg ttccggcatc tggaacctcc     60

cctaaacccg ggaagttcgg gacttggcta tcgagctcga gcccttccta caagcccaag    120

tcaaacccca gtggtggatt tcaggttaaa gcaaatgcca gtgctcatcc taaggctaac    180

ggttccgcag taagtctaaa gtctggcagc ctcaacactc aggagggcac ttcgtcgtcc    240

cctcctcctc ggacattcct taaccagttg cctgattgga gtaggcttct gactgcaatc    300

tcgaccgtct tcgtggcggc agagaagcag ttgactatgc tcgatcgaaa atctaagagg    360

cctgacatgc tcgtggactg gtttgggttg gagagtattg ttcaggatgg gctcgtgttc    420

agagagagtt attcgatcag gtcttacgaa ataagcgctg atcgaacagc ctctatagag    480

acggtgatga acctcttgca ggaaacatct ctcaatcatt gtaagagtat gggtattctc    540

aatgacggct ttggtcgtac ccggagatg tgcaaaaggg acctcatttg ggtgcttaca    600

aaaatgcaga tcttggtgaa tcgctatcca aattggggtg atactgtcga gatcaatagc    660

tggttctccc agtccgggaa aatcggtatg ggtcgcaatt ggctaataag tgattgcaac    720

acaggagaaa ttcttataag agcaacgagc atttgggcca tgatgaatca aaagacgaga    780

agattctcaa aacttccaaa tgaggttcgc caggagatag cgcctcattt tgtggacgcc    840

cctcctgtca ttgaagacaa tgatcgaaaa ttgcataagt ttgatgtgaa gactggtgat    900

tccatttgca agggtctaac accggagtgg aacgacttgg atgtcaatca gcacgtaagc    960

aacgtgaagt acattgggtg gattctcgag agtatgccaa aagaagtttt ggacacccag   1020

gagctatgct ctctcaccct tgaatatagg cgggaatgcg gaagggacag tgtgctggag   1080

tctgtgaccg ctatggatcc ctcaaaagtt ggagaccgat ctcagtacca gcaccttctg   1140

cggcttgaag atgggactga tatcatgaag ggcagaactg agtggcgacc aaagaatgca   1200

ggaaccaacg ggcgatatc aacaggaaag acttcaaatg gaaactcggt ctcttag      1257
```

<210> SEQ ID NO 63
<211> LENGTH: 1257
<212> TYPE: DNA

<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea heterophylla (Cht) FATB2f (R97L, H124L,
I132S, G152S, H165L, T211N variant) coding DNA sequence
codon optimized for Prototheca moriformis

<400> SEQUENCE: 63
atggtggtgg ccgccgccgc ctcctccgcc ttcttccccg tgcccgcctc cggcacctcc 60
cccaagcccg gcaagttcgg cacctggctg tcctcctcct ccccctccta caagcccaag 120
tccaacccct ccggcggctt ccaggtgaag gccaacgcct ccgcccaccc caaggccaac 180
ggctccgccg tgtccctgaa gtccggctcc ctgaacaccc aggagggcac ctcctcctcc 240
cccccccccc gcaccttcct gaaccagctg cccgactggt cccgcctgct gaccgccatc 300
tccaccgtgt tcgtggccgc cgagaagcag ctgaccatgc tggaccgcaa gtccaagcgc 360
cccgacatgc tggtggactg gttcggcctg gagtccatcg tgcaggacgg cctggtgttc 420
cgcgagtcct actccatccg ctcctacgag atctccgccg accgcaccgc ctccatcgag 480
accgtgatga acctgctgca ggagacctcc ctgaaccact gcaagtccat gggcatcctg 540
aacgacggct tcggccgcac ccccgagatg tgcaagcgcg acctgatctg ggtgctgacc 600
aagatgcaga tcctggtgaa ccgctacccc aactggggcg acaccgtgga gatcaactcc 660
tggttctccc agtccggcaa gatcggcatg ggccgcaact ggctgatctc cgactgcaac 720
accggcgaga tcctgatccg cgccacctcc atctgggcca tgatgaacca gaagacccgc 780
cgcttctcca agctgcccaa cgaggtgcgc caggagatcg ccccccactt cgtggacgcc 840
ccccccgtga tcgaggacaa cgaccgcaag ctgcacaagt tcgacgtgaa gaccggcgac 900
tccatctgca agggcctgac ccccgagtgg aacgacctgg acgtgaacca gcacgtgtcc 960
aacgtgaagt acatcggctg gatcctggag tccatgccca aggaggtgct ggacacccag 1020
gagctgtgct ccctgaccct ggagtaccgc cgcgagtgcg gccgcgactc cgtgctggag 1080
tccgtgaccg ccatggaccc ctccaaggtg ggcgaccgct cccagtacca gcacctgctg 1140
cgcctggagg acggcaccga catcatgaag ggccgcaccg agtggcgccc caagaacgcc 1200
ggcaccaacg gcgccatctc caccggcaag acctccaacg gcaactccgt gtcctga 1257

<210> SEQ ID NO 64
<211> LENGTH: 418
<212> TYPE: PRT
<213> ORGANISM: Cuphea heterophylla
<220> FEATURE:
<223> OTHER INFORMATION: Cuphea heterophylla (Cht) FATB2g (A6T, A16V,
S17P, G76D, R97L, H124L, I132S, S143I, G152S, A157T, H165L, T211N,
G414A variant) amino acid sequence

<400> SEQUENCE: 64

Met Val Val Ala Ala Thr Ala Ser Ser Ala Phe Phe Pro Val Pro Val
1               5                   10                  15

Pro Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

```
Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ile Tyr
    130                 135                 140

Ser Ile Arg Ser Tyr Glu Ile Ser Ala Asp Arg Thr Thr Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Ala Asn Ser
                405                 410                 415

Val Ser
```

<210> SEQ ID NO 65
<211> LENGTH: 1257
<212> TYPE: DNA
<213> ORGANISM: Cuphea heterophylla
<220> FEATURE:
<223> OTHER INFORMATION: Cuphea heterophylla (Cht) FATB2g (A6T, A16V, S17P, G76D, R97L, H124L, I132S, S143I, G152S, A157T, H165L, T211N, G414A variant) coding DNA sequence

<400> SEQUENCE: 65

```
atggtggtgg ctgctacagc aagttctgca ttcttccctg ttcctgtacc tggaacctcc      60
```

cctaaacccg gaaagttcgg gacttggcta tcgagctcga gcccttccta caagcccaag 120
tcaaacccca gtggtggatt tcaggttaag gcaaatgcca gtgctcatcc taaggctaac 180
ggttctgcag taagtctaaa gtctggcagc ctcaacactc aggaggacac ttcgtcgtcc 240
cctcctcctc ggacattcct taaccagttg cctgattgga gtaggcttct gactgcaatc 300
tcgaccgtct tcgtggcggc agagaagcag ttgactatgc tcgatcgaaa atctaagagg 360
cctgacatgc tcgtggactg gtttgggttg gagagtattg ttcaggatgg gctcgtgttc 420
agagagattt attcgatcag gtcttacgaa ataagcgctg atcgaacaac ctctatagag 480
acggtgatga acctcttgca ggaaacatct ctcaatcatt gtaagagtat gggtattctc 540
aatgacggct ttggtcgtac cccggagatg tgcaaaaggg acctcatttg ggtgcttaca 600
aaaatgcaga tcttggtgaa tcgctatcca aattggggtg atactgtcga gatcaatagc 660
tggttctccc agtccgggaa aatcggtatg ggtcgcaatt ggctaataag tgattgcaac 720
acaggagaaa ttcttataag agcaacgagc atttgggcca tgatgaatca aaagacgaga 780
agattctcaa aacttccaaa cgaggttcgc caggagatag cgcctcattt tgtggacgcc 840
cctcctgtca ttgaagacaa tgatcgaaaa ttgcataagt ttgatgtgaa gactggtgat 900
tccatttgca agggtctaac accggagtgg aatgacttgg atgtcaatca gcacgtaagc 960
aacgtgaagt acattgggtg gattctcgag agtatgccaa aagaagtttt ggacacccag 1020
gagctatgct ctctcaccct tgaatatagg cgggaatgcg gaagggacag tgtgctggag 1080
tctgtgaccg ctatggatcc ctcaaaagtt ggagaccgat ctcagtacca gcaccttctg 1140
cggcttgaag atgggactga tatcatgaag ggcagaactg agtggcgacc aaagaatgca 1200
ggaaccaacg ggcgatatc aacaggaaag acttcaaatg caaactcggt ctcttag 1257

<210> SEQ ID NO 66
<211> LENGTH: 1257
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB2g (A6T, A16V, S17P, G76D, R97L, H124L, I132S, S143I, G152S, A157T, H165L, T211N, G414A variant) coding DNA sequence codon optimized for Prototheca moriformis

<400> SEQUENCE: 66
atggtggtgg ccgccaccgc ctcctccgcc ttcttccccg tgcccgtgcc cggcacctcc 60
cccaagcccg gcaagttcgg cacctggctg tcctcctcct cccccctccta caagcccaag 120 tccaacccct ccggcggctt ccaggtgaag gccaacgcct ccgcccaccc caaggccaac 180
ggctccgccg tgtccctgaa gtccggctcc ctgaacaccc aggaggacac ctcctcctcc 240
cccccccccc gcaccttcct gaaccagctg cccgactggt cccgcctgct gaccgccatc 300
tccaccgtgt tcgtggccgc cgagaagcag ctgaccatgc tggaccgcaa gtccaagcgc 360
cccgacatgc tggtggactg gttcggcctg gagtccatcg tgcaggacgg cctggtgttc 420
cgcgagatct actccatccg ctcctacgag atctccgccg accgcaccac ctccatcgag 480
accgtgatga acctgctgca ggagacctcc ctgaaccact gcaagtccat gggcatcctg 540
aacgacggct tcggccgcac ccccgagatg tgcaagcgcg acctgatctg ggtgctgacc 600
aagatgcaga tcctggtgaa ccgctacccc aactggggcg acaccgtgga gatcaactcc 660

-continued

```
tggttctccc agtccggcaa gatcggcatg ggccgcaact ggctgatctc cgactgcaac    720

accggcgaga tcctgatccg cgccacctcc atctgggcca tgatgaacca gaagacccgc    780

cgcttctcca agctgcccaa cgaggtgcgc caggagatcg ccccccactt cgtggacgcc    840

ccccccgtga tcgaggacaa cgaccgcaag ctgcacaagt tcgacgtgaa gaccggcgac    900

tccatctgca agggcctgac ccccgagtgg aacgacctgg acgtgaacca gcacgtgtcc    960

aacgtgaagt acatcggctg gatcctggag tccatgccca aggaggtgct ggacacccag   1020

gagctgtgct ccctgaccct ggagtaccgc cgcgagtgcg gccgcgactc cgtgctggag   1080

tccgtgaccg ccatggaccc ctccaaggtg ggcgaccgct cccagtacca gcacctgctg   1140

cgcctggagg acggcaccga catcatgaag ggccgcaccg agtggcgccc caagaacgcc   1200

ggcaccaacg gcgccatctc caccggcaag acctccaacg ccaactccgt gtcctga      1257
```

<210> SEQ ID NO 67
<211> LENGTH: 414
<212> TYPE: PRT
<213> ORGANISM: Cuphea heterophylla
<220> FEATURE:
<223> OTHER INFORMATION: Cuphea heterophylla (Cht) FATB3aamino acid
      sequence

<400> SEQUENCE: 67

```
Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255
```

```
Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

```
<210> SEQ ID NO 68
<211> LENGTH: 1245
<212> TYPE: DNA
<213> ORGANISM: Cuphea heterophylla
<220> FEATURE:
<223> OTHER INFORMATION: Cuphea heterophylla (Cht) FATB3a coding DNA
      sequence

<400> SEQUENCE: 68

atggtggcca ccgctgcaag ttctgcattc ttcccggtgc cgtccccgga cacctcctct     60

agaccgggaa agctcggaaa tgggtcatca agcttgaggc ccctcaagcc caaatttgtt    120

gccaatgctg ggctgcaggt taaggcaaac gccagtgccc ctcctaagat caatggttcc    180

tcggtcagtc taaagtcttg cagtctcaag actcatgaag acactccttc agctcctcct    240

ccgcggactt ttatcaacca gttgcctgat tggagcatgc ttcttgctgc aatcactact    300

gtcttcttgg cagcagagaa gcagtggatg atgcttgatt ggaaaccaaa gaggcctgac    360

atgcttgtgg acccgttcgg attgggaagg attgttcagg atgggcttgt gttcaggcag    420

aatttttcga ttaggtccta tgaaataggc gctgatcgca ctgcatccat agagacggtg    480

atgaaccact tgcaggaaac ggctctcaat catgttaaga gtgcggggct tcttaatgaa    540

ggctttggtc gtactcctga gatgtataaa agggacctta tttgggttgt cgcgaaaatg    600

caggtcatgg ttaaccgcta tcctacttgg ggtgacacgg ttgaagtgaa tacttgggtt    660

gccaagtcag ggaaaaatgg tatgcgtcgt gattggctca taagtgattg caatacagga    720

gaaattctta caagggcatc aagtgtgtgg gtcatgatga atcaaaagac aagaaaattg    780

tcaaagattc cagatgaggt tcggcatgag atagagcctc attttgtgga ctctgctccc    840

gtcattgaag acgatgactg gaaacttccc aagctggatg agaaaactgc tgactccatc    900

cgcaagggtc taactccgaa gtggaatgac ttggatgtca atcagcacgt caacaacgtg    960

aagtacattg ggtggattct tgagagtact ccaccagaag ttctggagac ccaggagtta   1020

tgttccctta ccctggaata caggcgggaa tgcggaaggg agagtgtgct ggagtccctc   1080

actgctgtgg acccctctgg aaagggcttt gggccccagt ttcagcacct tctgaggctt   1140
```

gaggatggag gtgagatcgt aaaggggaga actgagtggc gacccaagac tgcaggtatc 1200
aatgggacga ttgcatctgg ggagacctca cctggaaact cttag 1245

<210> SEQ ID NO 69
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB3a coding DNA sequence codon optimized for Prototheca moriformis

<400> SEQUENCE: 69
atggtggcca ccgccgcctc ctccgccttc ttccccgtgc cctcccccga cacctcctcc 60
cgccccggca agctgggcaa cggctcctcc tccctgcgcc ccctgaagcc caagttcgtg 120
gccaacgccg gcctgcaggt gaaggccaac gcctccgccc cccccaagat caacggctcc 180
tccgtgtccc tgaagtcctg ctccctgaag acccacgagg acacccccctc cgcccccccc 240 ccccgcacct tcatcaacca gctgcccgac tggtccatgc tgctggccgc catcaccacc 300
gtgttcctgg ccgccgagaa gcagtggatg atgctggact ggaagcccaa gcgccccgac 360
atgctggtgg accccttcgg cctgggccgc atcgtgcagg acggcctggt gttccgccag 420
aacttctcca tccgctccta cgagatcggc gccgaccgca ccgcctccat cgagaccgtg 480
atgaaccacc tgcaggagac cgccctgaac cacgtgaagt ccgccggcct gctgaacgag 540
ggcttcggcc gcacccccga gatgtacaag cgcgacctga tctgggtggt ggccaagatg 600
caggtgatgg tgaaccgcta ccccacctgg ggcgacaccg tggaggtgaa cacctgggtg 660
gccaagtccg gcaagaacgg catgcgccgc gactggctga tctccgactg caacaccggc 720
gagatcctga cccgcgcctc ctccgtgtgg gtgatgatga accagaagac ccgcaagctg 780
tccaagatcc ccgacgaggt gcgccacgag atcgagcccc acttcgtgga ctccgccccc 840
gtgatcgagg acgacgactg gaagctgccc aagctggacg agaagaccgc cgactccatc 900
cgcaagggcc tgacccccaa gtggaacgac ctggacgtga accagcacgt gaacaacgtg 960
aagtacatcg gctggatcct ggagtccacc ccccccgagg tgctggagac ccaggagctg 1020
tgctccctga ccctggagta ccgccgcgag tgcggccgcg agtccgtgct ggagtccctg 1080
accgccgtgg acccctccgg caagggcttc ggcccccagt tccagcacct gctgcgcctg 1140
gaggacggcg gcgagatcgt gaagggccgc accgagtggc gccccaagac cgccggcatc 1200
aacggcacca tcgcctccgg cgagacctcc cccggcaact cctga 1245

<210> SEQ ID NO 70
<211> LENGTH: 414
<212> TYPE: PRT
<213> ORGANISM: Cuphea heterophylla
<220> FEATURE:
<223> OTHER INFORMATION: Cuphea heterophylla (Cht) FATB3b (C67G, H72Q, L128F, N179I variant) amino acid sequence

<400> SEQUENCE: 70

Met Val Ala Thr Ala Ala Ser Ser Ala Phe Phe Pro Val Pro Ser Pro
1 5 10 15

Asp Thr Ser Ser Arg Pro Gly Lys Leu Gly Asn Gly Ser Ser Ser Leu
20 25 30

Arg Pro Leu Lys Pro Lys Phe Val Ala Asn Ala Gly Leu Gln Val Lys
35 40 45

-continued

```
Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Phe
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Ile Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

<210> SEQ ID NO 71
<211> LENGTH: 1245
<212> TYPE: DNA
<213> ORGANISM: Cuphea heterophylla
<220> FEATURE:
<223> OTHER INFORMATION: Cuphea heterophylla (Cht) FATB3b (C67G, H72Q, L128F, N179I variant) coding DNA sequence

<400> SEQUENCE: 71
atggtggcca ccgctgcaag ttctgcattc ttcccggtgc catccccgga cacctcctct 60
agaccgggaa agctcggaaa tgggtcatca agcttgaggc ccctcaagcc caaatttgtt 120
gccaatgctg ggctgcaggt taaggcaaac gccagtgccc ctcctaagat caatggttcc 180
tcggtcagtc taaagtctgg cagtctcaag actcaggaag acactccttc ggctcctcct 240
ccgcggactt ttatcaacca gttgcctgat tggagcatgc ttcttgctgc aatcactact 300
gtcttcttgg cagcagagaa gcagtggatg atgcttgatt ggaaaccaaa gaggcctgac 360
atgcttgtgg acccgttcgg atttggaagg attgttcagg atgggcttgt gttcaggcag 420
aatttttcga ttaggtccta tgaaataggc gctgatcgca ctgcatctat agagacggtg 480
atgaaccact tgcaggaaac ggctctcaat catgttaaga gtgcggggct tcttattgaa 540
ggctttggtc gtactcctga gatgtataaa agggacctta tttgggttgt cgcgaaaatg 600
caggtcatgg ttaaccgcta tcctacttgg ggtgacacgg ttgaagtgaa tacttgggtt 660
gccaagtcag ggaaaaatgg tatgcgtcgt gattggctca taagtgattg caatacagga 720
gaaattctta ctagagcatc aagtgtgtgg gtcatgatga atcaaaagac aagaaaattg 780
tcaaagattc cagatgaggt tcggcatgag atagagcctc attttgtgga ctctgctccc 840
gtcattgaag acgatgactg gaaacttccc aagctggatg agaaaactgc tgactccatc 900
cgcaagggtc taactccgaa gtggaatgac ttggatgtca atcagcacgt caacaacgtg 960
aagtacattg ggtggattct tgagagtact ccaccagaag ttctggagac ccaggagtta 1020
tgttccctta ccctggaata caggcgggaa tgcggaaggg agagtgtgct ggagtccctc 1080
actgctgtgg acccctctgg aaagggcttt gggccccagt ttcagcacct tctgaggctt 1140
gaggatggag gtgagatcgt aaaggggaga actgagtggc gacccaagac tgcaggtatc 1200
aatgggacga ttgcatctgg ggagacctca cctggaaact cttag 1245

<210> SEQ ID NO 72
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea heterophylla (Cht) FATB3b (C67G, H72Q, L128F, N179I variant) coding DNA sequence codon optimized for Prototheca moriformis

<400> SEQUENCE: 72
atggtggcca ccgccgcctc ctccgccttc ttccccgtgc cctcccccga cacctcctcc 60
cgccccggca agctgggcaa cggctcctcc tccctgcgcc ccctgaagcc caagttcgtg 120
gccaacgccg gcctgcaggt gaaggccaac gcctccgccc cccccaagat caacggctcc 180
tccgtgtccc tgaagtccgg ctccctgaag acccaggagg acacccccctc cgcccccccc 240
ccccgcacct tcatcaacca gctgcccgac tggtccatgc tgctggccgc catcaccacc 300
gtgttcctgg ccgccgagaa gcagtggatg atgctggact ggaagcccaa gcgccccgac 360
atgctggtgg accccttcgg cttcggccgc atcgtgcagg acggcctggt gttccgccag 420
aacttctcca tccgctccta cgagatcggc gccgaccgca ccgcctccat cgagaccgtg 480
atgaaccacc tgcaggagac cgccctgaac cacgtgaagt ccgccggcct gctgatcgag 540
ggcttcggcc gcacccccga gatgtacaag cgcgacctga tctgggtggt ggccaagatg 600

-continued

```
caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgcaagctg    780

tccaagatcc ccgacgaggt gcgccacgag atcgagcccc acttcgtgga ctccgccccc    840

gtgatcgagg acgacgactg gaagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080

accgccgtgg accccctcgg caagggcttc ggcccccagt tccagcacct gctgcgcctg   1140

gaggacggcg gcgagatcgt gaagggccgc accgagtggc gccccaagac cgccggcatc   1200

aacggcacca tcgcctccgg cgagacctcc cccggcaact cctga                   1245
```

<210> SEQ ID NO 73
<211> LENGTH: 419
<212> TYPE: PRT
<213> ORGANISM: Cuphea viscosissima
<220> FEATURE:
<223> OTHER INFORMATION: Cuphea viscosissima (Cvis) FATB1 amino acid sequence

<400> SEQUENCE: 73

```
Met Val Ala Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg His Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Thr Ile Asn His Cys Lys Ser Leu
                165                 170                 175

Gly Leu His Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
```

-continued

```
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu Arg Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 74
<211> LENGTH: 1260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea viscosissima (Cvis) FATB1 coding DNA
      sequence codon optimized for Prototheca moriformis

<400> SEQUENCE: 74

atggtggccg ccgccgccac ctccgccttc ttccccgtgc ccgcccccgg cacctccccc     60

aagcccggca agtccggcaa ctggccctcc tccctgtccc ccaccttcaa gcccaagtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag tccatcgtgc gcgacggcct ggtgtcccgc    420

cactccttct ccatccgctc ctacgagatc ggcgccgacc gcaccgcctc catcgagacc    480

ctgatgaacc acctgcagga gaccaccatc aaccactgca agtccctggg cctgcacaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatggcc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccagaagctg cgcaagttcg acgtgaagac cggcgactcc    900

atccgcaagg gcctgacccc ccgctggaac gacctggacg tgaaccagca cgtgtccaac    960
```

```
gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgccg tggacccctc cgagaacggc ggccgctccc agtacaagca cctgctgcgc   1140

ctggaggacg gcaccgacat cgtgaagtcc cgcaccgagt ggcgccccaa gaacgccggc   1200

accaacggcg ccatctccac ctccaccgcc aagacctcca acggcaactc cgtgtcctga   1260


<210> SEQ ID NO 75
<211> LENGTH: 415
<212> TYPE: PRT
<213> ORGANISM: Cuphea viscosissima
<220> FEATURE:
<223> OTHER INFORMATION: Cuphea viscosissima (Cvis) FATB2 amino acid
      sequence

<400> SEQUENCE: 75

Met Val Ala Thr Ala Ala Ser Ser Ala Phe Phe Pro Val Pro Ser Ala
1               5                   10                  15

Asp Thr Ser Ser Arg Pro Gly Lys Leu Gly Asn Gly Pro Ser Ser Phe
            20                  25                  30

Ser Pro Leu Lys Pro Lys Ser Ile Pro Asn Gly Gly Leu Gln Val Lys
        35                  40                  45

Ala Ser Ala Ser Ala Pro Pro Lys Ile Asn Gly Ser Ser Val Gly Leu
    50                  55                  60

Lys Ser Gly Gly Leu Lys Thr His Asp Asp Ala Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Ala Phe Leu Ala Ala Glu Lys Gln Trp Met Met Leu
            100                 105                 110

Asp Arg Lys Pro Lys Arg Leu Asp Met Leu Glu Asp Pro Phe Gly Leu
        115                 120                 125

Gly Arg Val Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Thr Ala Gly
                165                 170                 175

Leu Ser Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg Arg Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Ser Ala Asp Ser Ile Arg Lys Gly Leu
    290                 295                 300
```

-continued

```
Thr Pro Arg Trp Asn Asp Leu Asp Val Asn Gln His Val Asn Asn Ala
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Glu
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Val Val Pro Ser Glu Glu Ser Ser Pro Gly Asp Tyr Ser
                405                 410                 415

<210> SEQ ID NO 76
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea viscosissima (Cvis) FATB2 coding DNA
      sequence codon optimized for Prototheca moriformis

<400> SEQUENCE: 76
atggtggcca ccgccgcctc ctccgccttc ttccccgtgc cctccgccga cacctcctcc      60
cgccccggca agctgggcaa cggcccctcc tccttctccc ccctgaagcc caagtccatc     120
cccaacggcg gcctgcaggt gaaggcctcc gcctccgccc cccccaagat caacggctcc     180
tccgtgggcc tgaagtccgg cggcctgaag acccacgacg acgccccctc cgcccccccc     240
ccccgcacct tcatcaacca gctgcccgac tggtccatgc tgctggccgc catcaccacc     300
gccttcctgg ccgccgagaa gcagtggatg atgctggacc gcaagcccaa gcgcctggac     360
atgctggagg accccttcgg cctgggccgc gtggtgcagg acggcctggt gttccgccag     420
aacttctcca tccgctccta cgagatcggc gccgaccgca ccgcctccat cgagaccgtg     480
atgaaccacc tgcaggagac cgccctgaac cacgtgaaga ccgccggcct gtccaacgac     540
ggcttcggcc gcacccccga gatgtacaag cgcgacctga tctgggtggt ggccaagatg     600
caggtgatgg tgaaccgcta ccccacctgg ggcgacaccg tggaggtgaa cacctgggtg     660
gccaagtccg gcaagaacgg catgcgccgc gactggctga tctccgactg caacaccggc     720
gagatcctga cccgcgcctc ctccgtgtgg gtgatgatga accagaagac ccgcaagctg     780
tccaagatcc ccgacgaggt gcgccgcgag atcgagcccc acttcgtgga ctccgccccc     840
gtgatcgagg acgacgaccg caagctgccc aagctggacg agaagtccgc cgactccatc     900
cgcaagggcc tgaccccccg ctggaacgac ctggacgtga accagcacgt gaacaacgcc     960
aagtacatcg gctggatcct ggagtccacc ccccccgagg tgctggagac ccaggagctg    1020
tgctccctga ccctggagta ccgccgcgag tgcggccgcg agtccgtgct ggagtccctg    1080
accgccgtgg acccctccgg cgagggctac ggctcccagt tccagcacct gctgcgcctg    1140
gaggacggcg gcgagatcgt gaagggccgc accgagtggc gccccaagaa cgccggcatc    1200
aacggcgtgg tgccctccga ggagtcctcc cccggcgact actcctga                 1248

<210> SEQ ID NO 77
```

-continued

```
<211> LENGTH: 412
<212> TYPE: PRT
<213> ORGANISM: Cuphea viscosissima
<220> FEATURE:
<223> OTHER INFORMATION: Cuphea viscosissima (Cvis) FATB3 amino acid
      sequence

<400> SEQUENCE: 77

Met Val Ala Ala Ala Ala Ser Ser Ala Phe Phe Ser Phe Pro Thr Pro
1               5                   10                  15

Gly Thr Ser Pro Lys Pro Gly Lys Phe Gly Asn Trp Pro Ser Ser Leu
            20                  25                  30

Ser Ile Pro Phe Asn Pro Lys Ser Asn His Asn Gly Gly Ile Gln Val
        35                  40                  45

Lys Ala Asn Ala Ser Ala His Pro Lys Ala Asn Gly Ser Ala Val Ser
    50                  55                  60

Leu Lys Ala Gly Ser Leu Glu Thr Gln Glu Asp Thr Ser Ser Pro Ser
65                  70                  75                  80

Pro Pro Pro Arg Thr Phe Ile Ser Gln Leu Pro Asp Trp Ser Met Leu
                85                  90                  95

Val Ser Ala Ile Thr Thr Val Phe Val Ala Ala Glu Lys Gln Trp Thr
            100                 105                 110

Met Leu Asp Arg Lys Ser Lys Arg Pro Asp Val Leu Val Glu Pro Phe
        115                 120                 125

Val Gln Asp Gly Val Ser Phe Arg Gln Ser Phe Ser Ile Arg Ser Tyr
    130                 135                 140

Glu Ile Gly Val Asp Arg Thr Ala Ser Ile Glu Thr Leu Met Asn Ile
145                 150                 155                 160

Phe Gln Glu Thr Ser Leu Asn His Cys Lys Ser Leu Gly Leu Leu Asn
                165                 170                 175

Asp Gly Phe Gly Arg Thr Pro Glu Met Cys Lys Arg Asp Leu Ile Trp
            180                 185                 190

Val Val Thr Lys Met Gln Ile Glu Val Asn Arg Tyr Pro Thr Trp Gly
        195                 200                 205

Asp Thr Ile Glu Val Thr Thr Trp Val Ser Glu Ser Gly Lys Asn Gly
    210                 215                 220

Met Ser Arg Asp Trp Leu Ile Ser Asp Cys His Ser Gly Glu Ile Leu
225                 230                 235                 240

Ile Arg Ala Thr Ser Val Trp Ala Met Met Asn Gln Lys Thr Arg Arg
                245                 250                 255

Leu Ser Lys Ile Pro Asp Glu Val Arg Gln Glu Ile Val Pro Tyr Phe
            260                 265                 270

Val Asp Ser Ala Pro Val Ile Glu Asp Asp Arg Lys Leu His Lys Leu
        275                 280                 285

Asp Val Lys Thr Gly Asp Ser Ile Arg Asn Gly Leu Thr Pro Arg Trp
    290                 295                 300

Asn Asp Phe Asp Val Asn Gln His Val Asn Asn Val Lys Tyr Ile Ala
305                 310                 315                 320

Trp Leu Leu Lys Ser Val Pro Thr Glu Val Phe Glu Thr Gln Glu Leu
                325                 330                 335

Cys Gly Leu Thr Leu Glu Tyr Arg Arg Glu Cys Arg Arg Asp Ser Val
            340                 345                 350

Leu Glu Ser Val Thr Ala Met Asp Pro Ser Lys Glu Gly Asp Arg Ser
        355                 360                 365

Leu Tyr Gln His Leu Leu Arg Leu Glu Asn Gly Ala Asp Ile Ala Leu
```

-continued 370 375 380

Gly Arg Thr Glu Trp Arg Pro Lys Asn Ala Gly Ala Thr Gly Ala Val
385 390 395 400

Ser Thr Gly Lys Thr Ser Asn Gly Asn Ser Val Ser
405 410

<210> SEQ ID NO 78
<211> LENGTH: 1239
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea viscosissima (Cvis) FATB3 coding DNA sequence codon optimized for Prototheca moriformis

<400> SEQUENCE: 78
atggtggccg ccgccgcctc ctccgccttc ttctccttcc ccacccccgg cacctccccc 60
aagcccggca agttcggcaa ctggccctcc tccctgtcca tcccctcaa ccccaagtcc 120 aaccacaacg gcggcatcca ggtgaaggcc aacgcctccg cccaccccaa ggccaacggc 180
tccgccgtgt ccctgaaggc cggctccctg gagacccagg aggacacctc ctcccctcc 240 ccccccccc gcaccttcat ctcccagctg cccgactggt ccatgctggt gtccgccatc 300
accaccgtgt tcgtggccgc cgagaagcag tggaccatgc tggaccgcaa gtccaagcgc 360
cccgacgtgc tggtggagcc cttcgtgcag gacggcgtgt ccttccgcca gtccttctcc 420
atccgctcct acgagatcgg cgtggaccgc accgcctcca tcgagaccct gatgaacatc 480
ttccaggaga cctccctgaa ccactgcaag tccctgggcc tgctgaacga cggcttcggc 540
cgcacccccg agatgtgcaa gcgcgacctg atctgggtgg tgaccaagat gcagatcgag 600
gtgaaccgct accccacctg gggcgacacc atcgaggtga ccacctgggt gtccgagtcc 660
ggcaagaacg gcatgtcccg cgactggctg atctccgact gccactccgg cgagatcctg 720
atccgcgcca cctccgtgtg ggccatgatg aaccagaaga cccgccgcct gtccaagatc 780
cccgacgagg tgcgccagga gatcgtgccc tacttcgtgg actccgcccc cgtgatcgag 840
gacgaccgca agctgcacaa gctggacgtg aagaccggcg actccatccg caacggcctg 900
accccccgct ggaacgactt cgacgtgaac cagcacgtga acaacgtgaa gtacatcgcc 960
tggctgctga agtccgtgcc caccgaggtg ttcgagaccc aggagctgtg cggcctgacc 1020
ctggagtacc gccgcgagtg ccgccgcgac tccgtgctgg agtccgtgac cgccatggac 1080
ccctccaagg agggcgaccg ctccctgtac cagcacctgc tgcgcctgga gaacggcgcc 1140
gacatcgccc tgggccgcac cgagtggcgc cccaagaacg ccggcgccac cggcgccgtg 1200
tccaccggca agacctccaa cggcaactcc gtgtcctga 1239

<210> SEQ ID NO 79
<211> LENGTH: 417
<212> TYPE: PRT
<213> ORGANISM: Cuphea calcarata
<220> FEATURE:
<223> OTHER INFORMATION: Cuphea calcarata (Ccalc) FATB1 amino acid sequence

<400> SEQUENCE: 79

Met Val Ala Ala Ser Ala Ser Ser Ala Phe Phe Ser Val Pro Thr Pro
1 5 10 15

Gly Thr Ser Pro Lys Pro Gly Lys Phe Gly Asn Trp Pro Ser Ser Leu

```
            20                  25                  30

Ser Val Pro Phe Lys Pro Arg Ser Asn Asn Ser Gly Gly Phe Gln Val
        35                  40                  45

Lys Ala Asn Ala Ser Ala His Pro Lys Ala Asn Gly Ser Ala Val Ser
    50                  55                  60

Leu Lys Ser Gly Ser Leu Glu Thr Gln Glu Asp Asn Ser Ser Ser Ser
65                  70                  75                  80

Arg Pro Pro Arg Thr Phe Ile Lys Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Phe Asp Arg Lys Ser Lys Arg Ser Asp Met Leu Val Asp Pro Phe
        115                 120                 125

Val Val Asp Arg Ile Val Gln Asp Gly Val Leu Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Met Gly Leu Leu Tyr Glu Gly Phe Gly Arg Thr Pro Glu Met Cys Lys
            180                 185                 190

Arg Asp Leu Ile Trp Val Val Thr Lys Ile His Ile Lys Val Asn Arg
        195                 200                 205

Tyr Pro Thr Trp Gly Asp Thr Ile Glu Val Thr Thr Trp Val Ser Glu
    210                 215                 220

Ser Gly Lys Asn Gly Met Gly Arg Asp Trp Leu Ile Ser Asp Cys His
225                 230                 235                 240

Thr Gly Glu Ile Leu Ile Arg Ala Thr Ser Val Trp Ala Met Met Asn
                245                 250                 255

Gln Thr Thr Arg Arg Leu Ser Lys Phe Pro Tyr Glu Leu Arg Gln Glu
            260                 265                 270

Ile Ala Pro His Phe Val Asp Ser Asp Pro Val Ile Glu Asp Asn Arg
        275                 280                 285

Arg Leu Leu Asn Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Asp Thr Arg Glu Leu Cys Gly Leu Thr Leu Glu Tyr Arg Gln Glu Cys
            340                 345                 350

Gly Arg Gly Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Pro Val Ser Thr Arg Lys Thr Thr Asn Gly Ser Ser Val
                405                 410                 415

Ser


<210> SEQ ID NO 80
<211> LENGTH: 1254
```

<212> TYPE: DNA
<213> ORGANISM: Cuphea calcarata
<220> FEATURE:
<223> OTHER INFORMATION: Cuphea calcarata (Ccalc) FATB1 coding DNA
sequence

<400> SEQUENCE: 80
atggtggctg cttcagcaag ttctgcattc ttctccgtcc caaccccggg aacctctcct 60
aaacccggga agttcggcaa ttggccatcg agcttgagcg tcccattcaa gcccagatca 120
aacaacagtg gcggctttca ggttaaggca aacgccagtg ctcatcctaa ggctaacggt 180
tctgcagtaa gtctaaagtc tgggagcctc gagactcagg aggacaattc gtcgtcgtct 240
cgtcctcctc ggactttcat taaacagttg ccggactgga gtatgcttct ttccgcgatc 300
acaaccgtct tcgtggcggc tgagaagcag tggacgatgt ttgatcggaa atctaagagg 360
tctgacatgc tcgtggaccc gtttgtggtt gacaggattg ttcaggatgg ggttctgttc 420
agacagagtt tttcgattag gtcttacgaa ataggcgctg atcgaacagc ctctattgag 480
acgctgatga acatcttcca ggaaacatct ctcaatcatt gtaagagtat gggtcttctc 540
tatgaaggct ttggtcgtac tcctgagatg tgtaagaggg acctcatttg ggtggttacg 600
aaaatacata tcaaggtgaa tcgctatccg acttggggtg atactatcga ggtcactact 660
tgggtctccg agtcgggcaa aaacggtatg ggtcgcgatt ggctgataag tgattgccat 720
acaggagaaa ttcttataag agcaacgagt gtgtgggcta tgatgaatca aacgacgaga 780
agattgtcga aatttccata tgagcttcga caggagatag cgccacattt tgtggactcg 840
gatcctgtca ttgaagacaa tcgaagattg ctcaactttg atgtgaagac gggtgattcc 900
attcgcaagg gtctaactcc aaggtggaat gacttggatg tcaatcagca cgttaacaat 960
gtgaagtaca ttgggtggat tctcgagagt gttccaacag aagttttcga tacccgggag 1020
ctatgcggcc tcacccttga gtataggcag gaatgcggaa gaggaagtgt gctggagtcc 1080
gtgaccgcta tggatccctc aaaagaggga gaccggtctc tgtaccagca ccttcttcgg 1140
cttgaggatg ggactgatat cgtgaagggc agaaccgagt ggcggccaaa gaatgcagga 1200
accaatgggc cagtatcaac aagaaagact acaaatggaa gctcagtctc ttag 1254

<210> SEQ ID NO 81
<211> LENGTH: 1254
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea calcarata (Ccalc) FATB1 coding DNA
sequence codon optimized for Prototheca moriformis

<400> SEQUENCE: 81
atggtggccg cctccgcctc ctccgccttc ttctccgtgc ccacccccgg cacctccccc 60
aagcccggca agttcggcaa ctggccctcc tccctgtccg tgcccttcaa gccccgctcc 120
aacaactccg gcggcttcca ggtgaaggcc aacgcctccg cccaccccaa ggccaacggc 180
tccgccgtgt ccctgaagtc cggctccctg gagacccagg aggacaactc ctcctcctcc 240
cgcccccccc gcaccttcat caagcagctg cccgactggt ccatgctgct gtccgccatc 300
accaccgtgt tcgtggccgc cgagaagcag tggaccatgt tcgaccgcaa gtccaagcgc 360
tccgacatgc tggtggaccc cttcgtggtg gaccgcatcg tgcaggacgg cgtgctgttc 420
cgccagtcct tctccatccg ctcctacgag atcggcgccg accgcaccgc ctccatcgag 480
accctgatga acatcttcca ggagacctcc ctgaaccact gcaagtccat gggcctgctg 540
tacgagggct tcggccgcac ccccgagatg tgcaagcgcg acctgatctg ggtggtgacc 600
aagatccaca tcaaggtgaa ccgctacccc acctggggcg acaccatcga ggtgaccacc 660
tgggtgtccg agtccggcaa gaacggcatg ggccgcgact ggctgatctc cgactgccac 720
accggcgaga tcctgatccg cgccacctcc gtgtgggcca tgatgaacca gaccacccgc 780
cgcctgtcca agttccccta cgagctgcgc caggagatcg ccccccactt cgtggactcc 840
gaccccgtga tcgaggacaa ccgccgcctg ctgaacttcg acgtgaagac cggcgactcc 900
atccgcaagg gcctgacccc ccgctggaac gacctggacg tgaaccagca cgtgaacaac 960
gtgaagtaca tcggctggat cctggagtcc gtgcccaccg aggtgttcga cacccgcgag 1020
ctgtgcggcc tgaccctgga gtaccgccag gagtgcggcc gcggctccgt gctggagtcc 1080
gtgaccgcca tggacccctc caaggagggc gaccgctccc tgtaccagca cctgctgcgc 1140
ctggaggacg gcaccgacat cgtgaagggc cgcaccgagt ggcgccccaa gaacgccggc 1200
accaacggcc ccgtgtccac ccgcaagacc accaacggct cctccgtgtc ctga 1254

<210> SEQ ID NO 82
<211> LENGTH: 415
<212> TYPE: PRT
<213> ORGANISM: Cuphea painteri
<220> FEATURE:
<223> OTHER INFORMATION: Cuphea painteri (Cpai) FATB1 amino acid sequence

<400> SEQUENCE: 82

Met Val Ala Ala Ala Ala Thr Ser Ala Phe Phe Pro Val Pro Ala Pro
1 5 10 15

Gly Thr Ser Pro Asn Pro Arg Lys Phe Gly Ser Trp Pro Ser Ser Leu
20 25 30

Ser Pro Ser Leu Pro Lys Ser Ile Pro Asn Gly Gly Phe Gln Val Lys
35 40 45

Ala Asn Ala Ser Ala His Pro Lys Ala Asn Gly Ser Ala Val Ser Leu
50 55 60

Lys Ser Gly Ser Leu Asn Thr Gln Glu Asn Thr Ser Ser Ser Pro Pro
65 70 75 80

Pro Arg Thr Phe Leu His Gln Leu Pro Asp Trp Ser Arg Leu Leu Thr
85 90 95

Ala Ile Thr Thr Val Phe Val Lys Ser Lys Arg Pro Asp Met His Asp
100 105 110

Arg Lys Ser Lys Arg Pro Asp Met Leu Val Asp Leu Phe Gly Leu Glu
115 120 125

Ser Ser Val Gln Asp Ala Leu Val Phe Arg Gln Ser Phe Ser Ile Arg
130 135 140

Ser Tyr Glu Ile Gly Thr Asp Arg Thr Ala Ser Ile Glu Thr Leu Met
145 150 155 160

Asn His Leu Gln Glu Thr Ser Leu Asn His Cys Lys Ser Thr Gly Ile
165 170 175

Leu Leu Asp Gly Phe Gly Arg Thr Leu Glu Met Cys Lys Arg Glu Leu
180 185 190

Ile Trp Val Val Ile Lys Met Gln Ile Gln Val Asn Arg Tyr Pro Ala
195 200 205

Trp Gly Asp Thr Val Glu Ile Asn Thr Arg Phe Ser Arg Leu Gly Lys
210 215 220

-continued

```
Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val His Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile Gln Lys Gly Leu Ser
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Gly Arg Ser Gln Tyr Gln His Leu Leu Arg Leu Glu Asp Gly Thr Ala
    370                 375                 380

Ile Val Asn Gly Ile Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

<210> SEQ ID NO 83
<211> LENGTH: 1248
<212> TYPE: DNA
<213> ORGANISM: Cuphea painteri
<220> FEATURE:
<223> OTHER INFORMATION: Cuphea painteri (Cpai) FATB1 coding DNA sequence

<400> SEQUENCE: 83

```
atggtggctg ctgcagcaac ttctgcattc ttccctgttc cagccccggg aacctcccca     60

aatcccagga aattcggaag ttggccatcg agcttgagcc cttccttgcc caagtcaatc    120

cccaatggcg gatttcaggt aaaggcaaat gccagtgccc atccgaaggc taacggttct    180

gcagttagtc taaagtctgg cagcctcaac actcaggaga acacttcgtc gtcccctcct    240

cctcggactt tccttcacca gttgcctgat tggagtaggc ttctgactgc aatcacgacc    300

gtgttcgtga aatctaagag gcctgacatg catgatcgga aatctaagag gcctgacatg    360

ctggtggact tgtttgggtt ggaaagtagt gttcaggatg cgctcgtgtt cagacagagt    420

ttttcgatta ggtcttatga aataggcact gatcgaacag cctctataga gacgctgatg    480

aaccacttgc aggaaacatc tctcaatcat tgtaaaagta ccggtattct ccttgacggc    540

ttcggtcgta ctcttgagat gtgtaaaagg gaactcattt gggtggtaat aaaaatgcaa    600

attcaggtga atcgctatcc agcatggggc gatactgtcg agatcaatac ccggttctcc    660

cggttgggga aaattggtat gggtcgcgat tggctaataa gtgattgcaa cacaggagaa    720

attctaataa gagcaacgag cgagtatgcc atgatgaatc aaaagacgag aagactctca    780

aaacttccat acgaggttca ccaggagata gcgcctcttt ttgtcgactc tcctcctgtg    840

attgaagaca atgatctgaa agtgcataaa tttgaagtga agactggtga ttccattcaa    900

aagggtctat ccccggggtg gaatgacttg gatgtcaatc agcacgtaag caacgtgaag    960
```

tacattgggt ggattctcga gagtatgcca acagaagttt tggagaccca ggagctatgc 1020
tctctcgccc ttgaatatag gcgggaatgc ggaagggaca gtgtgctgga gtccgtgacc 1080
gcaatggatc cctcaaaagt tggaggccgt tctcagtacc agcaccttct gcggcttgag 1140
gatgggactg ctatcgtgaa cggcataact gagtggcggc cgaagaatgc aggagctaat 1200
ggggcgatat caacgggaaa gacttcaaat ggaaactcgg tctcttag 1248

<210> SEQ ID NO 84
<211> LENGTH: 1248
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea painteri (Cpai) FATB1 coding DNA
sequence codon optimized for Prototheca moriformis

<400> SEQUENCE: 84
atggtggccg ccgccgccac ctccgccttc ttccccgtgc ccgcccccgg cacctccccc 60
aacccccgca agttcggctc ctggccctcc tccctgtccc cctccctgcc caagtccatc 120
cccaacggcg gcttccaggt gaaggccaac gcctccgccc accccaaggc caacggctcc 180
gccgtgtccc tgaagtccgg ctccctgaac acccaggaga acacctcctc ctcccccccc 240
ccccgcacct tcctgcacca gctgcccgac tggtcccgcc tgctgaccgc catcaccacc 300
gtgttcgtga agtccaagcg ccccgacatg cacgaccgca agtccaagcg ccccgacatg 360
ctggtggacc tgttcggcct ggagtcctcc gtgcaggacg ccctggtgtt ccgccagtcc 420
ttctccatcc gctcctacga gatcggcacc gaccgcaccg cctccatcga gaccctgatg 480
aaccacctgc aggagacctc cctgaaccac tgcaagtcca ccggcatcct gctggacggc 540
ttcggccgca ccctggagat gtgcaagcgc gagctgatct gggtggtgat caagatgcag 600
atccaggtga accgctaccc cgcctggggc gacaccgtgg agatcaacac ccgcttctcc 660
cgcctgggca agatcggcat gggccgcgac tggctgatct ccgactgcaa caccggcgag 720
atcctgatcc gcgccacctc cgagtacgcc atgatgaacc agaagacccg ccgcctgtcc 780
aagctgccct acgaggtgca ccaggagatc gccccccctgt tcgtggactc cccccccgtg 840
atcgaggaca acgacctgaa ggtgcacaag ttcgaggtga agaccggcga ctccatccag 900
aagggcctgt cccccggctg gaacgacctg gacgtgaacc agcacgtgtc caacgtgaag 960
tacatcggct ggatcctgga gtccatgccc accgaggtgc tggagaccca ggagctgtgc 1020
tccctggccc tggagtaccg ccgcgagtgc ggccgcgact ccgtgctgga gtccgtgacc 1080
gccatggacc cctccaaggt gggcggccgc tcccagtacc agcacctgct gcgcctggag 1140
gacggcaccg ccatcgtgaa cggcatcacc gagtggcgcc ccaagaacgc cggcgccaac 1200
ggcgccatct ccaccggcaa gacctccaac ggcaactccg tgtcctga 1248

<210> SEQ ID NO 85
<211> LENGTH: 414
<212> TYPE: PRT
<213> ORGANISM: Cuphea hookeriana
<220> FEATURE:
<223> OTHER INFORMATION: Cuphea hookeriana (Chook) FATB4 amino acid
sequence

<400> SEQUENCE: 85

Met Val Ala Ala Ala Ala Thr Ser Ala Phe Phe Pro Val Pro Ala Pro

```
1               5                   10                  15

Gly Thr Ser Pro Asn Pro Arg Lys Phe Gly Ser Trp Pro Ser Ser Leu
            20                  25                  30

Ser Pro Ser Leu Pro Asn Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Arg Phe Ser Ile Arg
    130                 135                 140

Ser Tyr Glu Ile Gly Thr Asp Arg Thr Ala Ser Met Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val Arg Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile His Lys Gly Leu Thr
    290                 295                 300

Pro Gly Trp Asn Asp Leu Asp Val Asn Gln His Val Asn Asn Val Lys
305                 310                 315                 320

Tyr Ile Gly Trp Ile Leu Glu Ser Thr Pro Pro Glu Val Leu Glu Thr
                325                 330                 335

Gln Glu Leu Cys Ser Leu Thr Leu Glu Tyr Arg Arg Glu Cys Gly Arg
            340                 345                 350

Glu Ser Val Leu Glu Ser Leu Thr Ala Met Asp Pro Ser Gly Gly Gly
        355                 360                 365

Tyr Gly Ser Gln Phe Gln His Leu Leu Arg Leu Glu Asp Gly Gly Glu
    370                 375                 380

Ile Val Lys Gly Arg Thr Glu Trp Arg Pro Lys Asn Gly Val Ile Asn
385                 390                 395                 400

Gly Val Val Pro Thr Gly Glu Ser Ser Pro Gly Asp Tyr Ser
                405                 410
```

<210> SEQ ID NO 86

<211> LENGTH: 1245
<212> TYPE: DNA
<213> ORGANISM: Cuphea hookeriana
<220> FEATURE:
<223> OTHER INFORMATION: Cuphea hookeriana (Chook) FATB4 coding DNA sequence

<400> SEQUENCE: 86

```
atggtggctg ctgcagcaac ttctgcattc ttccctgttc cagccccggg aacctcccct     60

aatcccagga aattcggaag ttggccatcg agcttgagcc cttccttgcc caactcaatc    120

cccaatggcg gatttcaggt aaaggcaaat gccagtgccc atccgaaggc taacggttct    180

gcagttagtc taaagtctgg cagcctcaac actcaggaga acacttcgtc gtcccctcct    240

cctcggactt tccttcacca gttgcctgat tggagtaggc ttctgactgc aatcacgacc    300

gtgttcgtga aatctaagag gcctgacatg catgatcgga aatctaagag gcctgacatg    360

ctggtggact tgtttgggtt ggagagtagt gttcaggatg cgctcgtgtt cagacagaga    420

ttttcgatta ggtcttatga aataggcact gatcgaacag cctctatgga gacgctgatg    480

aaccacttgc aggaaacatc tctcaatcat tgtaaaagta ccggtattct ccttgacggc    540

ttcggtcgta ctcttgagat gtgtaaaagg gaactcattt gggtggtaat aaaaatgcag    600

attcaggtga atcgctatcc agcatggggc gatactgtcg agatcaatac ccggttctcc    660

cggttgggga aaattggtat gggtcgcgat tggctaataa gtgattgcaa cacaggagaa    720

attcttataa gagcaacgag cgagtatgcc atgatgaatc aaaagacgag aagactctca    780

aaacttccat acgaggttcg ccaggagata gcgcctcttt ttgtcgactc tcctcctgtg    840

attgaagaca atgatctgaa agtgcataaa tttgaagtga agactggtga ttccattcac    900

aagggtctaa ctccggggtg gaatgacttg gatgtcaatc agcacgtcaa caacgtgaag    960

tacatcgggt ggattcttga gagtactcca ccagaagttc tggagaccca ggagttatgt   1020

tcccttactc tggaatacag gcgggaatgt ggaagggaga gcgtgctgga gtccctcact   1080

gctatggatc cctctggagg gggttatggg tcccagtttc agcaccttct gcggcttgag   1140

gatggaggtg agatcgtgaa ggggagaacc gagtggcgac ccaagaatgg tgtaatcaat   1200

ggggtggtac caaccgggga gtcctcacct ggagactact cttag                   1245
```

<210> SEQ ID NO 87
<211> LENGTH: 1245
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea hookeriana (Chook) FATB4 coding DNA sequence codon optimized for Prototheca moriformis

<400> SEQUENCE: 87

```
atggtggccg ccgccgccac ctccgccttc ttccccgtgc ccgcccccgg cacctccccc     60

aacccccgca agttcggctc ctggccctcc tccctgtccc cctccctgcc caactccatc    120

cccaacggcg gcttccaggt gaaggccaac gcctccgccc accccaaggc caacggctcc    180

gccgtgtccc tgaagtccgg ctccctgaac acccaggaga acacctcctc ctcccccccc    240

ccccgcacct tcctgcacca gctgcccgac tggtcccgcc tgctgaccgc catcaccacc    300

gtgttcgtga agtccaagcg ccccgacatg cacgaccgca agtccaagcg ccccgacatg    360

ctggtggacc tgttcggcct ggagtcctcc gtgcaggacg ccctggtgtt ccgccagcgc    420
```

```
ttctccatcc gctcctacga gatcggcacc gaccgcaccg cctccatgga gaccctgatg    480

aaccacctgc aggagacctc cctgaaccac tgcaagtcca ccggcatcct gctggacggc    540

ttcggccgca ccctggagat gtgcaagcgc gagctgatct gggtggtgat caagatgcag    600

atccaggtga accgctaccc cgcctggggc gacaccgtgg agatcaacac ccgcttctcc    660

cgcctgggca agatcggcat gggccgcgac tggctgatct ccgactgcaa caccggcgag    720

atcctgatcc gcgccacctc cgagtacgcc atgatgaacc agaagacccg ccgcctgtcc    780

aagctgccct acgaggtgcg ccaggagatc gcccccctgt tcgtggactc cccccccgtg    840

atcgaggaca acgacctgaa ggtgcacaag ttcgaggtga agaccggcga ctccatccac    900

aagggcctga cccccggctg gaacgacctg gacgtgaacc agcacgtgaa caacgtgaag    960

tacatcggct ggatcctgga gtccaccccc cccgaggtgc tggagaccca ggagctgtgc   1020

tccctgaccc tggagtaccg ccgcgagtgc ggccgcgagt ccgtgctgga gtccctgacc   1080

gccatggacc cctccggcgg cggctacggc tcccagttcc agcacctgct gcgcctggag   1140

gacggcggcg agatcgtgaa gggccgcacc gagtggcgcc ccaagaacgg cgtgatcaac   1200

ggcgtggtgc ccaccggcga gtcctccccc ggcgactact cctga                    1245
```

```
<210> SEQ ID NO 88
<211> LENGTH: 416
<212> TYPE: PRT
<213> ORGANISM: Cuphea avigera
<220> FEATURE:
<223> OTHER INFORMATION: Cuphea avigera var. pulcherrima (Ca) FATB1
      amino acid sequence

<400> SEQUENCE: 88

Met Val Ala Ala Ala Ala Ser Ser Ala Phe Phe Ser Val Pro Val Pro
1               5                   10                  15

Gly Thr Ser Pro Lys Pro Gly Lys Phe Arg Ile Trp Pro Ser Ser Leu
            20                  25                  30

Ser Pro Ser Phe Lys Pro Lys Pro Ile Pro Asn Gly Gly Leu Gln Val
        35                  40                  45

Lys Ala Asn Ser Arg Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Met Asp Ser Phe Gly Leu
        115                 120                 125

Glu Ser Ile Val Gln Glu Gly Leu Glu Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn Tyr Leu Gln Glu Thr Ser Leu Asn His Cys Lys Ser Thr Gly
                165                 170                 175

Ile Leu Leu Asp Gly Phe Gly Arg Thr Pro Glu Met Cys Lys Arg Asp
            180                 185                 190

Leu Ile Trp Val Val Thr Lys Met Lys Ile Lys Val Asn Arg Tyr Pro
        195                 200                 205

Ala Trp Gly Asp Thr Val Glu Ile Asn Thr Trp Phe Ser Arg Leu Gly
```

```
    210                 215                 220

Lys Ile Gly Lys Gly Arg Asp Trp Leu Ile Ser Asp Cys Asn Thr Gly
225                 230                 235                 240

Glu Ile Leu Ile Arg Ala Thr Ser Ala Tyr Ala Thr Met Asn Gln Lys
                245                 250                 255

Thr Arg Arg Leu Ser Lys Leu Pro Tyr Glu Val His Gln Glu Ile Ala
            260                 265                 270

Pro Leu Phe Val Asp Ser Pro Pro Val Ile Glu Asp Asn Asp Leu Lys
        275                 280                 285

Leu His Lys Phe Glu Val Lys Thr Gly Asp Ser Ile His Lys Gly Leu
    290                 295                 300

Thr Pro Gly Trp Asn Asp Leu Asp Val Asn Gln His Val Ser Asn Val
305                 310                 315                 320

Lys Tyr Ile Gly Trp Ile Leu Glu Ser Met Pro Thr Glu Val Leu Glu
                325                 330                 335

Thr Gln Glu Leu Cys Ser Leu Ala Leu Glu Tyr Arg Arg Glu Cys Gly
            340                 345                 350

Arg Asp Ser Val Leu Glu Ser Val Thr Ala Met Asp Pro Thr Lys Val
        355                 360                 365

Gly Gly Arg Ser Gln Tyr Gln His Leu Leu Arg Leu Glu Asp Gly Thr
    370                 375                 380

Asp Ile Val Lys Cys Arg Thr Glu Trp Arg Pro Lys Asn Pro Gly Ala
385                 390                 395                 400

Asn Gly Ala Ile Ser Thr Gly Lys Thr Ser Asn Gly Asn Ser Val Ser
                405                 410                 415


<210> SEQ ID NO 89
<211> LENGTH: 1251
<212> TYPE: DNA
<213> ORGANISM: Cuphea avigera
<220> FEATURE:
<223> OTHER INFORMATION: Cuphea avigera var. pulcherrima (Ca) FATB1
      coding DNA sequence

<400> SEQUENCE: 89

atggtggctg ctgcagcaag ttctgcattc ttctctgttc cagtcccggg aacctctcct     60

aaacccggga agttcagaat ttggccatcg agcttgagcc cttccttcaa gcccaagccg    120

atccccaatg gtggattgca ggttaaggca aattccaggg cacatccgaa ggctaacggt    180

tctgcagtta gtctaaagtc tggcagcctc aacactcagg aggacacttc gtcgtcccct    240

cctcctcgga ctttccttca ccagttgcct gattggagta ggcttctgac tgcaatcacg    300

accgtgttcg tgaaatctaa gaggcctgac atgcatgatc ggaaatctaa gaggcctgac    360

atgctgatgg actcgtttgg gttggagagt attgttcaag aagggctcga gttcagacag    420

agtttttcga ttaggtctta tgaaataggc actgatcgaa cagcctctat agagacgctg    480

atgaactact tgcaggaaac atctctcaat cattgtaaga gtaccggtat tctccttgac    540

ggctttggtc gtactcctga gatgtgtaaa agggacctca tttgggtggt aacaaaaatg    600

aagatcaagg tgaatcgcta tccagcttgg ggcgatactg tcgagatcaa tacctggttc    660

tcccggttgg ggaaaatcgg aaagggtcgc gattggctaa taagtgattg caacacagga    720

gaaattctta taagagcaac gagcgcgtat gccacgatga atcaaaagac gagaagactc    780

tcaaaacttc catacgaggt tcaccaggag atagcgcctc tctttgtcga ctctcctcct    840

gtcattgaag acaatgatct gaaattgcat aagtttgaag tgaagactgg tgattccatt    900
```

```
cacaagggtc taactccggg gtggaatgac ttggatgtca atcagcacgt aagcaacgtg    960

aagtacattg ggtggattct cgagagtatg ccaacagaag ttttggagac ccaggagcta   1020

tgctctctcg cccttgaata taggcgggaa tgcggaaggg acagtgtgct agagtccgtg   1080

acagctatgg atcccacaaa agttggaggc cggtctcagt accagcacct tctgcgactt   1140

gaggatggga ctgatatcgt gaagtgcaga actgagtggc ggccgaagaa tccaggagct   1200

aatggggcaa tatcaacggg aaagacttca aatggaaact cggtctctta g            1251
```

<210> SEQ ID NO 90
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea avigera var. pulcherrima (Ca) FATB1 coding DNA sequence codon optimized for Prototheca moriformis

<400> SEQUENCE: 90

```
atggtggccg ccgccgcctc ctccgccttc ttctccgtgc ccgtgcccgg cacctccccc     60

aagcccggca agttccgcat ctggccctcc tccctgtccc cctccttcaa gcccaagccc    120

atccccaacg gcggcctgca ggtgaaggcc aactcccgcg cccaccccaa ggccaacggc    180

tccgccgtgt ccctgaagtc cggctccctg aacacccagg aggacacctc ctcctccccc    240

cccccccgca ccttcctgca ccagctgccc gactggtccc gcctgctgac cgccatcacc    300

accgtgttcg tgaagtccaa gcgccccgac atgcacgacc gcaagtccaa gcgccccgac    360

atgctgatgg actccttcgg cctggagtcc atcgtgcagg agggcctgga gttccgccag    420

tccttctcca tccgctccta cgagatcggc accgaccgca ccgcctccat cgagaccctg    480

atgaactacc tgcaggagac ctccctgaac cactgcaagt ccaccggcat cctgctggac    540

ggcttcggcc gcacccccga gatgtgcaag cgcgacctga tctgggtggt gaccaagatg    600

aagatcaagg tgaaccgcta ccccgcctgg ggcgacaccg tggagatcaa cacctggttc    660

tcccgcctgg gcaagatcgg caagggccgc gactggctga tctccgactg caacaccggc    720

gagatcctga tccgcgccac ctccgcctac gccaccatga accagaagac ccgccgcctg    780

tccaagctgc cctacgaggt gcaccaggag atcgcccccc tgttcgtgga ctcccccccc    840

gtgatcgagg acaacgacct gaagctgcac aagttcgagg tgaagaccgg cgactccatc    900

cacaagggcc tgacccccgg ctggaacgac ctggacgtga accagcacgt gtccaacgtg    960

aagtacatcg gctggatcct ggagtccatg cccaccgagg tgctggagac ccaggagctg   1020

tgctccctgg ccctggagta ccgccgcgag tgcggccgcg actccgtgct ggagtccgtg   1080

accgccatgg accccaccaa ggtgggcggc cgctcccagt accagcacct gctgcgcctg   1140

gaggacggca ccgacatcgt gaagtgccgc accgagtggc gccccaagaa ccccggcgcc   1200

aacggcgcca tctccaccgg caagacctcc aacggcaact ccgtgtcc                1248
```

<210> SEQ ID NO 91
<211> LENGTH: 417
<212> TYPE: PRT
<213> ORGANISM: Cuphea paucipetala
<220> FEATURE:
<223> OTHER INFORMATION: Cuphea paucipetala (Cpau) FATB1 amino acid sequence

<400> SEQUENCE: 91

-continued

```
Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Ile Lys Pro Met Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Arg Asp Arg Lys Ser Lys Arg Pro Asp Met Leu Val Asp Ser Val Gly
        115                 120                 125

Leu Lys Ser Val Val Leu Asp Gly Leu Val Ser Arg Gln Ile Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser His Ser
    210                 215                 220

Gly Lys Ile Gly Met Ala Ser Asp Trp Leu Ile Thr Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Glu Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Pro Ser Asn Gly Asn Ser Val
                405                 410                 415

Ser
```

<210> SEQ ID NO 92
<211> LENGTH: 1254
<212> TYPE: DNA
<213> ORGANISM: Cuphea paucipetala
<220> FEATURE:
<223> OTHER INFORMATION: Cuphea paucipetala (Cpau) FATB1 coding DNA
sequence

<400> SEQUENCE: 92
atggtggctg ctgcagcaag ttctgcattc ttccctgttc cagcccccgg aacctcccct 60
aaacccggga agtccggcaa ctggccatca agcttgagcc cttccatcaa gcccatgtca 120
atccccaatg gcggatttca ggttaaggca aatgccagtg cccatcctaa ggctaacggt 180
tctgcagtaa atctaaagtc tggcagcctc aacactcagg aggacacttc gtcgtcccct 240
cctcctcggg ctttccttaa ccagttgcct gattggagta tgcttctgac tgcaatcacg 300
accgtcttcg tggcggcaga gaagcagtgg actatgcgtg atcggaaatc taagaggcct 360
gacatgctcg tggactcggt tgggttgaag agtgttgttc tggatgggct cgtgtccaga 420
cagatttttt cgattaggtc ttatgaaata ggcgctgatc gaactgcctc tatagagacg 480
ctgatgaacc acttgcagga aacatctatc aatcattgta agagtttggg tcttctcaat 540
gacggctttg gtcgtactcc tgggatgtgt aaaaatgacc tcatttgggt gcttacaaaa 600
atgcagatca tggtgaatcg ctacccaact tggggcgata ctgttgagat caatacctgg 660
ttctcccatt cggggaaaat tggtatggct agcgattggc taataactga ttgcaacaca 720
ggagaaattc ttataagagc aacgagcgtg tgggccatga tgaatcaaaa gacgagaaga 780
ttctcaagac ttccatacga ggttcgccag gagttaacgc ctcattatgt ggactctcct 840
catgtcattg aagataatga tcggaaattg cataagtttg atgtgaagac tggtgattcc 900
attcgtaagg gtctaactcc gaggtggaat gacttggatg tcaatcagca cgtaagcaac 960
gtgaagtaca ttgggtggat tctcgagagt atgccaatag aagttttgga gacccaggag 1020
ctatgctctc tcaccgttga atataggcgg gaatgcggaa tggacagtgt gctggagtcc 1080
gtgactgcta tggatccctc agaagatgaa ggccggtctc agtacaagca ccttctgcgg 1140
cttgaggatg ggactgacat cgtgaagggc agaactgagt ggcgaccgaa gaatgcagga 1200
actaacgggg cgatatcaac agcaaagcct tcaaatggaa actcggtctc ttag 1254

<210> SEQ ID NO 93
<211> LENGTH: 1254
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea paucipetala (Cpau) FATB1 coding DNA
sequence codon optimized for Prototheca moriformis

<400> SEQUENCE: 93
atggtggccg ccgccgcctc ctccgccttc ttccccgtgc ccgcccccgg cacctccccc 60
aagcccggca agtccggcaa ctggccctcc tccctgtccc cctccatcaa gcccatgtcc 120
atccccaacg gcggcttcca ggtgaaggcc aacgcctccg cccaccccaa ggccaacggc 180
tccgccgtga acctgaagtc cggctccctg aacacccagg aggacacctc ctcctccccc 240 ccccccgcg ccttcctgaa ccagctgccc gactggtcca tgctgctgac cgccatcacc 300
accgtgttcg tggccgccga gaagcagtgg accatgcgcg accgcaagtc caagcgcccc 360

```
gacatgctgg tggactccgt gggcctgaag tccgtggtgc tggacggcct ggtgtcccgc    420

cagatcttct ccatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccact ccggcaagat cggcatggcc tccgactggc tgatcaccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccactacgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgcca tggacccctc cgaggacgag ggccgctccc agtacaagca cctgctgcgc   1140

ctggaggacg gcaccgacat cgtgaagggc cgcaccgagt ggcgccccaa gaacgccggc   1200

accaacggcg ccatctccac cgccaagccc tccaacggca actccgtgtc ctga         1254
```

<210> SEQ ID NO 94
<211> LENGTH: 417
<212> TYPE: PRT
<213> ORGANISM: Cuphea procumbens
<220> FEATURE:
<223> OTHER INFORMATION: Cuphea procumbens (Cproc) FATB1 amino acid sequence

<400> SEQUENCE: 94

```
Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
```

```
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Ala Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asp Gly Gly Arg Ser Gln Tyr Asn His Leu Leu Arg Leu Glu Asp Gly
    370                 375                 380

Thr Asp Val Val Lys Gly Arg Thr Glu Trp Arg Pro Lys Asn Ala Glu
385                 390                 395                 400

Thr Asn Gly Ala Ile Ser Pro Gly Asn Thr Ser Asn Gly Asn Ser Ile
                405                 410                 415

Ser


<210> SEQ ID NO 95
<211> LENGTH: 1254
<212> TYPE: DNA
<213> ORGANISM: Cuphea procumbens
<220> FEATURE:
<223> OTHER INFORMATION: Cuphea procumbens (Cproc) FATB1 coding DNA
      sequence

<400> SEQUENCE: 95

atggtggctg ctgcagcaag ttctgcattc ttccctgctc cagccccggg atcctcacct      60

aaacccggga agtccggtaa ttggccatcg agcttgagcc cttccttcaa gtccaagtca     120

atcccctatg gccgatttca ggttaaggca aatgccagtg cccatcctaa ggctaacggt     180

tctgcagtaa atctaaagtc tggcagcctc aacactcagg aggacacttc gtcgtcccct     240

cctcctcggg ctttccttaa ccagttgcct gattggagta tgcttctgtc tgcaatcacg     300

actgtattcg tggcggcaga gaagcagtgg actatgcttg atcggaaatc taagaggcct     360

gacatgcttg tggactcggt tgggttgaag aatattgttc gggatgggct cgtgtccaga     420

cagagttttt tgattagatc ttatgaaata ggcgctgatc gaacagcttc tatagagaca     480

ctgatgaacc acttgcagga aacatctatc aatcattgta agagtttggg tcttctcaat     540

gacggctttg gtcgtactcc tgggatgtgt aaaaacgacc tcatttgggt gcttactaaa     600

atgcagatca tggtgaatcg ctacccagct tggggcgata ctgttgagat caatacctgg     660

ttctcccagt cggggaaaat cggtatgggt agcgattggc taataagtga ttgcaacaca     720

ggagaaattc ttataagagc aacgagcgtg tgggccatga tgaatcaaaa aacgagaaga     780
```

```
ttctcaagac ttccatacga ggttcgccag gagttaacgc ctcattttgt ggactctcct     840

catgtcattg aagacaatga tcggaaattg cataagttcg atgtgaagac tggtgattct     900

attcgcaagg gtctaactcc gaggtggaat gacttggatg tcaatcagca cgtgagcaac     960

gtgaagtaca ttgggtggat tctcgagagt atgccaatag aagttttgga ggcccaggaa    1020

ctatgctctc tcaccgttga atataggcgg gaatgcggaa tggacagtgt gctggagtcc    1080

gtgactgctg tagatccctc agaagatgga ggccggtctc agtacaatca ccttctgcgg    1140

cttgaggatg ggactgatgt cgtgaagggc agaactgagt ggcgaccgaa gaatgcagaa    1200

actaacgggg cgatatcacc aggaaacact tcaaatggaa actcgatctc ctag          1254
```

<210> SEQ ID NO 96
<211> LENGTH: 1254
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea procumbens (Cproc) FATB1 coding DNA sequence codon optimized for Prototheca moriformis

<400> SEQUENCE: 96

```
atggtggccg ccgccgcctc ctccgccttc ttccccgccc ccgcccccgg ctcctccccc      60

aagcccggca agtccggcaa ctggccctcc tccctgtccc cctccttcaa gtccaagtcc     120

atcccctacg gccgcttcca ggtgaaggcc aacgcctccg cccaccccaa ggccaacggc     180

tccgccgtga acctgaagtc cggctccctg aacacccagg aggacacctc ctcctccccc     240

ccccccgcg ccttcctgaa ccagctgccc gactggtcca tgctgctgtc cgccatcacc     300

accgtgttcg tggccgccga gaagcagtgg accatgctgg accgcaagtc caagcgcccc     360

gacatgctgg tggactccgt gggcctgaag aacatcgtgc gcgacggcct ggtgtcccgc     420

cagtccttcc tgatccgctc ctacgagatc ggcgccgacc gcaccgcctc catcgagacc     480

ctgatgaacc acctgcagga gacctccatc aaccactgca agtccctggg cctgctgaac     540

gacggcttcg gccgcacccc cggcatgtgc aagaacgacc tgatctgggt gctgaccaag     600

atgcagatca tggtgaaccg ctaccccgcc tggggcgaca ccgtggagat caacacctgg     660

ttctcccagt ccggcaagat cggcatgggc tccgactggc tgatctccga ctgcaacacc     720

ggcgagatcc tgatccgcgc cacctccgtg tgggccatga tgaaccagaa gacccgccgc     780

ttctcccgcc tgccctacga ggtgcgccag gagctgaccc cccacttcgt ggactccccc     840

cacgtgatcg aggacaacga ccgcaagctg cacaagttcg acgtgaagac cggcgactcc     900

atccgcaagg gcctgacccc ccgctggaac gacctggacg tgaaccagca cgtgtccaac     960

gtgaagtaca tcggctggat cctggagtcc atgcccatcg aggtgctgga ggcccaggag    1020

ctgtgctccc tgaccgtgga gtaccgccgc gagtgcggca tggactccgt gctggagtcc    1080

gtgaccgccg tggacccctc cgaggacggc ggccgctccc agtacaacca cctgctgcgc    1140

ctggaggacg gcaccgacgt ggtgaagggc cgcaccgagt ggcgccccaa gaacgccgag    1200

accaacggcg ccatctcccc cggcaacacc tccaacggca actccatctc ctga          1254
```

<210> SEQ ID NO 97
<211> LENGTH: 415
<212> TYPE: PRT
<213> ORGANISM: Cuphea procumbens
<220> FEATURE:

<223> OTHER INFORMATION: Cuphea procumbens (Cproc) FATB2 amino acid
      sequence

<400> SEQUENCE: 97

```
Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Gln Glu Cys
            340                 345                 350

Gly Arg Glu Ser Val Leu Glu Ser Leu Thr Ala Val Asp Pro Ser Gly
        355                 360                 365

Lys Gly Phe Gly Ser Gln Phe Gln His Leu Leu Arg Leu Glu Asp Gly
    370                 375                 380

Gly Glu Ile Val Lys Gly Arg Thr Glu Trp Arg Pro Lys Thr Ala Gly
385                 390                 395                 400
```

Ile Asn Gly Ala Ile Ala Ser Gly Glu Thr Ser Pro Gly Asp Phe
405 410 415

<210> SEQ ID NO 98
<211> LENGTH: 1248
<212> TYPE: DNA
<213> ORGANISM: Cuphea procumbens
<220> FEATURE:
<223> OTHER INFORMATION: Cuphea procumbens (Cproc) FATB2 coding DNA sequence

<400> SEQUENCE: 98
atggtggctg ctgcagcaag ttctgcattc ttccctgctc cagccccggg atcctcacct 60
aaacccggga agtccggtaa ttggccatcg agcttgagcc cttccttcaa gtccaagtca 120
atcccctatg gccgatttca ggttaaggca aatgccagtg cccatcctaa ggctaacggt 180
tctgcagtaa atctaaagtc tggcagcctc aacactcagg aggacacttc gtcgtcccct 240
cctcctcggg ctttccttaa ccagttgcct gattggagta tgcttctgtc tgcaatcacg 300
actgtattcg tggcggcaga gaagcagtgg actatgcttg atcggaaatc taagaggcct 360
gacatgcttg tggactcggt tgggttgaag aatattgttc gggatgggct cgtgtccaga 420
cagagttttt tgattagatc ttatgaaata ggcgctgatc gaacagcttc tatagagaca 480
ctgatgaacc acttgcagga aacatctatc aatcattgta agagtttggg tcttctcaat 540
gacggctttg gtcgtactcc tgggatgtgt aaaaacgacc tcatttgggt gcttactaaa 600
atgcagatca tggtgaatcg ctacccagct tggggcgata ctgttgagat caatacctgg 660
ttctcccagt cggggaaaat cggtatgggt agcgattggc taataagtga ttgcaacaca 720
ggagaaattc ttataagagc aacgagcgtg tgggccatga tgaatcaaaa aacgagaaga 780
ttctcaagac ttccatacga ggttcgccag gagttaacgc ctcattttgt ggactctcct 840
catgtcattg aagacaatga tcggaaattg cataagttcg atgtgaagac tggtgattct 900
attcgcaagg gtctaactcc gaggtggaat gacttggatg tcaatcagca cgtcaacaac 960
gtgaagtaca tcgggtggat tcttgagagt actccaccag aagttctgga gacccaggag 1020
ttatgttccc ttaccctgga atacaggcag gaatgcggaa gggagagcgt gctggagtcc 1080
ctcactgctg tggacccctc tggaaagggc tttgggtccc agttccaaca ccttctgagg 1140
cttgaggatg gaggtgagat cgtgaagggg agaactgagt ggcgacccaa gactgcaggt 1200
atcaatgggg cgatagcatc cggggagacc tcacctggag acttttag 1248

<210> SEQ ID NO 99
<211> LENGTH: 1248
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cuphea procumbens (Cproc) FATB2 coding DNA sequence codon optimized for Prototheca moriformis

<400> SEQUENCE: 99
atggtggccg ccgccgcctc ctccgccttc ttccccgccc ccgcccccgg ctcctccccc 60
aagcccggca agtccggcaa ctggccctcc tccctgtccc cctccttcaa gtccaagtcc 120
atcccctacg gccgcttcca ggtgaaggcc aacgcctccg cccaccccaa ggccaacggc 180
tccgccgtga acctgaagtc cggctccctg aacacccagg aggacacctc ctcctccccc 240

-continued

```
ccccccccgcg ccttcctgaa ccagctgccc gactggtcca tgctgctgtc cgccatcacc    300

accgtgttcg tggccgccga gaagcagtgg accatgctgg accgcaagtc caagcgcccc    360

gacatgctgg tggactccgt gggcctgaag aacatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccgcc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgaacaac    960

gtgaagtaca tcggctggat cctggagtcc acccccccg aggtgctgga gacccaggag   1020

ctgtgctccc tgaccctgga gtaccgccag gagtgcggcc gcgagtccgt gctggagtcc   1080

ctgaccgccg tggacccctc cggcaagggc ttcggctccc agttccagca cctgctgcgc   1140

ctggaggacg gcggcgagat cgtgaagggc cgcaccgagt ggcgccccaa gaccgccggc   1200

atcaacggcg ccatcgcctc cggcgagacc tcccccggcg acttctga               1248
```

```
<210> SEQ ID NO 100
<211> LENGTH: 410
<212> TYPE: PRT
<213> ORGANISM: Cuphea procumbens
<220> FEATURE:
<223> OTHER INFORMATION: Cuphea procumbens (Cproc) FATB3 amino acid
      sequence

<400> SEQUENCE: 100

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
```

```
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Gly Tyr Gly Ser Gln Phe Gln His Leu Leu Arg Leu Glu Asp
    370                 375                 380

Gly Gly Glu Ile Val Lys Gly Arg Thr Glu Trp Arg Pro Lys Asn Ala
385                 390                 395                 400

Gly Ile Asn Gly Val Leu Pro Thr Gly Glu
                405                 410


<210> SEQ ID NO 101
<211> LENGTH: 1233
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cuphea procumbens (Cproc) FATB3 coding DNA
      sequence

<400> SEQUENCE: 101

atggtggctg ctgcagcaag ttctgcattc ttccctgctc cagccccggg atcctcacct     60

aaacccggga agtccggtaa ttggccatcg agcttgagcc cttccttcaa gtccaagtca    120

atcccctatg gccgatttca ggttaaggca aatgccagtg cccatcctaa ggctaacggt    180

tctgcagtaa atctaaagtc tggcagcctc aacactcagg aggacacttc gtcgtcccct    240

cctcctcggg ctttccttaa ccagttgcct gattggagta tgcttctgtc tgcaatcacg    300

actgtattcg tggcggcaga gaagcagtgg actatgcttg atcggaaatc taagaggcct    360

gacatgcttg tggactcggt tgggttgaag aatattgttc gggatgggct cgtgtccaga    420

cagagttttt tgattagatc ttatgaaata ggcgctgatc gaacagcttc tatagagaca    480

ctgatgaacc acttgcagga aacatctatc aatcattgta agagtttggg tcttctcaat    540

gacggctttg gtcgtactcc tgggatgtgt aaaaacgacc tcatttgggt gcttactaaa    600

atgcagatca tggtgaatcg ctacccagct tggggcgata ctgttgagat caatacctgg    660
```

```
ttctcccagt cggggaaaat cggtatgggt agcgattggc taataagtga ttgcaacaca    720

ggagaaattc ttataagagc aacgagcgtg tgggccatga tgaatcaaaa aacgagaaga    780

ttctcaagac ttccatacga ggttcgccag gagttaacgc ctcattttgt ggactctcct    840

catgtcattg aagacaatga tcggaaattg cataagttcg atgtgaagac tggtgattct    900

attcgcaagg gtctaactcc gaggtggaat gacttggatg tcaatcagca cgtcaacaac    960

gtgaagtaca tcgggtggat tcttgagagt actccaccag aagttctgga gacccaggag   1020

ttatgttccc ttaccctgga atacaggcgg gaatgtggaa gggagagcgt gctggagtcc   1080

ctcactgctg tggacccctc tggagagggg ggctatggat cccagtttca gcaccttctg   1140

cggcttgagg atggaggtga gatcgtgaag gggagaactg agtggcgacc caagaatgct   1200

ggaatcaatg gggtgttacc aaccggggag tag                                1233
```

<210> SEQ ID NO 102
<211> LENGTH: 1233
<212> TYPE: DNA
<213> ORGANISM: Cuphea procumbens
<220> FEATURE:
<223> OTHER INFORMATION: Cuphea procumbens (Cproc) FATB3 coding DNA sequence codon optimized for Prototheca moriformis

<400> SEQUENCE: 102

```
atggtggccg ccgccgcctc ctccgccttc ttccccgccc ccgcccccgg ctcctccccc     60

aagcccggca agtccggcaa ctggccctcc tccctgtccc cctccttcaa gtccaagtcc    120

atcccctacg gccgcttcca ggtgaaggcc aacgcctccg cccaccccaa ggccaacggc    180

tccgccgtga acctgaagtc cggctccctg aacacccagg aggacacctc ctcctccccc    240

cccccccgcg ccttcctgaa ccagctgccc gactggtcca tgctgctgtc cgccatcacc    300

accgtgttcg tggccgccga gaagcagtgg accatgctgg accgcaagtc caagcgcccc    360

gacatgctgg tggactccgt gggcctgaag aacatcgtgc gcgacggcct ggtgtcccgc    420

cagtccttcc tgatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccgcc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780

ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgaacaac    960

gtgaagtaca tcggctggat cctggagtcc acccccccccg aggtgctgga gacccaggag   1020

ctgtgctccc tgaccctgga gtaccgccgc gagtgcggcc gcgagtccgt gctggagtcc   1080

ctgaccgccg tggacccctc cggcgagggc ggctacggct cccagttcca gcacctgctg   1140

cgcctggagg acggcggcga gatcgtgaag ggccgcaccg agtggcgccc caagaacgcc   1200

ggcatcaacg gcgtgctgcc caccggcgag tga                                1233
```

<210> SEQ ID NO 103
<211> LENGTH: 395
<212> TYPE: PRT
<213> ORGANISM: Cuphea ignea
<220> FEATURE:
<223> OTHER INFORMATION: Cuphea ignea (Cignea) FATB1 amino acid sequence

<400> SEQUENCE: 103

```
Pro Gly Thr Ser Arg Lys Thr Gly Lys Phe Gly Asn Trp Pro Ser Ser
1               5                   10                  15

Leu Ser Pro Ser Phe Lys Pro Lys Ser Ile Pro Asn Gly Gly Phe Gln
            20                  25                  30

Val Lys Ala Asn Ala Arg Ala His Pro Lys Ala Asn Gly Ser Ala Val
        35                  40                  45

Ser Leu Lys Ser Val Ser Leu Asn Thr Gln Glu Asp Thr Ser Leu Ser
    50                  55                  60

Pro Pro Pro Arg Ala Phe Leu Asn Gln Leu Pro Asp Trp Arg Met Leu
65                  70                  75                  80

Arg Thr Ala Leu Thr Thr Val Phe Val Ala Ala Glu Lys Gln Trp Thr
                85                  90                  95

Met Leu Asp Arg Lys Ser Lys Arg Pro Asp Met Leu Val Asp Ser Phe
            100                 105                 110

Gly Leu Glu Ser Ile Val Gln Glu Gly Leu Val Phe Arg Gln Ser Phe
        115                 120                 125

Ser Ile Arg Ser Tyr Glu Ile Gly Ile Asp Arg Thr Ala Ser Ile Glu
    130                 135                 140

Thr Leu Met Asn His Leu Gln Glu Thr Ser Leu Asn Gln Cys Lys Ser
145                 150                 155                 160

Ala Gly Ile Leu His Asp Gly Phe Gly Arg Thr Leu Glu Met Cys Lys
                165                 170                 175

Arg Asp Leu Ile Trp Val Val Thr Lys Met Gln Ile Lys Val Asn Arg
            180                 185                 190

Tyr Pro Ala Trp Gly Asp Thr Val Glu Ile Ser Thr Arg Phe Ser Arg
        195                 200                 205

Leu Gly Lys Ile Gly Met Gly Arg Asp Trp Leu Ile Cys Asp Cys Asn
    210                 215                 220

Thr Gly Glu Ile Leu Ile Arg Ala Thr Ser Ala Tyr Ala Met Met Asn
225                 230                 235                 240

Gln Lys Thr Arg Arg Leu Ser Lys Leu Pro Asn Glu Val Arg Gln Glu
                245                 250                 255

Ile Ala Pro Leu Phe Val Asp Ser Asp Pro Val Ile Glu Glu Asn Asp
            260                 265                 270

Met Lys Leu His Lys Phe Glu Val Lys Thr Gly Asp Ser Ile Cys Lys
        275                 280                 285

Gly Leu Thr Pro Arg Trp Ser Asp Leu Asp Val Asn Gln His Val Ser
    290                 295                 300

Asn Val Lys Tyr Ile Gly Trp Ile Leu Glu Ser Met Pro Thr Glu Val
305                 310                 315                 320

Leu Glu Thr Gln Glu Leu Cys Ser Leu Ala Leu Glu Tyr Arg Arg Glu
                325                 330                 335

Cys Gly Arg Asp Ser Val Leu Glu Ser Val Thr Ser Met Asp Pro Ser
            340                 345                 350

Lys Val Gly Gly Trp Ser Gln Tyr Gln His Leu Leu Arg Leu Glu Asp
        355                 360                 365

Gly Ala Asp Ile Val Lys Gly Arg Thr Glu Trp Arg Pro Lys Asn Ala
    370                 375                 380

Gly Ala Asn Gly Ala Ile Ser Thr Gly Lys Thr
385                 390                 395
```

<210> SEQ ID NO 104
<211> LENGTH: 1188
<212> TYPE: DNA
<213> ORGANISM: Cuphea ignea
<220> FEATURE:
<223> OTHER INFORMATION: Cuphea ignea (Cignea) FATB1 coding DNA sequence

<400> SEQUENCE: 104
ccgggaacct cacgtaaaac cgggaagttc ggcaattggc catcaagctt gagcccttcc 60
ttcaagccca agtcaatccc caatggcgga tttcaggtta aggctaatgc cagagcccat 120
cctaaggcta acggttctgc agtaagtcta aagtctgtca gcctcaacac tcaggaggac 180
acttcgttgt cccctcctcc tcgtgctttc cttaaccagt tgcctgattg gaggatgctt 240
cggactgcac tcacgaccgt ctttgtggcg gcagagaagc agtggactat gcttgatcgg 300
aaatctaaga ggcctgacat gctcgtggac tcgtttgggt tggagagtat tgttcaagaa 360
gggctcgtgt tcagacagag cttttcgatt aggtcttatg aaataggcat tgatcgaaca 420
gcctctatag agacgctgat gaaccacttg caggaaacat ctctcaatca atgtaagagt 480
gctggtattc tccatgacgg cttcggtcgt actcttgaga tgtgtaaaag ggacctcatt 540
tgggttgtta cgaaaatgca gatcaaggtg aatcgctatc cagcttgggg cgatactgtc 600
gagatcagta cccggttctc ccggttgggg aaaatcggta tgggtcgcga ttggctaata 660
tgtgattgca acacaggaga aattcttata agagcaacga gcgcgtatgc catgatgaat 720
caaaagacga gaagactctc aaaacttcca aacgaggttc gccaggagat agcgcctctt 780
tttgtggact ctgatcctgt cattgaagaa aatgatatga aattgcataa gtttgaagtg 840
aagactggtg attccatttg caagggtcta actccgaggt ggagtgactt ggatgtcaat 900
cagcacgtaa gcaacgtgaa gtacataggg tggattctcg agagtatgcc aacagaagtt 960
ttggagacac aggagctatg ctctctcgcc cttgaatata ggcgggaatg cggaagggac 1020
agtgtgctgg agtctgtgac ctctatggat ccctcaaaag ttggaggctg gtctcagtac 1080
cagcaccttc tgcgacttga ggatggggcg gatatcgtga agggcagaac tgagtggcgg 1140
ccgaagaatg caggagctaa cggggcgata tcaacaggaa agacttga 1188

<210> SEQ ID NO 105
<211> LENGTH: 1188
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Cuphea ignea (Cignea) FATB1 coding DNA sequence
codon optimized for Prototheca moriformis

<400> SEQUENCE: 105
cccggcacct cccgcaagac cggcaagttc ggcaactggc cctcctccct gtccccctcc 60
ttcaagccca agtccatccc caacggcggc ttccaggtga aggccaacgc ccgcgcccac 120
cccaaggcca acggctccgc cgtgtccctg aagtccgtgt ccctgaacac ccaggaggac 180
acctccctgt cccccccccc ccgcgccttc ctgaaccagc tgcccgactg gcgcatgctg 240
cgcaccgccc tgaccaccgt gttcgtggcc gccgagaagc agtggaccat gctggaccgc 300
aagtccaagc gccccgacat gctggtggac tccttcggcc tggagtccat cgtgcaggag 360
ggcctggtgt tccgccagtc cttctccatc cgctcctacg agatcggcat cgaccgcacc 420

```
gcctccatcg agaccctgat gaaccacctg caggagacct ccctgaacca gtgcaagtcc    480

gccggcatcc tgcacgacgg cttcggccgc accctggaga tgtgcaagcg cgacctgatc    540

tgggtggtga ccaagatgca gatcaaggtg aaccgctacc ccgcctgggg cgacaccgtg    600

gagatctcca cccgcttctc ccgcctgggc aagatcggca tgggccgcga ctggctgatc    660

tgcgactgca acaccggcga gatcctgatc cgcgccacct ccgcctacgc catgatgaac    720

cagaagaccc gccgcctgtc caagctgccc aacgaggtgc gccaggagat cgcccccctg    780

ttcgtggact ccgaccccgt gatcgaggag aacgacatga agctgcacaa gttcgaggtg    840

aagaccggcg actccatctg caagggcctg accccccgct ggtccgacct ggacgtgaac    900

cagcacgtgt ccaacgtgaa gtacatcggc tggatcctgg agtccatgcc caccgaggtg    960

ctggagaccc aggagctgtg ctccctggcc ctggagtacc gccgcgagtg cggccgcgac   1020

tccgtgctgg agtccgtgac ctccatggac ccctccaagg tgggcggctg gtcccagtac   1080

cagcacctgc tgcgcctgga ggacggcgcc gacatcgtga agggccgcac cgagtggcgc   1140

cccaagaacg ccggcgccaa cggcgccatc tccaccggca agacctga                1188
```

```
<210> SEQ ID NO 106
<211> LENGTH: 417
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: JcFatB1 consensus amino acid sequence

<400> SEQUENCE: 106

Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Phe Lys Pro Lys Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Arg Ile Val Gln Asp Gly Leu Val Ser Arg Gln Ser Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
```

```
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Gly Lys Thr Ser Asn Gly Asn Ser Val
                405                 410                 415

Ser


<210> SEQ ID NO 107
<211> LENGTH: 1254
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: JcFatB1 consensus DNA sequence codon optimized
      for Prototheca

<400> SEQUENCE: 107

atggtggccg ccgccgcctc ctccgccttc ttccccgtgc ccgcccccgg cacctccccc     60

aagcccggca agtccggcaa ctggccctcc tccctgtccc cctccttcaa gcccaagtcc    120

atccccaacg gcggcttcca ggtgaaggcc aacgcctccg cccaccccaa ggccaacggc    180

tccgccgtga acctgaagtc cggctccctg aacacccagg aggacacctc ctcctccccc    240

ccccccgcg ccttcctgaa ccagctgccc gactggtcca tgctgctgac cgccatcacc    300

accgtgttcg tggccgccga gaagcagtgg accatgctgg accgcaagtc caagcgcccc    360

gacatgctgg tggactccgt gggcctgaag cgcatcgtgc aggacggcct ggtgtcccgc    420

cagtccttct ccatccgctc ctacgagatc ggcgccgacc gcaccgcctc catcgagacc    480

ctgatgaacc acctgcagga gacctccatc aaccactgca agtccctggg cctgctgaac    540

gacggcttcg gccgcacccc cggcatgtgc aagaacgacc tgatctgggt gctgaccaag    600

atgcagatca tggtgaaccg ctaccccacc tggggcgaca ccgtggagat caacacctgg    660

ttctcccagt ccggcaagat cggcatgggc tccgactggc tgatctccga ctgcaacacc    720

ggcgagatcc tgatccgcgc cacctccgtg tgggccatga tgaaccagaa gacccgccgc    780
```

```
ttctcccgcc tgccctacga ggtgcgccag gagctgaccc cccacttcgt ggactccccc    840

cacgtgatcg aggacaacga ccgcaagctg cacaagttcg acgtgaagac cggcgactcc    900

atccgcaagg gcctgacccc ccgctggaac gacctggacg tgaaccagca cgtgtccaac    960

gtgaagtaca tcggctggat cctggagtcc atgcccatcg aggtgctgga gacccaggag   1020

ctgtgctccc tgaccgtgga gtaccgccgc gagtgcggca tggactccgt gctggagtcc   1080

gtgaccgcca tggacccctc cgagaacggc ggccgctccc agtacaagca cctgctgcgc   1140

ctggaggacg gcaccgacat cgtgaagggc cgcaccgagt ggcgccccaa gaacgccggc   1200

accaacggcg ccatctccac cggcaagacc tccaacggca actccgtgtc ctga         1254


<210> SEQ ID NO 108
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: JcFatB2 consensus amino acid sequence

<400> SEQUENCE: 108

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Ser Pro Leu Lys Pro Lys Ser Val Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
```

-continued

```
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Tyr Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Ala Ile Ala Ser Gly Glu Thr Ser Pro Gly Asp Ser Ser
                405                 410                 415


<210> SEQ ID NO 109
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: JcFatB2 consensus DNA sequence codon optimized
      for Prototheca

<400> SEQUENCE: 109

atggtggcca ccgccgcctc ctccgccttc ttccccgtgc cctcccccga cacctcctcc     60

cgcccccggca agctgggcaa cggctcctcc tccctgtccc ccctgaagcc caagtccgtg    120

gccaacggcg gcctgcaggt gaaggccaac gcctccgccc cccccaagat caacggctcc    180

tccgtgggcc tgaagtccgg ctccctgaag acccaggagg acacccccctc cgcccccccc    240

ccccgcacct tcatcaacca gctgcccgac tggtccatgc tgctggccgc catcaccacc    300

gtgttcctgg ccgccgagaa gcagtggatg atgctggact ggaagcccaa gcgccccgac    360

atgctggtgg accccttcgg cctgggccgc atcgtgcagg acggcctggt gttccgccag    420

aacttctcca tccgctccta cgagatcggc gccgaccgca ccgcctccat cgagaccgtg    480

atgaaccacc tgcaggagac cgccctgaac cacgtgaagt ccgccggcct gctgaacgac    540

ggcttcggcc gcacccccga gatgtacaag cgcgacctga tctgggtggt ggccaagatg    600

caggtgatgg tgaaccgcta ccccacctgg ggcgacaccg tggaggtgaa cacctgggtg    660

gccaagtccg gcaagaacgg catgcgccgc gactggctga tctccgactg caacaccggc    720

gagatcctga cccgcgcctc ctccgtgtgg gtgatgatga accagaagac ccgccgcctg    780

tccaagatcc ccgacgaggt gcgccacgag atcgagcccc acttcgtgga ctccgccccc    840

gtgatcgagg acgacgaccg caagctgccc aagctggacg agaagaccgc cgactccatc    900

cgcaagggcc tgacccccaa gtggaacgac ctggacgtga accagcacgt gaacaacgtg    960

aagtacatcg gctggatcct ggagtccacc ccccccgagg tgctggagac ccaggagctg   1020

tgctccctga ccctggagta ccgccgcgag tgcggccgcg agtccgtgct ggagtccctg   1080
```

-continued

```
accgccgtgg accccctccgg caagggctac ggctcccagt tccagcacct gctgcgcctg   1140

gaggacggcg gcgagatcgt gaagggccgc accgagtggc gccccaagac cgccggcatc   1200

aacggcgcca tcgcctccgg cgagacctcc cccggcgact cctcctga                 1248


<210> SEQ ID NO 110
<211> LENGTH: 419
<212> TYPE: PRT
<213> ORGANISM: Cuphea sp.
<220> FEATURE:
<223> OTHER INFORMATION: CuPSR23 FATB3 amino acid sequence

<400> SEQUENCE: 110

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Cys Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335
```

-continued

```
Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Val Ser


<210> SEQ ID NO 111
<211> LENGTH: 419
<212> TYPE: PRT
<213> ORGANISM: Cuphea sp.
<220> FEATURE:
<223> OTHER INFORMATION: CuPSR23 FATB3b amino acid sequence

<400> SEQUENCE: 111

Met Val Val Ala Ala Ala Thr Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Thr Phe Lys Pro Lys Ser Ile Pro Asn Ala Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Ser Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser Gln Ser
    210                 215                 220

Gly Lys Ile Gly Met Ala Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Gln
```

```
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asn Gly Gly Arg Ser Gln Tyr Lys His Leu Leu Arg Leu Glu Asp Gly
    370                 375                 380

Thr Asp Ile Val Lys Ser Arg Thr Glu Trp Arg Pro Lys Asn Ala Gly
385                 390                 395                 400

Thr Asn Gly Ala Ile Ser Thr Ser Thr Ala Lys Thr Ser Asn Gly Asn
                405                 410                 415

Ser Ala Ser


<210> SEQ ID NO 112
<211> LENGTH: 408
<212> TYPE: PRT
<213> ORGANISM: Cuphea wrightii
<220> FEATURE:
<223> OTHER INFORMATION: CwFATB3 amino acid sequence

<400> SEQUENCE: 112

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Pro Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125

Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220
```

Ser Gly Lys Ile Gly Met Gly Arg Asp Trp Leu Ile Ser Asp Cys Asn
225 230 235 240

Thr Gly Glu Ile Leu Val Arg Ala Thr Ser Ala Trp Ala Met Met Asn
245 250 255

Gln Lys Thr Arg Arg Phe Ser Lys Leu Pro Cys Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Cys Lys
290 295 300

Gly Leu Thr Pro Gly Trp Asn Asp Leu Asp Val Asn Gln His Val Ser
305 310 315 320

Asn Val Lys Tyr Ile Gly Trp Ile Leu Glu Ser Met Pro Thr Glu Val
325 330 335

Leu Glu Thr Gln Glu Leu Cys Ser Leu Thr Leu Glu Tyr Arg Arg Glu
340 345 350

Cys Gly Arg Glu Ser Val Val Glu Ser Val Thr Ser Met Asn Pro Ser
355 360 365

Lys Val Gly Asp Arg Ser Gln Tyr Gln His Leu Leu Arg Leu Glu Asp
370 375 380

Gly Ala Asp Ile Met Lys Gly Arg Thr Glu Trp Arg Pro Lys Asn Ala
385 390 395 400

Gly Thr Asn Arg Ala Ile Ser Thr
405

<210> SEQ ID NO 113
<211> LENGTH: 408
<212> TYPE: PRT
<213> ORGANISM: Cuphea wrightii
<220> FEATURE:
<223> OTHER INFORMATION: CwFATB3a amino acid sequence

<400> SEQUENCE: 113

Met Val Val Ala Ala Ala Ala Ser Ser Ala Phe Phe Pro Val Pro Ala
1 5 10 15

Pro Arg Thr Thr Pro Lys Pro Gly Lys Phe Gly Asn Trp Pro Ser Ser
20 25 30

Leu Ser Pro Pro Phe Lys Pro Lys Ser Asn Pro Asn Gly Arg Phe Gln
35 40 45

Val Lys Ala Asn Val Ser Pro His Pro Lys Ala Asn Gly Ser Ala Val
50 55 60

Ser Leu Lys Ser Gly Ser Leu Asn Thr Leu Glu Asp Pro Pro Ser Ser
65 70 75 80

Pro Pro Pro Arg Thr Phe Leu Asn Gln Leu Pro Asp Trp Ser Arg Leu
85 90 95

Arg Thr Ala Ile Thr Thr Val Phe Val Ala Ala Glu Lys Gln Phe Thr
100 105 110

Arg Leu Asp Arg Lys Ser Lys Arg Pro Asp Met Leu Val Asp Trp Phe
115 120 125

Gly Ser Glu Thr Ile Val Gln Asp Gly Leu Val Phe Arg Glu Arg Phe
130 135 140

Ser Ile Arg Ser Tyr Glu Ile Gly Ala Asp Arg Thr Ala Ser Ile Glu
145 150 155 160

Thr Leu Met Asn His Leu Gln Asp Thr Ser Leu Asn His Cys Lys Ser
165 170 175

```
Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Glu Ser Val Val Glu Ser Val Thr Ser Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Arg Ala Ile Ser Thr
                405


<210> SEQ ID NO 114
<211> LENGTH: 354
<212> TYPE: PRT
<213> ORGANISM: Cuphea wrightii
<220> FEATURE:
<223> OTHER INFORMATION: CwFATB3b amino acid sequence

<400> SEQUENCE: 114

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Leu Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Phe Thr
            100                 105                 110

Arg Leu Asp Arg Lys Ser Lys Arg Pro Asp Met Leu Val Asp Trp Phe
        115                 120                 125
```

```
Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Lys Phe Trp Arg Pro Arg
                325                 330                 335

Ser Tyr Ala Leu Ser Pro Leu Asn Ile Gly Gly Asn Val Glu Gly Lys
            340                 345                 350

Val Trp


<210> SEQ ID NO 115
<211> LENGTH: 354
<212> TYPE: PRT
<213> ORGANISM: Cuphea wrightii
<220> FEATURE:
<223> OTHER INFORMATION: CwFATB3c amino acid sequence

<400> SEQUENCE: 115

Met Val Val Ala Ala Ala Ala Ser Ser Ala Phe Phe Pro Val Pro Ala
1               5                   10                  15

Pro Arg Thr Thr Pro Lys Pro Gly Lys Phe Gly Asn Trp Pro Ser Ser
            20                  25                  30

Leu Ser Pro Pro Phe Lys Pro Lys Ser Asn Pro Asn Gly Arg Phe Gln
        35                  40                  45

Val Lys Ala Asn Val Ser Pro His Pro Lys Ala Asn Gly Ser Ala Val
    50                  55                  60

Ser Leu Lys Ser Gly Ser Leu Asn Thr Leu Glu Asp Leu Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Thr Glu Lys Gln Phe Thr
            100                 105                 110

Arg Leu Asp Arg Lys Ser Lys Arg Pro Asp Met Leu Val Asp Trp Phe
        115                 120                 125
```

```
Gly Ser Glu Thr Ile Val Gln Asp Gly Leu Val Phe Arg Glu Arg Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Ser Glu Met Cys Thr
            180                 185                 190

Arg Asp Leu Ile Trp Val Leu Thr Lys Met Gln Ile Val Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asp Trp Leu Ile Ser Asp Cys Asn
225                 230                 235                 240

Thr Gly Glu Ile Leu Val Arg Ala Thr Ser Ala Trp Ala Met Met Asn
                245                 250                 255

Gln Lys Thr Arg Arg Phe Ser Lys Leu Pro Cys Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Lys Phe Trp Arg Pro Arg
                325                 330                 335

Ser Tyr Ala Leu Ser Pro Leu Asn Ile Gly Gly Asn Val Glu Gly Lys
            340                 345                 350

Val Trp
```

<210> SEQ ID NO 116
<211> LENGTH: 416
<212> TYPE: PRT
<213> ORGANISM: Cuphea wrightii
<220> FEATURE:
<223> OTHER INFORMATION: CwFATB4a amino acid sequence

<400> SEQUENCE: 116

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
```

```
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415


<210> SEQ ID NO 117
<211> LENGTH: 416
<212> TYPE: PRT
<213> ORGANISM: Cuphea wrightii
<220> FEATURE:
<223> OTHER INFORMATION: CwFATB4a.1 amino acid sequence

<400> SEQUENCE: 117

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
```

-continued

```
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Trp Val Val Pro Ser Glu Glu Ser Ser Pro Gly Asp Phe Phe
                405                 410                 415
```

<210> SEQ ID NO 118
<211> LENGTH: 416
<212> TYPE: PRT
<213> ORGANISM: Cuphea wrightii
<220> FEATURE:
<223> OTHER INFORMATION: CwFATB4a.2 amino acid sequence:

<400> SEQUENCE: 118

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Asn Gly Pro Ser Ser
            20                  25                  30

Leu Ser Pro Leu Lys Pro Lys Ser Ile Pro Asn Gly Gly Leu Gln Val
```

```
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Ala Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415
```

<210> SEQ ID NO 119
<211> LENGTH: 416
<212> TYPE: PRT
<213> ORGANISM: Cuphea wrightii
<220> FEATURE:
<223> OTHER INFORMATION: CwFATB4a.3 amino acid sequence

<400> SEQUENCE: 119

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Gly Phe Lys Thr Gln Glu Asp Ser Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Asn Asp Gly Phe Gly Arg Thr Pro Glu Met Tyr Lys Arg
            180                 185                 190

Asp Leu Ile Trp Val Val Ala Lys Met Gln Val Met Val Asn Arg Tyr
        195                 200                 205

Pro Thr Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Ala
        355                 360                 365

Glu Gly Tyr Val Ser Arg Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Asp Phe Phe
                405                 410                 415
```

<210> SEQ ID NO 120
<211> LENGTH: 417
<212> TYPE: PRT
<213> ORGANISM: Cuphea wrightii
<220> FEATURE:
<223> OTHER INFORMATION: CwFATB4b amino acid sequence

<400> SEQUENCE: 120

```
Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Asn Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365
```

```
Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 121
<211> LENGTH: 417
<212> TYPE: PRT
<213> ORGANISM: Cuphea wrightii
<220> FEATURE:
<223> OTHER INFORMATION: CwFATB4b.1 amino acid sequence

<400> SEQUENCE: 121

Met Val Ala Thr Ala Ala Ser Ser Ala Phe Phe Pro Val Pro Ser Ala
1               5                   10                  15

Asp Thr Ser Ser Ser Arg Pro Gly Lys Leu Gly Ser Gly Pro Ser Ser
            20                  25                  30

Leu Ser Pro Leu Lys Pro Lys Ser Ile Pro Asn Gly Gly Leu Gln Val
        35                  40                  45

Lys Ala Asn Ala Ser Ala Pro Pro Lys Ile Asn Gly Ser Ser Val Gly
    50                  55                  60

Leu Lys Ser Gly Ser Phe Lys Thr Gln Glu Asp Ala Pro Ser Ala Pro
65                  70                  75                  80

Pro Pro Arg Thr Phe Ile Asn Gln Leu Pro Asp Trp Ser Met Leu Leu
                85                  90                  95

Ala Ala Ile Thr Thr Val Phe Leu Ala Ala Glu Lys Gln Trp Met Met
            100                 105                 110

Leu Asp Trp Lys Pro Lys Arg Pro Asp Met Leu Val Asp Pro Phe Gly
        115                 120                 125

Leu Gly Ser Ile Val Gln Asp Gly Leu Val Phe Arg Gln Asn Phe Ser
    130                 135                 140

Ile Arg Ser Tyr Glu Ile Gly Ala Asp Arg Thr Ala Ser Ile Glu Thr
145                 150                 155                 160

Val Met Asn His Leu Gln Glu Thr Ala Leu Asn His Val Lys Ile Ala
                165                 170                 175

Gly Leu Ser Ser Asp Gly Phe Gly Arg Thr Pro Ala Met Ser Lys Arg
            180                 185                 190

Asp Leu Ile Trp Val Val Ala Lys Met Gln Val Met Val Asn Arg Tyr
        195                 200                 205

Pro Ala Trp Gly Asp Thr Val Glu Val Asn Thr Trp Val Ala Lys Ser
    210                 215                 220

Gly Lys Asn Gly Met Arg Arg Asp Trp Leu Ile Ser Asp Cys Asn Thr
225                 230                 235                 240

Gly Glu Ile Leu Thr Arg Ala Ser Ser Val Trp Val Met Met Asn Gln
                245                 250                 255

Lys Thr Arg Arg Leu Ser Lys Ile Pro Asp Glu Val Arg Asn Glu Ile
            260                 265                 270

Glu Pro His Phe Val Asp Ser Ala Pro Val Val Glu Asp Asp Asp Arg
        275                 280                 285

Lys Leu Pro Lys Leu Asp Glu Asn Thr Ala Asp Ser Ile Arg Lys Gly
    290                 295                 300
```

-continued

```
Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Ala Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Asp Gly Ser Lys Phe Gln His Leu Leu Arg Leu Glu Asp Gly
    370                 375                 380

Gly Glu Ile Val Lys Ala Arg Thr Glu Trp Arg Pro Lys Asn Ala Gly
385                 390                 395                 400

Ile Asn Gly Val Val Pro Ser Glu Glu Ser Ser Pro Gly Gly Asp Phe
                405                 410                 415

Phe


<210> SEQ ID NO 122
<211> LENGTH: 413
<212> TYPE: PRT
<213> ORGANISM: Cuphea wrightii
<220> FEATURE:
<223> OTHER INFORMATION: CwFATB5 amino acid sequence

<400> SEQUENCE: 122

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
```

```
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410
```

<210> SEQ ID NO 123
<211> LENGTH: 413
<212> TYPE: PRT
<213> ORGANISM: Cuphea wrightii
<220> FEATURE:
<223> OTHER INFORMATION: CwFATB5a amino acid sequence

<400> SEQUENCE: 123

```
Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Phe Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Thr
            180                 185                 190

Trp Gly Asp Thr Ile Glu Val Asn Thr Trp Val Ser Glu Ser Gly Lys
```

```
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Arg Gly Trp Gln Pro Phe Arg Val Val Arg Leu Ile Phe
                405                 410


<210> SEQ ID NO 124
<211> LENGTH: 413
<212> TYPE: PRT
<213> ORGANISM: Cuphea wrightii
<220> FEATURE:
<223> OTHER INFORMATION: CwFATB5b amino acid sequence

<400> SEQUENCE: 124

Met Val Ala Ala Ala Ala Ser Ser Ala Phe Phe Ser Val Pro Thr Pro
1               5                   10                  15

Gly Thr Pro Pro Lys Pro Gly Lys Phe Gly Asn Trp Pro Ser Ser Leu
            20                  25                  30

Ser Val Pro Phe Lys Pro Asp Asn Gly Gly Phe His Val Lys Ala Asn
        35                  40                  45

Ala Ser Ala His Pro Lys Ala Asn Gly Ser Ala Val Asn Leu Lys Ser
    50                  55                  60

Gly Ser Leu Glu Thr Pro Pro Arg Ser Phe Ile Asn Gln Leu Pro Asp
65                  70                  75                  80

Leu Ser Val Leu Leu Ser Lys Ile Thr Thr Val Phe Gly Ala Ala Glu
                85                  90                  95

Lys Gln Trp Lys Arg Pro Gly Met Leu Val Glu Pro Phe Gly Val Asp
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
```

145 150 155 160

Leu Asn Asp Gly Phe Gly Arg Thr Pro Glu Met Cys Lys Arg Asp Leu
165 170 175

Ile Trp Val Val Thr Lys Ile Gln Val Glu Val Asn Arg Tyr Pro Thr
180 185 190

Trp Gly Asp Thr Ile Glu Val Asn Thr Trp Val Ser Glu Ser Gly Lys
195 200 205

Asn Gly Met Gly Arg Asp Trp Leu Ile Ser Asp Cys Arg Thr Gly Glu
210 215 220

Ile Leu Ile Arg Ala Thr Ser Val Trp Ala Met Met Asn Gln Asn Thr
225 230 235 240

Arg Arg Leu Ser Lys Phe Pro Tyr Glu Val Arg Gln Glu Ile Ala Pro
245 250 255

His Phe Val Asp Ser Ala Pro Val Ile Glu Asp Asp Gln Lys Leu Gln
260 265 270

Lys Leu Asp Val Lys Thr Gly Asp Ser Ile Arg Asp Gly Leu Thr Pro
275 280 285

Arg Trp Asn Asp Leu Asp Val Asn Gln His Val Asn Asn Val Lys Tyr
290 295 300

Ile Gly Trp Ile Leu Lys Ser Val Pro Ile Glu Val Phe Glu Thr Gln
305 310 315 320

Glu Leu Cys Gly Val Thr Leu Glu Tyr Arg Arg Glu Cys Gly Arg Asp
325 330 335

Ser Val Leu Glu Ser Val Thr Ala Met Asp Pro Ala Lys Glu Gly Asp
340 345 350

Arg Cys Val Tyr Gln His Leu Leu Trp Leu Glu Asp Gly Ala Asp Ile
355 360 365

Thr Ile Gly Arg Thr Glu Trp Arg Pro Lys Asn Ala Gly Ala Asn Gly
370 375 380

Ala Met Ser Ser Gly Lys Thr Ser Asn Gly Asn Cys Leu Ile Glu Gly
385 390 395 400

Arg Gly Trp Gln Pro Phe Arg Val Val Arg Leu Ile Phe
405 410

<210> SEQ ID NO 125
<211> LENGTH: 413
<212> TYPE: PRT
<213> ORGANISM: Cuphea wrightii
<220> FEATURE:
<223> OTHER INFORMATION: CwFATB5c amino acid sequence

<400> SEQUENCE: 125

Met Val Ala Ala Ala Ala Ser Ser Ala Phe Phe Ser Val Pro Thr Pro
1 5 10 15

Gly Thr Pro Pro Lys Pro Gly Lys Phe Gly Asn Trp Pro Ser Ser Leu
20 25 30

Ser Val Pro Phe Lys Pro Asp Asn Gly Gly Phe His Val Lys Ala Asn
35 40 45

Ala Ser Ala His Pro Lys Ala Asn Gly Ser Ala Val Asn Leu Lys Ser
50 55 60

Gly Ser Leu Glu Thr Pro Pro Arg Ser Phe Ile Asn Gln Leu Pro Asp
65 70 75 80

Leu Ser Val Leu Leu Ser Lys Ile Thr Thr Val Phe Gly Ala Ala Glu
85 90 95

Lys Gln Trp Lys Arg Pro Gly Met Leu Val Glu Pro Phe Gly Val Asp

```
            100                 105                 110

Arg Ile Phe Gln Asp Gly Val Phe Phe Arg Gln Ser Phe Ser Ile Arg
        115                 120                 125

Ser Tyr Glu Ile Gly Val Asp Arg Thr Ala Ser Ile Glu Thr Leu Met
    130                 135                 140

Asn Ile Phe Gln Glu Thr Ser Leu Asn His Cys Lys Ser Ile Gly Leu
145                 150                 155                 160

Leu Asn Asp Gly Phe Gly Arg Thr Pro Glu Met Cys Lys Arg Asp Leu
                165                 170                 175

Ile Trp Val Val Thr Lys Ile Gln Val Glu Val Asn Arg Tyr Pro Ile
            180                 185                 190

Trp Gly Asp Thr Ile Glu Val Asn Thr Trp Val Ser Glu Ser Gly Lys
        195                 200                 205

Asn Gly Met Gly Arg Asp Trp Leu Ile Ser Asp Cys Arg Thr Gly Glu
    210                 215                 220

Ile Leu Ile Arg Ala Thr Ser Val Trp Ala Met Met Asn Gln Asn Thr
225                 230                 235                 240

Arg Arg Leu Ser Lys Phe Pro Tyr Glu Val Arg Gln Glu Ile Ala Pro
                245                 250                 255

His Phe Val Asp Ser Ala Pro Val Ile Glu Asp Asp Gln Lys Leu Gln
            260                 265                 270

Lys Leu Asp Val Lys Thr Gly Asp Ser Ile Arg Asp Gly Leu Thr Pro
        275                 280                 285

Arg Trp Asn Asp Leu Asp Val Asn Gln His Val Asn Asn Val Lys Tyr
    290                 295                 300

Ile Gly Trp Ile Leu Lys Ser Val Pro Ile Glu Val Phe Glu Thr Gln
305                 310                 315                 320

Glu Leu Cys Gly Val Thr Leu Glu Tyr Arg Arg Glu Cys Gly Arg Asp
                325                 330                 335

Ser Val Leu Glu Ser Val Thr Ala Met Asp Pro Ala Lys Glu Gly Asp
            340                 345                 350

Arg Cys Val Tyr Gln His Leu Leu Arg Leu Glu Asp Gly Ala Asp Ile
        355                 360                 365

Thr Ile Gly Arg Thr Glu Trp Arg Pro Lys Asn Ala Gly Ala Asn Gly
    370                 375                 380

Ala Met Ser Ser Gly Lys Thr Ser Asn Gly Asn Cys Leu Ile Glu Gly
385                 390                 395                 400

Met Gly Trp Gln Pro Phe Arg Val Val Arg Leu Ile Phe
                405                 410


<210> SEQ ID NO 126
<211> LENGTH: 409
<212> TYPE: PRT
<213> ORGANISM: Cuphea wrightii
<220> FEATURE:
<223> OTHER INFORMATION: CwFATB5.1 amino acid sequence

<400> SEQUENCE: 126

Met Val Ala Ala Ala Ala Ser Ser Ala Phe Phe Ser Val Pro Thr Pro
1               5                   10                  15

Gly Thr Ser Pro Lys Pro Gly Lys Phe Arg Asn Trp Pro Ser Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
```

-continued

```
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350

Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380

Glu Trp Arg Pro Lys Asn Ala Gly Ala Asn Glu Ala Ile Ser Ser Gly
385                 390                 395                 400

Lys Thr Ser Asn Gly Asn Ser Ala Ser
                405


<210> SEQ ID NO 127
<211> LENGTH: 409
<212> TYPE: PRT
<213> ORGANISM: Cuphea wrightii
<220> FEATURE:
<223> OTHER INFORMATION: CwFATB5.1a amino acid sequence

<400> SEQUENCE: 127

Met Val Ala Ala Ala Ala Ser Ser Ala Phe Phe Ser Val Pro Thr Pro
```

-continued

```
1               5                   10                  15

Gly Thr Ser Pro Lys Pro Gly Lys Phe Arg Asn Trp Pro Leu Ser Leu
            20                  25                  30

Ser Val Pro Phe Lys Pro Glu Thr Asn His Asn Gly Gly Phe His Ile
        35                  40                  45

Lys Ala Asn Ala Ser Ala His Pro Lys Ala Asn Gly Ser Ala Leu Asn
    50                  55                  60

Leu Lys Ser Gly Ser Leu Glu Thr Gln Glu Asp Thr Ser Leu Ser Ser
65                  70                  75                  80

Pro Pro Arg Thr Phe Ile Lys Gln Leu Pro Asp Trp Ser Met Leu Leu
                85                  90                  95

Ser Lys Ile Thr Thr Val Phe Gly Ala Ala Glu Lys Gln Leu Lys Arg
            100                 105                 110

Pro Gly Met Leu Val Glu Pro Phe Gly Val Asp Arg Ile Phe Gln Asp
        115                 120                 125

Gly Val Phe Phe Arg Gln Ser Phe Ser Ile Arg Ser Tyr Glu Ile Gly
    130                 135                 140

Ala Asp Arg Thr Ala Ser Ile Glu Thr Leu Met Asn Ile Phe Gln Glu
145                 150                 155                 160

Thr Ser Leu Asn His Cys Lys Ser Ile Gly Leu Leu Asn Asp Gly Phe
                165                 170                 175

Gly Arg Thr Pro Glu Met Cys Lys Arg Asp Leu Ile Trp Val Val Thr
            180                 185                 190

Lys Ile Gln Val Glu Val Asn Arg Tyr Pro Thr Trp Gly Asp Thr Ile
        195                 200                 205

Glu Val Asn Thr Trp Val Ser Glu Ser Gly Lys Asn Gly Met Gly Arg
    210                 215                 220

Asp Trp Leu Ile Ser Asp Cys Arg Thr Gly Glu Ile Leu Ile Arg Ala
225                 230                 235                 240

Thr Ser Val Trp Ala Met Met Asn Gln Asn Thr Arg Arg Leu Ser Lys
                245                 250                 255

Phe Pro Tyr Glu Val Arg Gln Glu Ile Ala Pro His Phe Val Asp Ser
            260                 265                 270

Ala Pro Val Ile Glu Asp Asp Arg Lys Leu Tyr Lys Leu Asn Val Lys
        275                 280                 285

Thr Gly Asp Ser Ile Arg Asp Gly Leu Thr Pro Arg Trp Asn Asp Leu
    290                 295                 300

Asp Val Asn Gln His Val Asn Asn Val Lys Phe Ile Gly Trp Ile Leu
305                 310                 315                 320

Lys Ser Val Pro Thr Lys Val Phe Glu Thr Gln Glu Leu Cys Gly Val
                325                 330                 335

Thr Leu Glu Tyr Arg Arg Glu Cys Gly Lys Asp Ser Val Leu Glu Ser
            340                 345                 350

Val Thr Ala Met Asp Pro Ala Lys Glu Gly Asp Arg Ser Val Tyr Gln
        355                 360                 365

His Leu Leu Arg Leu Glu Asp Gly Ala Asp Ile Thr Ile Gly Arg Thr
    370                 375                 380

Glu Trp Arg Pro Lys Asn Ala Gly Ala Asn Glu Ala Ile Ser Ser Gly
385                 390                 395                 400

Lys Thr Ser Asn Gly Asn Ser Ala Ser
                405
```

<210> SEQ ID NO 128

<211> LENGTH: 357
<212> TYPE: PRT
<213> ORGANISM: Cinnamomum camphora
<220> FEATURE:
<223> OTHER INFORMATION: CcFATB2b amino acid sequence

<400> SEQUENCE: 128

```
Met Val Thr Thr Ser Leu Ala Ser Ala Tyr Phe Ser Met Lys Ala Val
1               5                   10                  15

Met Leu Ala Pro Asp Gly Arg Gly Ile Lys Pro Arg Ser Ser Gly Leu
            20                  25                  30

Gln Val Arg Ala Gly Asn Glu Arg Asn Ser Cys Lys Val Ile Asn Gly
        35                  40                  45

Thr Lys Val Lys Asp Thr Glu Gly Leu Lys Gly Cys Ser Thr Leu Gln
    50                  55                  60

Gly Gln Ser Met Leu Asp Asp His Phe Gly Leu His Gly Leu Val Phe
65                  70                  75                  80

Arg Arg Thr Phe Ala Ile Arg Cys Tyr Glu Val Gly Pro Asp Arg Ser
                85                  90                  95

Thr Ser Ile Met Ala Val Met Asn His Leu Gln Glu Ala Ala Arg Asn
            100                 105                 110

His Ala Glu Ser Leu Gly Leu Leu Gly Asp Gly Phe Gly Glu Thr Leu
        115                 120                 125

Glu Met Ser Lys Arg Asp Leu Ile Trp Val Val Arg Arg Thr His Val
    130                 135                 140

Ala Val Glu Arg Tyr Pro Ala Trp Gly Asp Thr Val Glu Val Glu Ala
145                 150                 155                 160

Trp Val Gly Ala Ser Gly Asn Thr Gly Met Arg Arg Asp Phe Leu Val
                165                 170                 175

Arg Asp Cys Lys Thr Gly His Ile Leu Thr Arg Cys Thr Ser Val Ser
            180                 185                 190

Val Met Met Asn Met Arg Thr Arg Arg Leu Ser Lys Ile Pro Gln Glu
        195                 200                 205

Val Arg Ala Glu Ile Asp Pro Leu Phe Ile Glu Lys Val Ala Val Lys
    210                 215                 220

Glu Gly Glu Ile Lys Lys Leu Gln Lys Leu Asn Asp Ser Thr Ala Asp
225                 230                 235                 240

Tyr Ile Gln Gly Gly Trp Thr Pro Arg Trp Asn Asp Leu Asp Val Asn
                245                 250                 255

Gln His Val Asn Asn Ile Ile Tyr Val Gly Trp Ile Phe Lys Ser Val
            260                 265                 270

Pro Asp Ser Ile Ser Glu Asn His His Leu Ser Ser Ile Thr Leu Glu
        275                 280                 285

Tyr Arg Arg Glu Cys Ile Arg Gly Asn Lys Leu Gln Ser Leu Thr Thr
    290                 295                 300

Val Cys Gly Gly Ser Ser Glu Ala Gly Ile Ile Cys Glu His Leu Leu
305                 310                 315                 320

Gln Leu Glu Asp Gly Ser Glu Val Leu Arg Ala Arg Thr Glu Trp Arg
                325                 330                 335

Pro Lys His Thr Asp Ser Phe Gln Gly Ile Ser Glu Arg Phe Pro Gln
            340                 345                 350

Gln Glu Pro His Lys
        355
```

<210> SEQ ID NO 129

```
<211> LENGTH: 419
<212> TYPE: PRT
<213> ORGANISM: Cinnamomum camphora
<220> FEATURE:
<223> OTHER INFORMATION: CcFATB3 amino acid sequence

<400> SEQUENCE: 129

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380
```

```
Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 130
<211> LENGTH: 419
<212> TYPE: PRT
<213> ORGANISM: Cinnamomum camphora
<220> FEATURE:
<223> OTHER INFORMATION: CcFATB3b amino acid sequence

<400> SEQUENCE: 130

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Leu Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320
```

-continued

```
Val Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 131
<211> LENGTH: 419
<212> TYPE: PRT
<213> ORGANISM: Cinnamomum camphora
<220> FEATURE:
<223> OTHER INFORMATION: CcFATB3c amino acid sequence

<400> SEQUENCE: 131

Met Val Ala Thr Ala Ala Ala Ser Ala Phe Phe Pro Val Gly Ala Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Leu Pro Glu Glu Val Arg Gly Glu Ile
```

```
            260                 265                 270

Gly Pro Tyr Phe Ile Glu Asp Val Ala Ile Ile Glu Glu Asp Asn Arg
        275                 280                 285

Lys Leu Gln Lys Leu Asn Glu Asn Thr Ala Asp Asn Val Arg Arg Gly
    290                 295                 300

Leu Thr Pro Arg Trp Ser Asp Leu Asp Val Asn Gln His Val Asn Asn
305                 310                 315                 320

Ala Lys Tyr Ile Gly Trp Ile Leu Glu Ser Ala Pro Gly Ser Ile Leu
                325                 330                 335

Glu Ser His Glu Leu Ser Cys Met Thr Leu Glu Tyr Arg Arg Glu Cys
            340                 345                 350

Gly Lys Asp Ser Val Leu Gln Ser Met Thr Ala Val Ser Gly Gly Gly
        355                 360                 365

Ser Ala Ala Gly Gly Ser Pro Glu Ser Ser Val Glu Cys Asp His Leu
    370                 375                 380

Leu Gln Leu Glu Ser Gly Pro Glu Val Val Arg Gly Arg Thr Glu Trp
385                 390                 395                 400

Arg Pro Lys Ser Ala Asn Asn Ser Arg Ser Ile Leu Glu Met Pro Ala
                405                 410                 415

Glu Ser Leu


<210> SEQ ID NO 132
<211> LENGTH: 410
<212> TYPE: PRT
<213> ORGANISM: Cuphea heterophylla
<220> FEATURE:
<223> OTHER INFORMATION: ChtFATB1a amino acid sequence

<400> SEQUENCE: 132

Met Val Ala Ala Ala Ala Ser Ser Ala Phe Phe Ser Val Pro Thr Pro
1               5                   10                  15

Gly Thr Ser Thr Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205
```

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410

<210> SEQ ID NO 133
<211> LENGTH: 410
<212> TYPE: PRT
<213> ORGANISM: Cuphea heterophylla
<220> FEATURE:
<223> OTHER INFORMATION: ChtFATB1a.1 amino acid sequence

<400> SEQUENCE: 133

Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg His Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

```
Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Gly Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Leu Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Leu Ser Thr
385                 390                 395                 400

Gly Lys Thr Ser Asn Gly Asn Ser Val Ser
                405                 410


<210> SEQ ID NO 134
<211> LENGTH: 410
<212> TYPE: PRT
<213> ORGANISM: Cuphea heterophylla
<220> FEATURE:
<223> OTHER INFORMATION: ChtFATB1a.2 amino acid sequence

<400> SEQUENCE: 134

Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Asn Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110
```

```
Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 135
<211> LENGTH: 410
<212> TYPE: PRT
<213> ORGANISM: Cuphea heterophylla
<220> FEATURE:
<223> OTHER INFORMATION: ChtFATB1a.3 amino acid sequence

<400> SEQUENCE: 135

```
Met Val Ala Ala Ala Ala Ser Ser Ala Phe Phe Ser Val Pro Thr Pro
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60
```

```
Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Gly Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Val Asn Gly Ala Ile Ser Thr
385                 390                 395                 400

Gly Lys Thr Ser Asn Glu Asn Ser Val Ser
                405                 410


<210> SEQ ID NO 136
<211> LENGTH: 410
<212> TYPE: PRT
<213> ORGANISM: Cuphea heterophylla
<220> FEATURE:
<223> OTHER INFORMATION: ChtFATB1a.4 amino acid sequence

<400> SEQUENCE: 136

Met Val Ala Ala Ala Ala Ser Ser Ala Phe Phe Ser Val Pro Thr Pro
1               5                   10                  15
```

```
Gly Thr Ser Pro Lys Pro Gly Asn Phe Gly Asn Trp Pro Ser Ser Leu
            20                  25                  30

Ser Val Pro Phe Lys Pro Glu Ser Asn His Asn Gly Gly Phe Arg Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Gly Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Ser Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380

Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410
```

<210> SEQ ID NO 137
<211> LENGTH: 410

```
<212> TYPE: PRT
<213> ORGANISM: Cuphea heterophylla
<220> FEATURE:
<223> OTHER INFORMATION: ChtFATB1b amino acid sequence

<400> SEQUENCE: 137

Met Val Ala Ala Ala Ala Ser Ser Ala Phe Phe Ser Val Pro Thr Ser
1               5                   10                  15

Gly Thr Ser Pro Lys Pro Gly Asn Phe Gly Asn Trp Pro Ser Ser Leu
            20                  25                  30

Ser Val Pro Phe Lys Pro Glu Ser Ser His Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Glu Thr Gln Glu Asp Thr Ser Ser Ser Ser
65                  70                  75                  80

Pro Pro Pro Arg Thr Phe Ile Lys Gln Leu Pro Asp Trp Ser Met Leu
                85                  90                  95

Leu Ser Lys Ile Thr Thr Val Phe Trp Ala Ala Glu Arg Gln Trp Lys
            100                 105                 110

Arg Pro Gly Met Leu Val Glu Pro Phe Gly Val Asp Arg Ile Phe Gln
        115                 120                 125

Asp Gly Val Phe Phe Arg Gln Ser Phe Ser Ile Arg Ser Tyr Glu Ile
    130                 135                 140

Gly Ala Asp Arg Thr Ala Ser Ile Glu Thr Leu Met Asn Ile Phe Gln
145                 150                 155                 160

Glu Thr Ser Leu Asn His Cys Lys Ser Ile Gly Leu Leu Asn Asp Gly
                165                 170                 175

Phe Gly Arg Thr Pro Glu Met Cys Lys Arg Asp Leu Ile Trp Val Val
            180                 185                 190

Thr Lys Ile Gln Val Glu Val Asn Arg Tyr Pro Thr Trp Gly Asp Thr
        195                 200                 205

Ile Glu Val Asn Thr Trp Val Ser Glu Ser Gly Lys Asn Gly Met Gly
    210                 215                 220

Arg Asp Trp Leu Ile Ser Asp Cys Arg Thr Gly Glu Ile Leu Ile Arg
225                 230                 235                 240

Ala Thr Ser Val Trp Ala Met Met Asn Arg Lys Thr Arg Arg Leu Ser
                245                 250                 255

Lys Phe Pro Tyr Glu Val Arg Gln Glu Ile Ala Pro His Phe Val Asp
            260                 265                 270

Ser Ala Pro Val Ile Glu Asp Asp Lys Lys Leu His Lys Leu Asp Val
        275                 280                 285

Lys Thr Gly Asp Phe Ile Arg Lys Gly Leu Thr Pro Arg Trp Asn Asp
    290                 295                 300

Phe Asp Val Asn Gln His Val Asn Asn Val Lys Tyr Ile Gly Trp Ile
305                 310                 315                 320

Leu Lys Ser Val Pro Ala Glu Val Phe Glu Thr Gln Glu Leu Cys Gly
                325                 330                 335

Val Thr Leu Glu Tyr Arg Arg Glu Cys Gly Arg Asp Ser Val Leu Glu
            340                 345                 350

Ser Val Thr Ala Met Asp Thr Ala Lys Glu Gly Asp Arg Ser Leu Tyr
        355                 360                 365

Gln His Leu Leu Arg Leu Glu Asp Gly Ala Asp Ile Thr Ile Gly Arg
    370                 375                 380
```

```
Thr Glu Trp Arg Pro Lys Asn Ala Gly Ala Asn Gly Ala Ile Ser Thr
385                 390                 395                 400

Gly Lys Thr Ser Asn Glu Asn Ser Val Ser
                405                 410


<210> SEQ ID NO 138
<211> LENGTH: 418
<212> TYPE: PRT
<213> ORGANISM: Cuphea heterophylla
<220> FEATURE:
<223> OTHER INFORMATION: ChtFATB2b amino acid sequence

<400> SEQUENCE: 138

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335
```

```
Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 139
<211> LENGTH: 418
<212> TYPE: PRT
<213> ORGANISM: Cuphea heterophylla
<220> FEATURE:
<223> OTHER INFORMATION: ChtFATB2a amino acid sequence

<400> SEQUENCE: 139

Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Ser Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Trp Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Leu Ile Glu Asp Asn Asp
```

```
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 140
<211> LENGTH: 418
<212> TYPE: PRT
<213> ORGANISM: Cuphea heterophylla
<220> FEATURE:
<223> OTHER INFORMATION: ChtFATB2c amino acid sequence

<400> SEQUENCE: 140

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Lys Glu Asp Thr Pro Ser Ser
65                  70                  75                  80

Pro Pro Pro Arg Thr Phe Leu Asn Gln Leu Pro Asp Trp Asn Arg Leu
                85                  90                  95

Arg Thr Ala Ile Thr Thr Val Phe Val Ala Ala Glu Lys Gln Leu Thr
            100                 105                 110

Met Leu Asp Arg Lys Ser Lys Lys Pro Asp Met His Val Asp Trp Phe
        115                 120                 125

Gly Leu Glu Ile Ile Val Gln Asp Gly Leu Val Phe Arg Glu Ser Phe
    130                 135                 140

Ser Ile Arg Ser Tyr Glu Ile Gly Ala Asp Arg Thr Ala Ser Ile Glu
145                 150                 155                 160

Thr Leu Met Asn His Leu Gln Asp Thr Ser Leu Asn His Cys Lys Ser
                165                 170                 175

Val Gly Leu Leu Asn Asp Gly Phe Gly Arg Thr Pro Glu Met Cys Lys
            180                 185                 190

Arg Asp Leu Ile Trp Val Leu Thr Lys Met Gln Ile Met Val Asn Arg
        195                 200                 205

Tyr Pro Thr Trp Gly Asp Thr Val Glu Ile Asn Ser Trp Phe Ser Gln
    210                 215                 220
```

```
Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 141
<211> LENGTH: 418
<212> TYPE: PRT
<213> ORGANISM: Cuphea heterophylla
<220> FEATURE:
<223> OTHER INFORMATION: ChtFATB2d amino acid sequence

<400> SEQUENCE: 141

Met Val Val Ala Ala Ala Ala Ser Ser Ala Phe Phe Pro Val Pro Ala
1               5                   10                  15

Pro Gly Thr Thr Ser Lys Pro Gly Lys Phe Gly Asn Trp Pro Ser Ser
            20                  25                  30

Leu Ser Pro Ser Phe Lys Pro Lys Ser Asn Pro Asn Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Leu Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Gly Ala Asp Arg Thr Ala Ser Ile Glu
145                 150                 155                 160
```

Thr Leu Met Asn His Leu Gln Asp Thr Ser Leu Asn His Cys Lys Ser
165 170 175

Val Gly Leu Leu Asn Asp Gly Phe Gly Arg Thr Pro Glu Met Cys Lys
180 185 190

Arg Asp Leu Ile Trp Val Leu Thr Lys Met Gln Ile Met Val Asn Arg
195 200 205

Tyr Pro Thr Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Asn Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Arg Lys
290 295 300

Gly Leu Thr Pro Gly Trp Asn Asp Leu Asp Val Asn Gln His Val Ser
305 310 315 320

Asn Val Lys Tyr Ile Gly Trp Ile Leu Glu Ser Met Pro Thr Glu Val
325 330 335

Leu Glu Thr Gln Glu Leu Cys Ser Leu Thr Leu Glu Tyr Arg Arg Glu
340 345 350

Cys Gly Arg Glu Ser Val Leu Glu Ser Val Thr Ala Met Asn Pro Ser
355 360 365

Lys Val Gly Asp Arg Ser Gln Tyr Gln His Leu Leu Arg Leu Glu Asp
370 375 380

Gly Ala Asp Ile Met Lys Gly Arg Thr Glu Trp Arg Pro Lys Asn Ala
385 390 395 400

Gly Thr Asn Gly Ala Ile Ser Thr Gly Lys Thr Ser Asn Gly Asn Ser
405 410 415

Val Ser

<210> SEQ ID NO 142
<211> LENGTH: 418
<212> TYPE: PRT
<213> ORGANISM: Cuphea heterophylla
<220> FEATURE:
<223> OTHER INFORMATION: ChtFATB2e amino acid sequence

<400> SEQUENCE: 142

Met Val Val Ala Ala Ala Ala Ser Ser Ala Phe Phe Pro Val Pro Ala
1 5 10 15

Ser Gly Thr Ser Pro Lys Pro Gly Lys Phe Gly Thr Trp Leu Ser Ser
20 25 30

Ser Ser Pro Ser Tyr Lys Pro Lys Ser Asn Pro Ser Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Asp Thr Ser Ser Ser
65 70 75 80

Pro Pro Pro Gln Thr Phe Leu Asn Gln Leu Pro Asp Trp Ser Arg Leu
85 90 95

Leu Thr Ala Ile Ser Thr Val Phe Val Ala Ala Glu Lys Gln Leu Thr

```
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Asn Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Arg Lys
    290                 295                 300

Gly Leu Thr Pro Gly Trp Asn Asp Leu Asp Val Asn Gln His Val Ser
305                 310                 315                 320

Asn Val Lys Tyr Ile Gly Trp Ile Leu Glu Ser Met Pro Thr Glu Val
                325                 330                 335

Leu Glu Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 143
<211> LENGTH: 418
<212> TYPE: PRT
<213> ORGANISM: Cuphea heterophylla
<220> FEATURE:
<223> OTHER INFORMATION: ChtFATB2f amino acid sequence

<400> SEQUENCE: 143

Met Val Val Ala Ala Ala Ala Ser Ser Ala Phe Phe Pro Val Pro Ala
1               5                   10                  15

Ser Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45
```

```
Val Lys Ala Asn Ala Ser Ala His Pro Lys Ala Asn Gly Ser Ala Val
    50                  55                  60

Ser Leu Lys Ser Gly Ser Leu Asn Thr Gln Glu Gly Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ser Tyr
    130                 135                 140

Ser Ile Arg Ser Tyr Glu Ile Ser Ala Asp Arg Thr Ala Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser
```

<210> SEQ ID NO 144
<211> LENGTH: 418
<212> TYPE: PRT
<213> ORGANISM: Cuphea heterophylla
<220> FEATURE:
<223> OTHER INFORMATION: ChtFATB2g amino acid sequence

<400> SEQUENCE: 144

Met Val Val Ala Ala Thr Ala Ser Ser Ala Phe Phe Pro Val Pro Val
1               5                   10                  15

Pro Gly Thr Ser Pro Lys Pro Gly Lys Phe Gly Thr Trp Leu Ser Ser
            20                  25                  30

Ser Ser Pro Ser Tyr Lys Pro Lys Ser Asn Pro Ser Gly Gly Phe Gln
        35                  40                  45

Val Lys Ala Asn Ala Ser Ala His Pro Lys Ala Asn Gly Ser Ala Val
    50                  55                  60

Ser Leu Lys Ser Gly Ser Leu Asn Thr Gln Glu Asp Thr Ser Ser Ser
65                  70                  75                  80

Pro Pro Pro Arg Thr Phe Leu Asn Gln Leu Pro Asp Trp Ser Arg Leu
                85                  90                  95

Leu Thr Ala Ile Ser Thr Val Phe Val Ala Ala Glu Lys Gln Leu Thr
            100                 105                 110

Met Leu Asp Arg Lys Ser Lys Arg Pro Asp Met Leu Val Asp Trp Phe
        115                 120                 125

Gly Leu Glu Ser Ile Val Gln Asp Gly Leu Val Phe Arg Glu Ile Tyr
    130                 135                 140

Ser Ile Arg Ser Tyr Glu Ile Ser Ala Asp Arg Thr Thr Ser Ile Glu
145                 150                 155                 160

Thr Val Met Asn Leu Leu Gln Glu Thr Ser Leu Asn His Cys Lys Ser
                165                 170                 175

Met Gly Ile Leu Asn Asp Gly Phe Gly Arg Thr Pro Glu Met Cys Lys
            180                 185                 190

Arg Asp Leu Ile Trp Val Leu Thr Lys Met Gln Ile Leu Val Asn Arg
        195                 200                 205

Tyr Pro Asn Trp Gly Asp Thr Val Glu Ile Asn Ser Trp Phe Ser Gln
    210                 215                 220

Ser Gly Lys Ile Gly Met Gly Arg Asn Trp Leu Ile Ser Asp Cys Asn
225                 230                 235                 240

Thr Gly Glu Ile Leu Ile Arg Ala Thr Ser Ile Trp Ala Met Met Asn
                245                 250                 255

Gln Lys Thr Arg Arg Phe Ser Lys Leu Pro Asn Glu Val Arg Gln Glu
            260                 265                 270

Ile Ala Pro His Phe Val Asp Ala Pro Pro Val Ile Glu Asp Asn Asp
        275                 280                 285

Arg Lys Leu His Lys Phe Asp Val Lys Thr Gly Asp Ser Ile Cys Lys
    290                 295                 300

Gly Leu Thr Pro Glu Trp Asn Asp Leu Asp Val Asn Gln His Val Ser
305                 310                 315                 320

Asn Val Lys Tyr Ile Gly Trp Ile Leu Glu Ser Met Pro Lys Glu Val
                325                 330                 335

Leu Asp Thr Gln Glu Leu Cys Ser Leu Thr Leu Glu Tyr Arg Arg Glu
            340                 345                 350

Cys Gly Arg Asp Ser Val Leu Glu Ser Val Thr Ala Met Asp Pro Ser
        355                 360                 365

Lys Val Gly Asp Arg Ser Gln Tyr Gln His Leu Leu Arg Leu Glu Asp
    370                 375                 380

Gly Thr Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Ala Asn Ser 405 410 415

Val Ser

<210> SEQ ID NO 145
<211> LENGTH: 418
<212> TYPE: PRT
<213> ORGANISM: Cuphea heterophylla
<220> FEATURE:
<223> OTHER INFORMATION: ChtFATB2h amino acid sequence

<400> SEQUENCE: 145

Met Val Val Ala Ala Ala Ala Ser Ser Ala Phe Phe Pro Val Pro Ala
1 5 10 15

Ser Gly Thr Ser Pro Lys Pro Gly Lys Phe Gly Thr Trp Leu Ser Ser
20 25 30

Ser Ser Pro Ser Tyr Lys Pro Lys Ser Asn Pro Ser Gly Gly Phe Gln
35 40 45

Val Lys Ala Asn Ala Ser Ala His Pro Lys Ala Asn Gly Ser Ala Val
50 55 60

Ser Leu Lys Ser Gly Ser Leu Asn Thr Gln Glu Gly Thr Ser Ser Ser
65 70 75 80

Pro Pro Pro Arg Thr Phe Leu Asn Gln Leu Pro Asp Trp Ser Arg Leu
85 90 95

Leu Thr Ala Ile Ser Thr Val Phe Val Ala Ala Glu Lys Gln Leu Thr
100 105 110

Met Leu Asp Arg Lys Ser Lys Arg Pro Asp Met Leu Val Asp Trp Phe
115 120 125

Gly Leu Glu Ser Ile Val Gln Asp Gly Leu Val Phe Arg Glu Ser Tyr
130 135 140

Ser Ile Arg Ser Tyr Glu Ile Ser Ala Asp Arg Thr Ala Ser Ile Glu
145 150 155 160

Thr Val Met Asn Leu Leu Gln Glu Thr Ser Leu Asn His Cys Lys Ser
165 170 175

Met Gly Ile Leu Asn Asp Gly Phe Gly Arg Thr Pro Glu Met Cys Lys
180 185 190

Arg Asp Leu Ile Trp Val Leu Thr Lys Met Gln Ile Leu Val Asn Arg
195 200 205

Tyr Pro Asn Trp Gly Asp Thr Val Glu Ile Asn Ser Trp Phe Ser Gln
210 215 220

Ser Gly Lys Ile Gly Met Gly Arg Asn Trp Leu Ile Ser Asp Cys Asn
225 230 235 240

Thr Gly Glu Ile Leu Ile Arg Ala Thr Ser Ile Trp Ala Met Met Asn
245 250 255

Gln Asn Thr Arg Arg Phe Ser Lys Leu Pro Asn Glu Val Arg Gln Glu
260 265 270

Ile Ala Pro His Phe Val Asp Ala Pro Pro Val Ile Glu Asp Asn Asp
275 280 285

Arg Lys Leu His Lys Phe Asp Val Lys Thr Gly Asp Ser Ile Arg Lys
290 295 300

Gly Leu Thr Pro Gly Trp Asn Asp Leu Asp Val Asn Gln His Val Ser
305 310 315 320

Asn Val Lys Tyr Ile Gly Trp Ile Leu Glu Ser Ile Pro Thr Glu Val
325 330 335

Leu Glu Thr Gln Glu Leu Cys Ser Leu Thr Leu Glu Tyr Arg Arg Glu
340 345 350

```
Cys Gly Arg Glu Ser Val Leu Glu Ser Val Thr Ala Met Asn Pro Ser
        355                 360                 365

Lys Val Gly Asp Arg Ser Gln Tyr Gln His Leu Leu Arg Leu Glu Asp
    370                 375                 380

Gly Ala Asp Ile Met Lys Gly Arg Thr Glu Trp Arg Pro Lys Asn Ala
385                 390                 395                 400

Gly Thr Asn Gly Ala Ile Ser Thr Gly Lys Thr Ser Asn Gly Asn Ser
                405                 410                 415

Val Ser


<210> SEQ ID NO 146
<211> LENGTH: 414
<212> TYPE: PRT
<213> ORGANISM: Cuphea heterophylla
<220> FEATURE:
<223> OTHER INFORMATION: ChtFATB3a amino acid sequence

<400> SEQUENCE: 146

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285
```

```
Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 147
<211> LENGTH: 414
<212> TYPE: PRT
<213> ORGANISM: Cuphea heterophylla
<220> FEATURE:
<223> OTHER INFORMATION: ChtFATB3b amino acid sequence

<400> SEQUENCE: 147

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Phe
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Ile Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240
```

```
Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 148
<211> LENGTH: 414
<212> TYPE: PRT
<213> ORGANISM: Cuphea heterophylla
<220> FEATURE:
<223> OTHER INFORMATION: ChtFATB3c amino acid sequence

<400> SEQUENCE: 148

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190
```

-continued

```
Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Glu Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Ala Ile Ala Phe Gly Glu Thr Ser Pro Gly Asp Ser
                405                 410


<210> SEQ ID NO 149
<211> LENGTH: 414
<212> TYPE: PRT
<213> ORGANISM: Cuphea heterophylla
<220> FEATURE:
<223> OTHER INFORMATION: ChtFATB3d amino acid sequence

<400> SEQUENCE: 149

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Cys Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140
```

```
Arg Ser Tyr Glu Ile Gly Ala Asp Arg Thr Ala Ser Ile Lys Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 150
<211> LENGTH: 414
<212> TYPE: PRT
<213> ORGANISM: Cuphea heterophylla
<220> FEATURE:
<223> OTHER INFORMATION: ChtFATB3e amino acid sequence

<400> SEQUENCE: 150

Met Val Ala Thr Ala Ala Ser Ser Ala Phe Phe Pro Val Pro Ser Pro
1               5                   10                  15

Asp Thr Ser Ser Arg Pro Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr His Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95
```

```
Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 151
<211> LENGTH: 414
<212> TYPE: PRT
<213> ORGANISM: Cuphea heterophylla
<220> FEATURE:
<223> OTHER INFORMATION: ChtFATB3f amino acid sequence

<400> SEQUENCE: 151

Met Val Ala Thr Ala Ala Ser Ser Ala Phe Phe Pro Val Pro Ser Pro
1               5                   10                  15

Asp Thr Ser Ser Arg Leu Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45
```

-continued

```
Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Pro Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Glu Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410


<210> SEQ ID NO 152
<211> LENGTH: 414
<212> TYPE: PRT
<213> ORGANISM: Cuphea heterophylla
<220> FEATURE:
<223> OTHER INFORMATION: ChtFATB3g amino acid sequence

<400> SEQUENCE: 152
```

-continued

```
Met Val Ala Thr Ala Ala Ser Ser Ala Phe Phe Pro Val Pro Ser Pro
1               5                   10                  15

Asp Thr Ser Ser Arg Ala Gly Lys Leu Gly Asn Gly Ser Ser Ser Leu
            20                  25                  30

Arg Pro Leu Lys Pro Lys Phe Val Ala Asn Ala Gly Leu Gln Val Lys
        35                  40                  45

Ala Asn Ala Ser Ala Pro Pro Lys Ile Asn Gly Ser Ser Val Ser Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Glu Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Lys Leu Ser Lys Ile Pro Asp Glu Val Arg His Glu Ile Glu
            260                 265                 270

Pro His Phe Val Asp Ser Ala Pro Val Ile Glu Asp Asp Asp Trp Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Phe Gly Pro Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Thr Ile Ala Ser Gly Glu Thr Ser Pro Gly Asn Ser
                405                 410
```

```
<210> SEQ ID NO 153
<211> LENGTH: 361
<212> TYPE: PRT
<213> ORGANISM: Cuphea hyssopifolia
<220> FEATURE:
<223> OTHER INFORMATION: ChsFATB1 amino acid sequence

<400> SEQUENCE: 153

Met Val Ala Thr Asn Ala Ala Ala Phe Ser Ala Tyr Thr Phe Phe Leu
1               5                   10                  15

Thr Ser Pro Thr His Gly Tyr Ser Ser Lys Arg Leu Ala Asp Thr Gln
            20                  25                  30

Asn Gly Tyr Pro Gly Thr Ser Leu Lys Ser Lys Ser Thr Pro Pro Pro
        35                  40                  45

Ala Ala Ala Ala Ala Arg Asn Gly Ala Leu Pro Leu Leu Ala Ser Ile
    50                  55                  60

Cys Lys Cys Pro Lys Lys Ala Asp Gly Ser Met Gln Leu Asp Ser Ser
65                  70                  75                  80

Leu Val Phe Gly Phe Gln Phe Tyr Ile Arg Ser Tyr Glu Val Gly Ala
                85                  90                  95

Asp Gln Thr Val Ser Ile Gln Thr Val Leu Asn Tyr Leu Gln Glu Ala
            100                 105                 110

Ala Ile Asn His Val Gln Ser Ala Gly Tyr Phe Gly Asp Ser Phe Gly
        115                 120                 125

Ala Thr Pro Glu Met Thr Lys Arg Asn Leu Ile Trp Val Ile Thr Lys
    130                 135                 140

Met Gln Val Leu Val Asp Arg Tyr Pro Ala Trp Gly Asp Val Val Gln
145                 150                 155                 160

Val Asp Thr Trp Thr Cys Ser Ser Gly Lys Asn Ser Met Gln Arg Asp
                165                 170                 175

Trp Phe Val Arg Asp Leu Lys Thr Gly Asp Ile Ile Thr Arg Ala Ser
            180                 185                 190

Ser Val Trp Val Leu Met Asn Arg Leu Thr Arg Lys Leu Ser Lys Ile
        195                 200                 205

Pro Glu Ala Val Leu Glu Glu Ala Lys Leu Phe Val Met Asn Thr Ala
    210                 215                 220

Pro Thr Val Asp Asp Asn Arg Lys Leu Pro Lys Leu Asp Gly Ser Ser
225                 230                 235                 240

Ala Asp Tyr Val Leu Ser Gly Leu Thr Pro Arg Trp Ser Asp Leu Asp
                245                 250                 255

Met Asn Gln His Val Asn Asn Val Lys Tyr Ile Ala Trp Ile Leu Glu
            260                 265                 270

Ser Val Pro Gln Ser Ile Pro Glu Thr His Lys Leu Ser Ala Ile Thr
        275                 280                 285

Val Glu Tyr Arg Arg Glu Cys Gly Lys Asn Ser Val Leu Gln Ser Leu
    290                 295                 300

Thr Asn Val Ser Gly Asp Gly Ile Thr Cys Gly Asn Ser Ile Ile Glu
305                 310                 315                 320

Cys His His Leu Leu Gln Leu Glu Thr Gly Pro Glu Ile Leu Leu Ala
                325                 330                 335

Arg Thr Glu Trp Ile Ser Lys Glu Pro Gly Phe Arg Gly Ala Pro Ile
            340                 345                 350

Gln Ala Glu Lys Val Tyr Asn Asn Lys
        355                 360
```

<210> SEQ ID NO 154
<211> LENGTH: 415
<212> TYPE: PRT
<213> ORGANISM: Cuphea hyssopifolia
<220> FEATURE:
<223> OTHER INFORMATION: ChsFATB2 amino acid sequence

<400> SEQUENCE: 154

```
Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
```

```
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 155
<211> LENGTH: 427
<212> TYPE: PRT
<213> ORGANISM: Cuphea hyssopifolia
<220> FEATURE:
<223> OTHER INFORMATION: ChsFatB2b amino acid sequence

<400> SEQUENCE: 155

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Lys Ser Gln Ile Met Leu Pro Leu
                245                 250                 255

His Tyr Cys Ser Val Trp Val Met Met Asn Gln Lys Thr Arg Arg Leu
            260                 265                 270

Ser Lys Ile Pro Asp Glu Val Arg His Glu Ile Glu Pro His Phe Val
        275                 280                 285

Asp Ser Ala Pro Val Ile Glu Asp Asp Asp Arg Lys Leu Pro Lys Leu
    290                 295                 300

Asp Glu Lys Thr Ala Asp Ser Ile Arg Lys Gly Leu Thr Pro Lys Trp
305                 310                 315                 320

Asn Asp Leu Asp Val Asn Gln His Val Asn Asn Val Lys Tyr Ile Gly
```

```
                325                 330                 335

Trp Ile Leu Glu Ser Thr Pro Pro Glu Val Leu Glu Thr Gln Glu Leu
            340                 345                 350

Cys Ser Leu Thr Leu Glu Tyr Arg Arg Glu Cys Gly Arg Glu Ser Val
        355                 360                 365

Leu Glu Ser Leu Thr Ala Val Asp Pro Ser Gly Lys Gly Ser Gly Ser
    370                 375                 380

Gln Phe Gln His Leu Leu Arg Leu Glu Asp Gly Gly Glu Ile Val Lys
385                 390                 395                 400

Gly Arg Thr Glu Trp Arg Pro Lys Thr Ala Gly Ile Asn Gly Pro Ile
                405                 410                 415

Ala Ser Gly Glu Thr Ser Pro Gly Asp Ser Ser
            420                 425


<210> SEQ ID NO 156
<211> LENGTH: 415
<212> TYPE: PRT
<213> ORGANISM: Cuphea hyssopifolia
<220> FEATURE:
<223> OTHER INFORMATION: ChsFatB2c amino acid sequence

<400> SEQUENCE: 156

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Leu Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
```

```
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Met Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 157
<211> LENGTH: 415
<212> TYPE: PRT
<213> ORGANISM: Cuphea hyssopifolia
<220> FEATURE:
<223> OTHER INFORMATION: ChsFatB2d amino acid sequence

<400> SEQUENCE: 157

Met Val Ala Thr Ala Ala Ser Ser Ala Phe Phe Pro Val Pro Ser Pro
1               5                   10                  15

Asp Ala Ser Ser Arg Pro Gly Lys Leu Gly Asn Gly Ser Ser Ser Leu
            20                  25                  30

Ser Pro Leu Lys Pro Lys Leu Met Ala Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Gly Ser Leu Lys Thr Gln Glu Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Val Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
```

```
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Arg Glu Ser Val Leu Glu Ser Leu Thr Ala Val Asp Pro Ser Gly Lys
        355                 360                 365

Gly Ser Gly Ser Gln Phe Gln His Leu Leu Arg Leu Glu Asp Gly Gly
    370                 375                 380

Glu Ile Val Lys Gly Arg Thr Glu Trp Arg Pro Lys Thr Ala Gly Ile
385                 390                 395                 400

Asn Gly Pro Ile Ala Ser Gly Glu Thr Ser Pro Gly Asp Ser Ser
                405                 410                 415


<210> SEQ ID NO 158
<211> LENGTH: 417
<212> TYPE: PRT
<213> ORGANISM: Cuphea hyssopifolia
<220> FEATURE:
<223> OTHER INFORMATION: Chs FATB3 amino acid sequence

<400> SEQUENCE: 158

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
```

```
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 159
<211> LENGTH: 417
<212> TYPE: PRT
<213> ORGANISM: Cuphea hyssopifolia
<220> FEATURE:
<223> OTHER INFORMATION: ChsFatb3b amino acid sequence

<400> SEQUENCE: 159

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110
```

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser

<210> SEQ ID NO 160
<211> LENGTH: 409
<212> TYPE: PRT
<213> ORGANISM: Cuphea hyssopifolia
<220> FEATURE:
<223> OTHER INFORMATION: ChsFatB3c amino acid sequence

<400> SEQUENCE: 160

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

-continued

```
Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

<210> SEQ ID NO 161
<211> LENGTH: 417
<212> TYPE: PRT
<213> ORGANISM: Cuphea hyssopifolia
<220> FEATURE:
<223> OTHER INFORMATION: ChsFATB3d amino acid sequence

<400> SEQUENCE: 161

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser
```

<210> SEQ ID NO 162
<211> LENGTH: 417
<212> TYPE: PRT
<213> ORGANISM: Cuphea hyssopifolia
<220> FEATURE:
<223> OTHER INFORMATION: ChsFATB3e amino acid sequence

<400> SEQUENCE: 162

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Val Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365
```

```
Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 163
<211> LENGTH: 417
<212> TYPE: PRT
<213> ORGANISM: Cuphea hyssopifolia
<220> FEATURE:
<223> OTHER INFORMATION: ChsFATB3f amino acid sequence

<400> SEQUENCE: 163

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300
```

```
Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 164
<211> LENGTH: 409
<212> TYPE: PRT
<213> ORGANISM: Cuphea hyssopifolia
<220> FEATURE:
<223> OTHER INFORMATION: ChsFATB3g amino acid sequence

<400> SEQUENCE: 164

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
```

```
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

<210> SEQ ID NO 165
<211> LENGTH: 409
<212> TYPE: PRT
<213> ORGANISM: Cuphea hyssopifolia
<220> FEATURE:
<223> OTHER INFORMATION: ChsFATB3h amino acid sequence

<400> SEQUENCE: 165

```
Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Ser Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Ala Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Ser Asp Met Leu Met Asp Pro Phe
        115                 120                 125

Gly Val Asp Arg Val Val Gln Asp Gly Val Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
```

```
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405


<210> SEQ ID NO 166
<211> LENGTH: 417
<212> TYPE: PRT
<213> ORGANISM: Cuphea hyssopifolia
<220> FEATURE:
<223> OTHER INFORMATION: ChsFATB3i amino acid sequence

<400> SEQUENCE: 166

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95

Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
```

-continued

```
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Val Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Cys His
225                 230                 235                 240

Thr Gly Glu Ile Leu Ile Arg Ala Thr Ser Met Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Arg Glu Cys
            340                 345                 350

Gly Gly Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Ala Asp Ile Ala Lys Gly Arg Thr Lys Trp Arg Pro Lys Asn Ala Gly
385                 390                 395                 400

Thr Asn Gly Ala Ile Ser Thr Gly Lys Thr Ser Asn Gly Asn Ser Ile
                405                 410                 415

Ser


<210> SEQ ID NO 167
<211> LENGTH: 409
<212> TYPE: PRT
<213> ORGANISM: Cuphea hyssopifolia
<220> FEATURE:
<223> OTHER INFORMATION: ChsFATB3j amino acid sequence

<400> SEQUENCE: 167

Met Val Ala Ala Glu Ala Ser Ser Ala Leu Phe Ser Val Arg Thr Pro
1               5                   10                  15

Gly Thr Ser Pro Lys Pro Gly Lys Phe Gly Asn Trp Pro Thr Ser Leu
            20                  25                  30

Ser Val Pro Phe Lys Ser Lys Ser Asn His Asn Gly Gly Phe Gln Val
        35                  40                  45

Lys Ala Asn Ala Ser Ala Arg Pro Lys Ala Asn Gly Ser Ala Val Ser
    50                  55                  60

Leu Lys Ser Gly Ser Leu Asp Thr Gln Glu Asp Thr Ser Ser Ser Ser
65                  70                  75                  80

Ser Pro Pro Arg Thr Phe Ile Asn Gln Leu Pro Asp Trp Ser Met Leu
                85                  90                  95
```

```
Leu Ser Ala Ile Thr Thr Val Phe Val Ala Ala Glu Lys Gln Trp Thr
            100                 105                 110

Met Leu Asp Arg Lys Ser Lys Arg Pro Asp Met Leu Met Asp Pro Phe
        115                 120                 125

Gly Val Asp Arg Val Val Gln Asp Gly Ala Val Phe Arg Gln Ser Phe
    130                 135                 140

Ser Ile Arg Ser Tyr Glu Ile Gly Ala Asp Arg Thr Ala Ser Ile Glu
145                 150                 155                 160

Thr Leu Met Asn Ile Phe Gln Glu Thr Ser Leu Asn His Cys Lys Ser
                165                 170                 175

Ile Gly Leu Leu Asn Asp Gly Phe Gly Arg Thr Pro Glu Met Cys Lys
            180                 185                 190

Arg Asp Leu Ile Trp Val Val Thr Lys Met His Ile Glu Val Asn Arg
        195                 200                 205

Tyr Pro Thr Trp Gly Asp Thr Ile Glu Val Asn Thr Trp Val Ser Glu
    210                 215                 220

Ser Gly Lys Thr Gly Met Gly Arg Asp Trp Leu Ile Ser Asp Phe His
225                 230                 235                 240

Thr Gly Asp Ile Leu Ile Arg Ala Thr Ser Val Cys Ala Met Met Asn
                245                 250                 255

Gln Lys Thr Arg Arg Phe Ser Lys Phe Pro Tyr Glu Val Arg Gln Glu
            260                 265                 270

Leu Ala Pro His Phe Val Asp Ser Ala Pro Val Ile Glu Asp Tyr Gln
        275                 280                 285

Lys Leu His Lys Leu Asp Val Lys Thr Gly Asp Ser Ile Cys Asn Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Val Pro Thr Glu Val Phe
                325                 330                 335

Glu Thr Gln Glu Leu Cys Gly Leu Thr Leu Glu Tyr Arg Gln Glu Cys
            340                 345                 350

Gly Arg Asp Ser Val Leu Glu Ser Val Thr Ala Met Asp Pro Ser Lys
        355                 360                 365

Glu Gly Asp Arg Ser Leu Tyr Gln His Leu Leu Arg Leu Glu Asp Gly
    370                 375                 380

Thr Asp Ile Ala Lys Gly Arg Thr Lys Trp Arg Pro Lys Asn Ala Gly
385                 390                 395                 400

Lys Thr Ser Asn Gly Asn Ser Ile Ser
                405
```

```
<210> SEQ ID NO 168
<211> LENGTH: 415
<212> TYPE: PRT
<213> ORGANISM: Cuphea calcarata
<220> FEATURE:
<223> OTHER INFORMATION: CcalcFATB1 (Cuphea calcarata FATB1)

<400> SEQUENCE: 168

Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Lys Ser Ile Pro Asn Gly Gly Phe Gln Val Lys
        35                  40                  45
```

```
Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Ser Phe Ser Ile Arg
    130                 135                 140

Ser Tyr Glu Ile Gly Thr Asp Arg Thr Ala Ser Ile Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val His Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile Gln Lys Gly Leu Ser
    290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365

Gly Arg Ser Gln Tyr Gln His Leu Leu Arg Leu Glu Asp Gly Thr Ala
    370                 375                 380

Ile Val Asn Gly Ile Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415
```

<210> SEQ ID NO 169
<211> LENGTH: 414
<212> TYPE: PRT
<213> ORGANISM: Cuphea hookeriana
<220> FEATURE:
<223> OTHER INFORMATION: ChookFATB4 (Cuphea hookeriana FATB4)

<400> SEQUENCE: 169

```
Met Val Ala Ala Ala Ala Thr Ser Ala Phe Phe Pro Val Pro Ala Pro
1               5                   10                  15

Gly Thr Ser Pro Asn Pro Arg Lys Phe Gly Ser Trp Pro Ser Ser Leu
            20                  25                  30

Ser Pro Ser Leu Pro Asn Ser Ile Pro Asn Gly Gly Phe Gln Val Lys
        35                  40                  45

Ala Asn Ala Ser Ala His Pro Lys Ala Asn Gly Ser Ala Val Ser Leu
    50                  55                  60

Lys Ser Gly Ser Leu Asn Thr Gln Glu Asn Thr Ser Ser Ser Pro Pro
65                  70                  75                  80

Pro Arg Thr Phe Leu His Gln Leu Pro Asp Trp Ser Arg Leu Leu Thr
                85                  90                  95

Ala Ile Thr Thr Val Phe Val Lys Ser Lys Arg Pro Asp Met His Asp
            100                 105                 110

Arg Lys Ser Lys Arg Pro Asp Met Leu Val Asp Leu Phe Gly Leu Glu
        115                 120                 125

Ser Ser Val Gln Asp Ala Leu Val Phe Arg Gln Arg Phe Ser Ile Arg
    130                 135                 140

Ser Tyr Glu Ile Gly Thr Asp Arg Thr Ala Ser Met Glu Thr Leu Met
145                 150                 155                 160

Asn His Leu Gln Glu Thr Ser Leu Asn His Cys Lys Ser Thr Gly Ile
                165                 170                 175

Leu Leu Asp Gly Phe Gly Arg Thr Leu Glu Met Cys Lys Arg Glu Leu
            180                 185                 190

Ile Trp Val Val Ile Lys Met Gln Ile Gln Val Asn Arg Tyr Pro Ala
        195                 200                 205

Trp Gly Asp Thr Val Glu Ile Asn Thr Arg Phe Ser Arg Leu Gly Lys
    210                 215                 220

Ile Gly Met Gly Arg Asp Trp Leu Ile Ser Asp Cys Asn Thr Gly Glu
225                 230                 235                 240

Ile Leu Ile Arg Ala Thr Ser Glu Tyr Ala Met Met Asn Gln Lys Thr
                245                 250                 255

Arg Arg Leu Ser Lys Leu Pro Tyr Glu Val Arg Gln Glu Ile Ala Pro
            260                 265                 270

Leu Phe Val Asp Ser Pro Pro Val Ile Glu Asp Asn Asp Leu Lys Val
        275                 280                 285

His Lys Phe Glu Val Lys Thr Gly Asp Ser Ile His Lys Gly Leu Thr
    290                 295                 300

Pro Gly Trp Asn Asp Leu Asp Val Asn Gln His Val Asn Asn Val Lys
305                 310                 315                 320

Tyr Ile Gly Trp Ile Leu Glu Ser Thr Pro Pro Glu Val Leu Glu Thr
                325                 330                 335

Gln Glu Leu Cys Ser Leu Thr Leu Glu Tyr Arg Arg Glu Cys Gly Arg
            340                 345                 350

Glu Ser Val Leu Glu Ser Leu Thr Ala Met Asp Pro Ser Gly Gly Gly
        355                 360                 365

Tyr Gly Ser Gln Phe Gln His Leu Leu Arg Leu Glu Asp Gly Gly Glu
    370                 375                 380

Ile Val Lys Gly Arg Thr Glu Trp Arg Pro Lys Asn Gly Val Ile Asn
385                 390                 395                 400

Gly Val Val Pro Thr Gly Glu Ser Ser Pro Gly Asp Tyr Ser
                405                 410
```

<210> SEQ ID NO 170
<211> LENGTH: 416
<212> TYPE: PRT
<213> ORGANISM: Cuphea avigera
<220> FEATURE:
<223> OTHER INFORMATION: CaFATB1 (Cuphea avigera var. pulcherrima FATB1)

<400> SEQUENCE: 170

```
Met Val Ala Ala Ala Ala Ser Ser Ala Phe Phe Ser Val Pro Val Pro
1               5                   10                  15

Gly Thr Ser Pro Lys Pro Gly Lys Phe Arg Ile Trp Pro Ser Ser Leu
            20                  25                  30

Ser Pro Ser Phe Lys Pro Lys Pro Ile Pro Asn Gly Gly Leu Gln Val
        35                  40                  45

Lys Ala Asn Ser Arg Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
            100                 105                 110

Asp Arg Lys Ser Lys Arg Pro Asp Met Leu Met Asp Ser Phe Gly Leu
        115                 120                 125

Glu Ser Ile Val Gln Glu Gly Leu Glu Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn Tyr Leu Gln Glu Thr Ser Leu Asn His Cys Lys Ser Thr Gly
                165                 170                 175

Ile Leu Leu Asp Gly Phe Gly Arg Thr Pro Glu Met Cys Lys Arg Asp
            180                 185                 190

Leu Ile Trp Val Val Thr Lys Met Lys Ile Lys Val Asn Arg Tyr Pro
        195                 200                 205

Ala Trp Gly Asp Thr Val Glu Ile Asn Thr Trp Phe Ser Arg Leu Gly
    210                 215                 220

Lys Ile Gly Lys Gly Arg Asp Trp Leu Ile Ser Asp Cys Asn Thr Gly
225                 230                 235                 240

Glu Ile Leu Ile Arg Ala Thr Ser Ala Tyr Ala Thr Met Asn Gln Lys
                245                 250                 255

Thr Arg Arg Leu Ser Lys Leu Pro Tyr Glu Val His Gln Glu Ile Ala
            260                 265                 270

Pro Leu Phe Val Asp Ser Pro Pro Val Ile Glu Asp Asn Asp Leu Lys
        275                 280                 285

Leu His Lys Phe Glu Val Lys Thr Gly Asp Ser Ile His Lys Gly Leu
    290                 295                 300

Thr Pro Gly Trp Asn Asp Leu Asp Val Asn Gln His Val Ser Asn Val
305                 310                 315                 320

Lys Tyr Ile Gly Trp Ile Leu Glu Ser Met Pro Thr Glu Val Leu Glu
                325                 330                 335

Thr Gln Glu Leu Cys Ser Leu Ala Leu Glu Tyr Arg Arg Glu Cys Gly
            340                 345                 350

Arg Asp Ser Val Leu Glu Ser Val Thr Ala Met Asp Pro Thr Lys Val
        355                 360                 365
```

```
Gly Gly Arg Ser Gln Tyr Gln His Leu Leu Arg Leu Glu Asp Gly Thr
    370                 375                 380

Asp Ile Val Lys Cys Arg Thr Glu Trp Arg Pro Lys Asn Pro Gly Ala
385                 390                 395                 400

Asn Gly Ala Ile Ser Thr Gly Lys Thr Ser Asn Gly Asn Ser Val Ser
                405                 410                 415


<210> SEQ ID NO 171
<211> LENGTH: 417
<212> TYPE: PRT
<213> ORGANISM: Cuphea paucipetala
<220> FEATURE:
<223> OTHER INFORMATION: CpauFATB1 (Cuphea paucipetala FATB1)

<400> SEQUENCE: 171

Met Val Ala Ala Ala Ala Ser Ser Ala Phe Phe Pro Val Pro Ala Pro
1               5                   10                  15

Gly Thr Ser Pro Lys Pro Gly Lys Ser Gly Asn Trp Pro Ser Ser Leu
            20                  25                  30

Ser Pro Ser Ile Lys Pro Met Ser Ile Pro Asn Gly Gly Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Arg Asp Arg Lys Ser Lys Arg Pro Asp Met Leu Val Asp Ser Val Gly
        115                 120                 125

Leu Lys Ser Val Val Leu Asp Gly Leu Val Ser Arg Gln Ile Phe Ser
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Thr Trp Gly Asp Thr Val Glu Ile Asn Thr Trp Phe Ser His Ser
    210                 215                 220

Gly Lys Ile Gly Met Ala Ser Asp Trp Leu Ile Thr Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Tyr Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320
```

```
Val Lys Tyr Ile Gly Trp Ile Leu Glu Ser Met Pro Ile Glu Val Leu
                325                 330                 335

Glu Thr Gln Glu Leu Cys Ser Leu Thr Val Glu Tyr Arg Arg Glu Cys
            340                 345                 350

Gly Met Asp Ser Val Leu Glu Ser Val Thr Ala Met Asp Pro Ser Glu
        355                 360                 365

Asp Glu Gly Arg Ser Gln Tyr Lys His Leu Leu Arg Leu Glu Asp Gly
    370                 375                 380

Thr Asp Ile Val Lys Gly Arg Thr Glu Trp Arg Pro Lys Asn Ala Gly
385                 390                 395                 400

Thr Asn Gly Ala Ile Ser Thr Ala Lys Pro Ser Asn Gly Asn Ser Val
                405                 410                 415

Ser


<210> SEQ ID NO 172
<211> LENGTH: 417
<212> TYPE: PRT
<213> ORGANISM: Cuphea procumbens
<220> FEATURE:
<223> OTHER INFORMATION: CprocFATB1 (Cuphea procumbens FATB1)

<400> SEQUENCE: 172

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
```

```
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Ser Asn
305                 310                 315                 320

Val Lys Tyr Ile Gly Trp Ile Leu Glu Ser Met Pro Ile Glu Val Leu
                325                 330                 335

Glu Ala Gln Glu Leu Cys Ser Leu Thr Val Glu Tyr Arg Arg Glu Cys
            340                 345                 350

Gly Met Asp Ser Val Leu Glu Ser Val Thr Ala Val Asp Pro Ser Glu
        355                 360                 365

Asp Gly Gly Arg Ser Gln Tyr Asn His Leu Leu Arg Leu Glu Asp Gly
    370                 375                 380

Thr Asp Val Val Lys Gly Arg Thr Glu Trp Arg Pro Lys Asn Ala Glu
385                 390                 395                 400

Thr Asn Gly Ala Ile Ser Pro Gly Asn Thr Ser Asn Gly Asn Ser Ile
                405                 410                 415

Ser


<210> SEQ ID NO 173
<211> LENGTH: 415
<212> TYPE: PRT
<213> ORGANISM: Cuphea procumbens
<220> FEATURE:
<223> OTHER INFORMATION: CprocFATB2 (Cuphea procumbens FATB2)

<400> SEQUENCE: 173

Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205
```

-continued

```
Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Gln Glu Cys
            340                 345                 350

Gly Arg Glu Ser Val Leu Glu Ser Leu Thr Ala Val Asp Pro Ser Gly
        355                 360                 365

Lys Gly Phe Gly Ser Gln Phe Gln His Leu Leu Arg Leu Glu Asp Gly
    370                 375                 380

Gly Glu Ile Val Lys Gly Arg Thr Glu Trp Arg Pro Lys Thr Ala Gly
385                 390                 395                 400

Ile Asn Gly Ala Ile Ala Ser Gly Glu Thr Ser Pro Gly Asp Phe
                405                 410                 415
```

```
<210> SEQ ID NO 174
<211> LENGTH: 410
<212> TYPE: PRT
<213> ORGANISM: Cuphea procumbens
<220> FEATURE:
<223> OTHER INFORMATION: CprocFATB3 (Cuphea procumbens FATB3)

<400> SEQUENCE: 174
```

```
Met Val Ala Ala Ala Ala Ser Ser Ala Phe Phe Pro Ala Pro Ala Pro
1               5                   10                  15

Gly Ser Ser Pro Lys Pro Gly Lys Ser Gly Asn Trp Pro Ser Ser Leu
            20                  25                  30

Ser Pro Ser Phe Lys Ser Lys Ser Ile Pro Tyr Gly Arg Phe Gln Val
        35                  40                  45

Lys Ala Asn Ala Ser Ala His Pro Lys Ala Asn Gly Ser Ala Val Asn
    50                  55                  60

Leu Lys Ser Gly Ser Leu Asn Thr Gln Glu Asp Thr Ser Ser Ser Pro
65                  70                  75                  80

Pro Pro Arg Ala Phe Leu Asn Gln Leu Pro Asp Trp Ser Met Leu Leu
                85                  90                  95

Ser Ala Ile Thr Thr Val Phe Val Ala Ala Glu Lys Gln Trp Thr Met
            100                 105                 110

Leu Asp Arg Lys Ser Lys Arg Pro Asp Met Leu Val Asp Ser Val Gly
        115                 120                 125

Leu Lys Asn Ile Val Arg Asp Gly Leu Val Ser Arg Gln Ser Phe Leu
    130                 135                 140

Ile Arg Ser Tyr Glu Ile Gly Ala Asp Arg Thr Ala Ser Ile Glu Thr
145                 150                 155                 160
```

```
Leu Met Asn His Leu Gln Glu Thr Ser Ile Asn His Cys Lys Ser Leu
                165                 170                 175

Gly Leu Leu Asn Asp Gly Phe Gly Arg Thr Pro Gly Met Cys Lys Asn
            180                 185                 190

Asp Leu Ile Trp Val Leu Thr Lys Met Gln Ile Met Val Asn Arg Tyr
        195                 200                 205

Pro Ala Trp Gly Asp Thr Val Glu Ile Asn Thr Trp Phe Ser Gln Ser
    210                 215                 220

Gly Lys Ile Gly Met Gly Ser Asp Trp Leu Ile Ser Asp Cys Asn Thr
225                 230                 235                 240

Gly Glu Ile Leu Ile Arg Ala Thr Ser Val Trp Ala Met Met Asn Gln
                245                 250                 255

Lys Thr Arg Arg Phe Ser Arg Leu Pro Tyr Glu Val Arg Gln Glu Leu
            260                 265                 270

Thr Pro His Phe Val Asp Ser Pro His Val Ile Glu Asp Asn Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Thr Pro Pro Glu Val Leu
                325                 330                 335

Glu Thr Gln Glu Leu Cys Ser Leu Thr Leu Glu Tyr Arg Arg Glu Cys
            340                 345                 350

Gly Arg Glu Ser Val Leu Glu Ser Leu Thr Ala Val Asp Pro Ser Gly
        355                 360                 365

Glu Gly Gly Tyr Gly Ser Gln Phe Gln His Leu Leu Arg Leu Glu Asp
    370                 375                 380

Gly Gly Glu Ile Val Lys Gly Arg Thr Glu Trp Arg Pro Lys Asn Ala
385                 390                 395                 400

Gly Ile Asn Gly Val Leu Pro Thr Gly Glu
                405                 410
```

<210> SEQ ID NO 175
<211> LENGTH: 395
<212> TYPE: PRT
<213> ORGANISM: Cuphea ignea
<220> FEATURE:
<223> OTHER INFORMATION: CigneaFATB1 (Cuphea ignea FATB1)

<400> SEQUENCE: 175

```
Pro Gly Thr Ser Arg Lys Thr Gly Lys Phe Gly Asn Trp Pro Ser Ser
1               5                   10                  15

Leu Ser Pro Ser Phe Lys Pro Lys Ser Ile Pro Asn Gly Gly Phe Gln
            20                  25                  30

Val Lys Ala Asn Ala Arg Ala His Pro Lys Ala Asn Gly Ser Ala Val
        35                  40                  45

Ser Leu Lys Ser Val Ser Leu Asn Thr Gln Glu Asp Thr Ser Leu Ser
    50                  55                  60

Pro Pro Pro Arg Ala Phe Leu Asn Gln Leu Pro Asp Trp Arg Met Leu
65                  70                  75                  80

Arg Thr Ala Leu Thr Thr Val Phe Val Ala Ala Glu Lys Gln Trp Thr
                85                  90                  95

Met Leu Asp Arg Lys Ser Lys Arg Pro Asp Met Leu Val Asp Ser Phe
            100                 105                 110
```

Gly Leu Glu Ser Ile Val Gln Glu Gly Leu Val Phe Arg Gln Ser Phe
115 120 125

Ser Ile Arg Ser Tyr Glu Ile Gly Ile Asp Arg Thr Ala Ser Ile Glu
130 135 140

Thr Leu Met Asn His Leu Gln Glu Thr Ser Leu Asn Gln Cys Lys Ser
145 150 155 160

Ala Gly Ile Leu His Asp Gly Phe Gly Arg Thr Leu Glu Met Cys Lys
165 170 175

Arg Asp Leu Ile Trp Val Val Thr Lys Met Gln Ile Lys Val Asn Arg
180 185 190

Tyr Pro Ala Trp Gly Asp Thr Val Glu Ile Ser Thr Arg Phe Ser Arg
195 200 205

Leu Gly Lys Ile Gly Met Gly Arg Asp Trp Leu Ile Cys Asp Cys Asn
210 215 220

Thr Gly Glu Ile Leu Ile Arg Ala Thr Ser Ala Tyr Ala Met Met Asn
225 230 235 240

Gln Lys Thr Arg Arg Leu Ser Lys Leu Pro Asn Glu Val Arg Gln Glu
245 250 255

Ile Ala Pro Leu Phe Val Asp Ser Asp Pro Val Ile Glu Glu Asn Asp
260 265 270

Met Lys Leu His Lys Phe Glu Val Lys Thr Gly Asp Ser Ile Cys Lys
275 280 285

Gly Leu Thr Pro Arg Trp Ser Asp Leu Asp Val Asn Gln His Val Ser
290 295 300

Asn Val Lys Tyr Ile Gly Trp Ile Leu Glu Ser Met Pro Thr Glu Val
305 310 315 320

Leu Glu Thr Gln Glu Leu Cys Ser Leu Ala Leu Glu Tyr Arg Arg Glu
325 330 335

Cys Gly Arg Asp Ser Val Leu Glu Ser Val Thr Ser Met Asp Pro Ser
340 345 350

Lys Val Gly Gly Trp Ser Gln Tyr Gln His Leu Leu Arg Leu Glu Asp
355 360 365

Gly Ala Asp Ile Val Lys Gly Arg Thr Glu Trp Arg Pro Lys Asn Ala
370 375 380

Gly Ala Asn Gly Ala Ile Ser Thr Gly Lys Thr
385 390 395

<210> SEQ ID NO 176
<211> LENGTH: 405
<212> TYPE: PRT
<213> ORGANISM: Cuphea calcarata
<220> FEATURE:
<223> OTHER INFORMATION: CcalcFATB1 (Cuphea calcarata FATB1)

<400> SEQUENCE: 176

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Ala Ala Ile Asn Ala Ser Ala His Pro Lys Ala Asn Gly
35 40 45

Ser Ala Val Ser Leu Lys Ser Gly Ser Leu Glu Thr Gln Glu Asp Asn
50 55 60

Ser Ser Ser Ser Arg Pro Pro Arg Thr Phe Ile Lys Gln Leu Pro Asp
65 70 75 80

Trp Ser Met Leu Leu Ser Ala Ile Thr Thr Val Phe Val Ala Ala Glu
85 90 95

Lys Gln Trp Thr Met Phe Asp Arg Lys Ser Lys Arg Ser Asp Met Leu
100 105 110

Val Asp Pro Phe Val Val Asp Arg Ile Val Gln Asp Gly Val Leu Phe
115 120 125

Arg Gln Ser Phe Ser Ile Arg Ser Tyr Glu Ile Gly Ala Asp Arg Thr
130 135 140

Ala Ser Ile Glu Thr Leu Met Asn Ile Phe Gln Glu Thr Ser Leu Asn
145 150 155 160

His Cys Lys Ser Met Gly Leu Leu Tyr Glu Gly Phe Gly Arg Thr Pro
165 170 175

Glu Met Cys Lys Arg Asp Leu Ile Trp Val Val Thr Lys Ile His Ile
180 185 190

Lys Val Asn Arg Tyr Pro Thr Trp Gly Asp Thr Ile Glu Val Thr Thr
195 200 205

Trp Val Ser Glu Ser Gly Lys Asn Gly Met Gly Arg Asp Trp Leu Ile
210 215 220

Ser Asp Cys His Thr Gly Glu Ile Leu Ile Arg Ala Thr Ser Val Trp
225 230 235 240

Ala Met Met Asn Gln Thr Thr Arg Arg Leu Ser Lys Phe Pro Tyr Glu
245 250 255

Leu Arg Gln Glu Ile Ala Pro His Phe Val Asp Ser Asp Pro Val Ile
260 265 270

Glu Asp Asn Arg Arg Leu Leu Asn Phe Asp Val Lys Thr Gly Asp Ser
275 280 285

Ile Arg Lys Gly Leu Thr Pro Arg Trp Asn Asp Leu Asp Val Asn Gln
290 295 300

His Val Asn Asn Val Lys Tyr Ile Gly Trp Ile Leu Glu Ser Val Pro
305 310 315 320

Thr Glu Val Phe Asp Thr Arg Glu Leu Cys Gly Leu Thr Leu Glu Tyr
325 330 335

Arg Gln Glu Cys Gly Arg Gly Ser Val Leu Glu Ser Val Thr Ala Met
340 345 350

Asp Pro Ser Lys Glu Gly Asp Arg Ser Leu Tyr Gln His Leu Leu Arg
355 360 365

Leu Glu Asp Gly Thr Asp Ile Val Lys Gly Arg Thr Glu Trp Arg Pro
370 375 380

Lys Asn Ala Gly Thr Asn Gly Pro Val Ser Thr Arg Lys Thr Thr Asn
385 390 395 400

Gly Ser Ser Val Ser
405

<210> SEQ ID NO 177
<211> LENGTH: 403
<212> TYPE: PRT
<213> ORGANISM: Cuphea hookeriana
<220> FEATURE:
<223> OTHER INFORMATION: ChookFATB4 (Cuphea hookeriana FATB4)

<400> SEQUENCE: 177

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

```
Pro Val Arg Ala Ala Ile Asn Ala Ser Ala His Pro Lys Ala Asn Gly
        35                  40                  45

Ser Ala Val Ser Leu Lys Ser Gly Ser Leu Asn Thr Gln Glu Asn Thr
    50                  55                  60

Ser Ser Ser Pro Pro Pro Arg Thr Phe Leu His Gln Leu Pro Asp Trp
65                  70                  75                  80

Ser Arg Leu Leu Thr Ala Ile Thr Thr Val Phe Val Lys Ser Lys Arg
                85                  90                  95

Pro Asp Met His Asp Arg Lys Ser Lys Arg Pro Asp Met Leu Val Asp
            100                 105                 110

Leu Phe Gly Leu Glu Ser Ser Val Gln Asp Ala Leu Val Phe Arg Gln
        115                 120                 125

Arg Phe Ser Ile Arg Ser Tyr Glu Ile Gly Thr Asp Arg Thr Ala Ser
    130                 135                 140

Met Glu Thr Leu Met Asn His Leu Gln Glu Thr Ser Leu Asn His Cys
145                 150                 155                 160

Lys Ser Thr Gly Ile Leu Leu Asp Gly Phe Gly Arg Thr Leu Glu Met
                165                 170                 175

Cys Lys Arg Glu Leu Ile Trp Val Val Ile Lys Met Gln Ile Gln Val
            180                 185                 190

Asn Arg Tyr Pro Ala Trp Gly Asp Thr Val Glu Ile Asn Thr Arg Phe
        195                 200                 205

Ser Arg Leu Gly Lys Ile Gly Met Gly Arg Asp Trp Leu Ile Ser Asp
    210                 215                 220

Cys Asn Thr Gly Glu Ile Leu Ile Arg Ala Thr Ser Glu Tyr Ala Met
225                 230                 235                 240

Met Asn Gln Lys Thr Arg Arg Leu Ser Lys Leu Pro Tyr Glu Val Arg
                245                 250                 255

Gln Glu Ile Ala Pro Leu Phe Val Asp Ser Pro Pro Val Ile Glu Asp
            260                 265                 270

Asn Asp Leu Lys Val His Lys Phe Glu Val Lys Thr Gly Asp Ser Ile
        275                 280                 285

His Lys Gly Leu Thr Pro Gly Trp Asn Asp Leu Asp Val Asn Gln His
    290                 295                 300

Val Asn Asn Val Lys Tyr Ile Gly Trp Ile Leu Glu Ser Thr Pro Pro
305                 310                 315                 320

Glu Val Leu Glu Thr Gln Glu Leu Cys Ser Leu Thr Leu Glu Tyr Arg
                325                 330                 335

Arg Glu Cys Gly Arg Glu Ser Val Leu Glu Ser Leu Thr Ala Met Asp
            340                 345                 350

Pro Ser Gly Gly Gly Tyr Gly Ser Gln Phe Gln His Leu Leu Arg Leu
        355                 360                 365

Glu Asp Gly Gly Glu Ile Val Lys Gly Arg Thr Glu Trp Arg Pro Lys
    370                 375                 380

Asn Gly Val Ile Asn Gly Val Val Pro Thr Gly Glu Ser Ser Pro Gly
385                 390                 395                 400

Asp Tyr Ser
```

<210> SEQ ID NO 178
<211> LENGTH: 404
<212> TYPE: PRT
<213> ORGANISM: Cuphea avigera
<220> FEATURE:
<223> OTHER INFORMATION: CaFATB1 (Cuphea avigera var. pulcherrima FATB1)

<400> SEQUENCE: 178

Met Ala Thr Ala Ser Thr Phe Ser Ala Phe Asn Ala Arg Cys Gly Asp
1 5 10 15

Leu Arg Arg Ser Ala Gly Ser Gly Pro Arg Arg Pro Ala Arg Pro Leu
20 25 30

Pro Val Arg Ala Ala Ile Asn Ser Arg Ala His Pro Lys Ala Asn Gly
35 40 45

Ser Ala Val Ser Leu Lys Ser Gly Ser Leu Asn Thr Gln Glu Asp Thr
50 55 60

Ser Ser Ser Pro Pro Pro Arg Thr Phe Leu His Gln Leu Pro Asp Trp
65 70 75 80

Ser Arg Leu Leu Thr Ala Ile Thr Thr Val Phe Val Lys Ser Lys Arg
85 90 95

Pro Asp Met His Asp Arg Lys Ser Lys Arg Pro Asp Met Leu Met Asp
100 105 110

Ser Phe Gly Leu Glu Ser Ile Val Gln Glu Gly Leu Glu Phe Arg Gln
115 120 125

Ser Phe Ser Ile Arg Ser Tyr Glu Ile Gly Thr Asp Arg Thr Ala Ser
130 135 140

Ile Glu Thr Leu Met Asn Tyr Leu Gln Glu Thr Ser Leu Asn His Cys
145 150 155 160

Lys Ser Thr Gly Ile Leu Leu Asp Gly Phe Gly Arg Thr Pro Glu Met
165 170 175

Cys Lys Arg Asp Leu Ile Trp Val Val Thr Lys Met Lys Ile Lys Val
180 185 190

Asn Arg Tyr Pro Ala Trp Gly Asp Thr Val Glu Ile Asn Thr Trp Phe
195 200 205

Ser Arg Leu Gly Lys Ile Gly Lys Gly Arg Asp Trp Leu Ile Ser Asp
210 215 220

Cys Asn Thr Gly Glu Ile Leu Ile Arg Ala Thr Ser Ala Tyr Ala Thr
225 230 235 240

Met Asn Gln Lys Thr Arg Arg Leu Ser Lys Leu Pro Tyr Glu Val His
245 250 255

Gln Glu Ile Ala Pro Leu Phe Val Asp Ser Pro Pro Val Ile Glu Asp
260 265 270

Asn Asp Leu Lys Leu His Lys Phe Glu Val Lys Thr Gly Asp Ser Ile
275 280 285

His Lys Gly Leu Thr Pro Gly Trp Asn Asp Leu Asp Val Asn Gln His
290 295 300

Val Ser Asn Val Lys Tyr Ile Gly Trp Ile Leu Glu Ser Met Pro Thr
305 310 315 320

Glu Val Leu Glu Thr Gln Glu Leu Cys Ser Leu Ala Leu Glu Tyr Arg
325 330 335

Arg Glu Cys Gly Arg Asp Ser Val Leu Glu Ser Val Thr Ala Met Asp
340 345 350

Pro Thr Lys Val Gly Gly Arg Ser Gln Tyr Gln His Leu Leu Arg Leu
355 360 365

Glu Asp Gly Thr Asp Ile Val Lys Cys Arg Thr Glu Trp Arg Pro Lys
370 375 380

Asn Pro Gly Ala Asn Gly Ala Ile Ser Thr Gly Lys Thr Ser Asn Gly
385 390 395 400

Asn Ser Val Ser

<210> SEQ ID NO 179
<211> LENGTH: 405
<212> TYPE: PRT
<213> ORGANISM: Cuphea paucipetala
<220> FEATURE:
<223> OTHER INFORMATION: CpauFATB1 (Cuphea paucipetala FATB1)

<400> SEQUENCE: 179

```
Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Thr Ala Ile Thr Thr Val Phe Val Ala Ala Glu Lys
                85                  90                  95

Gln Trp Thr Met Arg Asp Arg Lys Ser Lys Arg Pro Asp Met Leu Val
            100                 105                 110

Asp Ser Val Gly Leu Lys Ser Val Val Leu Asp Gly Leu Val Ser Arg
        115                 120                 125

Gln Ile Phe Ser Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Thr Trp Gly Asp Thr Val Glu Ile Asn Thr Trp
        195                 200                 205

Phe Ser His Ser Gly Lys Ile Gly Met Ala Ser Asp Trp Leu Ile Thr
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Tyr Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Ser Asn Val Lys Tyr Ile Gly Trp Ile Leu Glu Ser Met Pro
305                 310                 315                 320

Ile Glu Val Leu Glu Thr Gln Glu Leu Cys Ser Leu Thr Val Glu Tyr
                325                 330                 335

Arg Arg Glu Cys Gly Met Asp Ser Val Leu Glu Ser Val Thr Ala Met
            340                 345                 350

Asp Pro Ser Glu Asp Glu Gly Arg Ser Gln Tyr Lys His Leu Leu Arg
        355                 360                 365
```

Leu Glu Asp Gly Thr Asp Ile Val Lys Gly Arg Thr Glu Trp Arg Pro
    370                 375                 380

Lys Asn Ala Gly Thr Asn Gly Ala Ile Ser Thr Ala Lys Pro Ser Asn
385                 390                 395                 400

Gly Asn Ser Val Ser
                405

<210> SEQ ID NO 180
<211> LENGTH: 405
<212> TYPE: PRT
<213> ORGANISM: Cuphea procumbens
<220> FEATURE:
<223> OTHER INFORMATION: CprocFATB1 (Cuphea procumbens FATB1)

<400> SEQUENCE: 180

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Ser Ala Ile Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Val Gly Leu Lys Asn Ile Val Arg Asp Gly Leu Val Ser Arg
        115                 120                 125

Gln Ser Phe Leu Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Ala Trp Gly Asp Thr Val Glu Ile Asn Thr Trp
        195                 200                 205

Phe Ser Gln Ser Gly Lys Ile Gly Met Gly Ser Asp Trp Leu Ile Ser
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Phe Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Ser Asn Val Lys Tyr Ile Gly Trp Ile Leu Glu Ser Met Pro
305                 310                 315                 320

```
Ile Glu Val Leu Glu Ala Gln Glu Leu Cys Ser Leu Thr Val Glu Tyr
                325                 330                 335

Arg Arg Glu Cys Gly Met Asp Ser Val Leu Glu Ser Val Thr Ala Val
            340                 345                 350

Asp Pro Ser Glu Asp Gly Gly Arg Ser Gln Tyr Asn His Leu Leu Arg
        355                 360                 365

Leu Glu Asp Gly Thr Asp Val Val Lys Gly Arg Thr Glu Trp Arg Pro
    370                 375                 380

Lys Asn Ala Glu Thr Asn Gly Ala Ile Ser Pro Gly Asn Thr Ser Asn
385                 390                 395                 400

Gly Asn Ser Ile Ser
                405


<210> SEQ ID NO 181
<211> LENGTH: 403
<212> TYPE: PRT
<213> ORGANISM: Cuphea procumbens
<220> FEATURE:
<223> OTHER INFORMATION: CprocFATB2 (Cuphea procumbens FATB2)

<400> SEQUENCE: 181

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Ser Ala Ile Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Val Gly Leu Lys Asn Ile Val Arg Asp Gly Leu Val Ser Arg
        115                 120                 125

Gln Ser Phe Leu Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Ala Trp Gly Asp Thr Val Glu Ile Asn Thr Trp
        195                 200                 205

Phe Ser Gln Ser Gly Lys Ile Gly Met Gly Ser Asp Trp Leu Ile Ser
    210                 215                 220

Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Phe Val Asp Ser Pro His Val Ile Glu
            260                 265                 270
```

```
Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Asn Asn Val Lys Tyr Ile Gly Trp Ile Leu Glu Ser Thr Pro
305                 310                 315                 320

Pro Glu Val Leu Glu Thr Gln Glu Leu Cys Ser Leu Thr Leu Glu Tyr
                325                 330                 335

Arg Gln Glu Cys Gly Arg Glu Ser Val Leu Glu Ser Leu Thr Ala Val
            340                 345                 350

Asp Pro Ser Gly Lys Gly Phe Gly Ser Gln Phe Gln His Leu Leu Arg
        355                 360                 365

Leu Glu Asp Gly Gly Glu Ile Val Lys Gly Arg Thr Glu Trp Arg Pro
    370                 375                 380

Lys Thr Ala Gly Ile Asn Gly Ala Ile Ala Ser Gly Glu Thr Ser Pro
385                 390                 395                 400

Gly Asp Phe


<210> SEQ ID NO 182
<211> LENGTH: 398
<212> TYPE: PRT
<213> ORGANISM: Cuphea procumbens
<220> FEATURE:
<223> OTHER INFORMATION: CprocFATB3 (Cuphea procumbens FATB3)

<400> SEQUENCE: 182

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Ser Ala His Pro Lys Ala Asn Gly
        35                  40                  45

Ser Ala Val Asn Leu Lys Ser Gly Ser Leu Asn Thr Gln Glu Asp Thr
    50                  55                  60

Ser Ser Ser Pro Pro Pro Arg Ala Phe Leu Asn Gln Leu Pro Asp Trp
65                  70                  75                  80

Ser Met Leu Leu Ser Ala Ile Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Val Gly Leu Lys Asn Ile Val Arg Asp Gly Leu Val Ser Arg
        115                 120                 125

Gln Ser Phe Leu Ile Arg Ser Tyr Glu Ile Gly Ala Asp Arg Thr Ala
    130                 135                 140

Ser Ile Glu Thr Leu Met Asn His Leu Gln Glu Thr Ser Ile Asn His
145                 150                 155                 160

Cys Lys Ser Leu Gly Leu Leu Asn Asp Gly Phe Gly Arg Thr Pro Gly
                165                 170                 175

Met Cys Lys Asn Asp Leu Ile Trp Val Leu Thr Lys Met Gln Ile Met
            180                 185                 190

Val Asn Arg Tyr Pro Ala Trp Gly Asp Thr Val Glu Ile Asn Thr Trp
        195                 200                 205

Phe Ser Gln Ser Gly Lys Ile Gly Met Gly Ser Asp Trp Leu Ile Ser
    210                 215                 220
```

-continued

```
Asp Cys Asn Thr Gly Glu Ile Leu Ile Arg Ala Thr Ser Val Trp Ala
225                 230                 235                 240

Met Met Asn Gln Lys Thr Arg Arg Phe Ser Arg Leu Pro Tyr Glu Val
                245                 250                 255

Arg Gln Glu Leu Thr Pro His Phe Val Asp Ser Pro His Val Ile Glu
            260                 265                 270

Asp Asn Asp Arg Lys Leu His Lys Phe Asp Val Lys Thr Gly Asp Ser
        275                 280                 285

Ile Arg Lys Gly Leu Thr Pro Arg Trp Asn Asp Leu Asp Val Asn Gln
    290                 295                 300

His Val Asn Asn Val Lys Tyr Ile Gly Trp Ile Leu Glu Ser Thr Pro
305                 310                 315                 320

Pro Glu Val Leu Glu Thr Gln Glu Leu Cys Ser Leu Thr Leu Glu Tyr
                325                 330                 335

Arg Arg Glu Cys Gly Arg Glu Ser Val Leu Glu Ser Leu Thr Ala Val
            340                 345                 350

Asp Pro Ser Gly Glu Gly Gly Tyr Gly Ser Gln Phe Gln His Leu Leu
        355                 360                 365

Arg Leu Glu Asp Gly Gly Glu Ile Val Lys Gly Arg Thr Glu Trp Arg
    370                 375                 380

Pro Lys Asn Ala Gly Ile Asn Gly Val Leu Pro Thr Gly Glu
385                 390                 395


<210> SEQ ID NO 183
<211> LENGTH: 398
<212> TYPE: PRT
<213> ORGANISM: Cuphea ignea
<220> FEATURE:
<223> OTHER INFORMATION: CigneaFATB1 (Cuphea ignea FATB1)

<400> SEQUENCE: 183

Met Ala Thr Ala Ser Thr Phe Ser Ala Phe Asn Ala Arg Cys Gly Asp
1               5                   10                  15

Leu Arg Arg Ser Ala Gly Ser Gly Pro Arg Arg Pro Ala Arg Pro Leu
            20                  25                  30

Pro Val Arg Ala Ala Ile Asn Ala Arg Ala His Pro Lys Ala Asn Gly
        35                  40                  45

Ser Ala Val Ser Leu Lys Ser Val Ser Leu Asn Thr Gln Glu Asp Thr
    50                  55                  60

Ser Leu Ser Pro Pro Pro Arg Ala Phe Leu Asn Gln Leu Pro Asp Trp
65                  70                  75                  80

Arg Met Leu Arg Thr Ala Leu Thr Thr Val Phe Val Ala Ala Glu Lys
                85                  90                  95

Gln Trp Thr Met Leu Asp Arg Lys Ser Lys Arg Pro Asp Met Leu Val
            100                 105                 110

Asp Ser Phe Gly Leu Glu Ser Ile Val Gln Glu Gly Leu Val Phe Arg
        115                 120                 125

Gln Ser Phe Ser Ile Arg Ser Tyr Glu Ile Gly Ile Asp Arg Thr Ala
    130                 135                 140

Ser Ile Glu Thr Leu Met Asn His Leu Gln Glu Thr Ser Leu Asn Gln
145                 150                 155                 160

Cys Lys Ser Ala Gly Ile Leu His Asp Gly Phe Gly Arg Thr Leu Glu
                165                 170                 175

Met Cys Lys Arg Asp Leu Ile Trp Val Val Thr Lys Met Gln Ile Lys
            180                 185                 190
```

```
Val Asn Arg Tyr Pro Ala Trp Gly Asp Thr Val Glu Ile Ser Thr Arg
        195                 200                 205

Phe Ser Arg Leu Gly Lys Ile Gly Met Gly Arg Asp Trp Leu Ile Cys
    210                 215                 220

Asp Cys Asn Thr Gly Glu Ile Leu Ile Arg Ala Thr Ser Ala Tyr Ala
225                 230                 235                 240

Met Met Asn Gln Lys Thr Arg Arg Leu Ser Lys Leu Pro Asn Glu Val
                245                 250                 255

Arg Gln Glu Ile Ala Pro Leu Phe Val Asp Ser Asp Pro Val Ile Glu
            260                 265                 270

Glu Asn Asp Met Lys Leu His Lys Phe Glu Val Lys Thr Gly Asp Ser
        275                 280                 285

Ile Cys Lys Gly Leu Thr Pro Arg Trp Ser Asp Leu Asp Val Asn Gln
    290                 295                 300

His Val Ser Asn Val Lys Tyr Ile Gly Trp Ile Leu Glu Ser Met Pro
305                 310                 315                 320

Thr Glu Val Leu Glu Thr Gln Glu Leu Cys Ser Leu Ala Leu Glu Tyr
                325                 330                 335

Arg Arg Glu Cys Gly Arg Asp Ser Val Leu Glu Ser Val Thr Ser Met
            340                 345                 350

Asp Pro Ser Lys Val Gly Gly Trp Ser Gln Tyr Gln His Leu Leu Arg
        355                 360                 365

Leu Glu Asp Gly Ala Asp Ile Val Lys Gly Arg Thr Glu Trp Arg Pro
    370                 375                 380

Lys Asn Ala Gly Ala Asn Gly Ala Ile Ser Thr Gly Lys Thr
385                 390                 395


<210> SEQ ID NO 184
<211> LENGTH: 414
<212> TYPE: PRT
<213> ORGANISM: Cuphea glossostoma
<220> FEATURE:
<223> OTHER INFORMATION: CgFATB1 (Cuphea glossostoma FATB1)

<400> SEQUENCE: 184

Met Val Ala Ala Ala Ala Ser Ser Ala Phe Phe Pro Ser Pro Ala Pro
1               5                   10                  15

Gly Ser Ser Pro Lys Pro Gly Asn Arg Pro Ser Ser Leu Ser Pro Ser
            20                  25                  30

Phe Lys Pro Lys Ser Ile Pro Asn Gly Ala Phe Gln Val Lys Ala Asn
        35                  40                  45

Ala Ser Ala His Pro Lys Ala Asn Gly Ser Ala Val Asn Leu Lys Ser
    50                  55                  60

Gly Ser Leu Asn Thr Gln Glu Asp Ser Ser Ser Ser Pro Ser Pro Arg
65                  70                  75                  80

Ala Phe Leu Asn Gln Leu Pro Asp Trp Ser Val Leu Leu Thr Ala Ile
                85                  90                  95

Thr Thr Val Phe Val Ala Ala Glu Lys Gln Trp Thr Met Leu Asp Arg
            100                 105                 110

Lys Ser Lys Arg Pro Asp Val Leu Val Asp Ser Val Gly Leu Lys Ser
        115                 120                 125

Ile Val Gln Asp Gly Leu Val Ser Arg Gln Ser Phe Ser Ile Arg Ser
    130                 135                 140

Tyr Glu Ile Gly Ala Asp Arg Thr Ala Ser Ile Glu Thr Leu Met Asn
145                 150                 155                 160
```

```
His Leu Gln Glu Thr Ser Ile Asn His Cys Lys Ser Leu Gly Leu Leu
                165                 170                 175

Asn Asp Gly Phe Gly Arg Thr Pro Gly Met Cys Lys Asn Asp Leu Ile
            180                 185                 190

Trp Val Leu Thr Lys Met Gln Ile Met Val Asn Arg Tyr Pro Ala Trp
        195                 200                 205

Gly Asp Thr Val Glu Ile Asn Thr Trp Phe Ser Gln Ser Gly Lys Ile
    210                 215                 220

Gly Met Gly Ser Asp Trp Leu Ile Ser Asp Cys Asn Thr Gly Glu Ile
225                 230                 235                 240

Leu Ile Arg Ala Thr Ser Val Trp Ala Met Met Asn Gln Lys Thr Arg
                245                 250                 255

Arg Phe Ser Arg Leu Pro Tyr Glu Val Arg Gln Glu Leu Thr Pro His
            260                 265                 270

Phe Val Asp Ser Pro His Val Ile Glu Asp Asn Asp Arg Lys Leu His
        275                 280                 285

Lys Phe Asp Val Lys Thr Gly Asp Ser Ile Arg Lys Gly Leu Thr Pro
    290                 295                 300

Arg Trp Asn Asp Leu Asp Val Asn Gln His Val Ser Asn Val Lys Tyr
305                 310                 315                 320

Ile Gly Trp Ile Leu Glu Ser Met Pro Ile Glu Val Leu Glu Thr Gln
                325                 330                 335

Glu Leu Cys Ser Leu Thr Val Glu Tyr Arg Arg Glu Cys Gly Met Asp
            340                 345                 350

Ser Val Leu Glu Ser Val Thr Ala Met Asp Pro Ser Glu Asp Gly Gly
        355                 360                 365

Arg Ser Gln Tyr Asn His Leu Leu Arg Leu Glu Asp Gly Thr Asp Val
    370                 375                 380

Val Lys Gly Arg Thr Glu Trp Arg Pro Lys Asn Ala Gly Thr Asn Gly
385                 390                 395                 400

Ala Ile Ser Thr Thr Lys Thr Ser Asn Gly Asn Ser Val Ser
                405                 410


<210> SEQ ID NO 185
<211> LENGTH: 414
<212> TYPE: PRT
<213> ORGANISM: Cuphea glossostoma
<220> FEATURE:
<223> OTHER INFORMATION: CgFATB1b (Cuphea glossostoma FATB1
      C170F,M198T,T374S variant)

<400> SEQUENCE: 185

Met Val Ala Ala Ala Ala Ser Ser Ala Phe Phe Pro Ser Pro Ala Pro
1               5                   10                  15

Gly Ser Ser Pro Lys Pro Gly Asn Arg Pro Ser Ser Leu Ser Pro Ser
            20                  25                  30

Phe Lys Pro Lys Ser Ile Pro Asn Gly Ala Phe Gln Val Lys Ala Asn
        35                  40                  45

Ala Ser Ala His Pro Lys Ala Asn Gly Ser Ala Val Asn Leu Lys Ser
    50                  55                  60

Gly Ser Leu Asn Thr Gln Glu Asp Ser Ser Ser Ser Pro Ser Pro Arg
65                  70                  75                  80

Ala Phe Leu Asn Gln Leu Pro Asp Trp Ser Val Leu Leu Thr Ala Ile
                85                  90                  95

Thr Thr Val Phe Val Ala Ala Glu Lys Gln Trp Thr Met Leu Asp Arg
            100                 105                 110
```

```
Lys Ser Lys Arg Pro Asp Val Leu Val Asp Ser Val Gly Leu Lys Ser
        115                 120                 125

Ile Val Gln Asp Gly Leu Val Ser Arg Gln Ser Phe Ser Ile Arg Ser
    130                 135                 140

Tyr Glu Ile Gly Ala Asp Arg Thr Ala Ser Ile Glu Thr Leu Met Asn
145                 150                 155                 160

His Leu Gln Glu Thr Ser Ile Asn His Phe Lys Ser Leu Gly Leu Leu
                165                 170                 175

Asn Asp Gly Phe Gly Arg Thr Pro Gly Met Cys Lys Asn Asp Leu Ile
            180                 185                 190

Trp Val Leu Thr Lys Thr Gln Ile Met Val Asn Arg Tyr Pro Ala Trp
        195                 200                 205

Gly Asp Thr Val Glu Ile Asn Thr Trp Phe Ser Gln Ser Gly Lys Ile
    210                 215                 220

Gly Met Gly Ser Asp Trp Leu Ile Ser Asp Cys Asn Thr Gly Glu Ile
225                 230                 235                 240

Leu Ile Arg Ala Thr Ser Val Trp Ala Met Met Asn Gln Lys Thr Arg
                245                 250                 255

Arg Phe Ser Arg Leu Pro Tyr Glu Val Arg Gln Glu Leu Thr Pro His
            260                 265                 270

Phe Val Asp Ser Pro His Val Ile Glu Asp Asn Asp Arg Lys Leu His
        275                 280                 285

Lys Phe Asp Val Lys Thr Gly Asp Ser Ile Arg Lys Gly Leu Thr Pro
    290                 295                 300

Arg Trp Asn Asp Leu Asp Val Asn Gln His Val Ser Asn Val Lys Tyr
305                 310                 315                 320

Ile Gly Trp Ile Leu Glu Ser Met Pro Ile Glu Val Leu Glu Thr Gln
                325                 330                 335

Glu Leu Cys Ser Leu Thr Val Glu Tyr Arg Arg Glu Cys Gly Met Asp
            340                 345                 350

Ser Val Leu Glu Ser Val Ser Ala Met Asp Pro Ser Glu Asp Gly Gly
        355                 360                 365

Arg Ser Gln Tyr Asn His Leu Leu Arg Leu Glu Asp Gly Thr Asp Val
    370                 375                 380

Val Lys Gly Arg Thr Glu Trp Arg Pro Lys Asn Ala Gly Thr Asn Gly
385                 390                 395                 400

Ala Ile Ser Thr Thr Lys Thr Ser Asn Gly Asn Ser Val Ser
                405                 410
```

```
<210> SEQ ID NO 186
<211> LENGTH: 434
<212> TYPE: PRT
<213> ORGANISM: Umbellularia californica
<220> FEATURE:
<223> OTHER INFORMATION: Umbellularia californica UcFATB3 amino acid
      sequence

<400> SEQUENCE: 186

Met Val Ala Thr Ala Ala Ala Ser Ala Phe Phe Pro Val Gly Ser Pro
1               5                   10                  15

Ala Thr Ser Ser Ala Thr Ser Ala Lys Ala Ser Met Met Pro Asp Asn
            20                  25                  30

Leu Asp Ala Arg Gly Ile Lys Pro Lys Pro Ala Ser Ser Ser Gly Leu
        35                  40                  45

Gln Val Lys Ala Asn Ala His Ala Ser Pro Lys Ile Asn Gly Ser Lys
```

-continued

```
    50                  55                  60

Val Ser Thr Asp Thr Leu Lys Gly Glu Asp Thr Leu Thr Ser Ser Pro
65                  70                  75                  80

Ala Pro Arg Thr Phe Ile Asn Gln Leu Pro Asp Trp Ser Met Phe Leu
                85                  90                  95

Ala Ala Ile Thr Thr Ile Phe Leu Ala Ala Glu Lys Gln Trp Thr Asn
            100                 105                 110

Leu Asp Trp Lys Pro Arg Arg Pro Asp Met Leu Ala Asp Pro Phe Gly
        115                 120                 125

Ile Gly Arg Phe Met Gln Asp Gly Leu Ile Phe Arg Gln His Phe Ala
    130                 135                 140

Ile Arg Ser Tyr Glu Ile Gly Ala Asp Arg Thr Ala Ser Ile Glu Thr
145                 150                 155                 160

Leu Met Asn His Leu Gln Glu Thr Ala Leu Asn His Val Arg Ser Ala
                165                 170                 175

Gly Leu Leu Gly Asp Gly Phe Gly Ala Thr Pro Glu Met Ser Arg Arg
            180                 185                 190

Asp Leu Ile Trp Val Val Thr Arg Met Gln Val Leu Val Asp Arg Tyr
        195                 200                 205

Pro Ala Trp Gly Asp Ile Val Glu Val Glu Thr Trp Val Gly Ala Ser
    210                 215                 220

Gly Lys Asn Gly Met Arg Arg Asp Trp Leu Val Arg Asp Ser Gln Thr
225                 230                 235                 240

Gly Glu Ile Leu Thr Arg Ala Thr Ser Val Trp Val Met Met Asn Lys
                245                 250                 255

Arg Thr Arg Arg Leu Ser Lys Ile Pro Glu Glu Val Arg Gly Glu Ile
            260                 265                 270

Gly Pro Tyr Phe Met Glu Asn Val Ala Ile Ile Glu Glu Asp Ser Arg
        275                 280                 285

Lys Leu Gln Lys Leu Asn Glu Asn Ile Ile Glu Glu Asp Ser Arg Lys
    290                 295                 300

Leu Gln Lys Leu Asn Glu Asn Thr Ala Asp Asn Val Arg Arg Gly Leu
305                 310                 315                 320

Thr Pro Arg Trp Ser Asp Leu Asp Val Asn Gln His Val Asn Asn Val
                325                 330                 335

Lys Tyr Ile Gly Trp Ile Leu Glu Ser Ala Pro Gly Ser Ile Leu Glu
            340                 345                 350

Ser His Glu Leu Ser Cys Met Thr Leu Glu Tyr Arg Arg Glu Cys Gly
        355                 360                 365

Lys Asp Ser Val Leu Gln Ser Met Thr Val Val Ser Gly Gly Gly Ser
    370                 375                 380

Ala Ala Gly Gly Ser Pro Glu Ser Ser Val Glu Cys Asp His Leu Leu
385                 390                 395                 400

Gln Leu Glu Ser Gly Pro Glu Val Val Lys Ala Arg Thr Glu Trp Arg
                405                 410                 415

Pro Lys Ser Ala Asn Asn Pro Arg Ser Ile Leu Glu Met Pro Ala Glu
            420                 425                 430

Ser Ser


<210> SEQ ID NO 187
<211> LENGTH: 417
<212> TYPE: PRT
<213> ORGANISM: Cuphea carthagenensis
<220> FEATURE:
```

-continued

<223> OTHER INFORMATION: Cuphea carthagenensis CCrFATB2c (V138L variant
of FATB2)

<400> SEQUENCE: 187

```
Met Val Ala Ala Ala Ala Ser Ser Ala Phe Phe Pro Val Thr Thr Pro
1               5                   10                  15

Gly Thr Ser Arg Lys Pro Gly Lys Phe Gly Asn Trp Leu Ser Ser Leu
            20                  25                  30

Ser Pro Pro Phe Arg Pro Lys Ser Ile Pro Ser Gly Gly Phe Gln Val
        35                  40                  45

Lys Ala Asn Ala Ser Ala His Pro Lys Ala Asn Gly Ser Ala Val Ser
    50                  55                  60

Leu Lys Ser Gly Ser Leu Asn Thr Gln Glu Asp Thr Ser Ser Ser Pro
65                  70                  75                  80

Pro Pro Arg Ala Phe Ile Asn Gln Leu Pro Asp Trp Ser Met Leu Leu
                85                  90                  95

Thr Ala Ile Thr Thr Val Phe Val Ala Ala Glu Lys Gln Trp Thr Met
            100                 105                 110

Leu Asp Arg Lys Ser Lys Arg Ser Asp Met Leu Val Asp Ser Phe Gly
        115                 120                 125

Met Glu Arg Ile Val Gln Asp Gly Leu Leu Phe Arg Gln Ser Phe Ser
    130                 135                 140

Ile Arg Ser Tyr Glu Ile Gly Ala Asp Arg Arg Ala Ser Ile Glu Thr
145                 150                 155                 160

Leu Met Asn His Leu Gln Glu Thr Ser Leu Asn His Cys Lys Ser Ile
                165                 170                 175

Arg Leu Leu Asn Glu Gly Phe Gly Arg Thr Pro Glu Met Cys Lys Arg
            180                 185                 190

Asp Leu Ile Trp Val Val Thr Arg Met His Ile Met Val Asn Arg Tyr
        195                 200                 205

Pro Thr Trp Gly Asp Thr Val Glu Ile Asn Thr Trp Val Ser Gln Ser
    210                 215                 220

Gly Lys Asn Gly Met Gly Arg Asp Trp Leu Ile Ser Asp Cys Asn Thr
225                 230                 235                 240

Gly Glu Ile Leu Ile Arg Ala Thr Ser Ala Trp Ala Met Met Asn Gln
                245                 250                 255

Lys Thr Arg Arg Leu Ser Lys Leu Pro Tyr Glu Val Ser Gln Glu Ile
            260                 265                 270

Ala Pro His Phe Val Asp Ser Pro Pro Val Ile Glu Asp Gly Asp Arg
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Met Pro Thr Glu Val Leu
                325                 330                 335

Glu Thr His Glu Leu Cys Phe Leu Thr Leu Glu Tyr Arg Arg Glu Cys
            340                 345                 350

Gly Arg Asp Ser Val Leu Glu Ser Val Thr Ala Met Asp Pro Ser Asn
        355                 360                 365

Glu Gly Gly Arg Ser His Tyr Gln His Leu Leu Arg Leu Glu Asp Gly
    370                 375                 380

Thr Asp Ile Val Lys Gly Arg Thr Glu Trp Arg Pro Lys Asn Ala Arg
385                 390                 395                 400
```

Asn Ile Gly Ala Ile Ser Thr Gly Lys Thr Ser Asn Gly Asn Pro Ala
405 410 415

Ser

<210> SEQ ID NO 188
<211> LENGTH: 417
<212> TYPE: PRT
<213> ORGANISM: Cuphea carthagenensis
<220> FEATURE:
<223> OTHER INFORMATION: Cuphea carthagenensis CCrFATB2

<400> SEQUENCE: 188

Met Val Ala Ala Ala Ala Ser Ser Ala Phe Phe Pro Val Thr Thr Pro
1 5 10 15

Gly Thr Ser Arg Lys Pro Gly Lys Phe Gly Asn Trp Leu Ser Ser Leu
20 25 30

Ser Pro Pro Phe Arg Pro Lys Ser Ile Pro Ser Gly Gly Phe Gln Val
35 40 45

Lys Ala Asn Ala Ser Ala His Pro Lys Ala Asn Gly Ser Ala Val Ser
50 55 60

Leu Lys Ser Gly Ser Leu Asn Thr Gln Glu Asp Thr Ser Ser Ser Pro
65 70 75 80

Pro Pro Arg Ala Phe Ile Asn Gln Leu Pro Asp Trp Ser Met Leu Leu
85 90 95

Thr Ala Ile Thr Thr Val Phe Val Ala Ala Glu Lys Gln Trp Thr Met
100 105 110

Leu Asp Arg Lys Ser Lys Arg Ser Asp Met Leu Val Asp Ser Phe Gly
115 120 125

Met Glu Arg Ile Val Gln Asp Gly Leu Val Phe Arg Gln Ser Phe Ser
130 135 140

Ile Arg Ser Tyr Glu Ile Gly Ala Asp Arg Arg Ala Ser Ile Glu Thr
145 150 155 160

Leu Met Asn His Leu Gln Glu Thr Ser Leu Asn His Cys Lys Ser Ile
165 170 175

Arg Leu Leu Asn Glu Gly Phe Gly Arg Thr Pro Glu Met Cys Lys Arg
180 185 190

Asp Leu Ile Trp Val Val Thr Arg Met His Ile Met Val Asn Arg Tyr
195 200 205

Pro Thr Trp Gly Asp Thr Val Glu Ile Asn Thr Trp Val Ser Gln Ser
210 215 220

Gly Lys Asn Gly Met Gly Arg Asp Trp Leu Ile Ser Asp Cys Asn Thr
225 230 235 240

Gly Glu Ile Leu Ile Arg Ala Thr Ser Ala Trp Ala Met Met Asn Gln
245 250 255

Lys Thr Arg Arg Leu Ser Lys Leu Pro Tyr Glu Val Ser Gln Glu Ile
260 265 270

Ala Pro His Phe Val Asp Ser Pro Pro Val Ile Glu Asp Gly Asp Arg
275 280 285

Lys Leu His Lys Phe Asp Val Lys Thr Gly Asp Ser Ile Arg Lys Gly
290 295 300

Leu Thr Pro Arg Trp Asn Asp Leu Asp Val Asn Gln His Val Asn Asn
305 310 315 320

Val Lys Tyr Ile Gly Trp Ile Leu Glu Ser Met Pro Thr Glu Val Leu
325 330 335

Glu Thr His Glu Leu Cys Phe Leu Thr Leu Glu Tyr Arg Arg Glu Cys
340 345 350

Gly Arg Asp Ser Val Leu Glu Ser Val Thr Ala Met Asp Pro Ser Asn
355 360 365

Glu Gly Gly Arg Ser His Tyr Gln His Leu Leu Arg Leu Glu Asp Gly
370 375 380

Thr Asp Ile Val Lys Gly Arg Thr Glu Trp Arg Pro Lys Asn Ala Arg
385 390 395 400

Asn Ile Gly Ala Ile Ser Thr Gly Lys Thr Ser Asn Gly Asn Pro Ala
405 410 415

Ser

<210> SEQ ID NO 189
<211> LENGTH: 417
<212> TYPE: PRT
<213> ORGANISM: Cuphea carthagenensis
<220> FEATURE:
<223> OTHER INFORMATION: CcrFATB2b

<400> SEQUENCE: 189

Met Val Ala Ala Ala Ala Ser Ser Ala Phe Phe Pro Val Thr Thr Pro
1 5 10 15

Gly Thr Ser Arg Lys Pro Gly Lys Phe Gly Asn Trp Leu Ser Ser Leu
20 25 30

Ser Pro Pro Phe Arg Pro Lys Ser Ile Pro Ser Gly Gly Phe Gln Val
35 40 45

Lys Ala Asn Ala Ser Ala His Pro Lys Ala Asn Gly Ser Ala Val Ser
50 55 60

Leu Lys Ser Gly Ser Leu Asn Thr Gln Glu Asp Thr Ser Ser Ser Pro
65 70 75 80

Pro Pro Arg Ala Phe Ile Asn Gln Leu Pro Asp Trp Ser Met Leu Leu
85 90 95

Thr Ala Ile Thr Thr Val Phe Val Ala Ala Glu Lys Gln Trp Thr Met
100 105 110

Leu Asp Arg Lys Ser Lys Arg Ser Asp Met Leu Val Asp Ser Phe Gly
115 120 125

Met Glu Arg Ile Val Gln Asp Gly Leu Val Phe Arg Gln Ser Phe Ser
130 135 140

Ile Arg Ser Tyr Glu Ile Gly Ala Asp Arg Arg Ala Ser Ile Glu Thr
145 150 155 160

Leu Met Asn His Leu Gln Glu Thr Ser Leu Asn His Cys Lys Ser Ile
165 170 175

Arg Leu Leu Asn Glu Gly Phe Gly Arg Thr Pro Glu Met Cys Lys Arg
180 185 190

Asp Leu Ile Trp Val Phe Thr Arg Met His Ile Met Val Asn Arg Tyr
195 200 205

Pro Thr Trp Gly Asp Thr Val Glu Ile Asn Thr Trp Val Ser Gln Ser
210 215 220

Gly Lys Asn Gly Met Gly Arg Asp Trp Leu Ile Ser Asp Cys Asn Thr
225 230 235 240

Gly Glu Ile Leu Ile Arg Ala Thr Ser Ala Trp Ala Met Met Asn Gln
245 250 255

Lys Thr Arg Arg Leu Ser Lys Leu Pro Tyr Glu Val Ser Gln Glu Ile
260 265 270

Ala Pro His Phe Val Asp Ser Pro Pro Val Ile Glu Asp Gly Asp Arg

```
        275                 280                 285

Lys Leu His Lys Phe Asp Val Lys Thr Gly Asp Ser Ile Arg Lys Gly
    290                 295                 300

Leu Thr Pro Arg Trp Asn Asp Leu Asp Val Asn Gln His Val Asn Asn
305                 310                 315                 320

Val Lys Tyr Ile Gly Trp Ile Leu Glu Ser Met Pro Thr Glu Val Leu
                325                 330                 335

Glu Thr His Glu Leu Cys Phe Leu Thr Leu Glu Tyr Arg Arg Glu Cys
            340                 345                 350

Gly Arg Asp Ser Val Leu Glu Ser Val Thr Ala Met Asp Pro Ser Asn
        355                 360                 365

Glu Gly Gly Arg Ser His Tyr Gln His Leu Leu Arg Leu Glu Asp Gly
    370                 375                 380

Thr Asp Ile Val Lys Gly Arg Thr Glu Trp Arg Pro Lys Asn Ala Arg
385                 390                 395                 400

Asn Ile Gly Ala Ile Pro Thr Gly Lys Thr Ser Asn Gly Asn Pro Ala
                405                 410                 415

Ser


<210> SEQ ID NO 190
<211> LENGTH: 414
<212> TYPE: PRT
<213> ORGANISM: Cuphea carthagenensis
<220> FEATURE:
<223> OTHER INFORMATION: CcrFATB1

<400> SEQUENCE: 190

Met Val Ala Thr Ala Ala Ser Ser Ala Phe Phe Pro Val Pro Ser Pro
1               5                   10                  15

Asp Ser Ser Ser Arg Pro Gly Lys Leu Gly Asn Gly Pro Ser Ser Leu
            20                  25                  30

Ser Pro Leu Lys Pro Lys Ser Thr Pro Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Ser Ser Leu Lys Thr Gln Asp Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Thr Asp Pro Phe Gly Leu
        115                 120                 125

Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220
```

Lys Asn Gly Met Arg Arg Asp Trp Leu Ile Ser Asp Cys Asn Thr Gly
225 230 235 240

Glu Ile Leu Thr Arg Ala Ser Ser Val Trp Val Met Met Asn Gln Lys
245 250 255

Thr Arg Arg Leu Ser Lys Ile Pro Asp Glu Val Arg His Glu Ile Glu
260 265 270

Pro His Phe Val Asp Ser Ala Pro Val Ile Glu Asp Asp Asp Arg Lys
275 280 285

Leu Pro Lys Leu Asp Glu Lys Thr Ala Asp Ser Ile Arg Lys Gly Leu
290 295 300

Thr Pro Lys Trp Asn Asp Leu Asp Val Asn Gln His Val Asn Asn Val
305 310 315 320

Lys Tyr Ile Gly Trp Ile Leu Glu Ser Thr Pro Pro Glu Val Leu Glu
325 330 335

Thr Gln Glu Leu Cys Ser Leu Thr Leu Glu Tyr Arg Arg Glu Cys Gly
340 345 350

Lys Glu Ser Val Leu Glu Ser Leu Thr Ala Val Asp Pro Ser Gly Lys
355 360 365

Gly Trp Gly Ser His Phe Gln His Leu Leu Arg Leu Glu Asp Gly Gly
370 375 380

Glu Ile Val Lys Gly Arg Thr Glu Trp Arg Pro Lys Asn Ala Gly Ile
385 390 395 400

Asn Gly Ala Val Ala Phe Glu Glu Thr Ser Pro Gly Asp Ser
405 410

<210> SEQ ID NO 191
<211> LENGTH: 414
<212> TYPE: PRT
<213> ORGANISM: Cuphea carthagenensis
<220> FEATURE:
<223> OTHER INFORMATION: CcrFATB1b

<400> SEQUENCE: 191

Met Val Ala Thr Ala Ala Ser Ser Ala Phe Phe Pro Val Pro Ser Pro
1 5 10 15

Asp Ser Ser Ser Arg Pro Gly Lys Leu Gly Asn Gly Pro Ser Ser Leu
20 25 30

Ser Pro Leu Lys Pro Lys Ser Thr Pro Asn Gly Gly Leu Gln Val Lys
35 40 45

Ala Asn Ala Ser Ala Pro Pro Lys Ile Asn Gly Ser Ser Val Gly Leu
50 55 60

Lys Ser Ser Ser Leu Lys Thr Gln Asp Asp Thr Pro Ser Ala Pro Pro
65 70 75 80

Pro Arg Thr Phe Ile Asn Gln Leu Pro Asp Trp Ser Met Leu Leu Ala
85 90 95

Ala Ile Thr Thr Val Phe Leu Ala Ala Glu Lys Gln Trp Met Met Leu
100 105 110

Asp Trp Lys Pro Lys Arg Pro Asp Met Leu Thr Asp Pro Phe Gly Leu
115 120 125

Gly Arg Ile Ala Gln Asp Gly Leu Val Phe Arg Gln Asn Phe Ser Ile
130 135 140

Arg Ser Tyr Glu Ile Gly Ala Asp Arg Thr Ala Ser Ile Glu Thr Val
145 150 155 160

Met Asn His Leu Gln Glu Thr Ala Leu Asn His Val Lys Ser Ala Gly
165 170 175

```
Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Lys Glu Ser Val Leu Glu Ser Leu Thr Ala Val Asp Pro Ser Gly Lys
        355                 360                 365

Gly Trp Gly Ser His Phe Gln His Leu Leu Arg Leu Glu Asp Gly Gly
    370                 375                 380

Glu Ile Val Lys Gly Arg Thr Glu Trp Arg Pro Lys Asn Ala Gly Ile
385                 390                 395                 400

Asn Gly Ala Val Ala Phe Glu Glu Thr Ser Pro Gly Asp Ser
                405                 410
```

<210> SEQ ID NO 192
<211> LENGTH: 398
<212> TYPE: PRT
<213> ORGANISM: Cuphea carthagenensis
<220> FEATURE:
<223> OTHER INFORMATION: CCrFATB1c

<400> SEQUENCE: 192

```
Met Val Ala Thr Ala Ala Ser Ser Ala Phe Phe Pro Val Pro Ser Pro
1               5                   10                  15

Asp Ser Ser Ser Arg Pro Gly Lys Leu Gly Asn Gly Pro Ser Ser Leu
            20                  25                  30

Ser Pro Leu Lys Pro Lys Ser Thr Pro Asn Gly Gly Leu Gln Val Lys
        35                  40                  45

Ala Asn Ala Ser Ala Pro Pro Lys Ile Asn Gly Ser Ser Val Gly Leu
    50                  55                  60

Lys Ser Ser Ser Leu Lys Thr Gln Asp Asp Thr Pro Ser Ala Pro Pro
65                  70                  75                  80

Pro Arg Thr Phe Ile Asn Gln Leu Pro Asp Trp Ser Met Leu Leu Ala
                85                  90                  95

Ala Ile Thr Thr Val Phe Leu Ala Ala Glu Lys Gln Trp Met Met Leu
            100                 105                 110

Asp Trp Lys Pro Lys Arg Pro Asp Met Leu Thr Asp Pro Phe Gly Leu
        115                 120                 125
```

```
Gly Arg Ile Val Gln Asp Gly Leu Val Phe Arg Gln Asn Phe Ser Ile
    130                 135                 140

Arg Ser Tyr Glu Ile Gly Ala Asp Arg Thr Ala Ser Ile Glu Thr Val
145                 150                 155                 160

Met Asn His Leu Gln Glu Thr Ala Leu Asn His Val Lys Ser Ala Gly
                165                 170                 175

Leu Leu Asn Asp Gly Phe Gly Arg Thr Pro Glu Met Tyr Lys Arg Asp
            180                 185                 190

Leu Ile Trp Val Val Ala Lys Met Gln Val Met Val Asn Arg Tyr Pro
        195                 200                 205

Thr Trp Gly Asp Thr Val Glu Val Asn Thr Trp Val Ala Lys Ser Gly
    210                 215                 220

Lys Asn Gly Met Arg Arg Asp Trp Leu Ile Ser Asp Cys Asn Thr Gly
225                 230                 235                 240

Glu Ile Leu Thr Arg Ala Ser Ser Val Trp Val Met Met Asn Gln Lys
                245                 250                 255

Thr Arg Arg Leu Ser Lys Ile Pro Asp Glu Val Arg His Glu Ile Glu
            260                 265                 270

Pro His Phe Val Asp Ser Ala Pro Val Ile Glu Asp Asp Asp Arg Lys
        275                 280                 285

Leu Pro Lys Leu Asp Glu Lys Thr Ala Asp Ser Ile Arg Lys Gly Leu
    290                 295                 300

Thr Pro Lys Trp Asn Asp Leu Asp Val Asn Gln His Val Asn Asn Val
305                 310                 315                 320

Lys Tyr Ile Gly Trp Ile Leu Glu Ser Thr Pro Pro Glu Val Leu Glu
                325                 330                 335

Thr Gln Glu Leu Cys Ser Leu Thr Leu Glu Tyr Arg Arg Glu Cys Gly
            340                 345                 350

Lys Glu Ser Val Leu Glu Ser Leu Thr Ala Val Asp Pro Ser Gly Lys
        355                 360                 365

Gly Trp Gly Ser His Phe Gln His Leu Leu Arg Leu Glu Asp Gly Gly
    370                 375                 380

Glu Ile Val Lys Gly Arg Thr Glu Trp Arg Pro Lys Asn Ala
385                 390                 395


<210> SEQ ID NO 193
<211> LENGTH: 6541
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 193

gctcttcgcc gccgccactc ctgctcgagc gcgcccgcgc gtgcgccgcc agcgccttgg      60

ccttttcgcc gcgctcgtgc gcgtcgctga tgtccatcac caggtccatg aggtctgcct     120

tgcgccggct gagccactgc ttcgtccggg cggccaagag gagcatgagg gaggactcct     180

ggtccagggt cctgacgtgg tcgcggctct gggagcgggc cagcatcatc tggctctgcc     240

gcaccgaggc cgcctccaac tggtcctcca gcagccgcag tcgccgccga ccctggcaga     300

ggaagacagg tgaggggggt atgaattgta cagaacaacc acgagccttg tctaggcaga     360

atccctacca gtcatggctt tacctggatg acggcctgcg aacagctgtc cagcgaccct     420

cgctgccgcc gcttctcccg cacgcttctt tccagcaccg tgatggcgcg agccagcgcc     480
```

-continued

```
gcacgctggc gctgcgcttc gccgatctga ggacagtcgg ggaactctga tcagtctaaa     540
ccccccttgcg cgttagtgtt gccatccttt gcagaccggt gagagccgac ttgttgtgcg    600
ccacccccca caccacctcc tcccagacca attctgtcac ctttttggcg aaggcatcgg     660
cctcggcctg cagagaggac agcagtgccc agccgctggg ggttggcgga tgcacgctca     720
ggtacccttt cttgcgctat gacacttcca gcaaaaggta gggcgggctg cgagacggct     780
tcccggcgct gcatgcaaca ccgatgatgc ttcgaccccc cgaagctcct tcggggctgc     840
atgggcgctc cgatgccgct ccagggcgag cgctgtttaa atagccaggc ccccgattgc     900
aaagacatta tagcgagcta ccaaagccat attcaaacac ctagatcact accacttcta     960
cacaggccac tcgagcttgt gatcgcactc cgctaagggg gcgcctcttc ctcttcgttt    1020
cagtcacaac ccgcaaacgg cgcgccatgc tgctgcaggc cttcctgttc ctgctggccg    1080
gcttcgccgc caagatcagc gcctccatga cgaacgagac gtccgaccgc cccctggtgc    1140
acttcacccc caacaagggc tggatgaacg accccaacgg cctgtggtac gacgagaagg    1200
acgccaagtg gcacctgtac ttccagtaca acccgaacga caccgtctgg gggacgccct    1260
tgttctgggg ccacgccacg tccgacgacc tgaccaactg ggaggaccag cccatcgcca    1320
tcgccccgaa gcgcaacgac tccggcgcct tctccggctc catggtggtg gactacaaca    1380
acacctccgg cttcttcaac gacaccatcg acccgcgcca gcgctgcgtg gccatctgga    1440
cctacaacac cccggagtcc gaggagcagt acatctccta cagcctggac ggcggctaca    1500
ccttcaccga gtaccagaag aaccccgtgc tggccgccaa ctccacccag ttccgcgacc    1560
cgaaggtctt ctggtacgag ccctcccaga agtggatcat gaccgcggcc aagtcccagg    1620
actacaagat cgagatctac tcctccgacg acctgaagtc ctggaagctg gagtccgcgt    1680
tcgccaacga gggcttcctc ggctaccagt acgagtgccc cggcctgatc gaggtcccca    1740
ccgagcagga ccccagcaag tcctactggg tgatgttcat ctccatcaac cccggcgccc    1800
cggccggcgg ctccttcaac cagtacttcg tcggcagctt caacggcacc cacttcgagg    1860
ccttcgacaa ccagtcccgc gtggtggact tcggcaagga ctactacgcc ctgcagacct    1920
tcttcaacac cgacccgacc tacgggagcg ccctgggcat cgcgtgggcc tccaactggg    1980
agtactccgc cttcgtgccc accaacccct ggcgctcctc catgtccctc gtgcgcaagt    2040
tctccctcaa caccgagtac caggccaacc cggagacgga gctgatcaac ctgaaggccg    2100
agccgatcct gaacatcagc aacgccggcc cctggagccg gttcgccacc aacaccacgt    2160
tgacgaaggc caacagctac aacgtcgacc tgtccaacag caccggcacc ctggagttcg    2220
agctggtgta cgccgtcaac accacccaga cgatctccaa gtccgtgttc gcggacctct    2280
ccctctggtt caagggcctg gaggaccccg aggagtacct ccgcatgggc ttcgaggtgt    2340
ccgcgtcctc cttcttcctg gaccgcggga acagcaaggt gaagttcgtg aaggagaacc    2400
cctacttcac caaccgcatg agcgtgaaca accagccctt caagagcgag aacgacctgt    2460
cctactacaa ggtgtacggc ttgctggacc agaacatcct ggagctgtac ttcaacgacg    2520
gcgacgtcgt gtccaccaac acctacttca tgaccaccgg gaacgccctg ggctccgtga    2580
acatgacgac gggggtggac aacctgttct acatcgacaa gttccaggtg cgcgaggtca    2640
agtgacaatt ggcagcagca gctcggatag tatcgacaca ctctggacgc tggtcgtgtg    2700
atggactgtt gccgccacac ttgctgcctt gacctgtgaa tatccctgcc gcttttatca    2760
aacagcctca gtgtgtttga tcttgtgtgt acgcgctttt gcgagttgct agctgcttgt    2820
gctatttgcg aataccaccc ccagcatccc cttccctcgt ttcatatcgc ttgcatccca    2880
```

accgcaactt atctacgctg tcctgctatc cctcagcgct gctcctgctc ctgctcactg 2940
cccctcgcac agccttggtt tgggctccgc ctgtattctc ctggtactgc aacctgtaaa 3000
ccagcactgc aatgctgatg cacgggaagt agtgggatgg gaacacaaat ggaaagctgt 3060
atagggataa gaattcggcc gacaggacgc gcgtcaaagg tgctggtcgt gtatgccctg 3120
gccggcaggt cgttgctgct gctggttagt gattccgcaa ccctgatttt ggcgtcttat 3180
tttggcgtgg caaacgctgg cgcccgcgag ccgggccggc ggcgatgcgg tgccccacgg 3240
ctgccggaat ccaagggagg caagagcgcc cgggtcagtt gaagggcttt acgcgcaagg 3300
tacagccgct cctgcaaggc tgcgtggtgg aattggacgt gcaggtcctg ctgaagttcc 3360
tccaccgcct caccagcgga caaagcaccg gtgtatcagg tccgtgtcat ccactctaaa 3420
gaactcgact acgacctact gatggcccta gattcttcat caaaaacgcc tgagacactt 3480
gcccaggatt gaaactccct gaagggacca ccaggggccc tgagttgttc cttccccccg 3540
tggcgagctg ccagccaggc tgtacctgtg atcgaggctg gcgggaaaat aggcttcgtg 3600
tgctcaggtc atgggaggtg caggacagct catgaaacgc caacaatcgc acaattcatg 3660
tcaagctaat cagctatttc ctcttcacga gctgtaattg tcccaaaatt ctggtctacc 3720
gggggtgatc cttcgtgtac gggcccttcc ctcaacccta ggtatgcgcg catgcggtcg 3780
ccgcgcaact cgcgcgaggg ccgagggttt gggacgggcc gtcccgaaat gcagttgcac 3840
ccggatgcgt ggcacctttt ttgcgataat ttatgcaatg gactgctctg caaaattctg 3900
gctctgtcgc caaccctagg atcagcggcg taggatttcg taatcattcg tcctgatggg 3960
gagctaccga ctaccctaat atcagcccga ctgcctgacg ccagcgtcca cttttgtgca 4020
cacattccat tcgtgcccaa gacatttcat tgtggtgcga agcgtcccca gttacgctca 4080
cctgtttccc gacctcctta ctgttctgtc gacagagcgg gcccacaggc cggtcgcagc 4140
cactagtatg gccaccacct ccctggcctc cgccttctgc tccatgaagg ccgtgatgct 4200
ggcccgcgac ggccgcggcc tgaagccccg ctcctccgac ctgcagctgc gcgccggcaa 4260
cgcccagacc tccctgaaga tgatcaacgg caccaagttc tcctacaccg agtccctgaa 4320
gaagctgccc gactggtcca tgctgttcgc cgtgatcacc accatcttct ccgccgccga 4380
gaagcagtgg accaacctgg agtggaagcc caagcccaac cccccccagc tgctggacga 4440
ccacttcggc ccccacggcc tggtgttccg ccgcaccttc gccatccgct cctacgaggt 4500
gggccccgac cgctccacct ccatcgtggc cgtgatgaac cacctgcagg aggccgccct 4560
gaaccacgcc aagtccgtgg gcatcctggg cgacggcttc ggcaccaccc tggagatgtc 4620
caagcgcgac ctgatctggg tggtgaagcg cacccacgtg gccgtggagc gctaccccgc 4680
ctggggcgac accgtggagg tggagtgctg ggtgggcgcc tccggcaaca acggccgccg 4740
ccacgacttc ctggtgcgcg actgcaagac cggcgagatc ctgacccgct gcacctccct 4800
gtccgtgatg atgaacaccc gcacccgccg cctgtccaag atccccgagg aggtgcgcgg 4860
cgagatcggc cccgccttca tcgacaacgt ggccgtgaag gacgaggaga tcaagaagcc 4920
ccagaagctg aacgactcca ccgccgacta catccagggc ggcctgaccc cccgctggaa 4980
cgacctggac atcaaccagc acgtgaacaa catcaagtac gtggactgga tcctggagac 5040
cgtgcccgac tccatcttcg agtcccacca catctcctcc ttcaccatcg agtaccgccg 5100
cgagtgcacc cgcgactccg tgctgcagtc cctgaccacc gtgtccggcg gctcctccga 5160
ggccggcctg gtgtgcgagc acctgctgca gctggagggc ggctccgagg tgctgcgcgc 5220

-continued

```
caagaccgag tggcgcccca agctgtcctt ccgcggcatc tccgtgatcc ccgccgagtc   5280
ctccgtgatg gactacaagg accacgacgg cgactacaag gaccacgaca tcgactacaa   5340
ggacgacgac gacaagtgac tcgaggcagc agcagctcgg atagtatcga cacactctgg   5400
acgctggtcg tgtgatggac tgttgccgcc acacttgctg ccttgacctg tgaatatccc   5460
tgccgctttt atcaaacagc ctcagtgtgt ttgatcttgt gtgtacgcgc ttttgcgagt   5520
tgctagctgc ttgtgctatt tgcgaatacc acccccagca tccccttccc tcgtttcata   5580
tcgcttgcat cccaaccgca acttatctac gctgtcctgc tatccctcag cgctgctcct   5640
gctcctgctc actgcccctc gcacagcctt ggtttgggct ccgcctgtat tctcctggta   5700
ctgcaacctg taaaccagca ctgcaatgct gatgcacggg aagtagtggg atgggaacac   5760
aaatggaaag ctgtataggg ataacagggt aatgagctct tgttttccag aaggagttgc   5820
tccttgagcc tttcattctc agcctcgata acctccaaag ccgctctaat tgtggagggg   5880
gttcgaattt aaaagcttgg aatgttggtt cgtgcgtctg gaacaagccc agacttgttg   5940
ctcactggga aaaggaccat cagctccaaa aaacttgccg ctcaaaccgc gtacctctgc   6000
tttcgcgcaa tctgccctgt tgaaatcgcc accacattca tattgtgacg cttgagcagt   6060
ctgtaattgc ctcagaatgt ggaatcatct gccccctgtg cgagcccatg ccaggcatgt   6120
cgcgggcgag gacacccgcc actcgtacag cagaccatta tgctacctca caatagttca   6180
taacagtgac catatttctc gaagctcccc aacgagcacc tccatgctct gagtggccac   6240
cccccggccc tggtgcttgc ggagggcagg tcaaccggca tggggctacc gaaatccccg   6300
accggatccc accacccccg cgatgggaag aatctctccc cgggatgtgg gcccaccacc   6360
agcacaacct gctggcccag gcgagcgtca aaccatacca cacaaatatc cttggcatcg   6420
gccctgaatt ccttctgccg ctctgctacc cggtgcttct gtccgaagca ggggttgcta   6480
gggatcgctc cgagtccgca aacccttgtc gcgtggcggg gcttgttcga gcttgaagag   6540
c                                                                   6541
```

THIOESTERASES AND CELLS FOR PRODUCTION OF TAILORED OILS

CROSS REFERENCE TO RELATED APPLICATIONS

This application is a continuation of U.S. application Ser. No. 14/209,931, filed on Mar. 13, 2014 and issued as U.S. Pat. No. 9,783,836 on Oct. 10, 2017, which is a continuation-in-part of U.S. patent application Ser. No. 13/837,996, filed Mar. 15, 2013 and issued as U.S. Pat. No. 9,290,749 on Mar. 22, 2016, and claims the benefit of U.S. Provisional Patent Application Ser. No. 61/791,861, filed Mar. 15, 2013, and U.S. Provisional Patent Application Ser. No. 61/917,217, filed Dec. 17, 2013, all of which are hereby incorporated by reference herein in their entireties for all purposes.

SEQUENCE LISTING

The instant application contains a Sequence Listing which has been submitted electronically in ASCII format and is hereby incorporated by reference in its entirety. Said ASCII copy, created on Jun. 5, 2014, is named SOLAP019AUS_SL.txt and is 579,821 bytes in size.

BACKGROUND

Certain organisms including plants and some microalgae use a type II fatty acid biosynthetic pathway, characterized by the use of discrete, monofunctional enzymes for fatty acid synthesis. In contrast, mammals and fungi use a single, large, multifunctional protein.

Type II fatty acid biosynthesis typically involves extension of a growing acyl-ACP (acyl-carrier protein) chain by two carbon units followed by cleavage by an acyl-ACP thioesterase. In plants, two main classes of acyl-ACP thioesterases have been identified: (i) those encoded by genes of the FatA class, which tend to hydrolyze oleoyl-ACP into oleate (an 18:1 fatty acid) and ACP, and (ii) those encoded by genes of the FatB class, which liberate C8-C16 fatty acids from corresponding acyl-ACP molecules.

Different FatB genes from various plants have specificities for different acyl chain lengths. As a result, different gene products will produce different fatty acid profiles in plant seeds. See, U.S. Pat. Nos. 5,850,022; 5,723,761; 5,639,790; 5,807,893; 5,455,167; 5,654,495; 5,512,482; 5,298,421; 5,667,997; and 5,344,771; 5,304,481. Recently, FatB genes have been cloned into oleaginous microalgae to produce triglycerides with altered fatty acid profiles. See, WO2010/063032, WO2011/150411, WO2012/106560, and WO2013/158938.

SUMMARY

In various aspects, the invention(s) contemplated herein may include, but need not be limited to, any one or more of the following embodiments:

Embodiment 1

A nucleic acid construct including a regulatory element and a FatB gene expressing an active acyl-ACP thioesterase operable to produce an altered fatty acid profile in an oil produced by a cell expressing the nucleic acid construct, wherein the FatB gene expresses a protein having an amino acid sequence falling within clade 5 of Table 1a, the sequence having at least 94.6% sequence identity with each of SEQ ID NOs: 88, 82, 85, and 103, and optionally wherein the fatty acid of the oil is enriched in C8 and C10 fatty acids.

Embodiment 2

A nucleic acid construct including a regulatory element and a FatB gene expressing an active acyl-ACP thioesterase operable to produce an altered fatty acid profile in an oil produced by a cell expressing the nucleic acid construct, wherein the FatB gene expresses a protein having an amino acid sequence falling within one of clades 1-12 of Table 1a.

Embodiment 3

The nucleic acid construct of embodiment 2, wherein the FatB gene expresses a protein having an amino acid sequence falling within clade 1 of Table 1a, the sequence having at least 85.9% sequence identity with each of SEQ ID NOs: 19, 161, 22, and 160, and optionally wherein the fatty acid of the oil is enriched in C14 and C16 fatty acids.

Embodiment 4

The nucleic acid construct of embodiment 2, wherein the FatB gene expresses a protein having an amino acid sequence falling within clade 2 of Table 1a, the sequence having at least 89.5% sequence identity with each of SEQ ID NOs: 134-136, 132, 133, 137, 124, 122, 123, 125, and optionally wherein the fatty acid of the oil is enriched in C12 and C14 fatty acids.

Embodiment 5

The nucleic acid construct of embodiment 2, wherein the FatB gene expresses a protein having an amino acid sequence falling within clade 3 of Table 1a, the sequence having at least 92.5% sequence identity with each of SEQ ID NOs: 126 and 127, and optionally wherein the fatty acid of the oil is enriched in C12 and C14 fatty acids.

Embodiment 6

The nucleic acid construct of embodiment 2, wherein the FatB gene expresses a protein having an amino acid sequence falling within clade 4 of Table 1a, the sequence having at least 83.8% sequence identity with SEQ ID NO: 79, and optionally wherein the fatty acid of the oil is enriched in C12 and C14 fatty acids.

Embodiment 7

The nucleic acid construct of embodiment 2, wherein the FatB gene expresses a protein having an amino acid sequence falling within clade 6 of Table 1a, the sequence having at least 99.9% sequence identity with each of SEQ ID NOs: 111 and 110, and optionally wherein the fatty acid of the oil is enriched in C10 fatty acids.

Embodiment 8

The nucleic acid construct of embodiment 2, wherein the FatB gene expresses a protein having an amino acid sequence falling within clade 7 of Table 1a, the sequence having at least 89.5% sequence identity with each of SEQ ID NOs: 73, 106, 185, 172, 171, 173, 174, and optionally wherein the fatty acid of the oil is enriched in C10 and C12 fatty acids.

Embodiment 9

The nucleic acid construct of embodiment 2, wherein the FatB gene expresses a protein having an amino acid sequence falling within clade 8 of Table 1a, the sequence having at least 85.9% sequence identity with each of SEQ ID NOs: 112, 113, 142, 145, 143, 144, 139, 140, 138, 141, and optionally wherein the fatty acid of the oil is enriched in C12 and C14 fatty acids.

Embodiment 10

The nucleic acid construct of embodiment 2, wherein the FatB gene expresses a protein having an amino acid sequence falling within clade 9 of Table 1a, the sequence having at least 83.8% sequence identity with each of SEQ ID NOs: 187-189, and optionally wherein the fatty acid of the oil is enriched in C12 and C14 fatty acids.

Embodiment 11

The nucleic acid construct of embodiment 2, wherein the FatB gene expresses a protein having an amino acid sequence falling within clade 10 of Table 1a, the sequence having at least 95.9% sequence identity with each of SEQ ID NOs: 147, 149, 146, 150, 152, 151, 148, 154, 156, 155, 157, 108, 75, 190, 191, and 192, and optionally wherein the fatty acid of the oil is enriched in C14 and C16 fatty acids.

Embodiment 12

The nucleic acid construct of embodiment 2, wherein the FatB gene expresses a protein having an amino acid sequence falling within clade 11 of Table 1a, the sequence having at least 88.7% sequence identity with SEQ ID NO: 121, and optionally wherein the fatty acid of the oil is enriched in C14 and C16 fatty acids.

Embodiment 13

The nucleic acid construct of embodiment 2, wherein the FatB gene expresses a protein having an amino acid sequence falling within clade 12 of Table 1a, the sequence having at least 72.8% sequence identity with each of SEQ ID NOs: 129 and 186, and optionally wherein the fatty acid of the oil is enriched in C16 fatty acids.

Embodiment 14

An isolated nucleic acid or recombinant DNA construct including a nucleic acid, wherein the nucleic acid has at least 80% sequence identity to any of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107, 109 or any equivalent sequences by virtue of the degeneracy of the genetic code.

Embodiment 15

An isolated nucleic acid sequence encoding a protein or a host cell expressing a protein having at least 80% sequence identity to any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, 110-192 or a fragment thereof having acyl-ACP thioesterase activity.

Embodiment 16

The isolated nucleic acid of embodiment 15, wherein, the protein has acyl-ACP thioesterase activity operable to alter the fatty acid profile of an oil produced by a recombinant cell including that sequence.

Embodiment 17

A method of producing a recombinant cell that produces an altered fatty acid profile, the method including transforming the cell with a nucleic acid according to any of embodiments 1-3.

Embodiment 18

A host cell produced by the method of embodiment 17.

Embodiment 19

The host cell of embodiment 18, wherein the host cell is selected from a plant cell, a microbial cell, and a microalgal cell.

Embodiment 20

A method for producing an oil or oil-derived product, the method including cultivating a host cell of embodiment 5 or 6, and extracting oil produced thereby, optionally wherein the cultivation is heterotrophic growth on sugar.

Embodiment 21

The method of embodiment 20, further including producing a fatty acid, fuel, chemical, or other oil-derived product from the oil.

Embodiment 22

An oil produced by the method of embodiment 20, optionally having a fatty acid profile including at least 20% C8, C10, C12, C14 or C16 fatty acids.

Embodiment 23

An oil-derived product produced by the method of embodiment 21.

Embodiment 24

The oil of embodiment 23, wherein the oil is produced by a microalgae and optionally, lacks C24-alpha sterols.

DESCRIPTION OF ILLUSTRATIVE EMBODIMENTS OF THE INVENTION

Definitions

As used with respect to nucleic acids, the term “isolated” refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "natural oil" or "natural fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the natural oil or natural fat has not been subjected to interesterification or other synthetic process to obtain that regiospecific triglyceride profile, rather the regiospecificity is produced naturally, by a cell or population of cells. In connection with a natural oil or natural fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "natural oil" and "natural fat" encompass such oils obtained from an organism, where the oil has undergone minimal processing, including refining, bleaching and/or degumming, which does not substantially change its triglyceride profile. A natural oil can also be a "noninteresterified natural oil", which means that the natural oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell, for example, as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as Chlamydomonas, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

In connection with a natural oil, a "profile" is the distribution of particular species or triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

As used herein, an oil is said to be "enriched" in one or more particular fatty acids if there is at least a 10% increase in the mass of that fatty acid in the oil relative to the non-enriched oil. For example, in the case of a cell expressing a heterologous FatB gene described herein, the oil produced by the cell is said to be enriched in, e.g., C8 and C16 fatty acids if the mass of these fatty acids in the oil is at least 10% greater than in oil produced by a cell of the same type that does not express the heterologous FatB gene (e.g., wild type oil).

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant for the purposes of this invention. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

Embodiments of the present invention relate to the use of FatB genes isolated from plants, which can be expressed in a host cell in order to alter the fatty acid profile of an oil produced by the recombinant cell. Although the microalga, *Prototheca moriformis*, was used to screen the genes for ability to the alter fatty acid profile, the genes are useful in a wide variety of host cells. For example, the genes can be expressed in bacteria, other microalgae, or higher plants. The genes can be expressed in higher plants according to the methods of U.S. Pat. Nos. 5,850,022; 5,723,761; 5,639,790; 5,807,893; 5,455,167; 5,654,495; 5,512,482; 5,298,421; 5,667,997; 5,344,771; and 5,304,481. The fatty acids can be further converted to triglycerides, fatty aldehydes, fatty alcohols and other oleochemicals either synthetically or biosynthetically.

In specific embodiments, triglycerides are produced by a host cell expressing a novel FatB gene. A triglyceride-containing natural oil can be recovered from the host cell. The natural oil can be refined, degummed, bleached and/or deodorized. The oil, in its natural or processed form, can be used for foods, chemicals, fuels, cosmetics, plastics, and other uses. In other embodiments, the FatB gene may not be novel, but the expression of the gene in a microalga is novel.

The genes can be used in a variety of genetic constructs including plasmids or other vectors for expression or recombination in a host cell. The genes can be codon optimized for expression in a target host cell. The proteins produced by the genes can be used in vivo or in purified form.

For example, the gene can be prepared in an expression vector comprising an operably linked promoter and 5'UTR. Where a plastidic cell is used as the host, a suitably active plastid targeting peptide can be fused to the FATB gene, as in the examples below. Generally, for the newly identified FATB genes, there are roughly 50 amino acids at the N-terminal that constitute a plastid transit peptide, which are responsible for transporting the enzyme to the chloroplast. In the examples below, this transit peptide is replaced with a 38 amino acid sequence that is effective in the *Prototheca moriformis* host cell for transporting the enzyme to the plastids of those cells. Thus, the invention contemplates deletions and fusion proteins in order to optimize enzyme activity in a given host cell. For example, a transit peptide from the host or related species may be used instead of that of the newly discovered plant genes described here.

A selectable marker gene may be included in the vector to assist in isolating a transformed cell. Examples of selectable markers useful in microlagae include sucrose invertase and antibiotic resistance genes.

The gene sequences disclosed can also be used to prepare antisense, or inhibitory RNA (e.g., RNAi or hairpin RNA) to inhibit complementary genes in a plant or other organism.

FatB genes found to be useful in producing desired fatty acid profiles in a cell are summarized below in Table 1. Nucleic acids or proteins having the sequence of SEQ ID NOS: 1-109 can be used to alter the fatty acid profile of a recombinant cell. Variant nucleic acids can also be used; e.g., variants having at least 70, 80, 85, 90, 95, 96, 97, 98, or 99% sequence identity to SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107 or 109. Codon optimization of the genes for a variety of host organisms is contemplated, as is the use of gene fragments. Preferred codons for *Prototheca* strains and for *Chlorella protothecoides* are shown below in Tables 2 and 3, respectively. Codon usage for *Cuphea wrightii* is shown in Table 3a. Codon usage for *Arabidopsis* is shown in Table 3b; for example, the most preferred of codon for each amino acid can be selected. Codon tables for other organisms including microalgae and higher plants are known in the art. In some embodiments, the first and/or second most preferred *Prototheca* codons are employed for codon optimization. In specific embodiments, the novel amino acid sequences contained in the sequence listings below are converted into nucleic acid sequences according to the most preferred codon usage in *Prototheca, Chlorella, Cuphea wrightii*, or *Arabidopsis* as set forth in tables 2 through 3b or nucleic acid sequences having at least 70, 80, 85, 90, 95, 96, 97, 98, or 99% sequence identity to these derived nucleic acid sequences.

In embodiments of the invention, there is protein or a nucleic acid encoding a protein having any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192. In an embodiment, there is protein or a nucleic acid encoding a protein having at least 70, 75, 80, 85, 90, 91, 92, 93, 94, 95, 96, 97, 98, 99, or 100% sequence identity with any of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192. In certain embodiments, the invention encompasses a fragment any of the above-described proteins or nucleic acids (including fragments of protein or nucleic acid variants), wherein the protein fragment has acyl-ACP thioesterase activity or the nucleic acid fragment encodes such a protein fragment. In other embodiments, the fragment includes a domain of an acyl-ACP thioesterase that mediates a particular function, e.g., a specificity-determining domain. Illustrative fragments can be produced by C-terminal and/or N-terminal truncations and include at least 50%, 55%, 60%, 65%, 70%, 75%, 80%, 85%, 90%, 95%, 96%, 97%, 98%, or 99% of the full-length sequences disclosed herein.

In certain embodiments, percent sequence identity for variants of the nucleic acids or proteins discussed above can be calculated by using the full-length nucleic acid sequence (e.g., one of SEQ ID NOS: 2, 3, 5, 6, 8, 9, 11, 12, 14, 15, 17, 18, 20, 21, 23, 24, 26, 27, 29, 30, 32, 33, 35, 36, 38, 39, 41, 42, 44, 45, 47, 48, 50, 51, 53, 54, 56, 57, 59, 60, 62, 63, 65, 66, 68, 69, 71, 72, 74, 76, 78, 80, 81, 83, 84, 86, 87, 89, 90, 92, 93, 95, 96, 98, 99, 101, 102, 104, 105, 107 or 109) or full-length amino acid sequence (e.g., one of SEQ ID NOS: 1, 4, 7, 10, 13, 16, 19, 22, 25, 28, 31, 34, 37, 40, 43, 46, 49, 52, 55, 58, 61, 64, 67, 70, 73, 75, 77, 79, 82, 85, 88, 91, 94, 97, 100, 103, 106, 108, or 110-192) as the reference sequence and comparing the full-length test sequence to this reference sequence. In some embodiments relating to fragments, percent sequence identity for variants of nucleic acid or protein fragments can be calculated over the entire length of the fragment.

The nucleic acids can be in isolated form, or part of a vector or other construct, chromosome or host cell. It has been found that is many cases the full length gene (and protein) is not needed; for example, deletion of some or all of the N-terminal hydrophobic domain (typically an 18 amino acid domain starting with LPDW) yields a still-functional gene. In addition, fusions of the specificity determining regions of the genes in Table 1 with catalytic domains of other acyl-ACP thioesterases can yield functional genes. Thus, in certain embodiments, the invention encompasses functional fragments (e.g., specificity determining regions) of the disclosed nucleic acid or amino acids fused to heterologous acyl-ACP thioesterase nucleic acid or amino acid sequences, respectively.

TABLE 1

FatB genes according to embodiments of the present invention

| Species | Gene Name | Sequence Variant(relative to dominant transcript identified) | Amino Acid Sequence of CDS (no additional tags) | Native CDS nucleotide sequence (not codon-optimized, no additional cloning sites) | *Prototheca moriformis* codon-optimized nucleotide sequence of CDS |
|---|---|---|---|---|---|
| *Cinnamomum camphora* | CcFATB1b | M25L, M322R, ΔT367-D368 | SEQ ID NO: 1 | SEQ ID NO: 2 | SEQ ID NO: 3 |
| *Cinnamomum camphora* | CcFATB4 | “wild-type” | SEQ ID NO: 4 | SEQ ID NO: 5 | SEQ ID NO: 6 |
| *Cinnamomum camphora* | CcFATB3 | “wild-type” | SEQ ID NO: 7 | SEQ ID NO: 8 | SEQ ID NO: 9 |
| *Cuphea hyssopifolia* | ChsFATB1 | “wild-type” | SEQ ID NO: 10 | SEQ ID NO: 11 | SEQ ID NO: 12 |
| *Cuphea hyssopifolia* | ChsFATB2 | “wild-type” | SEQ ID NO: 13 | SEQ ID NO: 14 | SEQ ID NO: 15 |
| *Cuphea hyssopifolia* | ChsFATB2b | +a.a.248-259 | SEQ ID NO: 16 | SEQ ID NO: 17 | SEQ ID NO: 18 |
| *Cuphea hyssopifolia* | ChsFATB3 | “wild-type” | SEQ ID NO: 19 | SEQ ID NO: 20 | SEQ ID NO: 21 |
| *Cuphea hyssopifolia* | ChsFATB3b | V204I, C239F, E243D, M251V | SEQ ID NO: 22 | SEQ ID NO: 23 | SEQ ID NO: 24 |
| *Cuphea* PSR23 | CuPSR23FATB3 | “wild-type” | SEQ ID NO: 25 | SEQ ID NO: 26 | SEQ ID NO: 27 |
| *Cuphea wrightii* | CwFATB3 | “wild-type” | SEQ ID NO: 28 | SEQ ID NO: 29 | SEQ ID NO: 30 |
| *Cuphea wrightii* | CwFATB4a | “wild-type” | SEQ ID NO: 31 | SEQ ID NO: 32 | SEQ ID NO: 33 |
| *Cuphea wrightii* | CwFATB4b | “wild-type” | SEQ ID NO: 34 | SEQ ID NO: 35 | SEQ ID NO: 36 |
| *Cuphea wrightii* | CwFATB5 | “wild-type” | SEQ ID NO: 37 | SEQ ID NO: 38 | SEQ ID NO: 39 |
| *Cuphea heterophylla* | ChtFATB1a | “wild-type” | SEQ ID NO: 40 | SEQ ID NO: 41 | SEQ ID NO: 42 |
| *Cuphea heterophylla* | ChtFATB1b | P16S, T20P, G94S, G105W, S293F, L305F | SEQ ID NO: 43 | SEQ ID NO: 44 | SEQ ID NO: 45 |
| *Cuphea heterophylla* | ChtFATB2b | “wild-type” | SEQ ID NO: 46 | SEQ ID NO: 47 | SEQ ID NO: 48 |
| *Cuphea heterophylla* | ChtFATB2a | S17P, P21S, T28N, L30P, S33L, G76D, S78P, G137W | SEQ IDO NO: 49 | SEQ ID NO: 50 | SEQ ID NO: 51 |
| *Cuphea heterophylla* | ChtFATB2c | G76D, S78P | SEQ ID NO: 52 | SEQ ID NO: 53 | SEQ ID NO: 54 |
| *Cuphea heterophylla* | ChtFATB2d | S21P, T28N, L30P, S33L, G76D, R97L, H124L, W127L, I132S, K258N, C303R, E309G, K334T, T386A | SEQ ID NO: 55 | SEQ ID NO: 56 | SEQ ID NO: 57 |
| *Cuphea heterophylla* | ChtFATB2e | G76D, R97L, H124L, I132S, G152S, H165L, T211N, K258N, C303R, E309G, K334T, T386A | SEQ ID NO: 58 | SEQ ID NO: 59 | SEQ ID NO: 60 |
| *Cuphea heterophylla* | ChtFATB2f | R97L, H124L, I132S, G152S, H165L, T211N | SEQ ID NO: 61 | SEQ ID NO: 62 | SEQ ID NO: 63 |

TABLE 1-continued

FatB genes according to embodiments of the present invention

| Species | Gene Name | Sequence Variant(relative to dominant transcript identified) | Amino Acid Sequence of CDS (no additional tags) | Native CDS nucleotide sequence (not codon-optimized, no additional cloning sites) | *Prototheca moriformis* codon-optimized nucleotide sequence of CDS |
|---|---|---|---|---|---|
| *Cuphea heterophylla* | ChtFATB2g | A6T, A16V, S17P, G76D, R97L, H124L, I132S, S143I, G152S, A157T, H165L, T211N, G414A | SEQ ID NO: 64 | SEQ ID NO: 65 | SEQ ID NO: 66 |
| *Cuphea heterophylla* | ChtFATB3a | “wild-type” | SEQ ID NO: 67 | SEQ ID NO: 68 | SEQ ID NO: 69 |
| *Cuphea heterophylla* | ChtFATB3b | C67G, H72Q, L128F, N179I | SEQ ID NO: 70 | SEQ ID NO: 71 | SEQ ID NO: 72 |
| *Cuphea viscosissima* | CvisFATB1 | published | SEQ ID NO: 73 | N/A | SEQ ID NO: 74 |
| *Cuphea viscosissima* | CvisFATB2 | published | SEQ ID NO: 75 | N/A | SEQ ID NO: 76 |
| *Cuphea viscosissima* | CvisFATB3 | published | SEQ ID NO: 77 | N/A | SEQ ID NO: 78 |
| *Cuphea calcarata* | CcalcFATB1 | “wild-type” | SEQ ID NO: 79 | SEQ ID 80 | SEQ ID 81 |
| *Cuphea painteri* | CpaiFATB1 | “wild-type” | SEQ ID NO: 82 | SEQ ID 83 | SEQ ID 84 |
| *Cuphea hookeriana* | ChookFATB4 | “wild-type” | SEQ ID NO: 85 | SEQ ID 86 | SEQ ID 87 |
| *Cuphea avigera* var. *pulcherrima* | CaFATB1 | “wild-type” | SEQ ID NO: 88 | SEQ ID 89 | SEQ ID 90 |
| *Cuphea paucipetala* | CPauFATB1 | “wild-type” | SEQ ID NO: 91 | SEQ ID 92 | SEQ ID 93 |
| *Cuphea procumbens* | CprocFATB1 | “wild-type” | SEQ ID NO: 94 | SEQ ID 95 | SEQ ID 96 |
| *Cuphea procumbens* | CprocFATB2 | “wild-type” | SEQ ID NO: 97 | SEQ ID 98 | SEQ ID 99 |
| *Cuphea procumbens* | CprocFATB3 | “wild-type” | SEQ ID NO: 100 | SEQ ID 101 | SEQ ID 102 |
| *Cuphea ignea* | CigneaFATB1 | “wild-type”; partial (missing N-terminal portion of native transit peptide, fused to CpSAD1tp_trimmed transit peptide) | SEQ ID NO: 103 | SEQ ID 104 | SEQ ID 105 |
| Consensus | JcFATB1 | Consensus sequence | SEQ ID NO: 106 | None, can be codon optimized for a given host | SEQ ID NO: 107 |
| Consensus | JcFATB2 | Consensus sequence | SEQ ID NO: 108 | None, can be codon optimized for a given host | SEQ ID NO: 109 |

In certain embodiments, a host cell (e.g. plant or microalgal cell) is transformed to produce a recombinant FATB protein falling into one of clades 1-12 of Table 1a. These clades were determined by sequence alignment and observation of changes in fatty acid profile when expressed in *Prototheca*. See Example 5. The FATB amino acid sequence can fall within x % amino acid sequence identity of each sequence in that clade listed in Table 1a, where x is a first second or third cutoff value, also listed in Table 1a.

TABLE 1a

Groupings of Novel FatB genes into clades.

| Clade No. | Amino Acid SEQ ID Nos. in Clade | Example Function (see Table 6) | First Cutoff Value (minimum % amino acid identity to members of clade) | Second Cutoff Value | Third Cutoff Value |
|---|---|---|---|---|---|
| 1 | ChsFATB3 (SEQ ID NO: 19)<br>ChsFATB3d (SEQ ID NO: 161)<br>ChsFATB3b (SEQ ID NO: 22)<br>ChsFATB3c (SEQ ID NO: 160) | Increase C14/C16 fatty acids | 85.9 | 97.4 | 98 |
| 2 | ChtFATB1a.2 (SEQ ID NO: 134)<br>ChtFATB1a.3 (SEQ ID NO: 135)<br>ChtFATB1a.4 (SEQ ID NO: 136) | Increase C12/C14 fatty acids | 89.5 | 95 | 98 |

TABLE 1a-continued

Groupings of Novel FatB genes into clades.

| Clade No. | Amino Acid SEQ ID Nos. in Clade | Example Function (see Table 6) | First Cutoff Value (minimum % amino acid identity to members of clade) | Second Cutoff Value | Third Cutoff Value |
|---|---|---|---|---|---|
| | ChtFATB1a (SEQ ID NO: 132)__<br>ChtFATB1a.1 (SEQ ID NO: 133)<br>ChtFATB1b (SEQ ID NO: 137)<br>CwFATB5b (SEQ ID NO: 124)<br>CwFATB5 (SEQ ID NO: 122)<br>CwFATB5a (SEQ ID NO: 123)<br>CwFATB5c (SEQ ID NO: 125) | | | | |
| 3 | CwFATB5.1 (SEQ ID NO: 126)<br>CwFATB5.1a (SEQ ID NO: 127) | Increase C12/C14 fatty acids | 92.5 | 95 | 98 |
| 4 | CcalcFATB1 (SEQ ID NO: 79) | Increase C12/C14 fatty acids | 83.8 | 93 | 95 |
| 5 | CaFATB1 (SEQ ID NO: 88)<br>CpaiFATB1 (SEQ ID NO: 82)<br>ChookFATB4 (SEQ ID NO: 85)<br>CigneaFATB1 (SEQ ID NO: 103) | Increase C8/C10 fatty acids | 94.6 | 96 | 98 |
| 6 | CuPSR23FATB3b (SEQ ID NO: 111)<br>CuPSR23FATB3 (SEQ ID NO: 110) | Increase C10 fatty acids | 99.9 | | |
| 7 | CvisFATB1 (SEQ ID NO: 73)<br>JcFATB1/SzFATB1 (SEQ ID NO: 106)<br>CgFATB1b (SEQ ID NO: 185)<br>CprocFATB1 (SEQ ID NO: 172)<br>CpauFATB1 (SEQ ID NO: 171)<br>CprocFATB2 (SEQ ID NO: 173)<br>CprocFATB3 (SEQ ID NO: 174) | Increase C10/C12 fatty acids | 89.5 | 93 | 96 |
| 8 | CwFATB3 (SEQ ID NO: 112)<br>CwFATB3a (SEQ ID NO: 113)<br>ChtFATB2e (SEQ ID NO: 142)<br>ChtFATB2h (SEQ ID NO: 145)<br>ChtFATB2f (SEQ ID NO: 143)<br>ChtFATB2g (SEQ ID NO: 144)<br>ChtFATB2a (SEQ ID NO: 139)<br>ChtFATB2c (SEQ ID NO: 140)<br>ChtFATB2b (SEQ ID NO: 138)<br>ChtFATB2d (SEQ ID NO: 141) | Increase C12/C14 fatty acids | 85.9 | 98.9 | 99.5 |
| 9 | CcrFATB2c (SEQ ID NO: 187)<br>CcrFATB2 (SEQ ID NO: 188)<br>CcrFATB2b (SEQ ID NO: 189) | Increase C12/C14 fatty acids | 83.8 | 90 | 95 |
| 10 | ChtFATB3b (SEQ ID NO: 147)<br>ChtFATB3d (SEQ ID NO: 149)<br>ChtFATB3a (SEQ ID NO: 146)<br>ChtFATB3e (SEQ ID NO: 150)<br>ChtFATB3g (SEQ ID NO: 152)<br>ChtFATB3f (SEQ ID NO: 151)<br>ChtFATB3c (SEQ ID NO: 148)<br>ChsFATB2 (SEQ ID NO: 154)<br>ChsFATB2c (SEQ ID NO: 156)<br>ChsFATB2b (SEQ ID NO: 155)<br>ChsFATB2d (SEQ ID NO: 157)<br>JcFATB2/SzFATB2 (SEQ ID NO: 108)<br>CvisFATB2 (SEQ ID NO: 75)<br>CcrFATB1 (SEQ ID NO: 190 )<br>CcrFATB1b (SEQ ID NO: 191 )<br>CcrFATB1c (SEQ ID NO: 192 ) | Increase C14/C16 fatty acids | 95.9 | 98 | 99 |
| 11 | CwFATB4b.1 (SEQ ID NO: 121) | Increase C14/C16 fatty acids | 88.7 | 94.5 | 97 |
| 12 | CcFATB3 (SEQ ID NO: 129)<br>UcFATB3 (SEQ ID NO: 186) (predicted) | Increase C16 fatty acids | 72.8 | 85 | 90 |

TABLE 2

Preferred codon usage in *Prototheca* strains

| | | | | | |
|---|---|---|---|---|---|
| Ala | GCG | 345 (0.36) | Asn | AAT | 8 (0.04) |
| | GCA | 66 (0.07) | | AAC | 201 (0.96) |
| | GCT | 101 (0.11) | Pro | CCG | 161 (0.29) |
| | GCC | 442 (0.46) | | CCA | 49 (0.09) |
| Cys | TGT | 12 (0.10) | | CCT | 71 (0.13) |
| | TGC | 105 (0.90) | | CCC | 267 (0.49) |
| Asp | GAT | 43 (0.12) | Gln | CAG | 226 (0.82) |
| | GAC | 316 (0.88) | | CAA | 48 (0.18) |
| Glu | GAG | 377 (0.96) | Arg | AGG | 33 (0.06) |
| | GAA | 14 (0.04) | | AGA | 14 (0.02) |
| Phe | TTT | 89 (0.29) | | CGG | 102 (0.18) |
| | TTC | 216 (0.71) | | CGA | 49 (0.08) |
| Gly | GGG | 92 (0.12) | | CGT | 51 (0.09) |
| | GGA | 56 (0.07) | | CGC | 331 (0.57) |
| | GGT | 76 (0.10) | Ser | AGT | 16 (0.03) |
| | GGC | 559 (0.71) | | AGC | 123 (0.22) |
| His | CAT | 42 (0.21) | | TCG | 152 (0.28) |
| | CAC | 154 (0.79) | | TCA | 31 (0.06) |
| Ile | ATA | 4 (0.01) | | TCT | 55 (0.10) |
| | ATT | 30 (0.08) | | TCC | 173 (0.31) |
| | ATC | 338 (0.91) | Thr | ACG | 184 (0.38) |
| Lys | AAG | 284 (0.98) | | ACA | 24 (0.05) |
| | AAA | 7 (0.02) | | ACT | 21 (0.05) |

TABLE 2-continued

Preferred codon usage in *Prototheca* strains

| | | | | | |
|---|---|---|---|---|---|
| Leu | TTG | 26 (0.04) | | ACC | 249 (0.52) |
| | TTA | 3 (0.00) | Val | GTG | 308 (0.50) |
| | CTG | 447 (0.61) | | GTA | 9 (0.01) |
| | CTA | 20 (0.03) | | GTT | 35 (0.06) |
| | CTT | 45 (0.06) | | GTC | 262 (0.43) |
| | CTC | 190 (0.26) | Trp | TGG | 107 (1.00) |
| Met | ATG | 191 (1.00) | Tyr | TAT | 10 (0.05) |
| | | | | TAC | 180 (0.95) |
| | | | Stop | TGA/TAG/TAA | |

TABLE 3

Preferred codon usage in *Chlorella protothecoides*

| | | | |
|---|---|---|---|
| TTC (Phe) | TAG (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

TABLE 3a

Codon usage for *Cuphea wrightii*

| | | | |
|---|---|---|---|
| UUU F 0.48 19.5 (52) | UCU S 0.21 19.5 (52) | UAU Y 0.45 6.4 (17) | UGU C 0.41 10.5 (28) |
| UUC F 0.52 21.3 (57) | UCC S 0.26 23.6 (63) | UAC Y 0.55 7.9 (21) | UGC C 0.59 15.0 (40) |
| UUA L 0.07 5.2 (14) | UCA S 0.18 16.8 (45) | UAA * 0.33 0.7 (2) | UGA * 0.33 0.7 (2) |
| UUG L 0.19 14.6 (39) | UCG S 0.11 9.7 (26) | UAG * 0.33 0.7 (2) | UGG W 1.00 15.4 (41) |
| CUU L 0.27 21.0 (56) | CCU P 0.48 21.7 (58) | CAU H 0.60 11.2 (30) | CGU R 0.09 5.6 (15) |
| CUC L 0.22 17.2 (46) | CCC P 0.16 7.1 (19) | CAC H 0.40 7.5 (20) | CGC R 0.13 7.9 (21) |
| CUA L 0.13 10.1 (27) | CCA P 0.21 9.7 (26) | CAA Q 0.31 8.6 (23) | CGA R 0.11 6.7 (18) |
| CUG L 0.12 9.7 (26) | CCG P 0.16 7.1 (19) | CAG Q 0.69 19.5 (52) | CGG R 0.16 9.4 (25) |
| AUU I 0.44 22.8 (61) | ACU T 0.33 16.8 (45) | AAU N 0.66 31.4 (84) | AGU S 0.18 16.1 (43) |
| AUC I 0.29 15.4 (41) | ACC T 0.27 13.9 (37) | AAC N 0.34 16.5 (44) | AGC S 0.07 6.0 (16) |
| AUA I 0.27 13.9 (37) | ACA T 0.26 13.5 (36) | AAA K 0.42 21.0 (56) | AGA R 0.24 14.2 (38) |
| AUG M 1.00 28.1 (75) | ACG T 0.14 7.1 (19) | AAG K 0.58 29.2 (78) | AGG R 0.27 16.1 (43) |
| GUU V 0.28 19.8 (53) | GCU A 0.35 31.4 (84) | GAU D 0.63 35.9 (96) | GGU G 0.29 26.6 (71) |
| GUC V 0.21 15.0 (40) | GCC A 0.20 18.0 (48) | GAC D 0.37 21.0 (56) | GGC G 0.20 18.0 (48) |
| GUA V 0.14 10.1 (27) | GCA A 0.33 29.6 (79) | GAA E 0.41 18.3 (49) | GGA G 0.35 31.4 (84) |
| GUG V 0.36 25.1 (67) | GCG A 0.11 9.7 (26) | GAG E 0.59 26.2 (70) | GGG G 0.16 14.2 (38) |

TABLE 3b

Codon usage for *Arabidopsis*

| | | | |
|---|---|---|---|
| UUU F 0.51 21.8 (678320) | UCU S 0.28 25.2 (782818) | UAU Y 0.52 14.6 (455089) | UGU C 0.60 10.5 (327640) |
| UUC F 0.49 20.7 (642407) | UCC S 0.13 11.2 (348173) | UAC Y 0.48 13.7 (427132) | UGC C 0.40 7.2 (222769) |
| UUA L 0.14 12.7 (394867) | UCA S 0.20 18.3 (568570) | UAA * 0.36 0.9 (29405) | UGA * 0.44 1.2 (36260) |
| UUG L 0.22 20.9 (649150) | UCG S 0.10 9.3 (290158) | UAG * 0.20 0.5 (16417) | UGG W 1.00 12.5 (388049) |
| CUU L 0.26 24.1 (750114) | CCU P 0.38 18.7 (580962) | CAU H 0.61 13.8 (428694) | CGU R 0.17 9.0 (280392) |
| CUC L 0.17 16.1 (500524) | CCC P 0.11 5.3 (165252) | CAC H 0.39 8.7 (271155) | CGC R 0.07 3.8 (117543) |
| CUA L 0.11 9.9 (307000) | CCA P 0.33 16.1 (502101) | CAA Q 0.56 19.4 (604800) | CGA R 0.12 6.3 (195736) |
| CUG L 0.11 9.8 (305822) | CCG P 0.18 8.6 (268115) | CAG Q 0.44 15.2 (473809) | CGG R 0.09 4.9 (151572) |
| AUU I 0.41 21.5 (668227) | ACU T 0.34 17.5 (544807) | AAU N 0.52 22.3 (693344) | AGU S 0.16 14.0 (435738) |
| AUC I 0.35 18.5 (576287) | ACC T 0.20 10.3 (321640) | AAC N 0.48 20.9 (650826) | AGC S 0.13 11.3 (352568) |
| AUA I 0.24 12.6 (391867) | ACA T 0.31 15.7 (487161) | AAA K 0.49 30.8 (957374) | AGA R 0.35 19.0 (589788) |
| AUG M 1.00 24.5 (762852) | ACG T 0.15 7.7 (240652) | AAG K 0.51 32.7 (1016176) | AGG R 0.20 11.0 (340922) |
| GUU V 0.40 27.2 (847061) | GCU A 0.43 28.3 (880808) | GAU D 0.68 36.6 (1139637) | GGU G 0.34 22.2 (689891) |
| GUC V 0.19 12.8 (397008) | GCC A 0.16 10.3 (321500) | GAC D 0.32 17.2 (535668) | GGC G 0.14 9.2 (284681) |
| GUA V 0.15 9.9 (308605) | GCA A 0.27 17.5 (543180) | GAA E 0.52 34.3 (1068012) | GGA G 0.37 24.2 (751489) |
| GUG V 0.26 17.4 (539873) | GCG A 0.14 9.0 (280804) | GAG E 0.48 32.2 (1002594) | GGG G 0.16 10.2 (316620) |

Host Cells

The host cell can be a single cell (e.g., microalga, bacteria, yeast) or part of a multicellular organism such as a plant or fungus. Methods for expressing Fatb genes in a plant are given in U.S. Pat. Nos. 5,850,022; 5,723,761; 5,639,790; 5,807,893; 5,455,167; 5,654,495; 5,512,482; 5,298,421; 5,667,997; and 5,344,771; 5,304,481, or can be accomplished using other techniques generally known in plant biotechnology. Engineering of oleaginous microbes including those of Chlorophyta is disclosed in WO2010/063032, WO2011,150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic microalgae of the phylum Chlorophtya, the class Trebouxiophytae, the order Chlorellales, or the family Chlorellacae. Examples of oleaginous microalgae are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylosc metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012.

Oils and Related Products

The oleaginous cells express one or more exogenous genes encoding fatty acid biosynthesis enzymes. As a result, some embodiments feature natural oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. The oils produced may be refined, bleached and deodorized (RBD) as known in the art or as described in WO2010/120939. The raw or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments, the oils are derived from oleaginous organisms heterotrophically grown on sugar derived from a C4 plant such as corn or sugarcane. In some embodiments the δ13C (0/00) of the oil is from −10 to −17 0/00 or from −13 to −16 0/00.

The oils produced according to the above methods in some cases are made using a microalgal host cell. As described above, the microalga can be, without limitation, fall in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* was found to produce sterols that appeared to be brassicasterol, ergosterol, campesterol, stigmasterol, and β-sitosterol, when detected by GC-MS. However, it is believed that all sterols produced by *Chlorella* have C2413 stereoohemistry. Thus, it is believed that the molecules detected as campesterol, stigmasterol, and β-sitosterol, are actually 22,23-dihydrobrassicasterol, proferasterol and clionasterol, respectively. Thus, the oils produced by the microalgae described above can be distinguished from plant oils by the presence of sterols with C24β stereochemistry and the absence of C24α stereochemistry in the sterols present. For example, the oils produced may contain 22, 23-dihydrobrassicasterol while lacking campesterol; contain clionasterol, while lacking in β-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, b-sitosterol, and stigamsterol are common plant sterols, with b-sitosterol being a principle plant sterol. For example, b-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g):

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydrobrassica-sterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, β-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% β-sitosterol was found to be present. β-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of β-sitosterol as a percentage of total sterol content. Accordingly, the ratio of ergosterol: β-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% β-sitosterol. In other embodiments the oil is free from β-sitosterol.

In some embodiments, the oil is free from one or more of β-sitosterol, campesterol, or stigmasterol. In some embodiments the oil is free from β-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22, 23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5, 22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% β-sitosterol. In some embodiments, the oil content contains, as a percentage of total sterols, at least 25% ergosterol and less than 5% β-sitosterol. In some embodiments, the oil content further comprises brassicasterol.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols b-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than b-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In embodiments of the present invention, oleaginous cells expressing one or more of the genes of Table 1 can produce an oil with at least 20, 40, 60 or 70% of C8, C10, C12, C14 or C16 fatty acids. In a specific embodiment, the level of myristate (C14:0) in the oil is greater than 30%.

Thus, in embodiments of the invention, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

Example 1

Discovery of Novel FATB Sequences

Sequences of novel plant acyl-ACP thioesterases involved in seed-specific mid-chain (C8-C16) fatty acid biosynthesis in higher plants were isolated. Seed-specific lipid production genes were isolated through direct interrogation of RNA pools accumulating in oilseeds. Based on phylogenetic analysis, novel enzymes can be classified as members of FatB family of acyl-ACP thioesterases.

Seeds of oleaginous plants were obtained from local grocery stores or requested through USDA ARS National Plant Germplasm System (NPGS) from North Central Regional Plant Introduction Station (NCRIS) or USDA ARS North Central Soil Conservation Research Laboratory (Morris, Mich.). Dry seeds were homogenized in liquid nitrogen to powder, resuspended in cold extraction buffer containing 6-8M Urea and 3M LiCl and left on ice for a few hours to overnight at 4° C. The seed homogenate was passed through NucleoSpin Filters (Macherey-Nagel) by centrifugation at 20,000 g for 20 minutes in the refrigerated microcentrifuge (4° C.). The resulting RNA pellets were resuspended in the buffer containing 20 mM Tris HCl, pH7.5, 0.5% SDS, 100 mM NaCl, 25 mM EDTA, 2% PVPP) and RNA was subsequently extracted once with Phenol-Chloroform-Isoamyl Alcohol (25:24:1, v/v) and once with chloroform. RNA was finally precipitated with isopropyl alcohol (0.7 Vol.) in the presence of 150 mM of Na Acetate, pH51.2, washed with 80% ethanol by centrifugation, and dried. RNA samples were treated with Turbo DNAse (Lifetech) and purified further using RNeasy kits (Qiagen) following manufacturers' protocols. The resulting purified RNA samples were converted to pair-end cDNA libraries and subjected to next-generation sequencing (2×100 bp) using Illumina Hiseq 2000 platform. RNA sequence reads were assembled into corresponding seed transcriptomes using Trinity or Oases packages. Putative thioesterase-containg cDNA contigs were identified by mining transcriptomes for sequences with homology to known thioesterases. These in silico identified putative thioesterase cDNAs have been further verified by direct reverse transcription PCR analysis using seed RNA and primer pairs targeting full-length thioesterase cDNAs. The resulting amplified products were cloned and sequenced de novo to confirm authenticity of identified thioesterase genes.

To interrogate evolutionary and functional relationship between novel acyl-ACP thioesterases and the members of two existing thioesterase classes (FatA and FatB), we performed a phylogenetic analysis using published full-length (Mayer and Shanklin, 2007) and truncated (THYME database) amino acid thioesterase sequences. Novel proteins appear to group with known acyl-ACP FatB thioesterases involved in biosynthesis of C8-C16 fatty acids. Moreover, novel thioesterases appear to cluster into 3 predominant out-groups suggesting distinct functional similarity and evolutionary relatedness among members of each cluster.

The amino acid sequences of the FatB genes follow are shown in Table 4.

TABLE 4

| Amino acid sequences of FatB genes: | |
|---|---|
| CuPSR23 FATB3 | SEQ ID NO: 110 |
| CuPSR23 FATB3b | SEQ ID NO: 111 |
| CwFATB3 | SEQ ID NO: 112 |
| CwFATB3a | SEQ ID NO: 113 |
| CwFATB3b | SEQ ID NO: 114 |
| CwFATB3c | SEQ ID NO: 115 |
| CwFATB4a | SEQ ID NO: 116 |
| CwFATB4a.1 | SEQ ID NO: 117 |
| CwFATB4a.2 | SEQ ID NO: 118 |
| CwFATB4a.3 | SEQ ID NO: 119 |
| CwFATB4b | SEQ ID NO: 120 |
| CwFATB4b.1 | SEQ ID NO: 121 |
| CwFATB5 | SEQ ID NO: 122 |
| CwFATB5a | SEQ ID NO: 123 |
| CwFATB5b | SEQ ID NO: 124 |
| CwFATB5c | SEQ ID NO: 125 |
| CwFATB5.1 | SEQ ID NO: 126 |
| CwFATB5.1a | SEQ ID NO: 127 |
| CcFATB2b | SEQ ID NO: 128 |
| CcFATB3 | SEQ ID NO: 129 |
| CcFATB3b | SEQ ID NO: 130 |
| CcFATB3c | SEQ ID NO: 131 |
| ChtFATB1a | SEQ ID NO: 132 |
| ChtFATB1a.1 | SEQ ID NO: 133 |
| ChtFATB1a.2 | SEQ ID NO: 134 |
| ChtFATB1a.3 | SEQ ID NO: 135 |
| ChtFATB1a.4 | SEQ ID NO: 136 |
| ChtFATB1b | SEQ ID NO: 137 |
| ChtFATB2b | SEQ ID NO: 138 |

TABLE 4-continued

| Amino acid sequences of FatB genes: | |
|---|---|
| ChtFATB2a | SEQ ID NO: 139 |
| ChtFATB2c | SEQ ID NO: 140 |
| ChtFATB2d | SEQ ID NO: 141 |
| ChtFATB2e | SEQ ID NO: 142 |
| ChtFATB2f | SEQ ID NO: 143 |
| ChtFATB2g | SEQ ID NO: 144 |
| ChtFATB2h | SEQ ID NO: 145 |
| ChtFATB3a | SEQ ID NO: 146 |
| ChtFATB3b | SEQ ID NO: 147 |
| ChtFATB3c | SEQ ID NO: 148 |
| ChtFATB3d | SEQ ID NO: 149 |
| ChtFATB3e | SEQ ID NO: 150 |
| ChtFATB3f | SEQ ID NO: 151 |
| ChtFATB3g | SEQ ID NO: 152 |
| ChsFATB1 | SEQ ID NO: 153 |
| ChsFATB2 | SEQ ID NO: 154 |
| ChsFatB2b | SEQ ID NO: 155 |
| ChsFatB2c | SEQ ID NO: 156 |
| ChsFatB2d | SEQ ID NO: 157 |
| Chs FATB3 | SEQ ID NO: 158 |
| ChsFatb3b | SEQ ID NO: 159 |
| ChsFatB3c | SEQ ID NO: 160 |
| ChsFATB3d | SEQ ID NO: 161 |
| ChsFATB3e | SEQ ID NO: 162 |
| ChsFATB3f | SEQ ID NO: 163 |
| ChsFATB3g | SEQ ID NO: 164 |
| ChsFATB3h | SEQ ID NO: 165 |
| ChsFATB3i | SEQ ID NO: 166 |
| ChsFATB3j | SEQ ID NO: 167 |

ChsFATB3j:

```
MVAAEASSALFSVRTPGTSPKPGKFGNWPTSLSVPFKSKSNHNGGFQVKA

NASARPKANGSAVSLKSGSLDTQEDTSSSSSPPRTFINQLPDWSMLLSAI

TTVFVAAEKQWTMLDRKSKRPDMLMDPFGVDRVVQDGAVFRQSFSIRSYE

IGADRTASIETLMNIFQETSLNHCKSIGLLNDGFGRTPEMCKRDLIWVVT

KMHIEVNRYPTWGDTIEVNTWVSESGKTGMGRDWLISDFHTGDILIRATS

VCAMMNQKTRRFSKFPYEVRQELAPHFVDSAPVIEDYQKLHKLDVKTGDS

ICNGLTPRWNDLDVNQHVNNVKYIGWILESVPTEVFETQELCGLTLEYRQ

ECGRDSVLESVTAMDPSKEGDRSLYQHLLRLEDGTDIAKGRTKWRPKNAG

KTSNGNSIS (SEQ ID NO: 167)
```

Example 2

Cloning and Fatty Acid Analysis of Cells Transformed with Novel FATB Genes

In the example below, we detail the effect of expressing plant oilseed transcriptome-derived, heterologous thioesterases in the UTEX1435 (web.biosci.utexas.edu/utex/) strain, Strain A.

As in Example 1, RNA was extracted from dried plant seeds and submitted for paired-end sequencing using the Illumina Hiseq 2000 platform. RNA sequence reads were assembled into corresponding seed transcriptomes using Trinity or Oases packages and putative thioesterase-containing cDNA contigs were identified by mining transcriptomes for sequences with homology to known thioesterases. These in silico identified putative thioesterase cDNAs were verified by direct reverse transcription PCR analysis using seed RNA and primer pairs targeting full-length thioesterase cDNAs. The resulting amplified products were cloned and sequenced de novo to confirm authenticity of identified thioesterase genes and to identify sequence variants arising from expression of different gene alleles or diversity of sequences within a population of seeds. The resulting amino acid sequences were subjected to phylogenetic analysis using published full-length (Mayer and Shanklin, 2007) and truncated (THYME database) FatB sequences. The thioesterases that clustered with acyl-ACP FatB thioesterases, which are involved in biosynthesis of C8-C16 fatty acids, were pursued.

Construction of Transforming Vectors Expressing Acyl-ACP FatB Thioesterases 27 putative acyl-ACP FatB thioesterases from the species *Cinnamomum camphora, Cuphea hyssopifolia, Cuphea* PSR23, *Cuphea wrightii, Cuphea heterophylla*, and *Cuphea viscosissima* were synthesized in a codon-optimized form to reflect *Prototheca moriformis* (UTEX 1435) codon usage. Of the 27 genes synthesized, 24 were identified by our transcriptome sequencing efforts and the 3 genes from *Cuphea viscosissima*, were from published sequences in GenBank.

Transgenic strains were generated via transformation of the base strain Strain A (*Prototheca moriformis*, derived from UTEX 1435 by classical mutation and screening for high oil production) with a construct encoding 1 of the 27 FatB thioesterases. The construct pSZ2760 encoding *Cinnamomum camphora* (Cc) FATB1b is shown as an example, but identical methods were used to generate each of the remaining 26 constructs encoding the different respective thioesterases. Construct pSZ2760 can be written as 6S::CrTUB2:ScSUC2:CvNR::PmAMT3:CcFATB1b:CvNR::6S. The sequence of the transforming DNA is provided in Table 5 (pSZ2760). The relevant restriction sites in the construct from 5'-3', BspQ1, KpnI, AscI, MfeI, EcoRI, SpeI, XhoI, SacI, BspQ1, respectively, are indicated in lowercase, bold, and underlined. BspQ1 sites delimit the 5' and 3' ends of the transforming DNA. Bold, lowercase sequences at the 5' and 3' end of the construct represent genomic DNA from UTEX 1435 that target integration to the 6S locus via homologous recombination. Proceeding in the 5' to 3' direction, the selection cassette has the *C. reinhardtii* β-tubulin promoter driving expression of the *S. cerevisiae* gene SUC2 (conferring the ability to grow on sucrose) and the *Chlorella vulgaris* Nitrate Reductase (NR) gene 3' UTR. The promoter is indicated by lowercase, boxed text. The initiator ATG and terminator TGA for ScSUC2 are indicated by bold, uppercase italics, while the coding region is indicated with lowercase italics. The 3' UTR is indicated by lowercase underlined text. The spacer region between the two cassettes is indicated by upper case text. The second cassette containing the codon optimized CcFATB1b gene (Table 5; pSZ2760) from *Cinnamomum camphora* is driven by the *Prototheca moriformis* endogenous AMT3 promoter, and has the *Chlorella vulgaris* Nitrate Reductase (NR) gene 3' UTR. In this cassette, the AMT3 promoter is indicated by lowercase, boxed text. The initiator ATG and terminator TGA for the CcFATB1b gene are indicated in bold, uppercase italics, while the coding region is indicated by lowercase italics and the spacer region is indicated by upper case text. The 3' UTR is indicated by lowercase underlined text. The final construct was sequenced to ensure correct reading frame and targeting sequences.

TABLE 5

| pSZ2760 Transforming construct |
| --- |
| gctcttcgccgccgccactcctgctcgagcgcgcccgcgcgtgcgccgccagcgccttggccttttcgccgcgctcgtgcgcgtcgctgat |
| gtccatcaccaggtccatgaggtctgccttgcgccggctgagccactgcttcgtccgggcggccaagaggagcatgagggaggactcct |
| ggtccagggtcctgacgtggtcgcggctctgggagcgggccagcatcatctggctctgccgcaccgaggccgcctccaactggtcctcca |
| gcagccgcagtcgccgccgaccctggcagaggaagacaggtgaggggggtatgaattgtacagaacaaccacgagccttgtctaggca |
| gaatccctaccagtcatggctttacctggatgacggcctgcgaacagctgtccagcgaccctcgctgccgccgcttctcccgcacgcttcttt |
| ccagcaccgtgatggcgcgagccagcgccgcacgctggcgctgcgcttcgccgatctgaggacagtcggggaactctgatcagtctaaa |
| ccccccttgcgcgttagtgttgccatcctttgcagaccggtgagagccgacttgttgtgcgccaccccccacaccacctcctcccagaccaatt |
| ctgtcaccttttttggcgaaggcatcggcctcggcctgcagagaggacagcagtgcccagccgctggggggttggcggatgcacgctcaggt |
| accctttcttgcgctatgacacttccagcaaaaggtagggcgggctgcgagacggcttcccggcgctgcatgcaacaccgatgatgcttcg |
| acccccccgaagctccttcggggctgcatgggcgctccgatgccgctccagggcgagcgctgtttaaatagccaggcccccgattgcaaa |
| gacattatagcgagctaccaaagccatattcaaacacctagatcactaccacttctacacaggccactcgagcttgtgatcgcactccgctaa |
| gggggcgcctcttcctcttcgtttcagtcacaacccgcaaacggcgcgcc*ATGctgctgcaggccttcctgttcctgctggccggcttcgc* |
| *cgccaagatcagcgcctccatgacgaacgagacgtccgaccgcccccctggtgcacttcacccccaacaagggctggatgaacgacc* |
| *ccaacggcctgtggtacgacgagaaggacgccaagtggcacctgtacttccagtacaacccgaacgacaccgtctgggggacgccc* |
| *ttgttctggggccacgccacgtccgacgacctgaccaactgggaggaccagcccatcgccatcgccccgaagcgcaacgactccgg* |
| *cgccttctccggctccatggtggtggactacaacaacacctccggcttcttcaacgacaccatcgacccgcgccagcgctgcgtggcca* |
| *tctggacctacaacaccccggagtccgaggagcagtacatctcctacagcctggacggcggctacaccttcaccgagtaccagaaga* |
| *accccgtgctggccgccaactccacccagttccgcgacccgaaggtcttctggtacgagccctcccagaagtggatcatgaccgcggc* |
| *caagtcccaggactacaagatcgagatctactcctccgacgacctgaagtcctggaagctggagtccgcgttcgccaacgagggcttc* |
| *ctcggctaccagtacgagtgccccggcctgatcgaggtccccaccgagcaggaccccagcaagtcctactgggtgatgttcatctccat* |
| *caaccccggcgccccggccggcggctccttcaaccagtacttcgtcggcagcttcaacggcacccacttcgaggccttcgacaaccag* |
| *tcccgcgtggtggacttcggcaaggactactacgccctgcagaccttcttcaacaccgacccgacctacgggagcgccctgggcatcg* |
| *cgtgggcctccaactgggagtactccgccttcgtgcccaccaacccctggcgctcctccatgtccctcgtgcgcaagttctccctcaaca* |
| *ccgagtaccaggccaacccggagacggagctgatcaacctgaaggccgagccgatcctgaacatcagcaacgccggcccctgga* |
| *gccggttcgccaccaacaccacgttgacgaaggccaacagctacaacgtcgacctgtccaacagcaccggcaccctggagttcgag* |
| *ctggtgtacgccgtcaacaccacccagacgatctccaagtccgtgttcgcggacctctccctctggttcaagggcctggaggaccccga* |
| *ggagtacctccgcatgggcttcgaggtgtccgcgtcctccttcttcctggaccgcgggaacagcaaggtgaagttcgtgaaggagaac* |
| *ccctacttcaccaaccgcatgagcgtgaacaaccagcccttcaagagcgagaacgacctgtcctactacaaggtgtacggcttgctgg* |
| *accagaacatcctggagctgtacttcaacgacggcgacgtcgtgtccaccaacacctacttcatgaccaccgggaacgccctgggctc* |
| *cgtgaacatgacgacgggggtggacaacctgttctacatcgacaagttccaggtgcgcgaggtcaagTGA*caattggcagcagcag |
| ctcggatagtatcgacacactctggacgctggtcgtgtgatggactgttgccgccacacttgctgccttgacctgtgaatatccctgccgcttt |
| atcaaacagcctcagtgtgtttgatcttgtgtgtacgcgcttttgcgagttgctagctgcttgtgctatttgcgaataccacccccagcatcccctt |
| ccctcgtttcatatcgcttgcatcccaaccgcaacttatctacgctgtcctgctatccctcagcgctgctcctgctcctgctcactgcccctcgca |
| cagccttggtttgggctccgcctgtattctcctggtactgcaacctgtaaaccagcactgcaatgctgatgcacgggaagtagtgggatggg |
| aacacaaatggaAAGCTGTATAGGGATAAgaattcggccgacaggacgcgcgtcaaaggtgctggtcgtgtatgccctg |
| gccggcaggtcgttgctgctgctggttagtgattccgcaaccctgattttggcgtcttattttggcgtggcaaacgctggcgcccgcgagccg |
| ggccggcggcgatgcggtgccccacggctgccggaatccaagggaggcaagagcgcccgggtcagttgaagggctttacgcgcaag |
| gtacagccgctcctgcaaggctgcgtggtggaattggacgtgcaggtcctgctgaagttcctccaccgcctcaccagcggacaaagcacc |
| ggtgtatcaggtccgtgtcatccactctaaagaactcgactacgacctactgatggccctagattcttcatcaaaaacgcctgagacacttgcc |

TABLE 5-continued

| pSZ2760 Transforming construct |
|---|
| caggattgaaactccctgaagggaccaccaggggccctgagttgttccttccccccgtggcgagctgccagccaggctgtacctgtgatc |
| gaggctggcgggaaaataggcttcgtgtgctcaggtcatgggaggtgcaggacagctcatgaaacgccaacaatcgcacaattcatgtca |
| agctaatcagctatttcctcttcacgagctgtaattgtcccaaaattctggtctaccgggggtgatccttcgtgtacgggcccttccctcaaccct |
| aggtatgcgcgcatgcggtcgccgcgcaactcgcgcgagggccgagggtttgggacgggccgtcccgaaatgcagttgcacccggatg |
| cgtggcacctttttttgcgataatttatgcaatggactgctctgcaaaattctggctctgtcgccaaccctaggatcagcggcgtaggatttcgta |
| atcattcgtcctgatggggagctaccgactaccctaatatcagcccgactgcctgacgccagcgtccacttttgtgcacacattccattcgtgc |
| ccaagacatttcattgtggtgcgaagcgtccccagttacgctcacctgtttcccgacctccttactgttctgtcgacagagcgggcccacagg |
| ccggtcgcagccactagtATGgccaccacctccctggcctccgccttctgctccatgaaggccgtgatgctggcccgcgacggccgc |
| ggcctgaagccccgctcctccgacctgcagctgcgcgccggcaacgcccagacctccctgaagatgatcaacggcaccaagttctcc |
| tacaccgagtccctgaagaagctgcccgactggtccatgctgttcgccgtgatcaccaccatcttctccgccgccgagaagcagtggac |
| caacctggagtggaagcccaagcccaacccccccccagctgctggacgaccacttcggcccccacggcctggtgttccgccgcacctt |
| cgccatccgctcctacgaggtgggccccgaccgctccacctccatcgtggccgtgatgaaccacctgcaggaggccgccctgaacca |
| cgccaagtccgtgggcatcctgggcgacggcttcggcaccaccctggagatgtccaagcgcgacctgatctgggtggtgaagcgcac |
| ccacgtggccgtggagcgctaccccgcctggggcgacaccgtggaggtggagtgctgggtgggcgcctccggcaacaacggccgc |
| cgccacgacttcctggtgcgcgactgcaagaccggcgagatcctgacccgctgcacctccctgtccgtgatgatgaacacccgcaccc |
| gccgcctgtccaagatccccgaggaggtgcgcggcgagatcggccccgccttcatcgacaacgtggccgtgaaggacgaggagatc |
| aagaagccccagaagctgaacgactccaccgccgactacatccagggcggcctgacccccgctggaacgacctggacatcaacc |
| agcacgtgaacaacatcaagtacgtggactggatcctggagaccgtgcccgactccatcttcgagtcccaccacatctcctccttcacc |
| atcgagtaccgccgcgagtgcacccgcgactccgtgctgcagtccctgaccaccgtgtccggcggctcctccgaggccggcctggtgt |
| gcgagcacctgctgcagctggagggcggctccgaggtgctgcgcgccaagaccgagtggcgccccaagctgtccttccgcggcatct |
| ccgtgatccccgccgagtcctccgtgatggactacaaggaccacgacggcgactacaaggaccacgacatcgactacaaggacga |
| cgacgacaagTGActcgaggcagcagcagctcggatagtatcgacacactctggacgctggtcgtgtgatggactgttgccgccacac |
| ttgctgccttgacctgtgaatatccctgccgcttttatcaaacagcctcagtgtgtttgatcttgtgtgtacgcgcttttgcgagttgctagctgctt |
| gtgctatttgcgaataccacccccagcatccccttccctcgtttcatatcgcttgcatcccaaccgcaacttatctacgctgtcctgctatccctc |
| agcgctgctcctgctcctgctcactgcccctcgcacagccttggtttgggctccgcctgtattctcctggtactgcaacctgtaaaccagcact |
| gcaatgctgatgcacgggaagtagtgggatgggaacacaaatggaAAGCTGTATAGGGATAACAGGGTAATga |
| gctcttgttttccagaaggagttgctccttgagcctttcattctcagcctcgataacctccaaagccgctctaattgtggaggggggttcgaattta |
| aaagcttggaatgttggttcgtgcgtctggaacaagcccagacttgttgctcactgggaaaaggaccatcagctccaaaaaacttgccgctc |
| aaaccgcgtacctctgctttcgcgcaatctgccctgttgaaatcgccaccacattcatattgtgacgcttgagcagtctgtaattgcctcagaat |
| gtggaatcatctgcccccctgtgcgagcccatgccaggcatgtcgcgggcgaggacacccgccactcgtacagcagaccattatgctacct |
| cacaatagttcataacagtgaccatatttctcgaagctccccaacgagcacctccatgctctgagtggccaccccccggccctggtgcttgc |
| ggagggcaggtcaaccggcatggggctaccgaaatccccgaccggatcccaccacccccgcgatgggaagaatctctccccgggatgt |
| gggcccaccaccagcacaacctgctggcccaggcgagcgtcaaaccataccacacaaatatccttggcatcggccctgaattccttctgcc |
| gctctgctacccggtgcttctgtccgaagcaggggttgctagggatcgctccgagtccgcaaacccttgtcgcgtggcggggcttgttcgag |
| cttgaagagc(SEQ ID NO: 193) |

Constructs encoding the identified heterologous FatB genes, such as CcFATB1b from pSZ2760 in Table 6, were transformed into Strain A, and selected for the ability to grow on sucrose. Transformations, cell culture, lipid production and fatty acid analysis were all carried out as previously described. After cultivating on sucrose under low nitrogen conditions to accumulate oil, fatty acid profiles were determined by FAME-GC. The top performer from each transformation, as judged by the ability to produce the highest level of midchain fatty acids, is shown in Table 4

TABLE 6

Alteration of Fatty Acid Profiles in S3150 upon Expression of Heterologous FatB Thioesterases

| | | | FA profile of top performer from each transformation (%; primary lipid in Strain A background) | | | |
|---|---|---|---|---|---|---|
| Species | Gene Name | SZ Plasmid | Strain | C8:0 | C10:0 | C12:0 |
| *Cinnamomum camphora* | CcFATB1b | pSZ2760 | A; T526; D1670-13 | 0 | 0 | 1 |
| *Cinnamomum camphora* | CcFATB4 | pSZ2756 | A; T525; D1666-31 | 0 | 1 | 33 |
| *Cinnomomum camphora* | CcFATB3 | pSZ2755 | A; T525; D1665-4 | 0 | 0 | 0 |
| *Cuphea hyssopifolia* | ChsFATB1 | pSZ2778 | A; T535; D1689-30 | 0 | 0 | 0 |
| *Cuphea hyssopifolia* | ChsFATB2 | pSZ2796 | A; T537; D1700-46 | 0 | 0 | 0 |
| *Cuphea hyssopifolia* | ChsFATB2b | pSZ2792 | A; T537; D1696-9 | 0 | 0 | 0 |
| *Cuphea hyssopifolia* | ChsFATB3 | pSZ2797 | A; T537; D1701-48 | 0 | 0 | 8 |
| *Cuphea hyssopifolia* | ChsFATB3b | pSZ2795 | A; T537; D1699-1 | 0 | 0 | 7 |
| *Cuphea* PSR23 | CuPSR23FATB3 | pSZ2793 | A; T537; D1697-13 | 0 | 1 | 0 |
| *Cuphea wrightii* | CwFATB3 | pSZ2751 | A; T525; D1661-22 | 0 | 2 | 17 |
| *Cuphea wrightii* | CwFATB4a | pSZ2752 | A; T525; D1662-30 | 0 | 0 | 0 |
| *Cuphea wrightii* | CwFATB4b | pSZ2753 | A; T525; D1663-29 | 0 | 0 | 0 |
| *Cuphea wrightii* | CwFATB5 | pSZ2754 | A; T525; D1664-39 | 0 | 0 | 0 |
| *Cuphea heterophylla* | ChtFATB1a | pSZ2757 | A; T525; D1667-19 | 0 | 0 | 5 |
| *Cuphea heterophylla* | ChtFATB1b | pSZ2773 | A; T535; D1685-29 | 0 | 0 | 2 |
| *Cuphea heterophylla* | ChtFATB2b | pSZ2780 | A; T535; D1691-8 | 0 | 0 | 0 |
| *Cuphea heterophylla* | ChtFATB2a | pSZ2774 | A; T537; D1702-24 | 0 | 0 | 0 |
| *Cuphea heterophylla* | ChtFATB2c | pSZ2758 | A; T525; D1668-22 | 0 | 0 | 3 |
| *Cuphea heterophylla* | ChtFATB2d | pSZ2759 | A; T526; D1669-19 | 0 | 0 | 4 |
| *Cuphea heterophylla* | ChtFATB2e | pSZ2775 | A; T535; D1686-23 | 0 | 1 | 2 |
| *Cuphea heterophylla* | ChtFATB2f | pSZ2777 | A; T535; D1688-33 | 0 | 0 | 0 |
| *Cuphea heterophylla* | ChtFATB2g | pSZ2794 | A; T537; D1698-19 | 0 | 0 | 0 |
| *Cuphea heterophylla* | ChtFATB3a | pSZ2776 | A; T535; D1687-23 | 0 | 0 | 0 |
| *Cuphea heterophylla* | ChtFATB3b | pSZ2779 | A; T535; D1690-31 | 0 | 0 | 0 |
| *Cuphea viscosissima* | CvisFATB1 | pSZ2810 | A; T540; D1711-30 | 0 | 1 | 0 |
| *Cuphea viscosissima* | CvisFATB2 | pSZ2817 | A; T547; D1718-1 | 0 | 0 | 0 |
| *Cuphea viscosissima* | CvisFATB3 | pSZ2791 | A; T537; D1695-1 | 0 | 0 | 0 |
| | | | A (parent strain): | 0 | 0 | 0 |

| | | FA profile of top performer from each transformation (%; primary lipid in Strain A background) | | | | | |
|---|---|---|---|---|---|---|---|
| Species | Gene Name | C14:0 | C16:0 | C18:0 | C18:1 | C18:2 | C18:3α |
| *Cinnamomum camphora* | CcFATB1b | 15 | 26 | 2 | 46 | 9 | 1 |
| *Cinnamomum camphora* | CcFATB4 | 4 | 7 | 2 | 41 | 10 | 1 |
| *Cinnomomum camphora* | CcFATB3 | 3 | 44 | 3 | 41 | 8 | 0 |
| *Cuphea hyssopifolia* | ChsFATB1 | 2 | 22 | 4 | 63 | 8 | 1 |
| *Cuphea hyssopifolia* | ChsFATB2 | 6 | 53 | 3 | 32 | 6 | 0 |
| *Cuphea hyssopifolia* | ChsFATB2b | 5 | 26 | 2 | 56 | 9 | 1 |
| *Cuphea hyssopifolia* | ChsFATB3 | 34 | 27 | 2 | 24 | 5 | 1 |
| *Cuphea hyssopifolia* | ChsFATB3b | 29 | 27 | 1 | 28 | 6 | 1 |
| *Cuphea* PSR23 | CuPSR23FATB3 | 2 | 24 | 3 | 61 | 8 | 1 |
| *Cuphea wrightii* | CwFATB3 | 9 | 19 | 2 | 41 | 8 | 1 |
| *Cuphea wrightii* | CwFATB4a | 4 | 48 | 3 | 36 | 7 | 1 |
| *Cuphea wrightii* | CwFATB4b | 5 | 52 | 3 | 32 | 6 | 1 |
| *Cuphea wrightii* | CwFATB5 | 3 | 27 | 3 | 57 | 7 | 1 |
| *Cuphea heterophylla* | ChtFATB1a | 18 | 27 | 2 | 39 | 7 | 1 |
| *Cuphea heterophylla* | ChtFATB1b | 7 | 27 | 3 | 53 | 8 | 1 |
| *Cuphea heterophylla* | ChtFATB2b | 2 | 25 | 3 | 61 | 8 | 1 |
| *Cuphea heterophylla* | ChtFATB2a | 2 | 27 | 3 | 59 | 6 | 0 |
| *Cuphea heterophylla* | ChtFATB2c | 2 | 23 | 3 | 58 | 7 | 1 |
| *Cuphea heterophylla* | ChtFATB2d | 4 | 23 | 3 | 54 | 9 | 1 |
| *Cuphea heterophylla* | ChtFATB2e | 3 | 24 | 3 | 57 | 8 | 1 |
| *Cuphea heterophylla* | ChtFATB2f | 2 | 28 | 3 | 57 | 8 | 1 |
| *Cuphea heterophylla* | ChtFATB2g | 2 | 22 | 3 | 62 | 9 | 1 |
| *Cuphea heterophylla* | ChtFATB3a | 5 | 47 | 4 | 37 | 7 | 1 |
| *Cuphea heterophylla* | ChtFATB3b | 6 | 49 | 5 | 32 | 7 | 0 |
| *Cuphea viscosissima* | CvisFATB1 | 2 | 24 | 3 | 60 | 8 | 0 |
| *Cuphea viscosissima* | CvisFATB2 | 4 | 51 | 2 | 36 | 6 | 0 |
| *Cuphea viscosissima* | CvisFATB3 | 8 | 28 | 2 | 52 | 8 | 1 |
| | | 2 | 28 | 3 | 58 | 7 | 0 |

Many of the acyl-ACP FatB thioesterases were found to exhibit midchain activity when expressed in *Prototheca moriformis*. For example, expression of CcFATB1b causes an increase in myristate levels from 2% of total fatty acids in the parent, Strain A, to ~15% in the DI670-13 primary transformant. Other examples include CcFATB4, which exhibits an increase in laurate levels from 0% in Strain A to ~33%, and ChsFATB3, which exhibits an increase in myristate levels to ~34%. Although some of the acyl-ACP thioesterases did not exhibit dramatic effects on midchain levels in the current incarnation, efforts will likely develop to optimize some of these constructs.

Sequences of the Heterologous Acyl-ACP Thioesterases Identified and Transformed into *P. moriformis* (UTEX 1435)

A complete listing of relevant sequences for the transforming constructs, such as the deduced amino acid sequence of the encoded acyl-ACP thioesterase, the native CDS coding sequence, the *Prototheca moriformis* codon-optimized coding sequence, and the nature of the sequence variants examined, is provided as SEQ ID NOS: 1-78.

Example 3

Discovery and Cloning of Additional FATB Genes

Additional FATB genes were obtained from seeds as described above. The species and number of FatB genes identified were:

| Species | Accession Number | Novel FatB Thioesterase Genes |
|---|---|---|
| *Cuphea calcarata* | 534665 | 1 |
| *Cuphea painteri* | 288248 | 1 |
| *Cuphea hookeriana* | 534896 | 1 |
| *Cuphea avigera* var. *pulcherrima* | Ames 17868 | 1 |
| *Cuphea paucipetala* | 534877 | 1 |
| *Cuphea procumbens* | 534881 | 3 |
| *Cuphea ignea* | 534773 | 1 |

The thioesterases that clustered with acyl-ACP FatB thioesterases, which are involved in biosynthesis of C8-C16 fatty acids, were pursued. The native, putative plastid-targeting transit peptide sequence is indicated by underlining.

Construction of Transforming Vectors Expressing Acyl-ACP FatB Thioesterases. The nine putative Acyl-ACP FatB Thioesterases from the species *Cuphea calcarata, Cuphea painter, Cuphea hookeriana, Cuphea avigera* var. *pulcherrima, Cuphea paucipetala, Cuphea procumbens*, and *Cuphea ignea* were synthesized in a codon-optimized form to reflect UTEX 1435 codon usage. In contrast to the previous example, the new Acyl-ACP FatB thioesterases were synthesized with a modified transit peptide from *Chlorella protothecoides* (Cp) in place of the native transit peptide. The modified transit peptide derived from the CpSAD1 gene, "CpSAD1tp_trimmed", was synthesized as an in-frame, N-terminal fusion to the FatB acyl-ACP thioesterases in place of the native transit peptide; the resulting sequences are listed below. The novel FatB genes were cloned into *Prototheca moriformis* as described above. Constructs encoding heterologous FatB genes were transformed into strain S6165 (a descendant of S3150/Strain A) and selected for the ability to grow on sucrose. Transformations, cell culture, lipid production and fatty acid analysis were all carried out as previously described. The results for the nine novel FatB acyl-ACP thioesterases are displayed in the table immediately below.

| | | | FA profile of top performer from each transformation (%; primary lipid) | | | | | | | | | |
|---|---|---|---|---|---|---|---|---|---|---|---|---|
| Species | Gene Name | SZ Plasmid | Strain | C8:0 | C10:0 | C12:0 | C14:0 | C16:0 | C18:0 | C18:1 | C18:2 | C18:3α |
| *Cuphea colcarata* | CcalcFATB1 | pSZ3764 | S6165; T778; D2508-26 | 0 | 1 | 12 | 18 | 29 | 2 | 29 | 5 | 1 |
| *Cuphea painteri* | CpaiFATB1 | pSZ3838 | S6165; T841; D2796-22 | 8 | 17 | 1 | 2 | 18 | 2 | 43 | 6 | 1 |
| *Cuphea hookeriana* | ChookFATB4 | pSZ3837 | S6165; T788; D2552-18 | 0 | 0 | 0 | 2 | 32 | 2 | 54 | 7 | 1 |
| *Cuphea ovigera* var. *pulcherrima* | CaFATB1 | pSZ4084 | S6165; T841; D2800-7 | 22 | 9 | 0 | 2 | 15 | 2 | 42 | 6 | 1 |
| *Cuphea paucipetala* | CpauFATB1 | pSZ3762 | S6165; T778; D2506-46 | 0 | 9 | 1 | 3 | 28 | 2 | 47 | 7 | 1 |
| *Cuphea procumbens* | CprocFATB1 | pSZ3929 | S6165; T814; D2675-3 | 0 | 5 | 1 | 3 | 30 | 2 | 50 | 7 | 1 |
| *Cuphea procumbens* | CprocFATB2 | pSZ3839 | S6165; T788; D2553-2 | 0 | 0 | 0 | 2 | 32 | 3 | 55 | 6 | 1 |
| *Cuphea procumbens* | CprocFATB3 | pSZ3763 | S6165; T778; D2507-29 | 0 | 3 | 1 | 2 | 28 | 3 | 54 | 6 | 1 |
| *Cuphea ignea* | CigneaFATB1 | pSZ3930 | S6165; T814; D2676-34 | 0 | 8 | 1 | 4 | 24 | 2 | 51 | 8 | 1 |
| | | | S6165 (parent strain): | 0 | 0 | 0 | 2 | 29 | 3 | 58 | 6 | 1 |

Of particular note are: CpaiFATB1, which exhibits 17% C10:0 and 8% C8:0 fatty acid levels; CpauFATB1, which exhibits 9% C10:0 and 1% C12:0 fatty acid levels; CigneaFATB1, which exhibits 8% C10:0 and 1% C12:0 fatty acid levels; CcalcFATB1, which exhibits 18% C14:0 and 12% C12:0 levels; and CaFATB1, which exhibits 22% C8:0 and 9% C10:0 fatty acid levels.

CaFATB1, which exhibits high C8:0 and C10:0 levels, is of particular interest. CaFATB1 arose from two separate contigs that were assembled from the *Cupha avigera* var. *pulcherrima* transcriptome, S17_Cavig_trinity_7406 and S17_Cavig_trinity_7407. Although the two partial contigs exhibit only 17 nucleotides of overlap, we were able to assemble a putative full length transcript encoding CaFATB1 from the two contigs and then subsequently confirm the existence of the full-length transcript by direct reverse transcription PCR analysis using seed RNA and primer pairs targeting the full-length CaFATB1 thioesterase cDNA. Tjellstrom et al. (2013) discloses the expression of a newly identified fatty acyl-ACP thioesterase from *Cuphea pulcherrima* that they named "CpuFATB3" (Genbank accession number KC675178). The coding sequence of CpuFATB3 is 100% identical to the CaFATB1 gene we identified and contains one nucleotide difference in the RNA sequence outside the predicted coding region. Tjellstrom et al. (2013) showed that CpuFATB3 produces an average of 4.8% C8:0 when expressed in *Arabidopsis*, and further requires deletion of two acyl-ACP synthetases, AAE15/16, to produce an average of 9.2% C8:0 with a maximum level of ~12% C8.0. The CaFATB1 gene we identified was codon-optimized for expression in UTEX1435 and generated as a CpSAD1tp-trimmed transit peptide fusion before introduction into 56165. The CpSAD1tp_trimmed:CaFATB1 gene produces an average C8:0 level of 14% and a maximum level of 22% C8:0 without requiring the deletion of endogenous acyl-ACP synthetases.

TABLE 7

Amino Acid Sequences of Additional Novel FatB Acyl-ACP Thioesterases. In the appended sequence listings, the native, putative plastid-targeting transit peptide sequence is underlined:

| FatB | Sequence ID NO: |
|---|---|
| CcalcFATB1 (*Cuphea calcarata* FATB1) | SEQ ID NO: 168 |
| ChookFATB4 (*Cuphea hookeriana* FATB4) | SEQ ID NO: 169 |
| CaFATB1 (*Cuphea avigera* var. *pulcherrima* FATB1) | SEQ ID NO: 170 |
| CpauFATB1 (*Cuphea paucipetala* FATB1) | SEQ ID NO: 171 |
| CprocFATBl (*Cuphea procumbens* FATB1) | SEQ ID NO: 172 |
| CprocFATB2 (*Cuphea procumbens* FATB2) | SEQ ID NO: 173 |
| CprocFATB3 (*Cuphea procumbens* FATB3) | SEQ ID NO: 174 |
| CigneaFATB1 (*Cuphea ignea* FATB1) | SEQ ID NO: 175 |
| CcalcFATB1 (*Cuphea calcarata* FATB1) | SEQ ID NO: 176 |
| ChookFATB4 (*Cuphea hookeriana* FATB4) | SEQ ID NO: 177 |
| CaFATB1 (*Cuphea avigera* var. *pulcherrima* FATB1) | SEQ ID NO: 178 |
| CpauFATB1 (*Cuphea paucipetala* FATB1) | SEQ ID NO: 179 |
| CprocFATB1 (*Cuphea procumbens* FATB1) | SEQ ID NO: 180 |
| CprocFATB2 (*Cuphea procumbens* FATB2) | SEQ ID NO: 181 |
| CprocFATB3 (*Cuphea procumbens* FATB3) | SEQ ID NO: 182 |
| CigneaFATB1 (*Cuphea ignea* FATB1) | SEQ ID NO: 183 |

Example 4

FATB Consensus Sequences: Discovery, Cloning and Fatty Acid Profiles

In the course of testing several new putative midchain FatB thioesterases in UTEX1435, S3150 (Strain A above), we identified several thioesterases with increased C10:0 and C16:0 activity above the background midchain levels found in the strain. We reasoned that a consensus sequence could be obtained for an idealized C10:0 thioesterase and C16:0 thioesterase from aligning the best-performing C10:0 and C16:0 thioesterases. A consensus C10:0 specific thioesterase sequence was generated using the *C. palustris* FatB1 (CpFATB1), C. PSR23 FatB3 (CuPSR23FATB3), *C. viscosissima* FatB1 (CvisFATB1), *C. glossostoma* FatB1 (CgFATB1), and *C. carthagenensis* FatB2 (CcrFATB2) sequences as inputs resulting in a C10:0 specific consensus sequence termed JcFATB1/SzFATB1. A consensus C16:0 specific thioesterase sequence was generated using the *C. heterophylla* FatB3a (ChtFATB3a), *C. carthagenensis* FatB1 (CcrFATB1), *C. viscosissima* FatB2 (CvisFATB2), *C. hookeriana* FatB1 (ChFATB1; AAC48990), *C. hyssopifolia* FatB2 (ChsFATB2), *C. calophylla* FatB2 (CcalFATB2; ABB71581), *C. hookeriana* FatB1-1 (ChFATB1-1; AAC72882), *C. lanceolata* FatB1 (ClFATB1; CAC19933), and *C. wrightii* FatB4a (CwFATB4a) sequences as inputs resulting in a C16:0 specific consensus sequence termed JcFATB2/SzFATB2. The resulting consensus sequences were synthesized, cloned into a vector identical to that used to test other FatB thioesterases, and introduced into 53150 as described above. The consensus amino acid sequences are given as SEQ ID NOs. 106 and 107; the nucleic acid sequences were based on these amino acid sequences using codon optimization for *Prototheca moriformis*. The transformants were selected, cultivated and the oil was extracted and analyzed by FAME-GC-FID. The fatty acid profiles obtained are given in the table below.

| Species | Gene Name | SZ Plasmid | FA profile of top performer from each transformation (%; primary lipid) Strain | C8:0 | C10:0 | C12:0 | C14:0 | C16:0 | C18:0 | C18:1 | C18:2 | C18:3α |
|---|---|---|---|---|---|---|---|---|---|---|---|---|
| Consensus Sequence 1 | JcFATB1 | pSZ3187 | S3150; T617; D1930-18 | 0 | 2 | 0 | 2 | 26 | 3 | 57 | 8 | 1 |
| Consensus Sequence 2 | JcFATB2 | pSZ3100 | S3150; 1600; D1872-17 | 0 | 0 | 0 | 6 | 54 | 3 | 29 | 6 | 0 |
| | | | S3150 (parent strain): | 0 | 0 | 0 | 2 | 28 | 3 | 58 | 7 | 0 |

Example 5

Clade Analysis

Various novel FATB thioesterases were clustered according to a neighbor joining algorithm. These were found to form twelve clades as listed in Table 1a. Putative function was assigned based on expression in *Prototheca* as described above.

The described embodiments of the invention are intended to be merely exemplary and numerous variations and modifications will be apparent to those skilled in the art. All such variations and modifications are intended to be within the scope of the present invention.

Sequence Listing

SEQ ID NO 1:
*Cinnamomum camphora* (Cc) FATB1b variant M25L, M322R, ΔT367-D368 amino acid sequence
MATTSLASAFCSMKAVMLARDGRGLKPRSSDLQLRAGNAQTSLKMINGTKFSYTESLKKLPDWSMLFAVI

TTIFSAAEKQWTNLEWKPKPNPPQLLDDHFGPHGLVFRRTFAIRSYEVGPDRSTSIVAVMNHLQEAALNHA

KSVGILGDGFGTTLEMSKRDLIWVVKRTHVAVERYPAWGDTVEVECWVGASGNNGRRHDFLVRDCKTG

EILTRCTSLSVMMNTRTRRLSKIPEEVRGEIGPAFIDNVAVKDEEIKKPQKLNDSTADYIQGGLTPRWNDLDI

NQHVNNIKYVDWILETVPDSIFESHHISSFTIEYRRECTRDSVLQSLITVSGGSSEAGLVCEHLLQLEGGSEV

LRAKTEWRPKLSFRGISVIPAESSV*

SEQ ID NO 2:
*Cinnamomum camphora* (Cc) FATB1b variant M25L, M322R, ΔT367-D368 coding DNA sequence
TTAGCTTCTGCTTTCTGCTCGATGAAAGCTGTAATGTTGGCTCGTGATGGCAGGGGCTTGAAACCCAGG

AGCAGTGATTTGCAGCTGAGGGCGGGAAATGCACAAACCTCTTTGAAGATGATCAATGGGACCAAGTT

CAGTTACACAGAGAGCTTGAAAAAGTTGCCTGACTGGAGCATGCTCTTTGCAGTGATCACGACCATCT

TTTCGGCTGCTGAGAAGCAGTGGACCAATCTAGAGTGGAAGCCGAAGCCGAATCCACCCCAGTTGCTT

GATGACCATTTTGGGCCGCATGGGTTAGTTTTCAGGCGCACCTTTGCCATCAGATCGTATGAGGTGGG

ACCTGACCGCTCCACATCTATAGTGGCTGTTATGAATCACTTGCAGGAGGCTGCACTTAATCATGCGA

AGAGTGTGGGAATTCTAGGAGATGGATTCGGTACGACGCTAGAGATGAGTAAGAGAGATCTGATATG

GGTTGTGAAACGCACGCATGTTGCTGTGGAACGGTACCCTGCTTGGGGTGATACTGTTGAAGTAGAGT

GCTGGGTTGGTGCATCGGGAAATAATGGCAGGCGCCATGATTTCCTTGTCCGGGACTGCAAAACAGGC

GAAATTCTTACAAGATGTACCAGTCTTTCGGTGATGATGAATACAAGGACAAGGAGGTTGTCCAAAAT

CCCTGAAGAAGTTAGAGGGGAGATAGGGCCTGCATTCATTGATAATGTGGCTGTCAAGGACGAGGAA

ATTAAGAAACCACAGAAGCTCAATGACAGCACTGCAGATTACATCCAAGGAGGATTGACTCCTCGATG

GAATGATTTGGATATCAATCAGCACGTTAACAACATCAAATACGTTGACTGGATTCTTGAGACTGTCC

CAGACTCAATCTTTGAGAGTCATCATATTTCCAGCTTCACTATTGAATACAGGAGAGAGTGCACGAGG

GATAGCGTGCTGCAGTCCCTGACCACTGTCTCCGGTGGCTCGTCGGAAGCTGGGTTAGTGTGCGAGCA

CTTGCTCCAGCTTGAAGGTGGGTCTGAGGTATTGAGGGCAAAAACAGAGTGGAGGCCTAAGCTTAGTT

TCAGAGGGATTAGTGTGATACCCGCAGAATCGAGTGTCTAA

SEQ ID NO 3:
*Cinnamomum camphora* (Cc) FATB1b variant M25L, M322R, ΔT367-D368 coding DNA sequence codon optimized for *Prototheca moriformis*
TTAGCTTCTGCTTTCTGCTCGATGAAAGCTGTAATGTTGGCTCGTGATGGCAGGGGCTTGAAACCCAGG

AGCAGTGATTTGCAGCTGAGGGCGGGAAATGCACAAACCTCTTTGAAGATGATCAATGGGACCAAGTT

CAGTTACACAGAGAGCTTGAAAAAGTTGCCTGACTGGAGCATGCTCTTTGCAGTGATCACGACCATCT

TTTCGGCTGCTGAGAAGCAGTGGACCAATCTAGAGTGGAAGCCGAAGCCGAATCCACCCCAGTTGCTT

GATGACCATTTTGGGCCGCATGGGTTAGTTTTCAGGCGCACCTTTGCCATCAGATCGTATGAGGTGGG

ACCTGACCGCTCCACATCTATAGTGGCTGTTATGAATCACTTGCAGGAGGCTGCACTTAATCATGCGA

AGAGTGTGGGAATTCTAGGAGATGGATTCGGTACGACGCTAGAGATGAGTAAGAGAGATCTGATATG

-continued

GGTTGTGAAACGCACGCATGTTGCTGTGGAACGGTACCCTGCTTGGGGTGATACTGTTGAAGTAGAGT

GCTGGGTTGGTGCATCGGGAAATAATGGCAGGCGCCATGATTTCCTTGTCCGGGACTGCAAAACAGGC

GAAATTCTTACAAGATGTACCAGTCTTTCGGTGATGATGAATACAAGGACAAGGAGGTTGTCCAAAAT

CCCTGAAGAAGTTAGAGGGGAGATAGGGCCTGCATTCATTGATAATGTGGCTGTCAAGGACGAGGAA

ATTAAGAAACCACAGAAGCTCAATGACAGCACTGCAGATTACATCCAAGGAGGATTGACTCCTCGATG

GAATGATTTGGATATCAATCAGCACGTTAACAACATCAAATACGTTGACTGGATTCTTGAGACTGTCC

CAGACTCAATCTTTGAGAGTCATCATATTTCCAGCTTCACTATTGAATACAGGAGAGAGTGCACGAGG

GATAGCGTGCTGCAGTCCCTGACCACTGTCTCCGGTGGCTCGTCGGAAGCTGGGTTAGTGTGCGAGCA

CTTGCTCCAGCTTGAAGGTGGGTCTGAGGTATTGAGGGCAAAAACAGAGTGGAGGCCTAAGCTTAGTT

TCAGAGGGATTAGTGTGATACCCGCAGAATCGAGTGTCTAA

SEQ ID NO:4
*Cinnamomum camphora* (Cc) FATB4 amino acid sequence
MVITSLASAYFSMKAVMLAPDGRG1KPRSSGLQVRAGNERNSCKVINGTKVKDTEGLKGCSTLQGQSML

DDHFGLHGLVFRRTFAIRCYEVGPDRSTSIMAVMNHLQEAARNHAESLGLLGDGFGETLEMSKRDLIWVV

RRTHVAVERYPAWGDTVEVEAWVGASGNTGMRRDFLVRDCKTGHILTRCTSVSVMMNMRTRRLSKIPQE

VRAEIDPLFIEKVAVKEGEIKKLQKLNDSTADYIQGGWTPRWNDLDVNQHVNNIIYVGWIFKSVPDSISENH

HLSSITLEYRRECTRGNKLQSLTTVCGGSSEAGIICEHLLQLEDGSEVLRARTEWRPKHTDSFQGISERFPQQ

EPHK

SEQ ID NO: 5
*Cinnamomum camphora* (Cc) FATB4 coding DNA sequence
ATGGTCACCACCTCTTTAGCTTCCGCTTACTTCTCGATGAAAGCTGTAATGTTGGCTCCTGACGGCAGG

GGCATAAAGCCCAGGAGCAGTGGTTTGCAGGTGAGGGCGGGAAATGAACGAAACTCTTGCAAGGTGA

TCAATGGGACCAAGGTCAAAGACACGGAGGGCTTGAAAGGGTGCAGCACGTTGCAAGGCCAGAGCAT

GCTTGATGACCATTTTGGTCTGCATGGGCTAGTTTTCAGGCGCACCTTTGCAATCAGATGCTATGAGGT

TGGACCTGACCGCTCCACATCCATAATGGCTGTTATGAATCACTTGCAGGAAGCTGCACGTAATCATG

CGGAGAGTCTGGGACTTCTAGGAGATGGATTCGGTGAGACACTGGAGATGAGTAAGAGAGATCTGAT

ATGGGTTGTGAGACGCACGCATGTTGCTGTGGAACGGTACCCTGCTTGGGGCGATACTGTTGAAGTCG

AGGCCTGGGTGGGTGCATCAGGTAACACTGGCATGCGCCGCGATTTCCTTGTCCGCGACTGCAAAACT

GGCCACATTCTTACAAGATGTACCAGTGTTTCAGTGATGATGAATATGAGGACAAGGAGATTGTCCAA

AATTCCCCAAGAAGTTAGAGCGGAGATTGACCCTCTTTTCATTGAAAAGGTTGCTGTCAAGGAAGGGG

AAATTAAAAAATTACAGAAGTTGAATGATAGCACTGCAGATTACATTCAAGGGGGTTGGACTCCTCGA

TGGAATGATTTGGATGTCAATCAGCACGTGAACAATATCATATACGTTGGCTGGATTTTTAAGAGCGT

CCCAGACTCTATCTCTGAGAATCATCATCMCTAGCATCACTCTCGAATACAGGAGAGAGTGCACAA

GGGGCAACAAGCTGCAGTCCCTGACCACTGTTTGTGGTGGCTCGTCGGAAGCTGGGATCATATGTGAG

CACCTACTCCAGCTTGAGGATGGGTCTGAGGTTTTGAGGGCAAGAACAGAGTGGAGGCCCAAGCACA

CCGATAGTTTCCAAGGCATTAGTGAGAGATTCCCGCAGCAAGAACCGCATAAGTAA

SEQ ID NO: 6
*Cinnamomum camphora* (Cc) FATB4 coding DNA sequence codon optimized for *Prototheca moriformis*
ATGGTGACCACCTCCCtGGCCTCCGCCTACTTCTCCATGAAGGCCGTGATGCTGGCCCCCGACGGCCGC

GGCATCAAGCCCCGCTCCTCCGGCCTGCAGGTGCGCGCCGGCAACGAGCGCAACTCCTGCAAGGTGAT

CAACGGCACCAAGGTGAAGGACACCGAGGGCCTGAAGGGCTGCTCCACCCTGCAGGGCCAGTCCATG

CTGGACGACCACTTCGGCCTGCACGGCCTGGTGTTCCGCCGCACCTTCGCCATCCGCTGCTACGAGGTG

GGCCCCGACCGCTCCACCTCCATCATGGCCGTGATGAACCACCTGCAGGAGGCCGCCCGCAACCACGC

-continued

CGAGTCCCTGGGCCTGCTGGGCGACGGCTTCGGCGAGACCCTGGAGATGTCCAAGCGCGACCTGATCT

GGGTGGTGCGCCGCACCCACGTGGCCGTGGAGCGCTACCCCGCCTGGGGCGACACCGTGGAGGTGGA

GGCCTGGGTGGGCGCCTCCGGCAACACCGGCATGCGCCGCGACTTCCTGGTGCGCGACTGCAAGACCG

GCCACATCCTGACCCGCTGCACCTCCGTGTCCGTGATGATGAACATGCGCACCCGCCGCCTGTCCAAG

ATCCCCCAGGAGGTGCGCGCCGAGATCGACCCCCTGTTCATCGAGAAGGTGGCCGTGAAGGAGGGCG

AGATCAAGAAGCTGCAGAAGCTGAACGACTCCACCGCCGACTACATCCAGGGCGGCTGGACCCCCCG

CTGGAACGACCTGGACGTGAACCAGCACGTGAACAACATCATCTACGTGGGCTGGATCTTCAAGTCCG

TGCCCGACTCCATCTCCGAGAACCACCACCTGTCCTCCATCACCCTGGAGTACCGCCGCGAGTGCACC

CGCGGCAACAAGCTGCAGTCCCTGACCACCGTGTGCGGCGGCTCCTCCGAGGCCGGCATCATCTGCGA

GCACCTGCTGCAGCTGGAGGACGGCTCCGAGGTGCTGCGCGCCCGCACCGAGTGGCGCCCCAAGCAC

ACCGACTCCTTCCAGGGCATCTCCGAGCGCTTCCCCCAGCAGGAGCCCCACAAGTGA

SEQ ID NO: 7
*Cinnamomum camphora* (Cc) FATB3 amino acid sequence
MVATAAASAFFPVGAPATSSATSAKASMMPDNLDARGIKPKPASSSGLQVKANAHASPKINGSKVSTDTL

KGEDTLTSSPAPRTFINQLPDWSMFLAAITTIFLAAEKQWTNLDWKPRRPDMLADPFGIGRFMQDGLIFRQH

FAIRSYEIGADRTASIETLMNHLQETALNHVRSAGLLGDGFGATPEMSRRDLIWVVTRMQVLVDRYPAWG

DIVEVETWVGASGKNGMRRDWLVRDSQTGEILTRATSVWVMNINKRTRRLSKLPEEVRGEIGPYFIEDVAII

EEDNRKLQKLNENTADNVRRGLTPRWSDLDVNQHVNNVKYIGWILESAPGSILESHELSCMTLEYRRECG

KDSVLQSMTAVSGGGSAAGGSPESSVECDHLLQLESGPEVVRGRTEWRPKSANNSRSILEMPAESL

SEQ ID NO: 8
*Cinnamomum camphora* (Cc) FATB3 coding DNA sequence
ATGGTTGCCACCGCTGCTGCTTCTGCTTTCTTCCCGGTCGGTGCTCCGGCTACGTCATCTGCAACTTCAG

CCAAAGCGTCGATGATGCCTGATAATTTGGATGCCAGAGGCATCAAACCGAAGCCGGCTTCGTCCAGC

GGCTTGCAGGTTAAGGCAAATGCCCATGCCTCTCCCAAGATTAATGGTTCCAAGGTGAGCACGGATAC

CTTGAAGGGGGAAGACACCTTAACTTCCTCGCCCGCCCCACGGACCTTTATCAACCAATTGCCTGACT

GGAGCATGTTCCTTGCTGCCATCACAACTATTTTCTTGGCTGCCGAGAAGCAGTGGACGAATCTCGACT

GGAAGCCCAGAAGACCCGACATGCTTGCTGACCCGTTTGGCATCGGGAGGTTTATGCAGGATGGGCTG

ATTTTCAGGCAGCACTTTGCAATCAGATCTTATGAGATTGGGGCTGATAGAACGGCGTCTATAGAGAC

TTTAATGAATCACTTGCAGGAGACTGCACTTAATCATGTGAGGAGTGCTGGACTCCTAGGTGATGGAT

TTGGTGCGACACCTGAGATGAGTAGAAGAGATCTGATATGGGTTGTAACACGTATGCAGGTTCTTGTG

GACCGCTACCCTGCTTGGGGTGATATTGTTGAAGTAGAGACCTGGGTTGGTGCATCTGGAAAAAATGG

TATGCGCCGTGATTGGCTTGTTCGGGACAGCCAAACTGGTGAAATTCTCACACGAGCTACCAGTGTTT

GGGTGATGATGAATAAACGGACAAGGCGATTGTCCAAACTTCCTGAAGAAGTTAGAGGGGAAATAGG

GCCTTATTTTATAGAAGATGTTGCTATCATAGAGGAGGACAACAGGAAACTACAGAAGCTCAATGAAA

ACACTGCTGATAATGTTCGAAGGGGTTTGACTCCTCGCTGGAGTGATCTGGATGTTAATCAGCATGTG

AACAATGTCAAATACATTGG'TTGGATTCTTGAGAGTGCACCAGGATCCATCTTGGAGAGTCATGAGCT

TTCCTGCATGACCCTTGAATACAGGAGAGAATGTGGGAAGGACAGTGTGCTGCAGTCAATGACTGCTG

TCTCTGGTGGAGGCAGTGCAGCAGGTGGCTCACCAGAATCTAGCGTTGAGTGTGACCACTTGCTCCAG

CTAGAGAGTGGGCCTGAAGTTGTGAGGGGAAGAACCGAGTGGAGGCCCAAGAGTGCTAATAACTCGA

GGAGCATCCTGGAGATGCCGGCCGAGAGC

-continued

SEQ ID NO: 9
*Cinnamomum camphora* (Cc) FATB4 coding DNA sequence codon optimized for *Prototheca moriformis*
ATGGTGGCCACCGCCGCCGCCTCCGCCTTCTTCCCCGTGGGCGCCCCCGCCACCTCCTCCGCCACCTCC

GCCAAGGCCTCCATGATGCCCGACAACCTGGACGCCCGCGGCATCAAGCCCAAGCCCGCCTCCTCCTC

CGGCCTGCAGGTGAAGGCCAACGCCCACGCCTCCCCCAAGATCAACGGCTCCAAGGTGTCCACCGACA

CCCTGAAGGGCGAGGACACCCTGACCTCCTCCCCCGCCCCCCGCACCTTCATCAACCAGCTGCCCGAC

TGGTCCATGTTCCTGGCCGCCATCACCACCATCTTCCTGGCCGCCGAGAAGCAGTGGACCAACCTGGA

CTGGAAGCCCCGCCGCCCCGACATGCTGGCCGACCCCTTCGGCATCGGCCGCTTCATGCAGGACGGCC

TGATCTTCCGCCAGCACTTCGCCATCCGCTCCTACGAGATCGGCGCCGACCGCACCGCCTCCATCGAG

ACCCTGATGAACCACCTGCAGGAGACCGCCCTGAACCACGTGCGCTCCGCCGGCCTGCTGGGCGACGG

CTTCGGCGCCACCCCCGAGATGTCCCGCCGCGACCTGATCTGGGTGGTGACCCGCATGCAGGTGCTGG

TGGACCGCTACCCCGCCTGGGGCGACATCGTGGAGGTGGAGACCTGGGTGGGCGCCTCCGGCAAGAA

CGGCATGCGCCGCGACTGGCTGGTGCGCGACTCCCAGACCGGCGAGATCCTGACCCGCGCCACCTCCG

TGTGGGTGATGATGAACAAGCGCACCCGCCGCCTGTCCAAGCTGCCCGAGGAGGTGCGCGGCGAGAT

CGGCCCCTACTTCATCGAGGACGTGGCCATCATCGAGGAGGACAACCGCAAGCTGCAGAAGCTGAAC

GAGAACACCGCCGACAACGTGCGCCGCGGCCTGACCCCCCGCTGGTCCGACCTGGACGTGAACCAGC

ACGTGAACAACGTGAAGTACATCGGCTGGATCCTGGAGTCCGCCCCCGGCTCCATCCTGGAGTCCCAC

GAGCTGTCCTGCATGACCCTGGAGTACCGCCGCGAGTGCGGCAAGGACTCCGTGCTGCAGTCCATGAC

CGCCGTGTCCGGCGGCGGCTCCGCCGCCGGCGGCTCCCCCGAGTCCTCCGTGGAGTGCGACCACCTGC

TGCAGCTGGAGTCCGGCCCCGAGGTGGTGCGCGGCCGCACCGAGTGGCGCCCCAAGTCCGCCAACAA

CTCCCGCTCCATCCTGGAGATGCCCGCCGAGTCCCTGTGA

SEQ ID NO: 10
*Cuphea hyssopifolia* (Chs) FATB I amino acid sequence
MVATNAAAFSAYTFFLTSPTHGYSSKRLADTQNGYPGTSLKSKSTPPPAAAAARNGALPLLASICKCPKKA

DGSMQLDSSLVFGFQFYIRSYEVGADQTVSIQTVLNYLQEAAINHVQSAGYFGDSFGATPEMTKRNLIWVI

TKMQVLVDRYPAWGDVVQVDTWTCSSGKNSMQRDWFVRDLKTGDIITRASSVWVLMNRLTRKLSKIPE

AVLEEAKLFVMNTAPTVDDNRKLPKLDGSSADYVLSGLTPRWSDLDMNQHVNNVKYIAWILESVPQSIPE

THKLSAITVEYRRECGKNSVLQSLTNVSGDGITCGNSIIECHHLLQLETGPEILLARTEWISKEPGFRGAPIQA

EKVYNNK*

SEQ ID NO: 11
*Cuphea hyssopifolia* (Chs) FATB1 coding DNA sequence
ATGGTTGCCACTAATGCTGCTGCCTTTTCTGCTTATACTTTCTTCCTTACTTCACCAACTCATGGTTACT

CTTCCAAACGTCTCGCCGATACTCAAAATGGTTATCCGGGTACCTCCTTGAAATCGAAATCCACTCCTC

CACCAGCTGCTGCTGCTGCTCGTAACGGTGCATTGCCACTGCTGGCCTCCATCTGCAAATGCCCCAAAA

AGGCTGATGGGAGTATGCAACTAGACAGCTCCTTGGTCTTCGGGTTTCAATTTTACATTAGATCATATG

AAGTGGGTGCGGATCAAACCGTGTCAATACAGACAGTACTCAATTACTTACAGGAGGCAGCCATCAAT

CATGTTCAGAGTGCTGGCTATTTTGGTGATAGTTTTGGCGCCACCCCGGAAATGACCAAGAGGAACCT

CATCTGGGTTATCACTAAGATGCAGGTTTTGGTGGATCGCTATCCCGCTTGGGGCGATGTTGTTCAAGT

TGATACATGGACCTGTAGTTCTGGTAAAAACAGCATGCAGCGTGATTGGTTCGTACGGGATCTCAAAA

CTGGAGATATTATAACAAGAGCCTCGAGCGTGTGGGTGCTGATGAATAGACTCACCAGAAAATTATCA

AAAATTCCTGAAGCAGTTCTGGAAGAAGCAAAACTTTTTGTGATGAACACTGCCCCCACCGTAGATGA

CAACAGGAAGCTACCAAAGCTGGATGGCAGCAGTGCTGATTATGTCCTCTCTGGCTTAACTCCTAGAT

GGAGCGACTTAGATATGAACCAGCATGTCAACAATGTGAAGTACATAGCCTGGATCCTTGAGAGTGTC

-continued

CCTCAGAGCATACCGGAGACACACAAGCTGTCAGCGATAACCGTGGAGTACAGGAGAGAATGTGGCA

AGAACAGCGTCCTCCAGTCTCTGACCAACGTCTCCGGGGATGGAATCACATGTGGAAACAGTATTATC

GAGTGCCACCATTTGCTTCAACTTGAGACTGGCCCAGAGATTCTACTAGCGCGGACGGAGTGGATATC

CAAGGAACCTGGGTTCAGGGGAGCTCCAATCCAGGCAGAGAAAGTCTACAACAACAAATAA

SEQ ID NO: 12
*Cuphea hyssopifolia* (Chs) FATB1 coding DNA sequence codon optimized for *Prototheca moriformis*
ATGGTGGCCACCAACGCCGCCGCCTTCTCCGCCTACACCTTCTTCCTGACCTCCCCCACCCACGGCTAC

TCCTCCAAGCGCCTGGCCGACACCCAGAACGGCTACCCCGGCACCTCCCTGAAGTCCAAGTCCACCCC

CCCCCCCGCCGCCGCCGCCGCCCGCAACGGCGCCCTGCCCCTGCTGGCCTCCATCTGCAAGTGCCCCA

AGAAGGCCGACGGCTCCATGCAGCTGGACTCCTCCCTGGTGTTCGGCTTCCAGTTCTACATCCGCTCCT

ACGAGGTGGGCGCCGACCAGACCGTGTCCATCCAGACCGTGCTGAACTACCTGCAGGAGGCCGCCATC

AACCACGTGCAGTCCGCCGGCTACTTCGGCGACTCMCGGCGCCACCCCCGAGATGACCAAGCGCAA

CCTGATCTGGGTGATCACCAAGATGCAGGTGCTGGTGGACCGCTACCCCGCCTGGGGCGACGTGGTGC

AGGTGGACACCTGGACCTGCTCCTCCGGCAAGAACTCCATGCAGCGCGACTGGTTCGTGCGCGACCTG

AAGACCGGCGACATCATCACCCGCGCCTCCTCCGTGTGGGTGCTGATGAACCGCCTGACCCGCAAGCT

GTCCAAGATCCCCGAGGCCGTGCTGGAGGAGGCCAAGCTGTTCGTGATGAACACCGCCCCCACCGTGG

ACGACAACCGCAAGCTGCCCAAGCTGGACGGCTCCTCCGCCGACTACGTGCTGTCCGGCCTGACCCCC

CGCTGGTCCGACCTGGACATGAACCAGCACGTGAACAACGTGAAGTACATCGCCTGGATCCTGGAGTC

CGTGCCCCAGTCCATCCCCGAGACCCACAAGCTGTCCGCCATCACCGTGGAGTACCGCCGCGAGTGCG

GCAAGAACTCCGTGCTGCAGTCCCTGACCAACGTGTCCGGCGACGGCATCACCTGCGGCAACTCCATC

ATCGAGTGCCACCACCTGCTGCAGCTGGAGACCGGCCCCGAGATCCTGCTGGCCCGCACCGAGTGGAT

CTCCAAGGAGCCCGGCTTCCGCGGCGCCCCCATCCAGGCCGAGAAGGTGTACAACAACAAGTGA

SEQ ID NO: 13
*Cuphea hyssopifolia* (Chs) FATB2 amino acid sequence
MVATAASSAFFPVPSPDASSRPGKLGNGSSSLSPLKPKLMANGGLQVKANASAPPKINGSSVGLKSGSLKT

QEDTPSAPPPRTFINQLPDWSMLLAAITTVFLAAEKQWMMLDWKPKRPDMLVDPFGLGRIVQDGLVFRQN

FSIRSYEIGADRTASIETVMNHLQETALNHVKSAGLLNDGFGRTLEMYKRDLIWVVAKMQVMVNRYPTW

GDTVEVNTWVAKSGKNGMRRDWLISDCNTGEILTRASSVWVMNINQKTRRLSKIPDEVRHEIEPHFVDSAP

VIEDDDRKLPKLDEKTADSIRKGLTPKWNDLDVNQHVNNVKYIGWILESTPPEVLETQELCSLTLEYRREC

GRESVLESLTAVDPSGKGSGSQFQHLLRLEDGGEIVKGRTEWRPKTAGINGPIASGETSPGDSS*

SEQ ID NO: 14
*Cuphea hyssopifolia* (Chs) FATB2 coding DNA sequence
ATGGTGGCTACCGCTGCAAGTTCAGCATTCTTCCCTGTGCCGTCCCCCGACGCCTCCTCTAGACCTGGA

AAGCTCGGCAATGGGTCATCGAGCTTGAGCCCCCTCAAGCCCAAATTGATGGCCAATGGCGGGTTGCA

GGTTAAGGCAAACGCCAGTGCCCCTCCTAAGATCAATGGTTCTTCGGTCGGTCTAAAGTCCGGCAGTC

TCAAGACTCAGGAAGACACTCCTTCGGCGCCTCCTCCCCGGACTTTTATTAACCAGCTGCCTGATTGGA

GTATGCTTCTTGCTGCAATCACTACTGTCTTCTTGGCAGCAGAGAAGCAGTGGATGATGCTTGATTGGA

AACCCAAGAGGCCTGACATGCTTGTGGACCCGTTCGGATTGGGAAGGATTGTTCAAGATGGGCTTGTG

TTCAGGCAGAATTTTTCGATTAGGTCCTATGAAATAGGCGCTGATCGCACTGCGTCTATAGAGACGGT

GATGAACCACTTGCAGGAAACAGCTCTCAATCATGTTAAGAGTGCTGGGCTTCTTAATGACGGCTTTG

GTCGTACTCTTGAGATGTATAAAAGGGACCTTATTTGGGTTGTTGCAAAAATGCAGGTCATGGTTAAC

CGCTATCCTACTTGGGGCGACACGGTTGAAGTGAATACTTGGGTTGCCAAGTCAGGGAAAAATGGTAT

GCGTCGTGATTGGCTCATAAGTGATTGCAATACAGGAGAAATTCTTACTAGAGCATCAAGTGTGTGGG

-continued

TCATGATGAATCAAAAGACAAGAAGATTGTCAAAAATTCCAGATGAGGTTCGACATGAGATAGAGCC

TCATTTCGTGGACTCTGCTCCCGTCATTGAAGATGATGACCGGAAACTTCCCAAGCTGGATGAGAAGA

CTGCTGACTCCATCCGCAAGGGTCTAACTCCGAAGTGGAATGACTTGGATGTCAATCAGCACGTCAAC

AACGTGAAGTACATTGGGTGGATTCTTGAGAGTACTCCACCAGAAGTTCTGGAGACCCAGGAGTTATG

TTCCCTTACCCTGGAATATAGGCGGGAATGCGGAAGGGAGAGCGTGCTGGAGTCCCTCACTGCTGTGG

ACCCCTCTGGAAAGGGCTCTGGGTCTCAGTTCCAGCACCTTCTGCGGCTTGAGGATGGAGGTGAGATT

GTGAAGGGGAGAACTGAGTGGCGACCCAAGACTGCAGGAATCAATGGGCCAATAGCATCCGGGGAGA

CCTCACCTGGAGACTCTTCTTAG

SEQ ID NO: 15
*Cuphea hyssopifolia* (Chs) FATB2 coding DNA sequence codon optimized for *Prototheca moriformis*
ATGGTGGCCACCGCCGCCTCCTCCGCCTTCTTCCCCGTGCCCTCCCCCGACGCCTCCTCCCGCCCCGGC

AAGCTGGGCAACGGCTCCTCCTCCCTGTCCCCCCTGAAGCCCAAGCTGATGGCCAACGGCGGCCTGCA

GGTGAAGGCCAACGCCTCCGCCCCCCCAAGATCAACGGCTCCTCCGTGGGCCTGAAGTCCGGCTCCC

TGAAGACCCAGGAGGACACCCCCTCCGCCCCCCCCCCCCGCACCTTCATCAACCAGCTGCCCGACTGG

TCCATGCTGCTGGCCGCCATCACCACCGTGTTCCTGGCCGCCGAGAAGCAGTGGATGATGCTGGACTG

GAAGCCCAAGCGCCCCGACATGCTGGTGGACCCCTTCGGCCTGGGCCGCATCGTGCAGGACGGCCTGG

TGTTCCGCCAGAACTTCTCCATCCGCTCCTACGAGATCGGCGCCGACCGCACCGCCTCCATCGAGACC

GTGATGAACCACCTGCAGGAGACCGCCCTGAACCACGTGAAGTCCGCCGGCCTGCTGAACGACGGCTT

CGGCCGCACCCTGGAGATGTACAAGCGCGACCTGATCTGGGTGGTGGCCAAGATGCAGGTGATGGTG

AACCGCTACCCCACCTGGGGCGACACCGTGGAGGTGAACACCTGGGTGGCCAAGTCCGGCAAGAACG

GCATGCGCCGCGACTGGCTGATCTCCGACTGCAACACCGGCGAGATCCTGACCCGCGCCTCCTCCGTG

TGGGTGATGATGAACCAGAAGACCCGCCGCCTGTCCAAGATCCCCGACGAGGTGCGCCACGAGATCG

AGCCCCACTTCGTGGACTCCGCCCCCGTGATCGAGGACGACGACCGCAAGCTGCCCAAGCTGGACGAG

AAGACCGCCGACTCCATCCGCAAGGGCCTGACCCCCAAGTGGAACGACCTGGACGTGAACCAGCACG

TGAACAACGTGAAGTACATCGGCTGGATCCTGGAGTCCACCCCCCCCGAGGTGCTGGAGACCCAGGA

GCTGTGCTCCCTGACCCTGGAGTACCGCCGCGAGTGCGGCCGCGAGTCCGTGCTGGAGTCCCTGACCG

CCGTGGACCCCTCCGGCAAGGGCTCCGGCTCCCAGTTCCAGCACCTGCTGCGCCTGGAGGACGGCGGC

GAGATCGTGAAGGGCCGCACCGAGTGGCGCCCCAAGACCGCCGGCATCAACGGCCCCATCGCCTCCG

GCGAGACCTCCCCCGGCGACTCCTCCTGA

SEQ ID NO: 16
*Cuphea hyssopifolia* (Chs) FATB2b + a.a. 248-259 variant amino acid sequence
MVATAASSAFFPVPSPDASSRPGKLGNGSSSLSPLKPKLMANGGLQVKANASAPPKINGSSVGLKSGSLKT

QEDTPSAPPPRTFINQLPDWSMLLAAITTVFLAAEKQWMMLDWKPKRPDMLVDPFGLGRIVQDGLVFRQN

FSIRSYEIGADRTASIETVMNELQETALNHVKSAGLLNDGFGRTLEMYKRDLIWVVAKMQVMVNRYPTW

GDTVEVNTWVAKSGKNGMRRDWLISDCNTGEILTRASSKSQIMLPLHYCSVWVMMNQKTRRLSKIPDEV

RHEIEPHFVDSAPVIEDDDRKLPKLDEKTADSIRKGLTPKWNDLDVNQHVNNVKYIGWILESTPPEVLETQE

LCSLTLEYRRECGRESVLESLTAVDPSGKGSGSQFQHLLRLEDGGEIVKGRTEWRPKTAGINGPIASGETSP

GDSS*

SEQ ID NO: 17
*Cuphea hyssopifolia* (Chs) FATB2b + a.a. 248-259 variant coding DNA sequence
ATGGTGGCTACCGCTGCAAGTTCAGCATTCTTCCCTGTGCCGTCCCCCGACGCCTCCTCTAGACCTGGA

AAGCTCGGCAATGGGTCATCGAGCTTGAGCCCCCTCAAGCCCAAATTGATGGCCAATGGCGGGTTGCA

-continued

GGTTAAGGCAAACGCCAGTGCCCCTCCTAAGATCAATGGTTCTTCGGTCGGTCTAAAGTCCGGCAGTC

TCAAGACTCAGGAAGACACTCCTTCGGCGCCTCCTCCCCGGACTTTTATTAACCAGCTGCCTGATTGGA

GTATGCTTCTTGCTGCAATCACTACTGTCTTCTTGGCAGCAGAGAAGCAGTGGATGATGCTTGATTGGA

AACCCAAGAGGCCTGACATGCTTGTGGACCCGTTCGGATTGGGAAGGATTGTTCAAGATGGGCTTGTG

TTCAGGCAGAATTTTTCGATTAGGTCCTATGAAATAGGCGCTGATCGCACTGCGTCTATAGAGACGGT

GATGAACCACTTGCAGGAAACAGCTCTCAATCATGTTAAGAGTGCTGGGCTTCTTAATGACGGCTTTG

GTCGTACTCTTGAGATGTATAAAAGGGACCTTATTTGGGTTGTTGCAAAAATGCAGGTCATGGTTAAC

CGCTATCCTACTTGGGGCGACACGGTTGAAGTGAATACTTGGGTTGCCAAGTCAGGGAAAAATGGTAT

GCGTCGTGATTGGCTCATAAGTGATTGCAATACAGGAGAAATTCTTACTAGAGCATCAAGTAAAAGCC

AAATTATGTTACCCTTACATTATTGCAGTGTGTGGGTCATGATGAATCAAAAGACAAGAAGATTGTCA

AAAATTCCAGATGAGGTTCGACATGAGATAGAGCCTCATTTCGTGGACTCTGCTCCCGTCATTGAAGA

TGATGACCGGAAACTTCCCAAGCTGGATGAGAAGACTGCTGACTCCATCCGCAAGGGTCTAACTCCGA

AGTGGAATGACTTGGATGTCAATCAGCACGTCAACAACGTGAAGTACATTGGGTGGATTCTTGAGAGT

ACTCCACCAGAAGTTCTGGAGACCCAGGAGTTATGTTCCCTTACCCTGGAATATAGGCGGGAATGCGG

AAGGGAGAGCGTGCTGGAGTCCCTCACTGCTGTGGACCCCTCTGGAAAGGGCTCTGGGTCTCAGTTCC

AGCACCTTCTGCGGCTTGAGGATGGAGGTGAGATTGTGAAGGGGAGAACTGAGTGGCGACCCAAGAC

TGCAGGAATCAATGGGCCAATAGCATCCGGGGAGACCTCACCTGGAGACTCTTCTTAG

SEQ ID NO: 18
*Cuphea hyssopifolia* (Chs) FATB2b + a.a. 248-259 variant coding DNA sequence codon optimized for *Prototheca moriformis*
ATGGTGGCCACCGCCGCCTCCTCCGCCTTCTTCCCCGTGCCCTCCCCCGACGCCTCCTCCCGCCCCGGC

AAGCTGGGCAACGGCTCCTCCTCCCTGTCCCCCCTGAAGCCCAAGCTGATGGCCAACGGCGGCCTGCA

GGTGAAGGCCAACGCCTCCGCCCCCCCCAAGATCAACGGCTCCTCCGTGGGCCTGAAGTCCGGCTCCC

TGAAGACCCAGGAGGACACCCCCTCCGCCCCCCCCCCCCGCACCTTCATCAACCAGCTGCCCGACTGG

TCCATGCTGCTGGCCGCCATCACCACCGTGTTCCTGGCCGCCGAGAAGCAGTGGATGATGCTGGACTG

GAAGCCCAAGCGCCCCGACATGCTGGTGGACCCCTTCGGCCTGGGCCGCATCGTGCAGGACGGCCTGG

TGTTCCGCCAGAACTTCTCCATCCGCTCCTACGAGATCGGCGCCGACCGCACCGCCTCCATCGAGACC

GTGATGAACCACCTGCAGGAGACCGCCCTGAACCACGTGAAGTCCGCCGGCCTGCTGAACGACGGCTT

CGGCCGCACCCTGGAGATGTACAAGCGCGACCTGATCTGGGTGGTGGCCAAGATGCAGGTGATGGTG

AACCGCTACCCCACCTGGGGCGACACCGTGGAGGTGAACACCTGGGTGGCCAAGTCCGGCAAGAACG

GCATGCGCCGCGACTGGCTGATCTCCGACTGCAACACCGGCGAGATCCTGACCCGCGCCTCCTCCAAG

TCCCAGATCATGCTGCCCCTGCACTACTGCTCCGTGTGGGTGATGATGAACCAGAAGACCCGCCGCCT

GTCCAAGATCCCCGACGAGGTGCGCCACGAGATCGAGCCCCACTTCGTGGACTCCGCCCCCGTGATCG

AGGACGACGACCGCAAGCTGCCCAAGCTGGACGAGAAGACCGCCGACTCCATCCGCAAGGGCCTGAC

CCCCAAGTGGAACGACCTGGACGTGAACCAGCACGTGAACAACGTGAAGTACATCGGCTGGATCCTG

GAGTCCACCCCCCCCGAGGTGCTGGAGACCCAGGAGCTGTGCTCCCTGACCCTGGAGTACCGCCGCGA

GTGCGGCCGCGAGTCCGTGCTGGAGTCCCTGACCGCCGTGGACCCCTCCGGCAAGGGCTCCGGCTCCC

AGTTCCAGCACCTGCTGCGCCTGGAGGACGGCGGCGAGATCGTGAAGGGCCGCACCGAGTGGCGCCC

CAAGACCGCCGGCATCAACGGCCCCATCGCCTCCGGCGAGACCTCCCCCGGCGACTCCTCCTGA

SEQ ID NO: 19
*Cuphea hyssopifolia* (Chs) FATB3 amino acid sequence
MVAAEASSALFSVRTPGTSPKPGKFGNWPTSLSVPFKSKSNHNGGFQVKANASARPKANGSAVSLKSGSL

DTQEDTSSSSSPPRTFINQLPDWSMLLSAITTVFVAAEKQWTMLDRKSKRPDMLMDPFGVDRVVQDGAVF

-continued

RQSFSIRSYEIGADRTASIETLMNIFQETSLNHCKSIGLLNDGFGRTPEMCKRDLIWVVTKMHVEVNRYPTW

GDTIEVNTWVSESGKTGMGRDWLISDCHTGEILIRATSMCAMMNQKTRRFSKFPYEVRQELAPHFVDSAP

VIEDYQKLHKLDVKTGDSICNGLTPRWNDLDVNQHVNNVKYIGWILESVPTEVFETQELCGLTLEYRRECG

RDSVLESVTAMDPSKEGDRSLYQHLLRLEDGADIAKGRTKWRPKNAGTNGAISTGKTSNGNSIS*

SEQ ID NO: 20
*Cuphea hyssopifolia* (Chs) FATB3 coding DNA sequence
ATGGTGGCTGCCGAAGCAAGTTCTGCACTCTTCTCCGTTCGAACCCCGGGAACCTCCCCTAAACCCGG

GAAGTTCGGGAATTGGCCAACGAGCTTGAGCGTCCCCTTCAAGTCCAAATCAAACCACAATGGCGGCT

TTCAGGTTAAGGCAAACGCCAGTGCCCGTCCTAAGGCTAACGGTTCTGCAGTAAGTCTAAAGTCTGGC

AGCCTCGACACTCAGGAGGACACTTCATCGTCGTCCTCTCCTCCTCGGACTTTCATTAACCAGTTGCCC

GACTGGAGTATGCTGCTGTCCGCGATCACGACCGTCTTCGTGGCGGCTGAGAAGCAGTGGACGATGCT

TGATCGGAAATCTAAGAGGCCCGACATGCTCATGGACCCGTTTGGGGTTGACAGGGTTGTTCAGGATG

GGGCTGTGTTCAGACAGAGTTTTTCGATTAGGTCTTACGAAATAGGCGCTGATCGAACAGCCTCTATA

GAGACGCTGATGAACATCTTCCAGGAAACATCTCTCAATCATTGTAAGAGTATCGGTCTTCTCAATGA

CGGCTTTGGTCGTACTCCTGAGATGTGTAAGAGGGACCTCATTTGGGTGGTTACAAAAATGCACGTCG

AGGTTAATCGCTATCCTACTTGGGGTGATACTATCGAGGTCAATACTTGGGTCTCCGAGTCGGGGAAA

ACCGGTATGGGTCGTGATTGGCTGATAAGTGATTGTCATACAGGAGAAATTCTAATAAGAGCAACGAG

CATGTGTGCTATGATGAATCAAAAGACGAGAAGATTCTCAAAATTTCCATATGAGGTTCGACAGGAGT

TGGCGCCTCATTTTGTGGACTCTGCTCCTGTCATTGAAGACTATCAAAAATTGCACAAGCTTGATGTGA

AGACGGGTGATTCCATTTGCAATGGCCTAACTCCAAGGTGGAATGACTTGGATGTCAATCAGCACGTT

AACAATGTGAAGTACATTGGGTGGATTCTCGAGAGTGTTCCAACGGAAGTTTTCGAGACCCAGGAGCT

ATGTGGCCTCACCCTTGAGTATAGGCGGGAATGCGGAAGGGACAGTGTGCTGGAGTCCGTGACCGCTA

TGGATCCATCAAAAGAGGGAGACAGATCTCTGTACCAGCACCTTCTTCGGCTTGAGGATGGGGCTGAT

ATCGCGAAGGGCAGAACCAAGTGGCGGCCGAAGAATGCAGGAACCAATGGGGCAATATCAACAGGA

AAGACTTCAAATGGAAACTCGATCTCTTAG

SEQ ID NO: 21
*Cuphea hyssopifolia* (Chs) FATB3 coding DNA sequence codon optimized for
*Prototheca moriformis*
ATGGTGGCCGCCGAGGCCTCCTCCGCCCTGTTCTCCGTGCGCACCCCCGGCACCTCCCCCAAGCCCGGC

AAGTTCGGCAACTGGCCCACCTCCCTGTCCGTGCCCTTCAAGTCCAAGTCCAACCACAACGGCGGCTT

CCAGGTGAAGGCCAACGCCTCCGCCCGCCCCAAGGCCAACGGCTCCGCCGTGTCCCTGAAGTCCGGCT

CCCTGGACACCCAGGAGGACACCTCCTCCTCCTCCTCCCCCCCCCGCACCTTCATCAACCAGCTGCCCG

ACTGGTCCATGCTGCTGTCCGCCATCACCACCGTGTTCGTGGCCGCCGAGAAGCAGTGGACCATGCTG

GACCGCAAGTCCAAGCGCCCCGACATGCTGATGGACCCCTTCGGCGTGGACCGCGTGGTGCAGGACG

GCGCCGTGTTCCGCCAGTCCTTCTCCATCCGCTCCTACGAGATCGGCGCCGACCGCACCGCCTCCATCG

AGACCCTGATGAACATCTTCCAGGAGACCTCCCTGAACCACTGCAAGTCCATCGGCCTGCTGAACGAC

GGCTTCGGCCGCACCCCCGAGATGTGCAAGCGCGACCTGATCTGGGTGGTGACCAAGATGCACGTGGA

GGTGAACCGCTACCCCACCTGGGGCGACACCATCGAGGTGAACACCTGGGTGTCCGAGTCCGGCAAG

ACCGGCATGGGCCGCGACTGGCTGATCTCCGACTGCCACACCGGCGAGATCCTGATCCGCGCCACCTC

CATGTGCGCCATGATGAACCAGAAGACCCGCCGCTTCTCCAAGTTCCCCTACGAGGTGCGCCAGGAGC

TGGCCCCCCACTTCGTGGACTCCGCCCCCGTGATCGAGGACTACCAGAAGCTGCACAAGCTGGACGTG

AAGACCGGCGACTCCATCTGCAACGGCCTGACCCCCCGCTGGAACGACCTGGACGTGAACCAGCACGT

GAACAACGTGAAGTACATCGGCTGGATCCTGGAGTCCGTGCCCACCGAGGTGTTCGAGACCCAGGAG

-continued

CTGTGCGGCCTGACCCTGGAGTACCGCCGCGAGTGCGGCCGCGACTCCGTGCTGGAGTCCGTGACCGC

CATGGACCCCTCCAAGGAGGGCGACCGCTCCCTGTACCAGCACCTGCTGCGCCTGGAGGACGGCGCCG

ACATCGCCAAGGGCCGCACCAAGTGGCGCCCCAAGAACGCCGGCACCAACGGCGCCATCTCCACCGG

CAAGACCTCCAACGGCAACTCCATCTCCTGA

SEQ ID NO: 22
*Cuphea hyssopifolia* (Chs) FATB3b (V204I, C239F, E243D, M251V variant)
amino acid sequence
MVAAEASSALFSVRTPGTSPKPGKFGNWPTSLSVPFKSKSNHNGGFQVKANASARPKANGSAVSLKSGSL

DTQEDTSSSSSPPRTFINQLPDWSMLLSAITTVFVAAEKQWTMLDRKSKRPDMLMDPFGVDRVVQDGAVF

RQSFSIRSYEIGADRTASIETLMNIFQETSLNHCKSIGLLNDGFGRTPEMCKRDLIWVVTICMHIEVNRYPTW

GDTIEVNTWVSESGKTGMGRDWLISDFHTGDILIRATSVCAMMNQKTRRFSKFPYEVRQELAPHFVDSAPV

IEDYQKLHKLDVKTGDSICNGLTPRWNDLDVNQHVNNVKYIGWILESVPTEVFETQELCGLTLEYRRECGR

DSVLESVTAMDPSKEGDRSLYQHLLRLEDGADIAKGRTKWRPKNAGTNGAISTGKTSNGNSIS*

SEQ ID NO: 23
*Cuphea hyssopifolia* (Chs) FATB3b (V204I, C239F, E243D, M251V variant)
coding DNA sequence
ATGGTGGCTGCCGAAGCAAGTTCTGCACTCTTCTCCGTTCGAACCCCGGGAACCTCCCCTAAACCCGG

GAAGTTCGGGAATTGGCCAACGAGCTTGAGCGTCCCCTTCAAGTCCAAATCAAACCACAATGGCGGCT

TTCAGGTTAAGGCAAACGCCAGTGCCCGTCCTAAGGCTAACGGTTCTGCAGTAAGTCTAAAGTCTGGC

AGCCTCGACACTCAGGAGGACACTTCATCGTCGTCCTCTCCTCCTCGGACTTTCATTAACCAGTTGCCC

GACTGGAGTATGCTGCTGTCCGCGATCACGACCGTCTTCGTGGCGGCTGAGAAGCAGTGGACGATGCT

TGATCGGAAATCTAAGAGGCCCGACATGCTCATGGACCCGTTTGGGGTTGACAGGGTTGTTCAGGATG

GGGCTGTGTTCAGACAGAGTTTTTCGATTAGGTCTTACGAAATAGGCGCTGATCGAACAGCCTCTATA

GAGACGCTGATGAACATMCCAGGAAACATCTCTCAATCATTGTAAGAGTATCGGTCTTCTCAATGA

CGGCTTTGGTCGTACTCCTGAGATGTGTAAGAGGGACCTCATTTGGGTGGTTACAAAAATGCACATCG

AGGTTAATCGCTATCCTACTTGGGGTGATACTATCGAGGTCAATACTTGGGTCTCCGAGTCGGGGAAA

ACCGGTATGGGTCGTGATTGGCTGATAAGTGATTTTCATACAGGAGACATTCTAATAAGAGCAACGAG

CGTGTGTGCTATGATGAATCAAAAGACGAGAAGATTCTCAAAATTTCCATATGAGGTTCGACAGGAGT

TAGCGCCTCATTTTGTGGACTCTGCTCCAGTCATTGAAGACTATCAAAAATTGCACAAGCTTGATGTGA

AGACGGGTGATTCCATTTGCAATGGCCTAACTCCAAGGTGGAATGACTTGGATGTCAATCAGCACGTT

AACAATGTGAAGTACATTGGGTGGATTCTCGAGAGTGTTCCAACGGAAGTTTTCGAGACCCAGGAGCT

ATGTGGCCTCACCCTTGAGTATAGGCGGGAATGCGGAAGGGACAGTGTGCTGGAGTCCGTGACCGCTA

TGGATCCCTCAAAAGAGGGAGACAGATCTCTGTACCAGCACCTTCTTCGGCTTGAGGATGGGGCTGAT

ATCGCGAAGGGCAGAACCAAGTGGCGGCCGAAGAATGCAGGAACCAATGGGGCAATATCAACAGGA

AAGACTTCAAATGGAAACTCGATCTCTTAG

SEQ ID NO: 24
*Cuphea hyssopifolia* (Chs) FATB3b (V204I, C239F, E243D, M251V variant)
coding DNA sequence codon optimized for *Prototheca moriformis*
ATGGTGGCCGCCGAGGCCTCCTCCGCCCTGTTCTCCGTGCGCACCCCCGGCACCTCCCCCAAGCCCGGC

AAGTTCGGCAACTGGCCCACCTCCCTGTCCGTGCCCTTCAAGTCCAAGTCCAACCACAACGGCGGCTT

CCAGGTGAAGGCCAACGCCTCCGCCCGCCCCAAGGCCAACGGCTCCGCCGTGTCCCTGAAGTCCGGCT

CCCTGGACACCCAGGAGGACACCTCCTCCTCCTCCTCCCCCCCCCGCACCTTCATCAACCAGCTGCCCG

ACTGGTCCATGCTGCTGTCCGCCATCACCACCGTGTTCGTGGCCGCCGAGAAGCAGTGGACCATGCTG

GACCGCAAGTCCAAGCGCCCCGACATGCTGATGGACCCCTTCGGCGTGGACCGCGTGGTGCAGGACG

GCGCCGTGTTCCGCCAGTCCTTCTCCATCCGCTCCTACGAGATCGGCGCCGACCGCACCGCCTCCATCG

-continued

AGACCCTGATGAACATCTTCCAGGAGACCTCCCTGAACCACTGCAAGTCCATCGGCCTGCTGAACGAC

GGCTTCGGCCGCACCCCCGAGATGTGCAAGCGCGACCTGATCTGGGTGGTGACCAAGATGCACATCGA

GGTGAACCGCTACCCCACCTGGGGCGACACCATCGAGGTGAACACCTGGGTGTCCGAGTCCGGCAAG

ACCGGCATGGGCCGCGACTGGCTGATCTCCGACTTCCACACCGGCGACATCCTGATCCGCGCCACCTC

CGTGTGCGCCATGATGAACCAGAAGACCCGCCGCTTCTCCAAGTTCCCCTACGAGGTGCGCCAGGAGC

TGGCCCCCCACTTCGTGGACTCCGCCCCCGTGATCGAGGACTACCAGAAGCTGCACAAGCTGGACGTG

AAGACCGGCGACTCCATCTGCAACGGCCTGACCCCCCGCTGGAACGACCTGGACGTGAACCAGCACGT

GAACAACGTGAAGTACATCGGCTGGATCCTGGAGTCCGTGCCCACCGAGGTGTTCGAGACCCAGGAG

CTGTGCGGCCTGACCCTGGAGTACCGCCGCGAGTGCGGCCGCGACTCCGTGCTGGAGTCCGTGACCGC

CATGGACCCCTCCAAGGAGGGCGACCGCTCCCTGTACCAGCACCTGCTGCGCCTGGAGGACGGCGCCG

ACATCGCCAAGGGCCGCACCAAGTGGCGCCCCAAGAACGCCGGCACCAACGGCGCCATCTCCACCGG

CAAGACCTCCAACGGCAACTCCATCTCCTGA

SEQ ID NO: 25
*Cuphea PSR23* (Cu) FATB3 amino acid sequence
MVVAAATSAFFPVPAPGTSPKPGKSGNWPSSLSPTFKPKSIPNAGFQVKANASAHPKANGSAVNLKSGSLN

TQEDTSSSPPPRAFLNQLPDWSMLLTAITTVFVAAEKQWTMLDRKSKRPDMLVDSVGLKCIVRDGLVSRQ

SFLIRSYEIGADRTASIETLMNFILQETSINHCKSLGLLNDGFGRTPGMCKNDLIWVLTKMQIMVNRYPTWG

DTVEINTWFSQSGKIGMASDWLISDCNTGEILIRATSVWAMMNQKTRRFSRLPYEVRQELTPHFVDSPHVIE

DNDQKLHKFDVKTGDSIRKGLTPRWNDLDVNQHVSNVKYIGWILESMPIEVLETQELCSLTVEYRRECGM

DSVLESVTAVDPSENGGRSQYKHLLRLEDGTDIVKSRTEWRPKNAGTNGAISTSTAKTSNGNSVS*

SEQ ID NO: 26
*Cuphea PSR23* (Cu) FATB3 coding DNA sequence
ATGGTGGTGGCTGCAGCAACTTCTGCATTCTTCCCCGTTCCAGCCCCGGGAACCTCCCCTAAACCCGGG

AAGTCCGGCAACTGGCCATCGAGCTTGAGCCCTACCTTCAAGCCCAAGTCAATCCCCAATGCCGGATT

TCAGGTTAAGGCAAATGCCAGTGCCCATCCTAAGGCTAACGGTTCTGCAGTAAATCTAAAGTCTGGCA

GCCTCAACACTCAGGAGGACACTTCGTCGTCCCCTCCTCCCCGGGCTTTCCTTAACCAGTTGCCTGATT

GGAGTATGCTTCTGACTGCAATCACGACCGTCTTCGTGGCGGCAGAGAAGCAGTGGACTATGCTTGAT

AGGAAATCTAAGAGGCCTGACATGCTCGTGGACTCGGTTGGGTTGAAGTGTATTGTTCGGGATGGGCT

CGTGTCCAGACAGAGTTTTTTGATTAGATCTTATGAAATAGGCGCTGATCGAACAGCCTCTATAGAGA

CGCTGATGAACCACTTGCAGGAAACATCTATCAATCATTGTAAGAGTTTGGGTCTTCTCAATGACGGCT

TTGGTCGTACTCCTGGGATGTGTAAAAACGACCTCATTTGGGTGCTTACAAAAATGCAGATCATGGTG

AATCGCTACCCAACTTGGGGCGATACTGTTGAGATCAATACCTGGTTCTCTCAGTCGGGGAAAATCGG

TATGGCTAGCGATTGGCTAATAAGTGATTGCAACACAGGAGAAATTCTTATAAGAGCAACGAGCGTGT

GGGCTATGATGAATCAAAAGACGAGAAGATTCTCAAGACTTCCATACGAGGTTCGCCAGGAGTTAAC

GCCTCATTTTGTGGACTCTCCTCATGTCATTGAAGACAATGATCAGAAATTGCATAAGTTTGATGTGAA

GACTGGTGATTCCATTCGCAAGGGTCTAACTCCGAGGTGGAACGACTTGGATGTGAATCAGCACGTAA

GCAACGTGAAGTACATTGGGTGGATTCTCGAGAGTATGCCAATAGAAGTTTTGGAGACACAGGAGCTA

TGCTCTCTCACCGTAGAATATAGGCGGGAATGCGGAATGGACAGTGTGCTGGAGTCCGTGACTGCTGT

GGATCCCTCAGAAAATGGAGGCCGGTCTCAGTACAAGCACCTTCTGCGGCTTGAGGATGGGACTGATA

TCGTGAAGAGCAGAACTGAGTGGCGACCGAAGAATGCAGGAACTAACGGGGCGATATCAACATCAAC

AGCAAAGACTTCAAATGGAAACTCGGTCTCTTAG

-continued

SEQ ID NO: 27
*Cuphea PSR23* (Cu) FATB3 coding DNA sequence codon optimized for
*Prototheca moriformis*
ATGGTGGTGGCCGCCGCCACCTCCGCCTTCTTCCCCGTGCCCGCCCCCGGCACCTCCCCCAAGCCCGGC

AAGTCCGGCAACTGGCCCTCCTCCCTGTCCCCCACCTTCAAGCCCAAGTCCATCCCCAACGCCGGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGACCGCCATCACCACCGTGTTCGTGGCCGCCGAGAAGCAGTGGACCATGCTGGACC

GCAAGTCCAAGCGCCCCGACATGCTGGTGGACTCCGTGGGCCTGAAGTGCATCGTGCGCGACGGCCTG

GTGTCCCGCCAGTCCTTCCTGATCCGCTCCTACGAGATCGGCGCCGACCGCACCGCCTCCATCGAGACC

CTGATGAACCACCTGCAGGAGACCTCCATCAACCACTGCAAGTCCCTGGGCCTGCTGAACGACGGCTT

CGGCCGCACCCCCGGCATGTGCAAGAACGACCTGATCTGGGTGCTGACCAAGATGCAGATCATGGTGA

ACCGCTACCCCACCTGGGGCGACACCGTGGAGATCAACACCTGGTTCTCCCAGTCCGGCAAGATCGGC

ATGGCCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCAGAAGCTGCACAAGTTCGACGTGAAG

ACCGGCGACTCCATCCGCAAGGGCCTGACCCCCCGCTGGAACGACCTGGACGTGAACCAGCACGTGTC

CAACGTGAAGTACATCGGCTGGATCCTGGAGTCCATGCCCATCGAGGTGCTGGAGACCCAGGAGCTGT

GCTCCCTGACCGTGGAGTACCGCCGCGAGTGCGGCATGGACTCCGTGCTGGAGTCCGTGACCGCCGTG

GACCCCTCCGAGAACGGCGGCCGCTCCCAGTACAAGCACCTGCTGCGCCTGGAGGACGGCACCGACA

TCGTGAAGTCCCGCACCGAGTGGCGCCCCAAGAACGCCGGCACCAACGGCGCCATCTCCACCTCCACC

GCCAAGACCTCCAACGGCAACTCCGTGTCCTGA

SEQ ID NO: 28
*Cuphea wrightii* (Cw) FATB3 amino acid sequence
MVVAAAASSAFFPVPAPRTTPKPGKFGNWPSSLSPPFKPKSNPNGRFQVKANVSPHPKANGSAVSLKSGSL

NTLEDPPSSPPPRTFLNQLPDWSRLRTAITTVFVAAEKQFTRLDRKSKRPDMLVDWFGSETIVQDGLVFRER

FSIRSYEIGADRTASIETLMNHLQDTSLNHCKSVGLLNDGFGRTSEMCIRDLIWVLTKMQIVVNRYPTWGD

TVEINSWFSQSGKEGMGRDWLISDCNTGEILVRATSAWAMMNQKTRRFSKLPCEVRQEIAPHFVDAPPVIE

DNDRKLHKFDVKTGDSICKGLTPGWNDLDVNQHVSNVKYIGWILESMPTEVLETQELCSLTLEYRRECGR

ESVVESVISMNPSKVGDRSQYQHLLRLEDGADIMKGRTEWRPKNAGTNRAIST*

SEQ ID NO: 29
*Cuphca wrightii* (Cw) FATB3 coding DNA sequence
ATGGTGGTGGCTGCTGCAGCAAGTTCTGCATTCTTCCCTGTTCCAGCACCTAGAACCACGCCTAAACCC

GGGAAGTTCGGCAATTGGCCATCGAGCTTGAGCCCGCCCTTCAAGCCCAAGTCAAACCCCAATGGTAG

ATTTCAGGTTAAGGCAAATGTCAGTCCTCATCCTAAGGCTAACGGTTCTGCAGTAAGTCTAAAGTCTG

GCAGCCTCAACACTCTGGAGGACCCTCCGTCGTCCCCTCCTCCTCGGACTTTCCTTAACCAGTTGCCTG

ATTGGAGTAGGCTTCGGACTGCAATCACGACCGTCTTCGTGGCGGCAGAGAAGCAGTTCACTAGGCTC

GATCGAAAATCTAAGAGGCCTGACATGCTAGTGGACTGGTTTGGGTCAGAGACTATTGTTCAGGATGG

GCTCGTGTTCAGAGAGAGATTTTCGATCAGGTCTTACGAAATAGGCGCTGATCGAACAGCCTCTATAG

AGACGCTGATGAACCACTTGCAGGACACATCTCTGAATCATTGTAAGAGTGTGGGTCTTCTCAATGAC

GGCTTTGGTCGTACCTCGGAGATGTGTACAAGAGACCTCATTTGGGTGCTTACAAAAATGCAGATCGT

GGTGAATCGCTATCCAACTTGGGGCGATACTGTCGAGATCAATAGCTGGTTCTCCCAGTCGGGGAAAA

TCGGTATGGGTCGCGATTGGCTAATAAGTGATTGCAACACAGGAGAAATTCTTGTAAGAGCAACGAGC

GCTTGGGCCATGATGAATCAAAAGACGAGAAGATTCTCAAAACTTCCATGCGAGGTTCGCCAGGAGAT

-continued

AGCGCCTCATTTTGTGGACGCTCCTCCTGTCATTGAAGACAATGATCGGAAATTGCATAAGTTTGATGT

GAAGACTGGTGATTCCATTTGCAAGGGTCTAACTCCGGGGTGGAATGACTTGGATGTCAATCAGCACG

TAAGCAACGTGAAGTACATTGGGTGGATTCTCGAGAGTATGCCTACAGAAGTTTTGGAGACCCAGGAG

CTATGCTCTCTCACCCTTGAATATAGGCGGGAATGTGGAAGGGAAAGTGTGGTAGAGTCCGTGACCTC

TATGAATCCCTCAAAAGTTGGAGACCGGTCTCAGTACCAACACCTTCTGCGGCTTGAGGATGGGGCTG

ATATCATGAAGGGCAGAACTGAGTGGAGACCAAAGAATGCAGGAACCAACCGGGCGATATCAACATG

A

SEQ ID NO: 30
*Cuphea wrightii* (Cw) FATB3 coding DNA sequence codon optimized for
*Prototheca moriformis*
ATGGTGGTGGCCGCCGCCGCCTCCTCCGCCTTCTTCCCCGTGCCCGCCCCCCGCACCACCCCCAAGCCC

GGCAAGTTCGGCAACTGGCCCTCCTCCCTGTCCCCCCCCTTCAAGCCCAAGTCCAACCCCAACGGCCG

CTTCCAGGTGAAGGCCAACGTGTCCCCCCACCCCAAGGCCAACGGCTCCGCCGTGTCCCTGAAGTCCG

GCTCCCTGAACACCCTGGAGGACCCCCCCTCCTCCCCCCCCCCCCGCACCTTCCTGAACCAGCTGCCCG

ACTGGTCCCGCCTGCGCACCGCCATCACCACCGTGTTCGTGGCCGCCGAGAAGCAGTTCACCCGCCTG

GACCGCAAGTCCAAGCGCCCCGACATGCTGGTGGACTGGTTCGGCTCCGAGACCATCGTGCAGGACGG

CCTGGTGTTCCGCGAGCGCTTCTCCATCCGCTCCTACGAGATCGGCGCCGACCGCACCGCCTCCATCGA

GACCCTGATGAACCACCTGCAGGACACCTCCCTGAACCACTGCAAGTCCGTGGGCCTGCTGAACGACG

GCTTCGGCCGCACCTCCGAGATGTGCACCCGCGACCTGATCTGGGTGCTGACCAAGATGCAGATCGTG

GTGAACCGCTACCCCACCTGGGGCGACACCGTGGAGATCAACTCCTGGTTCTCCCAGTCCGGCAAGAT

CGGCATGGGCCGCGACTGGCTGATCTCCGACTGCAACACCGGCGAGATCCTGGTGCGCGCCACCTCCG

CCTGGGCCATGATGAACCAGAAGACCCGCCGCTTCTCCAAGCTGCCCTGCGAGGTGCGCCAGGAGATC

GCCCCCCACTTCGTGGACGCCCCCCCCGTGATCGAGGACAACGACCGCAAGCTGCACAAGTTCGACGT

GAAGACCGGCGACTCCATCTGCAAGGGCCTGACCCCCGGCTGGAACGACCTGGACGTGAACCAGCAC

GTGTCCAACGTGAAGTACATCGGCTGGATCCTGGAGTCCATGCCCACCGAGGTGCTGGAGACCCAGGA

GCTGTGCTCCCTGACCCTGGAGTACCGCCGCGAGTGCGGCCGCGAGTCCGTGGTGGAGTCCGTGACCT

CCATGAACCCCTCCAAGGTGGGCGACCGCTCCCAGTACCAGCACCTGCTGCGCCTGGAGGACGGCGCC

GACATCATGAAGGGCCGCACCGAGTGGCGCCCCAAGAACGCCGGCACCAACCGCGCCATCTCCACCT

GA

SEQ ID NO: 31
*Cuphea wrightii* (Cw) FATB4a amino acid sequence
MVATAASSAFFPVPSADTSSSRPGKLGSGPSSLSPLKPKSIPNGGLQVKANASAPPKINGSSVGLKSGGFKTQ

EDSPSAPPPRTFINQLPDWSMLLAAITTVFLAAEKQWMMLDWKPKRPDMLVDPFGLGSIVQDGLVFRQNF

SIRSYEIGADRTASIETVMNHLQETALNHVKIAGLSNDGFGRTPEMYKRDLIWVVAKMQVMVNRYPTWG

DTVEVNTWVAKSGKNGMRRDWLISDCNTGEILTRASSVWVMMNQKTRRLSKIPDEVRNEIEPHFVDSAPV

VEDDDRKLPKLDENTADSIRKGLTPRWNDLDVNQHVNNVKYIGWILESTPPEVLETQELCSLTLEYRRECG

RESVLESLTAVDPSAEGYASRFQHLLRLEDGGEIVKARTEWRPKNAGINGVVPSEESSPGDFF*

SEQ ID NO: 32
*Cuphea wrightii* (Cw)FATB4a coding DNA sequence
TTGGTGGCTACCGCTGCAAGTTCTGCATTTTTCCCCGTGCCATCCGCCGACACCTCCTCCTCGAGACCC

GGAAAGCTCGGCAGTGGACCATCGAGCTTGAGCCCCCTCAAGCCCAAATCGATCCCCAATGGCGGCTT

GCAGGTTAAGGCAAACGCCAGTGCCCCTCCTAAGATCAATGGTTCCTCGGTCGGTCTAAAGTCGGGCG

GTTTCAAGACTCAGGAAGACTCTCCTTCGGCCCCTCCTCCGCGGACTTTTATCAACCAGTTGCCTGATT

GGAGTATGCTTCTTGCTGCAATCACTACTGTCTTCTTGGCTGCAGAGAAGCAGTGGATGATGCTTGATT

-continued
GGAAACCTAAGAGGCCTGACATGCTCGTGGACCCGTTCGGATTGGGAAGTATTGTTCAGGATGGGCTT

GTGTTCAGGCAGAATTTTTCAATTAGGTCCTACGAAATAGGCGCCGATCGAACTGCGTCTATAGAGAC

GGTGATGAACCATTTGCAGGAAACAGCTCTCAATCATGTCAAGATTGCTGGGC'TTTCTAATGACGGCT

TTGGTCGTACTCCTGAGATGTATAAAAGAGACCTTATTTGGGTTGTTGCAAAAATGCAGGTCATGGTTA

ACCGCTATCCTACTTGGGGTGACACGGTTGAAGTGAATACTTGGGTTGCCAAGTCAGGGAAAAATGGT

ATGCGTCGTGACTGGCTCATAAGTGATTGCAATACTGGAGAGATTCTTACAAGAGCATCAAGCGTGTG

GGTCATGATGAATCAAAAGACAAGAAGATTGTCAAAAATTCCAGATGAGGTTCGAAATGAGATAGAG

CCTCATTTTGTGGACTCTGCTCCCGTCGTTGAAGATGATGATCGGAAACTTCCCAAGCTGGATGAGAAC

ACTGCTGACTCCATCCGCAAGGGTCTAACTCCGAGGTGGAATGACTTGGATGTCAATCAGCACGTCAA

CAACGTGAAGTACATCGGATGGATTCTTGAGAGTACTCCACCAGAAGTTCTGGAGACCCAGGAGTTAT

GCTCCCTGACCCTGGAATACAGGCGGGAATGTGGAAGGGAGAGCGTGCTGGAGTCCCTCACTGCTGTC

GACCCGTCTGCAGAGGGCTATGCGTCCCGGTTTCAGCACCTTCTGCGGCTTGAGGATGGAGGTGAGAT

CGTGAAGGCGAGAACTGAGTGGCGACCCAAGAATGCTGGAATCAATGGGGTGGTACCATCCGAGGAG

TCCTCACCTGGAGACTTCTTTTAG

SEQ ID NO: 33
*Cuphea wrightii* (Cw) FATB4a coding DNA sequence codon optimized for *Prototheca moriformis*
ATGGTGGCCACCGCCGCCTCCTCCGCCTTCTTCCCCGTGCCCTCCGCCGACACCTCCTCCTCCCGCCCC

GGCAAGCTGGGCTCCGGCCCCTCCTCCCTGTCCCCCCTGAAGCCCAAGTCCATCCCCAACGGCGGCCT

GCAGGTGAAGGCCAACGCCTCCGCCCCCCCCAAGATCAACGGCTCCTCCGTGGGCCTGAAGTCCGGCG

GCTTCAAGACCCAGGAGGACTCCCCCTCCGCCCCCCCCCCCCGCACCTTCATCAACCAGCTGCCCGACT

GGTCCATGCTGCTGGCCGCCATCACCACCGTGTTCCTGGCCGCCGAGAAGCAGTGGATGATGCTGGAC

TGGAAGCCCAAGCGCCCCGACATGCTGGTGGACCCCTTCGGCCTGGGCTCCATCGTGCAGGACGGCCT

GGTGTTCCGCCAGAACTTCTCCATCCGCTCCTACGAGATCGGCGCCGACCGCACCGCCTCCATCGAGA

CCGTGATGAACCACCTGCAGGAGACCGCCCTGAACCACGTGAAGATCGCCGGCCTGTCCAACGACGG

CTTCGGCCGCACCCCCGAGATGTACAAGCGCGACCTGATCTGGGTGGTGGCCAAGATGCAGGTGATGG

TGAACCGCTACCCCACCTGGGGCGACACCGTGGAGGTGAACACCTGGGTGGCCAAGTCCGGCAAGAA

CGGCATGCGCCGCGACTGGCTGATCTCCGACTGCAACACCGGCGAGATCCTGACCCGCGCCTCCTCCG

TGTGGGTGATGATGAACCAGAAGACCCGCCGCCTGTCCAAGATCCCCGACGAGGTGCGCAACGAGAT

CGAGCCCCACTTCGTGGACTCCGCCCCCGTGGTGGAGGACGACGACCGCAAGCTGCCCAAGCTGGACG

AGAACACCGCCGACTCCATCCGCAAGGGCCTGACCCCCCGCTGGAACGACCTGGACGTGAACCAGCA

CGTGAACAACGTGAAGTACATCGGCTGGATCCTGGAGTCCACCCCCCCCGAGGTGCTGGAGACCCAGG

AGCTGTGCTCCCTGACCCTGGAGTACCGCCGCGAGTGCGGCCGCGAGTCCGTGCTGGAGTCCCTGACC

GCCGTGGACCCCTCCGCCGAGGGCTACGCCTCCCGCTTCCAGCACCTGCTGCGCCTGGAGGACGGCGG

CGAGATCGTGAAGGCCCGCACCGAGTGGCGCCCCAAGAACGCCGGCATCAACGGCGTGGTGCCCTCC

GAGGAGTCCTCCCCCGGCGACTTCTTCTGA

SEQ ID NO: 34
*Cuphea wrightii* (Cw) FATB4b amino acid sequence
MVATAASSAFFPVPSADTSSSRPGICLGNGPSSLSPLKPKSIPNGGLQVKANASAPPKINGSSVGLKSGSFKTQ

EDAPSAPPPRTFINQLPDWSMLLAAITTVFLAAEKQWMMLDWKPKRPDMLVDPFGLGSIVQDGLVFRQNF

SIRSYEIGADRIASIETVMNFILQETALNHVKIAGLSSDGFGRTPAMSKRDLIWVVAKMQVMVNRYPAWGD

TVEVNTWVAKSGKNGMRRDWLISDCNTGEILTRASSVWVMMNQKTRRLSKIPDEVRNEIEPHFVDSAPVV

-continued

EDDDRKLPKLDENTADSIRKGLTPRWNDLDVNQHVNNVKYIGWILESTPAEVLETQELCSLTLEYRRECGR

ESVLESLTAVDPSGEGDGSKFQHLLRLEDGGEIVKARTEWRPKNAGINGVVPSEESSPGGDFF*

SEQ ID NO: 35
*Cuphea wrightii* (Cw) FATB4b coding DNA sequence
TTGGTGGCTACCGCTGCAAGTTCTGCATTTTTCCCCGTACCATCCGCCGACACCTCCTCATCGAGACCC

GGAAAGCTCGGCAATGGGCCATCGAGCTTGAGCCCCCTCAAGCCGAAATCGATCCCCAATGGCGGGTT

GCAGGTTAAGGCAAACGCCAGTGCCCCTCCTAAGATCAATGGTTCCTCGGTCGGTCTGAAGTCGGGCA

GTTTCAAGACTCAGGAAGACGCTCCTTCGGCCCCTCCTCCTCGGACTTTTATCAACCAGTTGCCTGATT

GGAGTATGCTTCTTGCTGCAATCACTACTGTCTTCTTGGCTGCAGAGAAGCAGTGGATGATGCTTGATT

GGAAACCTAAGAGGCCTGACATGCTTGTCGACCCGTTCGGATTGGGAAGTATTGTTCAGGATGGGCTT

GTTTTCAGGCAGAATTTCTCGATTAGGTCCTACGAAATAGGCGCTGATCGCACTGCGTCTATAGAGAC

GGTGATGAACCATTTGCAGGAAACAGCTCTCAATCATGTTAAGATTGCTGGGCTTTCTAGTGATGGCTT

TGGTCGTACTCCTGCGATGTCTAAACGGGACCTCATTTGGGTTGTTGCGAAAATGCAGGTCATGGTTAA

CCGCTACCCTGCTTGGGGTGACACGGTTGAAGTGAATACTTGGGTTGCCAAGTCAGGGAAAAATGGTA

TGCGTCGTGACTGGCTCATAAGTGATTGCAACACTGGAGAGATTCTTACAAGAGCATCAAGCGTGTGG

GTCATGATGAATCAAAAGACAAGAAGATTGTCAAAAATTCCAGATGAGGTTCGAAATGAGATAGAGC

CTCATTTTGTGGACTCTGCGCCCGTCGTTGAAGACGATGACCGGAAACTTCCCAAGCTGGATGAGAAC

ACTGCTGACTCCATCCGCAAGGGTCTAACTCCGAGGTGGAATGACTTGGATGTCAATCAGCACGTCAA

CAACGTGAAGTACATTGGGTGGATTCTTGAGAGTACTCCAGCAGAAGTTCTGGAGACCCAGGAATTAT

GTTCCCTGACCCTGGAATACAGGCGGGAATGTGGAAGGGAGAGCGTGCTGGAGTCCCTCACTGCTGTA

GATCCGTCTGGAGAGGGCGATGGGTCCAAGTTCCAGCACCTTCTGCGGCTTGAGGATGGAGGTGAGAT

CGTGAAGGCGAGAACTGAGTGGCGACCAAAGAATGCTGGAATCAATGGGGTGGTACCATCCGAGGAG

TCCTCACCTGGTGGAGACTTCTTTTAA

SEQ ID NO: 36
*Cuphea wrightii* (Cw) FATB4b coding DNA sequence codon optimized for
*Prototheca moriformis*
ATGGTGGCCACCGCCGCCTCCTCCGCCTTCTTCCCCGTGCCCTCCGCCGACACCTCCTCCTCCCGCCCC

GGCAAGCTGGGCAACGGCCCCTCCTCCCTGTCCCCCCTGAAGCCCAAGTCCATCCCCAACGGCGGCCT

GCAGGTGAAGGCCAACGCCTCCGCCCCCCCCAAGATCAACGGCTCCTCCGTGGGCCTGAAGTCCGGCT

CCTTCAAGACCCAGGAGGACGCCCCCTCCGCCCCCCCCCCCCGCACCTTCATCAACCAGCTGCCCGAC

TGGTCCATGCTGCTGGCCGCCATCACCACCGTGTTCCTGGCCGCCGAGAAGCAGTGGATGATGCTGGA

CTGGAAGCCCAAGCGCCCCGACATGCTGGTGGACCCCTTCGGCCTGGGCTCCATCGTGCAGGACGGCC

TGGTGTTCCGCCAGAACTTCTCCATCCGCTCCTACGAGATCGGCGCCGACCGCACCGCCTCCATCGAG

ACCGTGATGAACCACCTGCAGGAGACCGCCCTGAACCACGTGAAGATCGCCGGCCTGTCCTCCGACGG

CTTCGGCCGCACCCCCGCCATGTCCAAGCGCGACCTGATCTGGGTGGTGGCCAAGATGCAGGTGATGG

TGAACCGCTACCCCGCCTGGGGCGACACCGTGGAGGTGAACACCTGGGTGGCCAAGTCCGGCAAGAA

CGGCATGCGCCGCGACTGGCTGATCTCCGACTGCAACACCGGCGAGATCCTGACCCGCGCCTCCTCCG

TGTGGGTGATGATGAACCAGAAGACCCGCCGCCTGTCCAAGATCCCCGACGAGGTGCGCAACGAGAT

CGAGCCCCACTTCGTGGACTCCGCCCCCGTGGTGGAGGACGACGACCGCAAGCTGCCCAAGCTGGACG

AGAACACCGCCGACTCCATCCGCAAGGGCCTGACCCCCCGCTGGAACGACCTGGACGTGAACCAGCA

CGTGAACAACGTGAAGTACATCGGCTGGATCCTGGAGTCCACCCCCGCCGAGGTGCTGGAGACCCAG

GAGCTGTGCTCCCTGACCCTGGAGTACCGCCGCGAGTGCGGCCGCGAGTCCGTGCTGGAGTCCCTGAC

CGCCGTGGACCCCTCCGGCGAGGGCGACGGCTCCAAGTTCCAGCACCTGCTGCGCCTGGAGGACGGCG

-continued

GCGAGATCGTGAAGGCCCGCACCGAGTGGCGCCCCAAGAACGCCGGCATCAACGGCGTGGTGCCCTC

CGAGGAGTCCTCCCCCGGCGGCGACTTCTTCTGA

SEQ ID NO: 37
*Cuphea wrightii* (Cw) FATB5 amino acid sequence
MVAAAASSAFFSVPTPGIPPKPGKFGNVVPSSLSVPFKPDNGGFHVKANASAHPKANGSAVNLKSGSLETPP

RSFINQLPDLSVLLSKITTVFGAAEKQWKRPGMLVEPFGVDRIFQDGVFFRQSFSIRSYEIGVDRTASIETLM

NIFQETSLNHCKSIGLLNDGFGRTPEMCKRDLIWVVTKIQVEVNRYPTWGDTIEVNTWVSESGKNGMGRD

WLISDCRTGEILIRATSVWAMMNQNTRRLSKFPYEVRQEIAPHFVDSAPVIEDDQKLQKLDVKIGDSIRDG

LTPRWNDLDVNQHVNNVKYIGWILKSVPIEVFETQELCGVTLEYRRECGRDSVLESVTAMDPAKEGDRCV

YQHLLRLEDGADITIGRTEWRPKNAGANGAMSSGKTSNGNCLIEGRGWQPFRVVRLIF*

SEQ ID NO: 38
*Cuphea wrightii* (Cw) FATB5 coding DNA sequence
ATGGTGGCTGCCGCAGCAAGTTCTGCATTCTTCTCTGTTCCAACCCCGGGAACGCCCCCTAAACCCGGG

AAGTTCGGTAACTGGCCATCGAGCTTGAGCGTCCCCTTCAAGCCCGACAATGGTGGCTTTCATGTCAA

GGCAAACGCCAGTGCCCATCCTAAGGCTAATGGTTCTGCGGTAAATCTAAAGTCTGGCAGCCTCGAGA

CTCCTCCTCGGAGTTTCATTAACCAGCTGCCGGACTTGAGTGTGCTTCTGTCCAAAATCACGACTGTCT

TCGGGGCGGCTGAGAAGCAGTGGAAGAGGCCCGGCATGCTCGTGGAACCGTTTGGGGTTGACAGGAT

TTTTCAGGATGGTGTTTTTTTCAGACAGAGTTTTTCTATCAGGTCTTACGAAATAGGCGTTGATCGAAC

AGCCTCGATAGAGACACTGATGAACATCTTCCAGGAAACATCTTTGAATCATTGCAAGAGTATCGGTC

TTCTCAACGATGGCTTTGGTCGTACTCCTGAGATGTGTAAGAGGGACCTCATTTGGGTGGTTACGAAA

ATTCAGGTCGAGGTGAATCGCTATCCTACTTGGGGTGACACTATCGAAGTCAATACTTGGGTCTCGGA

GTCGGGGAAAAACGGTATGGGTCGGGATTGGCTGATAAGTGATTGCCGTACTGGAGAGATTCTTATAA

GAGCAACGAGCGTGTGGGCGATGATGAATCAAAACACGAGAAGATTGTCAAAATTTCCATATGAGGT

TCGACAGGAGATAGCGCCTCATTTTGTGGACTCTGCTCCTGTCATTGAAGACGATCAAAAGTTGCAGA

AGCTTGATGTGAAGACAGGTGATTCCATTCGCGATGGTCTAACTCCGAGATGGAATGACTTGGATGTC

AATCAACACGTTAACAATGTGAAGTACATTGGATGGATTCTCAAGAGTGTTCCAATAGAAGTTTTCGA

GACACAGGAGCTATGCGGCGTCACACTTGAATATAGGCGGGAATGCGGAAGGGACAGTGTGCTGGAG

TCAGTGACCGCTATGGATCCAGCAAAAGAGGGAGACCGGTGTGTGTACCAGCACCTTCTTCGGCTTGA

GGATGGAGCTGATATCACTATAGGCAGAACCGAGTGGCGGCCGAAGAATGCAGGAGCCAATGGTGCA

ATGTCATCAGGAAAGACTTCAAATGGAAACTGTCTCATAGAAGGAAGGGGTTGGCAACCTTTCCGAGT

TGTGCGTTTAATTTTCTGA

SEQ ID NO: 39
*Cuphea wrightii* (Cw) FATB5 coding DNA sequence codon optimized for
*Prototheca moriformis*
ATGGTGGCCGCCGCCGCCTCCTCCGCCTTCTTCTCCGTGCCCACCCCCGGCACCCCCCCCAAGCCCGGC

AAGTTCGGCAACTGGCCCTCCTCCCTGTCCGTGCCCTTCAAGCCCGACAACGGCGGCTTCCACGTGAA

GGCCAACGCCTCCGCCCACCCCAAGGCCAACGGCTCCGCCGTGAACCTGAAGTCCGGCTCCCTGGAGA

CCCCCCCCCGCTCCTTCATCAACCAGCTGCCCGACCTGTCCGTGCTGCTGTCCAAGATCACCACCGTGT

TCGGCGCCGCCGAGAAGCAGTGGAAGCGCCCCGGCATGCTGGTGGAGCCCTTCGGCGTGGACCGCAT

CTTCCAGGACGGCGTGTTCTTCCGCCAGTCCTTCTCCATCCGCTCCTACGAGATCGGCGTGGACCGCAC

CGCCTCCATCGAGACCCTGATGAACATCTTCCAGGAGACCTCCCTGAACCACTGCAAGTCCATCGGCC

TGCTGAACGACGGCTTCGGCCGCACCCCCGAGATGTGCAAGCGCGACCTGATCTGGGTGGTGACCAAG

ATCCAGGTGGAGGTGAACCGCTACCCCACCTGGGGCGACACCATCGAGGTGAACACCTGGGTGTCCG

AGTCCGGCAAGAACGGCATGGGCCGCGACTGGCTGATCTCCGACTGCCGCACCGGCGAGATCCTGATC

-continued

CGCGCCACCTCCGTGTGGGCCATGATGAACCAGAACACCCGCCGCCTGTCCAAGTTCCCCTACGAGGT

GCGCCAGGAGATCGCCCCCCACTTCGTGGACTCCGCCCCCGTGATCGAGGACGACCAGAAGCTGCAGA

AGCTGGACGTGAAGACCGGCGACTCCATCCGCGACGGCCTGACCCCCCGCTGGAACGACCTGGACGT

GAACCAGCACGTGAACAACGTGAAGTACATCGGCTGGATCCTGAAGTCCGTGCCCATCGAGGTGTTCG

AGACCCAGGAGCTGTGCGGCGTGACCCTGGAGTACCGCCGCGAGTGCGGCCGCGACTCCGTGCTGGA

GTCCGTGACCGCCATGGACCCCGCCAAGGAGGGCGACCGCTGCGTGTACCAGCACCTGCTGCGCCTGG

AGGACGGCGCCGACATCACCATCGGCCGCACCGAGTGGCGCCCCAAGAACGCCGGCGCCAACGGCGC

CATGTCCTCCGGCAAGACCTCCAACGGCAACTGCCTGATCGAGGGCCGCGGCTGGCAGCCCTTCCGCG

TGGTGCGCCTGATCTTCTGA

SEQ ID NO: 40
*Cuphea heterophylla* (Cht) FATBla amino acid sequence
MVAAAASSAFFSVPTPGTSTKPGNFGNWPSSLSVPFKPESNHNGGFRVKANASAHPKANGSAVNLKSGSLE

TQEDTSSSSPPPRTFIKQLPDWGMLLSKITTVFGAAERQWKRPGMLVEPFGVDRIFQDGVFFRQSFSIRSYEI

GADRTASIETLMNIFQETSLNHCKSIGLLNDGFGRTPEMCKRDLIWVVTKIQVEVNRYPTWGDTIEVNTWV

SESGKNGMGRDWLISDCRTGEILIRATSVWAMMNRKTRRLSKFPYEVRQEIAPHFVDSAPVIEDDKKLHKL

DVKTGDSIRKGLTPRWNDLDVNQHVNNVKYIGWILKSVPAEVFETQELCGVTLEYRRECGRDSVLESVTA

MDTAKEGDRSLYQHLLRLEDGADITIGRTEWRPKNAGANGAISTGKTSNENSVS*

SEQ ID NO: 41
*Cuphea heterophylla* (Cht) FATBla coding DNA sequence
ATGGTGGCTGCCGCAGCAAGTTCTGCATTCTTCTCCGTTCCAACCCCGGGAACCTCCACTAAACCCGGG

AACTTCGGCAATTGGCCATCGAGCTTGAGCGTCCCCTTCAAGCCCGAATCAAACCACAATGGTGGCTT

TCGGGTCAAGGCAAACGCCAGTGCTCATCCTAAGGCTAACGGTTCTGCAGTAAATCTAAAGTCTGGCA

GCCTCGAGACTCAGGAGGACACTTCATCGTCGTCCCCTCCTCCTCGGACTTTTATTAAGCAGTTGCCCG

ACTGGGGTATGCTTCTGTCCAAAATCACGACTGTCTTCGGGGCGGCTGAGAGGCAGTGGAAGAGGCCC

GGCATGCTTGTGGAACCGTTTGGGGTTGACAGGATTTTTCAGGATGGGGTTTTTTTCAGACAGAGTTTT

TCGATCAGGTCTTACGAAATAGGCGCTGATCGAACAGCCTCAATAGAGACGCTGATGAACATCTTCCA

GGAAACATCTCTGAATCATTGTAAGAGTATCGGTC'TTCTCAATGACGGCTTTGGTCGTACTCCTGAGAT

GTGTAAGAGGGACCTCATTTGGGTGGTTACGAAAATTCAGGTCGAGGTGAATCGCTATCCTACTTGGG

GTGATACTATTGAGGTCAATACTTGGGTCTCAGAGTCGGGGAAAAACGGTATGGGTCGTGATTGGCTG

ATAAGCGATTGCCGTACCGGAGAAATTCTTATAAGAGCAACGAGCGTGTGGGCTATGATGAATCGAA

AGACGAGAAGATTGTCAAAATTTCCATATGAGGTTCGACAGGAGATAGCGCCTCATTTTGTGGACTCT

GCTCCTGTCATTGAAGACGATAAAAAATTGCACAAGCTTGATGTTAAGACGGGTGATTCCATTCGCAA

GGGTCTAACTCCAAGGTGGAATGACTTGGATGTCAATCAGCACGTTAACAATGTGAAGTACATTGGGT

GGATTCTCAAGAGTGTTCCAGCAGAAGTTTTCGAGACCCAGGAGCTATGCGGAGTCACCCTTGAGTAC

AGGCGGGAATGTGGAAGGGACAGTGTGCTGGAGTCCGTGACCGCTATGGATACCGCAAAAGAGGGAG

ACCGGTCTCTGTACCAGCACCTTCTTCGGCTTGAGGATGGGGCTGATATCACCATAGGCAGAACCGAG

TGGCGGCCGAAGAATGCAGGAGCCAATGGGGCAATATCAACAGGAAAGACTTCAAATGAAAACTCTG

TCTCTTAG

SEQ ID NO: 42
Cuphea *heterophylla* (Cht) FATBla coding DNA sequence codon optimized for *Prototheca moriformis*
ATGGTGGCCGCCGCCGCCTCCTCCGCCTTCTTCTCCGTGCCCACCCCCGGCACCTCCACCAAGCCCGGC

AACTTCGGCAACTGGCCCTCCTCCCTGTCCGTGCCCTTCAAGCCCGAGTCCAACCACAACGGCGGCTTC

CGCGTGAAGGCCAACGCCTCCGCCCACCCCAAGGCCAACGGCTCCGCCGTGAACCTGAAGTCCGGCTC

-continued

CCTGGAGACCCAGGAGGACACCTCCTCCTCCTCCCCCCCCCCCCGCACCTTCATCAAGCAGCTGCCCG

ACTGGGGCATGCTGCTGTCCAAGATCACCACCGTGTTCGGCGCCGCCGAGCGCCAGTGGAAGCGCCCC

GGCATGCTGGTGGAGCCCTTCGGCGTGGACCGCATCTTCCAGGACGGCGTGTTCTTCCGCCAGTCCTTC

TCCATCCGCTCCTACGAGATCGGCGCCGACCGCACCGCCTCCATCGAGACCCTGATGAACATCTTCCA

GGAGACCTCCCTGAACCACTGCAAGTCCATCGGCCTGCTGAACGACGGCTTCGGCCGCACCCCCGAGA

TGTGCAAGCGCGACCTGATCTGGGTGGTGACCAAGATCCAGGTGGAGGTGAACCGCTACCCCACCTGG

GGCGACACCATCGAGGTGAACACCTGGGTGTCCGAGTCCGGCAAGAACGGCATGGGCCGCGACTGGC

TGATCTCCGACTGCCGCACCGGCGAGATCCTGATCCGCGCCACCTCCGTGTGGGCCATGATGAACCGC

AAGACCCGCCGCCTGTCCAAGTTCCCCTACGAGGTGCGCCAGGAGATCGCCCCCCACTTCGTGGACTC

CGCCCCCGTGATCGAGGACGACAAGAAGCTGCACAAGCTGGACGTGAAGACCGGCGACTCCATCCGC

AAGGGCCTGACCCCCCGCTGGAACGACCTGGACGTGAACCAGCACGTGAACAACGTGAAGTACATCG

GCTGGATCCTGAAGTCCGTGCCCGCCGAGGTGTTCGAGACCCAGGAGCTGTGCGGCGTGACCCTGGAG

TACCGCCGCGAGTGCGGCCGCGACTCCGTGCTGGAGTCCGTGACCGCCATGGACACCGCCAAGGAGG

GCGACCGCTCCCTGTACCAGCACCTGCTGCGCCTGGAGGACGGCGCCGACATCACCATCGGCCGCACC

GAGTGGCGCCCCAAGAACGCCGGCGCCAACGGCGCCATCTCCACCGGCAAGACCTCCAACGAGAACT

CCGTGTCCTGA

SEQ ID NO: 43
*Cuphea heterophylla* (Cht) FATB1b (P16*S*, T20P, G94*S*, G105W, *S*293F, L305F variant) amino acid sequence
MVAAAASSAFFSVPTSGTSPKPGNFGNWPSSLSVPFKPESSHNGGFQVKANASAHPKANGSAVNLKSGSLE

TQEDTSSSSPPPRTFIKQLPDWSMLLSKITTVFWAAERQWKRPGMLVEPFGVDRIFQDGVFFRQSFSIRSYEI

GADRTASIETLMNIFQETSLNHCKSIGLLNDGFGRTPEMCKRDLIWVVTKIQVEVNRYPTWGDTIEVNTWV

SESGKNGMGRDWLISDCRTGEILIRATSVWAMMNRKTRRLSKFPYEVRQEIAPHFVDSAPVIEDDKKLHKL

DVKTGDFIRKGLTPRWNDFDVNQHVNNVKYIGWILKSVPAEVFETQELCGVTLEYRRECGRDSVLESVTA

MDTAKEGDRSLYQHLLRLEDGADITIGRTEWRPKNAGANGAISTGKTSNENSVS*

SEQ ID NO: 44
*Cuphea heterophylla* (Cht) FATB1b(P16*S*, T20P, G94*S*, G105W, *S*293F, L305F variant) coding DNA sequence
ATGGTGGCTGCCGCAGCAAGTTCTGCATTCTTCTCCGTTCCAACCTCGGGAACCTCCCCTAAACCCGGG

AACTTCGGCAATTGGCCATCGAGCTTGAGCGTCCCCTTCAAGCCCGAATCAAGCCACAATGGTGGCTT

TCAGGTCAAGGCAAACGCCAGTGCCCATCCTAAGGCTAACGGTTCTGCAGTAAATCTAAAGTCTGGCA

GCCTCGAGACTCAGGAGGACACTTCATCGTCGTCCCCTCCTCCTCGGACTTTTATTAAGCAGTTGCCCG

ACTGGAGTATGCTTCTGTCCAAAATCACGACTGTCTTCTGGGCGGCTGAGAGGCAGTGGAAGAGGCCC

GGCATGCTTGTGGAACCGTTTGGGGTTGACAGGATTTTTCAGGATGGGGTTTTTTTCAGACAGAGTTTT

TCGATCAGGTCTTACGAAATAGGCGCTGATCGAACAGCCTCAATAGAGACGCTGATGAACATCTTCCA

GGAAACATCTCTGAATCATTGTAAGAGTATCGGTCTTCTCAATGACGGCTTTGGTCGTACTCCTGAGAT

GTGTAAGAGGGACCTCATTTGGGTGGTTACGAAAATTCAGGTCGAGGTGAATCGCTATCCTACTTGGG

GTGATACTATTGAGGTCAATACTTGGGTCTCAGAGTCGGGGAAAAACGGTATGGGTCGTGATTGGCTG

ATAAGCGATTGCCGTACCGGAGAAATTCTTATAAGAGCAACGAGCGTGTGGGCTATGATGAATCGAA

AGACGAGAAGATTGTCAAAATTTCCATATGAGGTTCGACAGGAGATAGCGCCTCATTTTGTGGACTCT

GCTCCTGTCATTGAAGACGATAAAAAATTGCACAAGCTTGATGTTAAGACGGGTGATTTCATTCGCAA

GGGTCTAACTCCAAGGTGGAATGACTTTGATGTCAATCAGCACGTTAACAATGTGAAGTACATTGGGT

GGATTCTCAAGAGTGTTCCAGCAGAAGTTTTCGAGACCCAGGAGCTATGCGGAGTCACCCTTGAGTAT

-continued
AGGCGGGAATGTGGAAGGGACAGTGTGCTGGAGTCCGTGACCGCTATGGATACCGCAAAAGAGGGAG

ACCGGTCTCTGTACCAGCACCTTCTTCGGCTTGAGGATGGGGCTGATATCACCATAGGCAGAACCGAG

TGGCGGCCGAAGAATGCAGGAGCCAATGGGGCAATATCAACAGGAAAGACTTCAAATGAAAACTCTG

TCTCTTAG

SEQ ID NO: 45
*Cuphea heterophylla* (Cht) FATB1b (P16S, T20P, G94S, G105W, S293F, L305F variant) coding DNA sequence codon optimized for *Prototheca moriformis*
ATGGTGGCCGCCGCCGCCTCCTCCGCCTTCTTCTCCGTGCCCACCTCCGGCACCTCCCCCAAGCCCGGC

AACTTCGGCAACTGGCCCTCCTCCCTGTCCGTGCCCTTCAAGCCCGAGTCCTCCCACAACGGCGGCTTC

CAGGTGAAGGCCAACGCCTCCGCCCACCCCAAGGCCAACGGCTCCGCCGTGAACCTGAAGTCCGGCTC

CCTGGAGACCCAGGAGGACACCTCCTCCTCCTCCCCCCCCCCCCGCACCTTCATCAAGCAGCTGCCCG

ACTGGTCCATGCTGCTGTCCAAGATCACCACCGTGTTCTGGGCCGCCGAGCGCCAGTGGAAGCGCCCC

GGCATGCTGGTGGAGCCCTTCGGCGTGGACCGCATCTTCCAGGACGGCGTGTTCTTCCGCCAGTCCTTC

TCCATCCGCTCCTACGAGATCGGCGCCGACCGCACCGCCTCCATCGAGACCCTGATGAACATCTTCCA

GGAGACCTCCCTGAACCACTGCAAGTCCATCGGCCTGCTGAACGACGGCTTCGGCCGCACCCCCGAGA

TGTGCAAGCGCGACCTGATCTGGGTGGTGACCAAGATCCAGGTGGAGGTGAACCGCTACCCCACCTGG

GGCGACACCATCGAGGTGAACACCTGGGTGTCCGAGTCCGGCAAGAACGGCATGGGCCGCGACTGGC

TGATCTCCGACTGCCGCACCGGCGAGATCCTGATCCGCGCCACCTCCGTGTGGGCCATGATGAACCGC

AAGACCCGCCGCCTGTCCAAGTTCCCCTACGAGGTGCGCCAGGAGATCGCCCCCCACTTCGTGGACTC

CGCCCCCGTGATCGAGGACGACAAGAAGCTGCACAAGCTGGACGTGAAGACCGGCGACTTCATCCGC

AAGGGCCTGACCCCCCGCTGGAACGACTTCGACGTGAACCAGCACGTGAACAACGTGAAGTACATCG

GCTGGATCCTGAAGTCCGTGCCCGCCGAGGTGTTCGAGACCCAGGAGCTGTGCGGCGTGACCCTGGAG

TACCGCCGCGAGTGCGGCCGCGACTCCGTGCTGGAGTCCGTGACCGCCATGGACACCGCCAAGGAGG

GCGACCGCTCCCTGTACCAGCACCTGCTGCGCCTGGAGGACGGCGCCGACATCACCATCGGCCGCACC

GAGTGGCGCCCCAAGAACGCCGGCGCCAACGGCGCCATCTCCACCGGCAAGACCTCCAACGAGAACT

CCGTGTCCTGA
SEQ ID NO: 46
*Cuphea heterophylla* (Cht) FATB2b amino acid sequence
MVVAAAASSAFFPVPASGTSPKPGIUGTWLSSSSPSYKPKSNPSGGFQVKANASAHPKANGSAVSLKSGSL NTQEGTSSSPPPRTFLNQLPDWSRLRTAITTVFVAAEKQLTMLDRKSKKPDIvIHVDWFGLEIIVQDGLVFRE

SFSIRSYEIGADRTASIETLMNELQDTSLNHCKSVGLLNDGFGRTPEMCKRDLIWVLTKMQ1MVNRYPTWG

DTVEINSWFSQSGKIGMGRNWLISDCNTGEILTRATSIWAMMNQKTRRFSKLPNEVRQEIAPHFVDAPPVIE

DNDRKLHKFDVKTGDSICKGLTPEWNDLDVNQHVSNVKY1GWILESMPKEVLDTQELCSLTLEYRRECGR

DSVLESVTAMDPSKVGDRSQYQHLLRLEDGTDIMKGRTEWRPKNAGTNGAISTGKTSNGNSVS*

SEQ ID NO: 47
*Cuphea heterophylla* (Cht) FATB2b coding DNA sequence
ATGGTGGTGGCTGCTGCAGCAAGCTCTGCATTCTTCCCTGTTCCGGCATCTGGAACCTCCCCTAAACCC

GGGAAGTTCGGGACTTGGCTATCGAGCTCGAGCCCTTCCTACAAGCCCAAGTCAAACCCCAGTGGTGG

ATTTCAGGTTAAGGCAAATGCCAGTGCTCATCCTAAGGCTAACGGTTCCGCAGTAAGTCTAAAGTCTG

GCAGCCTCAACACTCAGGAGGGCACTTCGTCGTCCCCTCCTCCTCGGACTTTCCTTAACCAGTTGCCTG

ATTGGAGTAGGCTTCGGACTGCAATCACGACCGTCTTCGTGGCGGCAGAGAAGCAGTTGACTATGCTC

GATCGAAAGTCTAAGAAGCCTGACATGCACGTGGACTGGTTTGGGTTGGAGATTATTGTTCAGGATGG

GCTCGTGTTCAGAGAGAGTTTTTCGATCAGGTCTTACGAAATAGGCGCTGATCGAACAGCCTCTATAG

AAACGTTGATGAACCATTTGCAGGACACATCTTTGAACCATTGTAAGAGTGTGGGTCTTCTCAATGAC

GGCTTTGGTCGTACCCCGGAGATGTGTAAAAGGGACCTCATTTGGGTGCTTACAAAAATGCAGATCAT

-continued

GGTGAATCGCTATCCAACTTGGGGCGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAAGACGAGAAGATTCTCAAAACTTCCAAACGAGGTTCGCCAGGAGA

TAGCGCCTCATTTTGTGGACGCCCCTCCTGTCATTGAAGACAATGATCGAAAATTGCATAAGTTTGATG

TGAAGACTGGTGATTCCATTTGC'AAGGGTCTAACACCGGAGTGGAATGACTTGGATGTCAATCAGCAC

GTAAGCAACGTGAAGTACATTGGGTGGATTCTCGAGAGTATGCCAAAAGAAGTTTTGGACACCCAGG

AGCTATGCTCTCTCACCCTTGAATATAGGCGGGAATGCGGAAGGGATAGTGTGCTGGAGTCTGTGACC

GCTATGGATCCCTCAAAAGTTGGAGACCGATCTCAGTACCAGCACCTTCTGCGGCTTGAAGATGGGAC

TGATATCATGAAGGGCAGAACTGAGTGGCGACCAAAGAATGCAGGAACCAACGGGGCTATATCAACA

GGAAAGACTTCAAATGGAAACTCGGTCTCTTAG

SEQ ID NO: 48
*Cuphea heterophylla* (Cht) FATB2b coding DNA sequence codon optimized for *Prototheca moriformis*
ATGGTGGTGGCCGCCGCCGCCTCCTCCGCCTTCTTCCCCGTGCCCGCCTCCGGCACCTCCCCCAAGCCC

GGCAAGTTCGGCACCTGGCTGTCCTCCTCCTCCCCCTCCTACAAGCCCAAGTCCAACCCCTCCGGCGGC

TTCCAGGTGAAGGCCAACGCCTCCGCCCACCCCAAGGCCAACGGCTCCGCCGTGTCCCTGAAGTCCGG

CTCCCTGAACACCCAGGAGGGCACCTCCTCCTCCCCCCCCCCCCGCACCTTCCTGAACCAGCTGCCCGA

CTGGTCCCGCCTGCGCACCGCCATCACCACCGTGTTCGTGGCCGCCGAGAAGCAGCTGACCATGCTGG

ACCGCAAGTCCAAGAAGCCCGACATGCACGTGGACTGGTTCGGCCTGGAGATCATCGTGCAGGACGG

CCTGGTGTTCCGCGAGTCCTTCTCCATCCGCTCCTACGAGATCGGCGCCGACCGCACCGCCTCCATCGA

GACCCTGATGAACCACCTGCAGGACACCTCCCTGAACCACTGCAAGTCCGTGGGCCTGCTGAACGACG

GCTTCGGCCGCACCCCCGAGATGTGCAAGCGCGACCTGATCTGGGTGCTGACCAAGATGCAGATCATG

GTGAACCGCTACCCCACCTGGGGCGACACCGTGGAGATCAACTCCTGGTTCTCCCAGTCCGGCAAGAT

CGGCATGGGCCGCAACTGGCTGATCTCCGACTGCAACACCGGCGAGATCCTGATCCGCGCCACCTCCA

TCTGGGCCATGATGAACCAGAAGACCCGCCGCTTCTCCAAGCTGCCCAACGAGGTGCGCCAGGAGATC

GCCCCCCACTTCGTGGACGCCCCCCCCGTGATCGAGGACAACGACCGCAAGCTGCACAAGTTCGACGT

GAAGACCGGCGACTCCATCTGCAAGGGCCTGACCCCCGAGTGGAACGACCTGGACGTGAACCAGCAC

GTGTCCAACGTGAAGTACATCGGCTGGATCCTGGAGTCCATGCCCAAGGAGGTGCTGGACACCCAGGA

GCTGTGCTCCCTGACCCTGGAGTACCGCCGCGAGTGCGGCCGCGACTCCGTGCTGGAGTCCGTGACCG

CCATGGACCCCTCCAAGGTGGGCGACCGCTCCCAGTACCAGCACCTGCTGCGCCTGGAGGACGGCACC

GACATCATGAAGGGCCGCACCGAGTGGCGCCCCAAGAACGCCGGCACCAACGGCGCCATCTCCACCG

GCAAGACCTCCAACGGCAACTCCGTGTCCTGA

SEQ ID NO: 49
*Cuphea heterophylla* (Cht) FATB2a (S17P, P21S, T28N, L30P, S33L, G76D, S78P, G137W variant) amino acid sequence
MVVAAAASSAFFPVPAPGTTSKPGKFGNWPSSLSPSFKPKSNPNGGFQVKANASAHPKANGSAVSLKSGSL

NTKEDTPSSPPPRTFLNQLPDWSRLRTAITTVFVAAEKQLTMLDRKSKKPDMHVDWFGLEIIVQDWLVFRE

SFS1RSYEIGADRTASIETLMNHLQDTSLNHCKSVGLLNDGFGRTPEMCKRDLIWVLTKMQIMVNRYPTWG

DTVEINSWFSQSGKIGMGRNWLISDCNTGEILIRATSIWAMMNQKTRRFSKLPNEVRQEIAPHFVDAPPLIE

DNDRKLHKFDVKTGDSICKGLTPEWNDLDVNQHVSNVKYIGWILESMPKEVLDTQELCSLTLEYRRECGR

DSVLESVTAMDPSKVGDRSQYQHLLRLEDGTDIMKGRTEWRPKNAGTNGAISTGKTSNGNSVS*

-continued

SEQ ID NO: 50
*Cuphea heterophylla* (Cht) FATB2a (S17P, P21S, T28N, L30P, S33L, G76D, S78P, G137W variant) coding DNA sequence
ATGGTGGTGGCTGCTGCAGCAAGTTCTGCATTCTTCCCTGTTCCAGCACCTGGAACCACGTCTAAACCC

GGGAAGTTCGGCAATTGGCCATCGAGCTTGAGCCCTTCCTTCAAGCCCAAGTCAAACCCCAATGGTGG

ATTTCAGGTTAAGGCAAATGCCAGCGCTCATCCTAAGGCTAACGGGTCTGCAGTAAGTCTAAAGTCTG

GCAGCCTCAACACTAAGGAGGACACTCCGTCGTCCCCTCCTCCTCGGACTTTCCTTAACCAGTTGCCTG

ATTGGAGTAGGCTTCGGACTGCAATCACGACCGTCTTCGTGGCGGCAGAGAAGCAGTTGACTATGCTC

GATCGAAAGTCTAAGAAGCCTGACATGCACGTGGACTGGTTTGGGTTGGAGATTATTGTTCAGGATTG

GCTCGTGTTCAGAGAGAGTTTTTCGATCAGGTCTTACGAAATAGGCGCTGATCGAACAGCCTCTATAG

AAACGTTGATGAACCATTTGCAGGACACATCTTTGAACCATTGTAAGAGTGTGGGTCTTCTCAATGAC

GGCTTTGGTCGTACCCCGGAGATGTGTAAAAGGGACCTCATTTGGGTGCTTACAAAAATGCAGATCAT

GGTGAATCGCTATCCAACTTGGGGCGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAAGACGAGAAGATTCTCAAAACTTCCAAACGAGGTTCGCCAGGAGA

TAGCTCCTCATTTTGTGGACGCCCCTCCTCTCATTGAAGACAATGATCGAAAATTGCATAAGTTTGATG

TGAAGACTGGTGATTCCATTTGCAAGGGTCTAACACCGGAGTGGAATGACTTGGATGTCAATCAGCAC

GTAAGCAACGTGAAGTACATTGGGTGGATTCTCGAGAGTATGCCAAAAGAAGTTTTGGACACCCAGG

AGCTATGCTCTCTCACCCTTGAATATAGGCGGGAATGCGGAAGGGACAGTGTGCTGGAGTCTGTGACC

GCTATGGATCCCTCAAAAGTTGGAGACCGATCTCAGTACCAGCACCTTCTGCGGCTTGAAGATGGGAC

TGATATCATGAAGGGCAGAACTGAGTGGCGACCAAAGAATGCAGGAACCAACGGGGCGATATCAACA

GGAAAGACTTCAAATGGAAACTCGGTCTCTTAG

SEQ ID NO: 51
*Cuphea heterophylla* (Cht) FATB2a (S17P, P21S, T28N, L30P, S33L, G76D, S78P, G137W variant) coding DNA sequence codon optimized for *Prototheca moriformis*
ATGGTGGTGGCCGCCGCCGCCTCCTCCGCCTTCTTCCCCGTGCCCGCCCCCGGCACCACCTCCAAGCCC

GGCAAGTTCGGCAACTGGCCCTCCTCCCTGTCCCCCTCCTTCAAGCCCAAGTCCAACCCCAACGGCGG

CTTCCAGGTGAAGGCCAACGCCTCCGCCCACCCCAAGGCCAACGGCTCCGCCGTGTCCCTGAAGTCCG

GCTCCCTGAACACCAAGGAGGACACCCCCTCCTCCCCCCCCCCCCGCACCTTCCTGAACCAGCTGCCC

GACTGGTCCCGCCTGCGCACCGCCATCACCACCGTGTTCGTGGCCGCCGAGAAGCAGCTGACCATGCT

GGACCGCAAGTCCAAGAAGCCCGACATGCACGTGGACTGGTTCGGCCTGGAGATCATCGTGCAGGAC

TGGCTGGTGTTCCGCGAGTCCTTCTCCATCCGCTCCTACGAGATCGGCGCCGACCGCACCGCCTCCATC

GAGACCCTGATGAACCACCTGCAGGACACCTCCCTGAACCACTGCAAGTCCGTGGGCCTGCTGAACGA

CGGCTTCGGCCGCACCCCCGAGATGTGCAAGCGCGACCTGATCTGGGTGCTGACCAAGATGCAGATCA

TGGTGAACCGCTACCCCACCTGGGGCGACACCGTGGAGATCAACTCCTGG'TTCTCCCAGTCCGGCAAG

ATCGGCATGGGCCGCAACTGGCTGATCTCCGACTGCAACACCGGCGAGATCCTGATCCGCGCCACCTC

CATCTGGGCCATGATGAACCAGAAGACCCGCCGCTTCTCCAAGCTGCCCAACGAGGTGCGCCAGGAG

ATCGCCCCCCACTTCGTGGACGCCCCCCCCCTGATCGAGGACAACGACCGCAAGCTGCACAAGTTCGA

CGTGAAGACCGGCGACTCCATCTGCAAGGGCCTGACCCCCGAGTGGAACGACCTGGACGTGAACCAG

CACGTGTCCAACGTGAAGTACATCGGCTGGATCCTGGAGTCCATGCCCAAGGAGGTGCTGGACACCCA

GGAGCTGTGCTCCCTGACCCTGGAGTACCGCCGCGAGTGCGGCCGCGACTCCGTGCTGGAGTCCGTGA

CCGCCATGGACCCCTCCAAGGTGGGCGACCGCTCCCAGTACCAGCACCTGCTGCGCCTGGAGGACGGC

-continued

ACCGACATCATGAAGGGCCGCACCGAGTGGCGCCCCAAGAACGCCGGCACCAACGGCGCCATCTCCA

CCGGCAAGACCTCCAACGGCAACTCCGTGTCCTGA

SEQ ID NO: 52
*Cuphea heterophylla* (Cht) FATB2c (G76D, S78P variant) amino acid sequence
MVVAAAASSAFFPVPASGTSPKPGKFGTWLSSSSPSYKPKSNPSGGFQVKANASAHPKANGSAVSLKSGSL

NTKEDTPSSPPPRTFLNQLPDWNRLRTAITTVFVAAEKQLTMLDRKSKKPDMHVDWFGLEIIVQDGLVFRE

SFSIRSYEIGADRIASIETLMNHLQDTSLNHCKSVGLLNDGFGRTPEMCKRDLIWVLIKMQIMVNRYPTWG

DTVEINSWFSQSGKIGMGRNWLISDCNTGEILIRATSIWAMMNQKTRRFSKLPNEVRQEIAPHFVDAPPVIE

DNDRKIHKFDVKTGDSICKGLIPEWNDLDVNQHVSNVKYIGWILESMPKEVLDTQELCSLTLEYRRECGR

DSVLESVTAMDPSKVGDRSQYQHLLRLEDGTDIMKGRTEWRPKNAGTNGAISTGKTSNGNSVS*

SEQ ID NO: 53
*Cuphea heterophylla* (Cht) FATB2c (G76D, S78P variant) coding DNA sequence
ATGGTGGTGGCTGCTGCAGCAAGCTCTGCATTCTTCCCTGTTCCGGCATCTGGAACCTCCCCTAAACCC

GGGAAGTTCGGGACTTGGCTATCGAGCTCGAGCCCTTCCTACAAGCCCAAGTCAAACCCCAGTGGTGG

ATTTCAGGTTAAGGCAAATGCCAGTGCTCATCCTAAGGCTAACGGTTCCGCAGTAAGTCTAAAGTCTG

GCAGCCTCAACACTAAGGAGGACACTCCGTCGTCCCCTCCTCCTCGGACTTTCCTTAACCAGTTGCCTG

ATTGGAATAGGCTTCGGACTGCAATCACGACCGTCTTCGTGGCGGCAGAGAAGCAGTTGACTATGCTC

GATCGAAAGTCTAAGAAGCCTGACATGCACGTGGACTGGTTTGGGTTGGAGATTATTGTTCAGGATGG

GCTCGTGTTCAGAGAGAGTTTTTCGATCAGGTCTTACGAAATAGGCGCTGATCGAACAGCCTCTATAG

AAACGTTGATGAACCATTTGCAGGACACATCTTTGAACCATTGTAAGAGTGTGGGTMCTCAATGAC

GGCTTTGGTCGTACCCCGGAGATGTGTAAAAGGGACCTCATTTGGGTGCTTACAAAAATGCAGATCAT

GGTGAATCGCTATCCAACTTGGGGCGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAAGACGAGAAGATTCTCAAAACTTCCAAACGAGGTTCGCCAGGAGA

TAGCGCCTCATTTTGTGGACGCCCCTCCTGTCATTGAAGACAATGATCGAAAATTGCATAAGTTTGATG

TGAAGACTGGTGATTCCATTTGCAAGGGTCTAACACCGGAGTGGAATGACTTGGATGTCAATCAGCAC

GTAAGCAACGTGAAGTACATTGGGTGGATTCTCGAGAGTATGCCAAAAGAAGTTTTGGACACCCAGG

AGCTATGCTCTCTCACCCTTGAATATAGGCGGGAATGCGGAAGGGACAGTGTGCTGGAGTCTGTGACC

GCTATGGATCCCTCAAAAGTTGGGGACCGATCTCAGTACCAGCACCTTCTGCGGCTTGAAGATGGGAC

TGATATCATGAAGGGCAGAACTGAGTGGCGACCAAAGAATGCAGGAACCAACGGGGCTATATCAACA

GGAAAGACTTCAAATGGAAACTCGGTCTCTTAG

SEQ ID NO: 54
*Cuphea heterophylla* (Cht) FATB2c (G76D, S78P variant) coding DNA sequence codon optimized for *Prototheca moriformis*
ATGGTGGTGGCCGCCGCCGCCTCCTCCGCCTTCTTCCCCGTGCCCGCCTCCGGCACCTCCCCCAAGCCC

GGCAAGTTCGGCACCTGGCTGTCCTCCTCCTCCCCCTCCTACAAGCCCAAGTCCAACCCCTCCGGCGGC

TTCCAGGTGAAGGCCAACGCCTCCGCCCACCCCAAGGCCAACGGCTCCGCCGTGTCCCTGAAGTCCGG

CTCCCTGAACACCAAGGAGGACACCCCCTCCTCCCCCCCCCCCCGCACCTTCCTGAACCAGCTGCCCG

ACTGGAACCGCCTGCGCACCGCCATCACCACCGTGTTCGTGGCCGCCGAGAAGCAGCTGACCATGCTG

GACCGCAAGTCCAAGAAGCCCGACATGCACGTGGACTGGTTCGGCCTGGAGATCATCGTGCAGGACG

GCCTGGTGTTCCGCGAGTCCTTCTCCATCCGCTCCTACGAGATCGGCGCCGACCGCACCGCCTCCATCG

AGACCCTGATGAACCACCTGCAGGACACCTCCCTGAACCACTGCAAGTCCGTGGGCCTGCTGAACGAC

GGCTTCGGCCGCACCCCCGAGATGTGCAAGCGCGACCTGATCTGGGTGCTGACCAAGATGCAGATCAT

GGTGAACCGCTACCCCACCTGGGGCGACACCGTGGAGATCAACTCCTGGTTCTCCCAGTCCGGCAAGA

-continued

TCGGCATGGGCCGCAACTGGCTGATCTCCGACTGCAACACCGGCGAGATCCTGATCCGCGCCACCTCC

ATCTGGGCCATGATGAACCAGAAGACCCGCCGCTTCTCCAAGCTGCCCAACGAGGTGCGCCAGGAGAT

CGCCCCCCACTTCGTGGACGCCCCCCCCGTGATCGAGGACAACGACCGCAAGCTGCACAAGTTCGACG

TGAAGACCGGCGACTCCATCTGCAAGGGCCTGACCCCCGAGTGGAACGACCTGGACGTGAACCAGCA

CGTGTCCAACGTGAAGTACATCGGCTGGATCCTGGAGTCCATGCCCAAGGAGGTGCTGGACACCCAGG

AGCTGTGCTCCCTGACCCTGGAGTACCGCCGCGAGTGCGGCCGCGACTCCGTGCTGGAGTCCGTGACC

GCCATGGACCCCTCCAAGGTGGGCGACCGCTCCCAGTACCAGCACCTGCTGCGCCTGGAGGACGGCAC

CGACATCATGAAGGGCCGCACCGAGTGGCGCCCCAAGAACGCCGGCACCAACGGCGCCATCTCCACC

GGCAAGACCTCCAACGGCAACTCCGTGTCCTGA

SEQ ID NO: 55
*Cuphea heterophylla* (Cht) FATB2d (S21P, T28N, L30P, S33L, G76D, R97L, H124L, W127L, I132S, K258N, C303R, E309G, K334T, T386A variant) amino acid sequence
MVVAAAASSAFFPVPAPGTTSKPGKFGNWPSSLSPSFKPKSNPNGGFQVKANASAHPKANGSAVSLKSGSL

NTQEDTSSSPPPRTFLNQLPDWSRLLTAISTVFVAAEKQLTMLDRICSKRPDMLVDLFGLESIVQDGLVFRES

YSIRSYEIGADRTASIETLMNHLQDTSLNHCKSVGLLNDGFGRTPEMCKRDLIWVLTKMQIMVNRYPTWG

DTVEINSWFSQSGKIGMGRNWLISDCNTGEILIRATSIWAMMNQNTRRFSKLPNEVRQEIAPHFVDAPPVIE

DNDRKLFfKIDVKTGDSIRKGLTPGWNDLDVNQHVSNVKYIGWILESMPTEVLETQELCSLTLEYRRECGR

ESVLESVTAMNPSKVGDRSQYQHLLRLEDGADIMKGRTEWRPKNAGTNGAISTGKTSNGNSVS*

SEQ ID NO: 56
*Cuphea heterophylla* (Cht) FATB2d (S21P, T28N, L30P, S33L, G76D, R97L, H124L, W127L, I132S, K258N, C303R, E309G, K334T, T386A variant) coding DNA sequence
ATGGTGGTGGCTGCTGCAGCAAGTTCTGCATTCTTCCCTGTTCCAGCACCTGGAACCACGTCTAAACCC

GGGAAGTTCGGCAATTGGCCATCGAGCTTGAGCCCTTCCTTCAAGCCCAAGTCAAACCCCAATGGTGG

ATTTCAGGTTAAGGCAAATGCCAGTGCTCATCCTAAGGCTAACGGTTCTGCGGTAAGTCTAAAGTCTG

GCAGCCTCAACACTCAGGAGGACACTTCGTCGTCCCCTCCTCCTCGGACATTCCTTAACCAGTTGCCTG

ATTGGAGTAGGCTTCTGACTGCAATCTCGACCGTCTTCGTGGCGGCAGAGAAGCAGTTGACTATGCTC

GATCGAAAATCTAAGAGGCCTGACATGCTCGTGGACTTGTTTGGGTTGGAGAGTATTGTTCAGGATGG

GCTCGTGTTCAGAGAGAGTTATTCGATCAGGTCTTACGAAATAGGCGCTGATCGAACAGCCTCTATAG

AAACGTTGATGAACCATTTGCAGGACACATCTTTGAACCATTGTAAGAGTGTGGGTCTTCTCAATGAC

GGCTTTGGTCGTACCCCGGAGATGTGTAAAAGGGACCTCATTTGGGTGCTTACAAAAATGCAGATCAT

GGTGAATCGCTATCCAACTTGGGGCGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAATACGAGAAGATTCTCAAAACTTCCAAACGAGGTTCGCCAGGAGAT

AGCGCCTCATTTTGTTGACGCTCCTCCTGTCATTGAAGACAATGATCGAAAATTGCATAAGTTTGATGT

GAAGACTGGTGATTCCATTCGCAAGGGTCTAACTCCGGGGTGGAATGACTTGGATGTCAATCAGCACG

TAAGCAACGTGAAGTACATTGGGTGGATTCTCGAGAGTATGCCAACAGAAGTTTTGGAGACCCAGGA

GCTATGCTCTCTCACCCTTGAATATAGGCGGGAATGCGGAAGGGAAAGTGTGCTGGAGTCCGTGACCG

CTATGAATCCCTCAAAAGTTGGAGACCGGTCTCAGTACCAGCACCTTCTACGGCTTGAGGATGGGGCT

GATATCATGAAGGGCAGAACTGAGTGGCGACCAAAGAATGCAGGAACCAACGGGGCGATATCAACAG

GAAAGACTTCAAATGGAAACTCGGTCTCTTAG

-continued

SEQ ID NO: 57
*Cuphea heterophylla* (Cht) FATB2d (S21P, T28N, L30P, S33L, G76D, R97L, H124L, W127L, I132S, K258N, C303R, E309G, K334T, T386A variant) coding DNA sequence codon optimized for *Prototheca moriformis*
ATGGTGGTGGCCGCCGCCGCCTCCTCCGCCTTCTTCCCCGTGCCCGCCCCCGGCACCACCTCCAAGCCC

GGCAAGTTCGGCAACTGGCCCTCCTCCCTGTCCCCCTCCTTCAAGCCCAAGTCCAACCCCAACGGCGG

CTTCCAGGTGAAGGCCAACGCCTCCGCCCACCCCAAGGCCAACGGCTCCGCCGTGTCCCTGAAGTCCG

GCTCCCTGAACACCCAGGAGGACACCTCCTCCTCCCCCCCCCCCCGCACCTTCCTGAACCAGCTGCCCG

ACTGGTCCCGCCTGCTGACCGCCATCTCCACCGTGTTCGTGGCCGCCGAGAAGCAGCTGACCATGCTG

GACCGCAAGTCCAAGCGCCCCGACATGCTGGTGGACCTGTTCGGCCTGGAGTCCATCGTGCAGGACGG

CCTGGTGTTCCGCGAGTCCTACTCCATCCGCTCCTACGAGATCGGCGCCGACCGCACCGCCTCCATCGA

GACCCTGATGAACCACCTGCAGGACACCTCCCTGAACCACTGCAAGTCCGTGGGCCTGCTGAACGACG

GCTTCGGCCGCACCCCCGAGATGTGCAAGCGCGACCTGATCTGGGTGCTGACCAAGATGCAGATCATG

GTGAACCGCTACCCCACCTGGGGCGACACCGTGGAGATCAACTCCTGGTTCTCCCAGTCCGGCAAGAT

CGGCATGGGCCGCAACTGGCTGATCTCCGACTGCAACACCGGCGAGATCCTGATCCGCGCCACCTCCA

TCTGGGCCATGATGAACCAGAACACCCGCCGCTTCTCCAAGCTGCCCAACGAGGTGCGCCAGGAGATC

GCCCCCCACTTCGTGGACGCCCCCCCCGTGATCGAGGACAACGACCGCAAGCTGCACAAGTTCGACGT

GAAGACCGGCGACTCCATCCGCAAGGGCCTGACCCCCGGCTGGAACGACCTGGACGTGAACCAGCAC

GTGTCCAACGTGAAGTACATCGGCTGGATCCTGGAGTCCATGCCCACCGAGGTGCTGGAGACCCAGGA

GCTGTGCTCCCTGACCCTGGAGTACCGCCGCGAGTGCGGCCGCGAGTCCGTGCTGGAGTCCGTGACCG

CCATGAACCCCTCCAAGGTGGGCGACCGCTCCCAGTACCAGCACCTGCTGCGCCTGGAGGACGGCGCC

GACATCATGAAGGGCCGCACCGAGTGGCGCCCCAAGAACGCCGGCACCAACGGCGCCATCTCCACCG

GCAAGACCTCCAACGGCAACTCCGTGTCCTGA

SEQ ID NO: 58
*Cuphea heterophylla* (Cht) FATB2e (G76D, R97L, H124L, I132S, G152S, H165L, T211N, K258N, C303R, E309G, K334T, T386A variant) amino acid sequence
MVVAAAASSAFFPVPASGTSPKPGKFGTWLSSSSPSYKPKSNPSGGFQVKANASAHPKANGSAVSLKSGSL

NTQEDTSSSPPPQTFLNQLPDWSRLLTAISTVFVAAEKQLTMLDRKSKRPDMLVDWFGLESIVQDGLVFRE

SYSIRSYEISADRTASIETVMNLLQETSLNHCKSMGILNDGFGRTPEMCKRDLIWVLTKMQILVNRYPNWG

DTVEINSWFSQSGKIGMGRNWLISDCNTGEILIRATSIWAMMNQNTRRFSKLPNEVRQEIAPHFVDAPPVIE

DNDRKLHKFDVKTGDSIRKGLTPGWNDLDVNQHVSNVKYIGWILESMPTEVLETQELCSLTLEYRRECGR

DSVLESVTAMNPSKVGDRSQYQHLLRLEDGADIMKGRTEWRPKNAGTNGAISTGKTSNGNSVS*

SEQ ID NO: 59
*Cuphea heterophylla* (Cht) FATB2e (G76D, R97L, H124L, I132S, G152S, H165L, T211N, K258N, C303R, E309G, K334T, T386A variant) coding DNA sequence

ATGGTGGTGGCTGCTGCAGCAAGCTCTGCATTCTTCCCTUTTCCGGCATCTGGAACCTCCCCTAAACCC

GGGAAGTTCGGGACTTGGCTATCGAGCTCGAGCCCTTCCTACAAGCCCAAGTCAAACCCCAGTGGTGG

ATTTCAGGTTAAGGCAAATGCCAGTGCTCATCCTAAGGCTAACGGTTCTGCAGTAAGTCTAAAGTCTG

GCAGCCTCAACACTCAGGAGGACACTTCGTCGTCCCCTCCTCCTCAGACATTCCTTAACCAGTTGCCTG

ATTGGAGTAGGCTTCTGACAGCAATCTCGACCGTCTTCGTGGCGGCAGAGAAGCAGTTGACTATGCTC

GATCGAAAATCTAAAAGGCCTGACATGCTCGTGGACTGGTTTGGGTTGGAGAGTATTGTTCAGGATGG

GCTCGTGTTCAGAGAGAGTTATTCGATCAGGTCTTACGAAATAAGCGCTGATCGAACAGCCTCTATAG

AGACGGTGATGAACCTCTTGCAGGAAACATCTCTCAATCATTGTAAGAGTATGGGTATTCTCAATGAC

GGCTTTGGTCGTACCCCGGAGATGTGCAAAAGGGACCTCATTTGGGTGCTTACAAAAATGCAGATCTT

GGTGAATCGCTATCCAAATTGGGGTGATACTGTCGAGATCAATAGCTGGTTCTCCCAGTCCGGGAAAA

-continued

TCGGTATGGGTCGCAATTGGCTAATAAGTGATTGCAACACAGGAGAAATTCTTATAAGAGCAACGAGC

ATTTGGGCCATGATGAATCAAAATACGAGAAGATTCTCAAAACTTCCAAACGAGGTTCGCCAGGAGAT

AGCGCCTCATTTTGTTGACGCTCCTCCTGTCATTGAAGACAATGATCGAAAATTGCATAAGTTTGATGT

GAAGACTGGTGATTCCATTCGCAAGGGTCTAACTCCGGGGTGGAATGACTTGGATGTCAATCAGCACG

TAAGCAACGTGAAGTACATTGGGTGGATTCTCGAGAGTATGCCAACAGAAGTTTTGGAGACCCAGGA

GCTATGCTCTCTCACCCTTGAATATAGGCGGGAATGCGGAAGGGACAGTGTGCTGGAGTCCGTGACCG

CTATGAATCCCTCAAAAGTTGGAGACCGGTCTCAGTACCAGCACCTTCTACGGCTTGAGGATGGGGCT

GATATCATGAAGGGCAGAACTGAGTGGCGACCAAAGAATGCAGGAACCAACGGGGCGATATCAACAG

GAAAGACTTCAAATGGAAACTCGGTCTCTTAG

SEQ ID NO: 60
*Cuphea heterophylla* (Cht) FATB2e (G76D, R97L, H124L, I132S, G152S, H165L, T211N, K258N, C303R, E309G, K334T, T386A variant) coding DNA sequence codon optimized for *Prototheca moriformis*
ATGGTGGTGGCCGCCGCCGCCTCCTCCGCCTTCTTCCCCGTGCCCGCCTCCGGCACCTCCCCCAAGCCC

GGCAAGTTCGGCACCTGGCTGTCCTCCTCCTCCCCCTCCTACAAGCCCAAGTCCAACCCCTCCGGCGGC

TTCCAGGTGAAGGCCAACGCCTCCGCCCACCCCAAGGCCAACGGCTCCGCCGTGTCCCTGAAGTCCGG

CTCCCTGAACACCCAGGAGGACACCTCCTCCTCCCCCCCCCCCAGACCTTCCTGAACCAGCTGCCCGA

CTGGTCCCGCCTGCTGACCGCCATCTCCACCGTGTTCGTGGCCGCCGAGAAGCAGCTGACCATGCTGG

ACCGCAAGTCCAAGCGCCCCGACATGCTGGTGGACTGGTTCGGCCTGGAGTCCATCGTGCAGGACGGC

CTGGTGTTCCGCGAGTCCTACTCCATCCGCTCCTACGAGATCTCCGCCGACCGCACCGCCTCCATCGAG

ACCGTGATGAACCTGCTGCAGGAGACCTCCCTGAACCACTGCAAGTCCATGGGCATCCTGAACGACGG

CTTCGGCCGCACCCCCGAGATGTGCAAGCGCGACCTGATCTGGGTGCTGACCAAGATGCAGATCCTGG

TGAACCGCTACCCCAACTGGGGCGACACCGTGGAGATCAACTCCTGGTTCTCCCAGTCCGGCAAGATC

GGCATGGGCCGCAACTGGCTGATCTCCGACTGCAACACCGGCGAGATCCTGATCCGCGCCACCTCCAT

CTGGGCCATGATGAACCAGAACACCCGCCGCTTCTCCAAGCTGCCCAACGAGGTGCGCCAGGAGATCG

CCCCCCACTTCGTGGACGCCCCCCCCGTGATCGAGGACAACGACCGCAAGCTGCACAAGTTCGACGTG

AAGACCGGCGACTCCATCCGCAAGGGCCTGACCCCCGGCTGGAACGACCTGGACGTGAACCAGCACG

TGTCCAACGTGAAGTACATCGGCTGGATCCTGGAGTCCATGCCCACCGAGGTGCTGGAGACCCAGGAG

CTGTGCTCCCTGACCCTGGAGTACCGCCGCGAGTGCGGCCGCGACTCCGTGCTGGAGTCCGTGACCGC

CATGAACCCCTCCAAGGTGGGCGACCGCTCCCAGTACCAGCACCTGCTGCGCCTGGAGGACGGCGCCG

ACATCATGAAGGGCCGCACCGAGTGGCGCCCCAAGAACGCCGGCACCAACGGCGCCATCTCCACCGG

CAAGACCTCCAACGGCAACTCCGTGTCCTGA

SEQ ID NO: 61
*Cuphea heterophylla* (Cht) FATB2f (R97L, H124L, I132S, G152S, H165L, T211N variant) amino acid sequence
MVVAAAASSAFFPVPASGTSPKPGKFGTWLSSSSPSYKPKSNPSGGFQVKANASAFIPKANGSAVSLKSGSL

NTQEGTSSSPPPRTFLNQLPDWSRLLTAISTVFVAAEKQLTMLDRKSKRPDMLVDWFGLESIVQDGLVFRES

YSIRSYEISADRTASIETVMNLLQETSLNHCKSMGILNDGFGRTPEMCKRDLIWVLTKMQILVNRYPNWGD

TVEINSWFSQSGKIGMGRNWLISDCNTGEILIRATSIWAMMNQKTRRFSKLPNEVRQEIAPHFVDAPPVIED

NDRKLHKFDVKTGDSICKGLIPEWNDLDVNQHVSNVKYIGWILESMPKEVLDTQELCSLTLEYRRECGRD

SVLESVTAMDPSKyGDRSQYQHLLRLEDGTDIMKGRTEWRPKNAGTNGAISTGKTSNGNSVS*

SEQ ID NO: 62
*Cuphea heterophylla* (Cht) FATB2f (R97L, H124L, I132S, G152S, H165L, T211N variant) coding DNA sequence
ATGGTGGTGGCTGCTGCAGCAAGCTCTGCATTCTTCCCTGTTCCGGCATCTGGAACCTCCCCTAAACCC

GGGAAGTTCGGGACTTGGCTATCGAGCTCGAGCCCTTCCTACAAGCCCAAGTCAAACCCCAGTGGTGG

-continued

ATTTCAGGTTAAAGCAAATGCCAGTGCTCATCCTAAGGCTAACGGTTCCGCAGTAAGTCTAAAGTCTG

GCAGCCTCAACACTCAGGAGGGCACTTCGTCGTCCCCTCCTCCTCGGACATTCCTTAACCAGTTGCCTG

ATTGGAGTAGGCTTCTGACTGCAATCTCGACCGTCTTCGTGGCGGCAGAGAAGCAGTTGACTATGCTC

GATCGAAAATCTAAGAGGCCTGACATGCTCGTGGACTGGTTTGGGTTGGAGAGTATTGTTCAGGATGG

GCTCGTGTTCAGAGAGAGTTATTCGATCAGGTCTTACGAAATAAGCGCTGATCGAACAGCCTCTATAG

AGACGGTGATGAACCTCTTGCAGGAAACATCTCTCAATCATTGTAAGAGTATGGGTATTCTCAATGAC

GGCTTTGGTCGTACCCCGGAGATGTGCAAAAGGGACCTCATTTGGGTGCTTACAAAAATGCAGATCTT

GGTGAATCGCTATCCAAATTGGGGTGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAAGACGAGAAGATTCTCAAAACTTCCAAATGAGGTTCGCCAGGAGAT

AGCGCCTCATTTTGTGGACGCCCCTCCTGTCATTGAAGACAATGATCGAAAATTGCATAAGTTTGATGT

GAAGACTGGTGATTCCATTTGCAAGGGTCTAACACCGGAGTGGAACGACTTGGATGTCAATCAGCACG

TAAGCAACGTGAAGTACATTGGGTGGATTCTCGAGAGTATGCCAAAAGAAGTTTTGGACACCCAGGA

GCTATGCTCTCTCACCCTTGAATATAGGCGGGAATGCGGAAGGGACAGTGTGCTGGAGTCTGTGACCG

CTATGGATCCCTCAAAAGTTGGAGACCGATCTCAGTACCAGCACCTTCTGCGGCTTGAAGATGGGACT

GATATCATGAAGGGCAGAACTGAGTGGCGACCAAAGAATGCAGGAACCAACGGGGCGATATCAACAG

GAAAGACTTCAAATGGAAACTCGGTCTCTTAG

SEQ ID NO: 63
*Cuphea heterophylla* (Cht) FATB2f (R97L, H124L, I132S, G152S, H165L, T211N variant) coding DNA sequence codon optimized for *Prototheca moriformis*
ATGGTGGTGGCCGCCGCCGCCTCCTCCGCCTTCTTCCCCGTGCCCGCCTCCGGCACCTCCCCCAAGCCC

GGCAAGTTCGGCACCTGGCTGTCCTCCTCCTCCCCCTCCTACAAGCCCAAGTCCAACCCCTCCGGCGGC

TTCCAGGTGAAGGCCAACGCCTCCGCCCACCCCAAGGCCAACGGCTCCGCCGTGTCCCTGAAGTCCGG

CTCCCTGAACACCCAGGAGGGCACCTCCTCCTCCCCCCCCCCCCGCACCTTCCTGAACCAGCTGCCCGA

CTGGTCCCGCCTGCTGACCGCCATCTCCACCGTGTTCGTGGCCGCCGAGAAGCAGCTGACCATGCTGG

ACCGCAAGTCCAAGCGCCCCGACATGCTGGTGGACTGGTTCGGCCTGGAGTCCATCGTGCAGGACGGC

CTGGTGTTCCGCGAGTCCTACTCCATCCGCTCCTACGAGATCTCCGCCGACCGCACCGCCTCCATCGAG

ACCGTGATGAACCTGCTGCAGGAGACCTCCCTGAACCACTGCAAGTCCATGGGCATCCTGAACGACGG

CTTCGGCCGCACCCCCGAGATGTGCAAGCGCGACCTGATCTGGGTGCTGACCAAGATGCAGATCCTGG

TGAACCGCTACCCCAACTGGGGCGACACCGTGGAGATCAACTCCTGGTTCTCCCAGTCCGGCAAGATC

GGCATGGGCCGCAACTGGCTGATCTCCGACTGCAACACCGGCGAGATCCTGATCCGCGCCACCTCCAT

CTGGGCCATGATGAACCAGAAGACCCGCCGCTTCTCCAAGCTGCCCAACGAGGTGCGCCAGGAGATC

GCCCCCCACTTCGTGGACGCCCCCCCCGTGATCGAGGACAACGACCGCAAGCTGCACAAGTTCGACGT

GAAGACCGGCGACTCCATCTGCAAGGGCCTGACCCCCGAGTGGAACGACCTGGACGTGAACCAGCAC

GTGTCCAACGTGAAGTACATCGGCTGGATCCTGGAGTCCATGCCCAAGGAGGTGCTGGACACCCAGGA

GCTGTGCTCCCTGACCCTGGAGTACCGCCGCGAGTGCGGCCGCGACTCCGTGCTGGAGTCCGTGACCG

CCATGGACCCCTCCAAGGTGGGCGACCGCTCCCAGTACCAGCACCTGCTGCGCCTGGAGGACGGCACC

GACATCATGAAGGGCCGCACCGAGTGGCGCCCCAAGAACGCCGGCACCAACGGCGCCATCTCCACCG

GCAAGACCTCCAACGGCAACTCCGTGTCCTGA

-continued

SEQ ID NO: 64
*Cuphea heterophylla* (Cht) FATB2g (A6T, A16V, S17P, G76D, R97L, H124L, I132S, S143I, G152S, A157T, H165L, T211N, G414A variant) amino acid sequence
MVVAATASSAFFPVPVPGTSPKPGKFGTWLSSSSPSYKPKSNPSGGFQVKANASAHPKANGSAVSLKSGSL

NTQEDTSSSPPPRTFLNQLPDWSRLLTAISTVFVAAEKQLTMLDRKSKRPDMLVDWFGLESIVQDGLVFREI

YSIRSYEISADRTTSIETVMNLLQETSLNHCKSMGILNDGFGRTPEMCKRDLIWVLTKMQILVNRYPNWGD

TVEINSWFSQSGKIGMGRNWLISDCNTGEILIRATSIWAMMNQKTRRFSKLPNEVRQEIAPHFVDAPPVIED

NDRKLHKFDVKTGDSICKGLTFEWNDLDVNQHVSNVKYIGWILESMPKEVLDTQELCSLTLEYRRECGRD

SVLESVTAMDPSKVGDRSQYQHLLRLEDGTDIMKGRTEWRPKNAGINGAISTGKTSNANSVS*

SEQ ID NO: 65
Cuphea heterophylla (Cht) FATB2g (A6T, A16V, S17P, G76D, R97L, H124L, I132S, S143I, G152S, A157T, H165L, T211N, G414A variant) coding DNA sequence
ATGGTGGTGGCTGCTACAGCAAGTTCTGCATTCTTCCCTGTTCCTGTACCTGGAACCTCCCCTAAACCC

GGAAAGTTCGGGACTTGGCTATCGAGCTCGAGCCCTTCCTACAAGCCCAAGTCAAACCCCAGTGGTGG

ATTTCAGGTTAAGGCAAATGCCAM'CiCTCATCCTAAGGCTAACGGTTCTGCAGTAAGTCTAAAGTCTG

GCAGCCTCAACACTCAGGAGGACACTTCGTCGTCCCCTCCTCCTCGGACATTCCTTAACCAGTTGCCTG

ATTGGAGTAGGCTTCTGACTGCAATCTCGACCGTCTTCGTGGCGGCAGAGAAGCAGTTGACTATGCTC

GATCGAAAATCTAAGAGGCCTGACATGCTCGTGGACTGGTTTGGGTTGGAGAGTATTGTTCAGGATGG

GCTCGTGTTCAGAGAGATTTATTCGATCAGGTCTTACGAAATAAGCGCTGATCGAACAACCTCTATAG

AGACGGTGATGAACCTCTTGCAGGAAACATCTCTCAATCATTGTAAGAGTATGGGTATTCTCAATGAC

GGCTTTGGTCGTACCCCGGAGATGTGCAAAAGGGACCTCATTTGGGTGCTTACAAAAATGCAGATCTT

GGTGAATCGCTATCCAAATTGGGGTGATACTGTCGAGATCAATAGCTGGTTCTCCCAGTCCGGGAAAA

TCGGTATGGGTCGCAATTGGCTAATAAGTGATTGCAACACAGGAGAAATTCTTATAAGAGCAACGAGC

ATTTGGGCCATGATGAATCAAAAGACGAGAAGATTCTCAAAACTTCCAAACGAGGTTCGCCAGGAGA

TAGCGCCTCATTTTGTGGACGCCCCTCCTGTCATTGAAGACAATGATCGAAAATTGCATAAGTTTGATG

TGAAGACTGGTGATTCCATTTGCAAGGGTCTAACACCGGAGTGGAATGACTTGGATGTCAATCAGCAC

GTAAGCAACGTGAAGTACATTGGGTGGATTCTCGAGAGTATGCCAAAAGAAGTTTTGGACACCCAGG

AGCTATGCTCTCTCACCCTTGAATATAGGCGGGAATGCGGAAGGGACAGTGTGCTGGAGTCTGTGACC

GCTATGGATCCCTCAAAAGTTGGAGACCGATCTCAGTACCAGCACCTTCTGCGGCTTGAAGATGGGAC

TGATATCATGAAGGGCAGAACTGAGTGGCGACCAAAGAATGCAGGAACCAACGGGGCGATATCAACA

GGAAAGACTTCAAATGCAAACTCGGTCTCTTAG

SEQ ID NO: 66
*Cuphea heterophylla* (Cht) FATB2g (A6T, A16V, S17P, G76D, R97L, H124L, I132S, S143I, G152S, AI57T, H165L, T211N, G414A variant) coding DNA sequence codon optimized for *Prototheca moriformis*
ATGGTGGTGGCCGCCACCGCCTCCTCCGCCTTCTTCCCCGTGCCCGTGCCCGGCACCTCCCCCAAGCCC

GGCAAGTTCGGCACCTGGCTGTCCTCCTCCTCCCCCTCCTACAAGCCCAAGTCCAACCCCTCCGGCGGC

TTCCAGGTGAAGGCCAACGCCTCCGCCCACCCCAAGGCCAACGGCTCCGCCGTGTCCCTGAAGTCCGG

CTCCCTGAACACCCAGGAGGACACCTCCTCCTCCCCCCCCCCCCGCACCTTCCTGAACCAGCTGCCCGA

CTGGTCCCGCCTGCTGACCGCCATCTCCACCGTGTTCGTGGCCGCCGAGAAGCAGCTGACCATGCTGG

ACCGCAAGTCCAAGCGCCCCGACATGCTGGTGGACTGGTTCGGCCTGGAGTCCATCGTGCAGGACGGC

CTGGTGTTCCGCGAGATCTACTCCATCCGCTCCTACGAGATCTCCGCCGACCGCACCACCTCCATCGAG

ACCGTGATGAACCTGCTGCAGGAGACCTCCCTGAACCACTGCAAGTCCATGGGCATCCTGAACGACGG

CTTCGGCCGCACCCCCGAGATGTGCAAGCGCGACCTGATCTGGGTGCTGACCAAGATGCAGATCCTGG

TGAACCGCTACCCCAACTGGGGCGACACCGTGGAGATCAACTCCTGGTTCTCCCAGTCCGGCAAGATC

-continued

GGCATGGGCCGCAACTGGCTGATCTCCGACTGCAACACCGGCGAGATCCTGATCCGCGCCACCTCCAT

CTGGGCCATGATGAACCAGAAGACCCGCCGCTTCTCCAAGCTGCCCAACGAGGTGCGCCAGGAGATC

GCCCCCCACTTCGTGGACGCCCCCCCCGTGATCGAGGACAACGACCGCAAGCTGCACAAGTTCGACGT

GAAGACCGGCGACTCCATCTGCAAGGGCCTGACCCCCGAGTGGAACGACCTGGACGTGAACCAGCAC

GTGTCCAACGTGAAGTACATCGGCTGGATCCTGGAGTCCATGCCCAAGGAGGTGCTGGACACCCAGGA

GCTGTGCTCCCTGACCCTGGAGTACCGCCGCGAGTGCGGCCGCGACTCCGTGCTGGAGTCCGTGACCG

CCATGGACCCCTCCAAGGTGGGCGACCGCTCCCAGTACCAGCACCTGCTGCGCCTGGAGGACGGCACC

GACATCATGAAGGGCCGCACCGAGTGGCGCCCCAAGAACGCCGGCACCAACGGCGCCATCTCCACCG

GCAAGACCTCCAACGCCAACTCCGTGTCCTGA

SEQ ID NO: 67
*Cuphea heterophylla* (Cht) FATB3aamino acid sequence
MVATAASSAFFPVPSPDTSSRPGKLGNGSSSLRPLKPKEVANAGLQVKANASAPPKINGSSVSLKSCSLKTH

EDTPSAPPPRTFINQLPDWSMLLAAITTVFLAAEKQWMMLDWKPKRPDMLVDPFGLGRIVQDGLVERQNF

SIRSYEIGADRTASIETVMNHLQETALNHVKSAGLLNEGFGRTPEMYKRDLIWVVAKMQVMVNRYPTWG

DTVEVNTWVAKSGKNGMRRDWLISDCNTGEILTRASSVWVMMNQKTRKLSKIPDEVRHEIEPHFVDSAPV

IEDDDWKLPKLDEKTADSIRKGLTPKWNDLDVNQHVNNVKYIGWILESTPPEVLETQELCSLTLEYRRECG

RESVLESLTAVDPSGKGFGPQFQHLLRIEDGGEIVKGRTEWRPKTAGINGTIASGETSPGNS*

SEQ ID NO: 68
*Cuphea heterophylla* (Cht) FATB3a coding DNA sequence
ATGGTGGCCACCGCTGCAAGTTCTGCATTCTTCCCGGTGCCGTCCCCGGACACCTCCTCTAGACCGGGA

AAGCTCGGAAATGGGTCATCAAGCTTGAGGCCCCTCAAGCCCAAATTTGTTGCCAATGCTGGGCTGCA

GGTTAAGGCAAACGCCAGTGCCCCTCCTAAGATCAATGGTTCCTCGGTCAGTCTAAAGTCTTGCAGTCT

CAAGACTCATGAAGACACTCCTTCAGCTCCTCCTCCGCGGACTTTTATCAACCAGTTGCCTGATTGGAG

CATGCTTCTTGCTGCAATCACTACTGTCTTCTTGGCAGCAGAGAAGCAGTGGATGATGCTTGATTGGAA

ACCAAAGAGGCCTGACATGCTTGTGGACCCGTTCGGATTGGGAAGGATTGTTCAGGATGGGCTTGTGT

TCAGGCAGAATTTTTCGATTAGGTCCTATGAAATAGGCGCTGATCGCACTGCATCCATAGAGACGGTG

ATGAACCACTTGCAGGAAACGGCTCTCAATCATGTTAAGAGTGCGGGGCTTCTTAATGAAGGCTTTGG

TCGTACTCCTGAGATGTATAAAAGGGACCTTATTTGGGTTGTCGCGAAAATGCAGGTCATGGTTAACC

GCTATCCTACTTGGGGTGACACGGTTGAAGTGAATACTTGGGTTGCCAAGTCAGGGAAAAATGGTATG

CGTCGTGATTGGCTCATAAGTGATTGCAATACAGGAGAAATTCTTACAAGGGCATCAAGTGTGTGGGT

CATGATGAATCAAAAGACAAGAAAATTGTCAAAGATTCCAGATGAGGTTCGGCATGAGATAGAGCCT

CATTTTGTGGACTCTGCTCCCGTCATTGAAGACGATGACTGGAAACTTCCCAAGCTGGATGAGAAAAC

TGCTGACTCCATCCGCAAGGGTCTAACTCCGAAGTGGAATGACTTGGATGTCAATCAGCACGTCAACA

ACGTGAAGTACATTGGGTGGATTCTTGAGAGTACTCCACCAGAAGTTCTGGAGACCCAGGAGTTATGT

TCCCTTACCCTGGAATACAGGCGGGAATGCGGAAGGGAGAGTGTGCTGGAGTCCCTCACTGCTGTGGA

CCCCTCTGGAAAGGGCTTTGGGCCCCAGTTTCAGCACCTTCTGAGGCTTGAGGATGGAGGTGAGATCG

TAAAGGGGAGAACTGAGTGGCGACCCAAGACTGCAGGTATCAATGGGACGATTGCATCTGGGGAGAC

CTCACCTGGAAACTCTTAG

SEQ ID NO: 69
*Cuphea heterophylla* (Cht) FATB3a coding DNA sequence codon optimized for *Prototheca moriformis*
ATGGTGGCCACCGCCGCCTCCTCCGCCTTCTTCCCCGTGCCCTCCCCCGACACCTCCTCCCGCCCCGGC

AAGCTGGGCAACGGCTCCTCCTCCCTGCGCCCCCTGAAGCCCAAGTTCGTGGCCAACGCCGGCCTGCA

GGTGAAGGCCAACGCCTCCGCCCCCCCCAAGATCAACGGCTCCTCCGTGTCCCTGAAGTCCTGCTCCCT

-continued

GAAGACCCACGAGGACACCCCCTCCGCCCCCCCCCCCCGCACCTTCATCAACCAGCTGCCCGACTGGT

CCATGCTGCTGGCCGCCATCACCACCGTGTTCCTGGCCGCCGAGAAGCAGTGGATGATGCTGGACTGG

AAGCCCAAGCGCCCCGACATGCTGGTGGACCCMCGGCCTGGGCCGCATCGTGCAGGACGGCCTGGT

GTTCCGCCAGAACTTCTCCATCCGCTCCTACGAGATCGGCGCCGACCGCACCGCCTCCATCGAGACCG

TGATGAACCACCTGCAGGAGACCGCCCTGAACCACGTGAAGTCCGCCGGCCTGCTGAACGAGGGCTTC

GGCCGCACCCCCGAGATGTACAAGCGCGACCTGATCTGGGTGGTGGCCAAGATGCAGGTGATGGTGA

ACCGCTACCCCACCTGGGGCGACACCGTGGAGGTGAACACCTGGGTGGCCAAGTCCGGCAAGAACGG

CATGCGCCGCGACTGGCTGATCTCCGACTGCAACACCGGCGAGATCCTGACCCGCGCCTCCTCCGTGT

GGGTGATGATGAACCAGAAGACCCGCAAGCTGTCCAAGATCCCCGACGAGGTGCGCCACGAGATCGA

GCCCCACTTCGTGGACTCCGCCCCCGTGATCGAGGACGACGACTGGAAGCTGCCCAAGCTGGACGAGA

AGACCGCCGACTCCATCCGCAAGGGCCTGACCCCCAAGTGGAACGACCTGGACGTGAACCAGCACGT

GAACAACGTGAAGTACATCGGCTGGATCCTGGAGTCCACCCCCCCCGAGGTGCTGGAGACCCAGGAG

CTGTGCTCCCTGACCCTGGAGTACCGCCGCGAGTGCGGCCGCGAGTCCGTGCTGGAGTCCCTGACCGC

CGTGGACCCCTCCGGCAAGGGCTTCGGCCCCCAGTTCCAGCACCTGCTGCGCCTGGAGGACGGCGGCG

AGATCGTGAAGGGCCGCACCGAGTGGCGCCCCAAGACCGCCGGCATCAACGGCACCATCGCCTCCGG

CGAGACCTCCCCCGGCAACTCCTGA

SEQ ID NO: 70
*Cuphea heterophylla* (Cht) FATB3b (C67G, H72Q, L128F, N179I variant) amino acid sequence
MVATAASSAFFPVPSPDTSSRPGKLGNGSSSLRPLKPKFVANAGLQVKANASAPPK1NGSSVSLKSGSLKTQ

EDTPSAPPPRTFINQLPDWSMLLAAITTVFLAAEKQWMMLDWKPKRPDMLVDPFGFGRIVQDGLVFRQNF

SIRSYEIGADRTASIETVMNHLQETALNTIVKSAGLLIEGFGRTPEMYKRDLIWVVAKMQVMVNRYPTWGD

TVEVNTWVAKSGKNGIARRDWLISDCNTGEILTRASSVWVMMNQKTRKLSKIPDEVRHEIEPHFVDSAPVI

EDDDWKLPKIDEKTADSIRKGLTPKWNDLDVNQHVNNVKYIGWILESTPPEVLETQELCSLTLEYRRECG

RESVLESLTAVDPSGKGFGPQFQHLLRLEDGGEIVKGRTEWRPKTAGINGTIASGETSPGNS*

SEQ ID NO: 71
Cuphea *heterophylla* (Cht) FATB3b (C67G, H72Q, L128F, N179I variant) coding DNA sequence
ATGGTGGCCACCGCTGCAAGTTCTGCATTCTTCCCGGTGCCATCCCCGGACACCTCCTCTAGACCGGGA

AAGCTCGGAAATGGGTCATCAAGCTTGAGGCCCCTCAAGCCCAAATTTGTTGCCAATGCTGGGCTGCA

GGTTAAGGCAAACGCCAGTGCCCCTCCTAAGATCAATGGTTCCTCGGTCAGTCTAAAGTCTGGCAGTC

TCAAGACTCAGGAAGACACTCCTTCGGCTCCTCCTCCGCGGACTTTTATCAACCAGTTGCCTGATTGGA

GCATGCTTCTTGCTGCAATCACTACTGTCTTCTTGGCAGCAGAGAAGCAGTGGATGATGCTTGATTGGA

AACCAAAGAGGCCTGACATGCTTGTGGACCCGTTCGGATTTGGAAGGATTGTTCAGGATGGGCTTGTG

TTCAGGCAGAATTTTTCGATTAGGTCCTATGAAATAGGCGCTGATCGCACTGCATCTATAGAGACGGT

GATGAACCACTTGCAGGAAACGGCTCTCAATCATGTTAAGAGTGCGGGGCTTCTTATTGAAGGCTTTG

GTCGTACTCCTGAGATGTATAAAAGGGACCTTATTTGGGTTGTCGCGAAAATGCAGGTCATGGTTAAC

CGCTATCCTACTTGGGGTGACACGGTTGAAGTGAATACTTGGGTTGCCAAGTCAGGGAAAAATGGTAT

GCGTCGTGATTGGCTCATAAGTGATTGCAATACAGGAGAAATTCTTACTAGAGCATCAAGTGTGTGGG

TCATGATGAATCAAAAGACAAGAAAATTGTCAAAGATTCCAGATGAGGTTCGGCATGAGATAGAGCC

TCATTTTGTGGACTCTGCTCCCGTCATTGAAGACGATGACTGGAAACTTCCCAAGCTGGATGAGAAAA

CTGCTGACTCCATCCGCAAGGGTCTAACTCCGAAGTGGAATGACTTGGATGTCAATCAGCACGTCAAC

AACGTGAAGTACATTGGGTGGATTCTTGAGAGTACTCCACCAGAAGTTCTGGAGACCCAGGAGTTATG

-continued

TTCCCTTACCCTGGAATACAGGCGGGAATGCGGAAGGGAGAGTGTGCTGGAGTCCCTCACTGCTGTGG

ACCCCTCTGGAAAGGGCTTTGGGCCCCAGTTTCAGCACCTTCTGAGGCTTGAGGATGGAGGTGAGATC

GTAAAGGGGAGAACTGAGTGGCGACCCAAGACTGCAGGTATCAATGGGACGATTGCATCTGGGGAGA

CCTCACCTGGAAACTCTTAG

SEQ ID NO: 72
*Cuphea heterophylla* (Cht) FATB3b (C67G, H72Q, L128F, N179I variant)
coding DNA sequence codon optimized for *Prototheca moriformis*
ATGGTGGCCACCGCCGCCTCCTCCGCCTTCTTCCCCGTGCCCTCCCCCGACACCTCCTCCCGCCCCGGC

AAGCTGGGCAACGGCTCCTCCTCCCTGCGCCCCCTGAAGCCCAAGTTCGTGGCCAACGCCGGCCTGCA

GGTGAAGGCCAACGCCTCCGCCCCCCCCAAGATCAACGGCTCCTCCGTGTCCCTGAAGTCCGGCTCCC

TGAAGACCCAGGAGGACACCCCCTCCGCCCCCCCCCCCCGCACCTTCATCAACCAGCTGCCCGACTGG

TCCATGCTGCTGGCCGCCATCACCACCGTGTTCCTGGCCGCCGAGAAGCAGTGGATGATGCTGGACTG

GAAGCCCAAGCGCCCCGACATGCTGGTGGACCCCTTCGGCTTCGGCCGCATCGTGCAGGACGGCCTGG

TGTTCCGCCAGAACTTCTCCATCCGCTCCTACGAGATCGGCGCCGACCGCACCGCCTCCATCGAGACC

GTGATGAACCACCTGCAGGAGACCGCCCTGAACCACGTGAAGTCCGCCGGCCTGCTGATCGAGGGCTT

CGGCCGCACCCCCEGAGATGTACAAGCGCGACCTGATCTGGGTGGTGGCCAAGATGCAGGTGATGGTG

AACCGCTACCCCACCTGGGGCGACACCGTGGAGGTGAACACCTGGGTGGCCAAGTCCGGCAAGAACG

GCATGCGCCGCGACTGGCTGATCTCCGACTGCAACACCGGCGAGATCCTGACCCGCGCCTCCTCCGTG

TGGGTGATGATGAACCAGAAGACCCGCAAGCTGTCCAAGATCCCCGACGAGGTGCGCCACGAGATCG

AGCCCCACTTCGTGGACTCCGCCCCCGTGATCGAGGACGACGACTGGAAGCTGCCCAAGCTGGACGAG

AAGACCGCCGACTCCATCCGCAAGGGCCTGACCCCCAAGTGGAACGACCTGGACGTGAACCAGCACG

TGAACAACGTGAAGTACATCGGCTGGATCCTGGAGTCCACCCCCCCCGAGGTGCTGGAGACCCAGGA

GCTGTGCTCCCTGACCCTGGAGTACCGCCGCGAGTGCGGCCGCGAGTCCGTGCTGGAGTCCCTGACCG

CCGTGGACCCCTCCGGCAAGGGCTTCGGCCCCCAGTTCCAGCACCTGCTGCGCCTGGAGGACGGCGGC

GAGATCGTGAAGGGCCGCACCGAGTGGCGCCCCAAGACCGCCGGCATCAACGGCACCATCGCCTCCG

GCGAGACCTCCCCCGGCAACTCCTGA

SEQ ID NO: 73
*Cuphea viscosissima* (Cvis) FATB1 amino acid sequence
MVAAAATSAFFPVPAPGTSPKPGKSGNWPSSLSPTFKPKSIPNGGFQVKANASAHPKANGSAVNLKSGSLN

TQEDTSSSPPPRAFLNQLPDWSMLLTAITTVFVAAEKQWTMLDRKSKRPDMLVDSVGLKSIVRDGLVSRHS

FSIRSYEIGADRTASIETLMNHLQETTINHCKSLGLHNDGFGRTPGMCKNDLIWVLTKMQIMVNRYPTWGD

TVEINTWFSQSGKIGMASDWLISDCNTGEILIRATSVWAMMNQKTRRFSRLPYEVRQELTPHFVDSPHVIED

NDQKLRKFDVKTGDSIRKGLTPRWNDLDVNQHVSNVKYIGWILESMPIEVLETQELCSLTVEYRRECGMD

SVLESVTAVDPSENGGRSQYKHLLRLEDGTDIVKSRTEWRPKNAGINGAISTSTAKTSNGNSVS

SEQ ID NO: 74
*Cuphea viscosissima* (Cvis) FATB1 coding DNA sequence codon optimized for
*Prototheca moriformis*
ATGGTGGCCGCCGCCGCCACCTCCGCCTTCTTCCCCGTGCCCGCCCCCGGCACCTCCCCCAAGCCCGGC

AAGTCCGGCAACTGGCCCTCCTCCCTGTCCCCCACCTTCAAGCCCAAGTCCATCCCCAACGGCGGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGACCGCCATCACCACCGTGTTCGTGGCCGCCGAGAAGCAGTGGACCATGCTGGACC

GCAAGTCCAAGCGCCCCGACATGCTGGTGGACTCCGTGGGCCTGAAGTCCATCGTGCGCGACGGCCTG

GTGTCCCGCCACTCCTTCTCCATCCGCTCCTACGAGATCGGCGCCGACCGCACCGCCTCCATCGAGACC

CTGATGAACCACCTGCAGGAGACCACCATCAACCACTGCAAGTCCCTGGGCCTGCACAACGACGGCTT

-continued

CGGCCGCACCCCCGGCATGTGCAAGAACGACCTGATCTGGGTGCTGACCAAGATGCAGATCATGGTGA

ACCGCTACCCCACCTGGGGCGACACCGTGGAGATCAACACCTGGTTCTCCCAGTCCGGCAAGATCGGC

ATGGCCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCAGAAGCTGCGCAAGTTCGACGTGAAG

ACCGGCGACTCCATCCGCAAGGGCCTGACCCCCCGCTGGAACGACCTGGACGTGAACCAGCACGTGTC

CAACGTGAAGTACATCGGCTGGATCCTGGAGTCCATGCCCATCGAGGTGCTGGAGACCCAGGAGCTGT

GCTCCCTGACCGTGGAGTACCGCCGCGAGTGCGGCATGGACTCCGTGCTGGAGTCCGTGACCGCCGTG

GACCCCTCCGAGAACGGCGGCCGCTCCCAGTACAAGCACCTGCTGCGCCTGGAGGACGGCACCGACA

TCGTGAAGTCCCGCACCGAGTGGCGCCCCAAGAACGCCGGCACCAACGGCGCCATCTCCACCTCCACC

GCCAAGACCTCCAACGGCAACTCCGTGTCCTGA

SEQ ID NO: 75
*Cuphea viscosissima* (Cvis) FATB2 amino acid sequence
MVATAASSAFFPVPSADTSSRPGKLGNGPSSFSPLKPKSIPNGGLQVKASASAPPKINGSSVGLKSGGLKTH

DDAPSAPPPRTFINQLPDWSMLLAAITTAFLAAEKQWMMLDRKPKRLDMLEDPFGLGRVVQDGLVFRQNF

SIRSYEIGADRTASIETVMNHLQETALNHVKTAGLSNDGFGRTPEMYKRDLIWVVAKMQVMVNRYPTWG

DTVEVNTWVAKSGKNGMRRDWLISDCNTGEILTRASSVWVMMNQKTRKLSKIPDEVRREIEPHFVDSAPV

IEDDDRKLPKLDEKSADSIRKGLTPRWNDLDVNQHVNNAKYIGWILESTPPEVLETQELCSLTLEYRRECGR

ESVLESLTAVDPSGEGYGSQFQHLLRLEDGGEIVKGRTEWRPKNAGINGVVPSEESSPGDYS

SEQ ID NO: 76
*Cuphea viscosissima* (Cvis) FATB2 coding DNA sequence codon optimized for *Prototheca moriformis*
ATGGTGGCCACCGCCGCCTCCTCCGCCTTCTTCCCCGTGCCCTCCGCCGACACCTCCTCCCGCCCCGGC

AAGCTGGGCAACGGCCCCTCCTCCTTCTCCCCCCTGAAGCCCAAGTCCATCCCCAACGGCGGCCTGCA

GGTGAAGGCCTCCGCCTCCGCCCCCCCCAAGATCAACGGCTCCTCCGTGGGCCTGAAGTCCGGCGGCC

TGAAGACCCACGACGACGCCCCCTCCGCCCCCCCCCCCCGCACCTTCATCAACCAGCTGCCCGACTGG

TCCATGCTGCTGGCCGCCATCACCACCGCCTTCCTGGCCGCCGAGAAGCAGTGGATGATGCTGGACCG

CAAGCCCAAGCGCCTGGACATGCTGGAGGACCCCTTCGGCCTGGGCCGCGTGGTGCAGGACGGCCTG

GTGTTCCGCCAGAACTTCTCCATCCGCTCCTACGAGATCGGCGCCGACCGCACCGCCTCCATCGAGAC

CGTGATGAACCACCTGCAGGAGACCGCCCTGAACCACGTGAAGACCGCCGGCCTGTCCAACGACGGC

TTCGGCCGCACCCCCGAGATGTACAAGCGCGACCTGATCTGGGTGGTGGCCAAGATGCAGGTGATGGT

GAACCGCTACCCCACCTGGGGCGACACCGTGGAGGTGAACACCTGGGTGGCCAAGTCCGGCAAGAAC

GGCATGCGCCGCGACTGGCTGATCTCCGACTGCAACACCGGCGAGATCCTGACCCGCGCCTCCTCCGT

GTGGGTGATGATGAACCAGAAGACCCGCAAGCTGTCCAAGATCCCCGACGAGGTGCGCCGCGAGATC

GAGCCCCACTTCGTGGACTCCGCCCCCGTGATCGAGGACGACGACCGCAAGCTGCCCAAGCTGGACGA

GAAGTCCGCCGACTCCATCCGCAAGGGCCTGACCCCCCGCTGGAACGACCTGGACGTGAACCAGCAC

GTGAACAACGCCAAGTACATCGGCTGGATCCTGGAGTCCACCCCCCCCGAGGTGCTGGAGACCCAGG

AGCTGTGCTCCCTGACCCTGGAGTACCGCCGCGAGTGCGGCCGCGAGTCCGTGCTGGAGTCCCTGACC

GCCGTGGACCCCTCCGGCGAGGGCTACGGCTCCCAGTTCCAGCACCTGCTGCGCCTGGAGGACGGCGG

CGAGATCGTGAAGGGCCGCACCGAGTGGCGCCCCAAGAACGCCGGCATCAACGGCGTGGTGCCCTCC

GAGGAGTCCTCCCCCGGCGACTACTCCTGA

-continued

SEQ ID NO: 77
*Cuphea viscosissima* (Cvis) FATB3 amino acid sequence
MVAAAASSAFFSFPTPGTSPKPGKFGNWPSSLSIPFNPKSNHNGGIQVKANASAHPKANGSAVSLKAGSLET

QEDTSSPSPPPRTFISQLPDWSMLVSAITTVFVAAEKQWTMLDRKSKRPDVLVEPFVQDGVSFRQSFSIRSYE

IGVDRTASIETLMNIFQETSLNHCKSLGLLNDGFGRTPEMCKRDLIWVVTKMQIEVNRYPTWGDTIEVTTW

VSESGKNGMSRDWLISDCHSGEILIRATSVWAMMNQKTRRLSKIPDEVRQEIVPYFVDSAPVIEDDRKLHK

LDVKTGDSIRNGLTPRWNDFDVNQHVNNVKYIAWLLKSVPTEVFETQELCGLTLEYRRECRRDSVLESVT

AMDPSKEGDRSLYQHLLRLENGADIALGRTEWRPKNAGATGAVSTGKTSNGNSVS

SEQ ID NO: 78
*Cuphea viscosissima* (Cvis) FATB3 coding DNA sequence codon optimized for *Prototheca moriformis*
ATGGTGGCCGCCGCCGCCTCCTCCGCCTTCTTCTCCTTCCCCACCCCCGGCACCTCCCCCAAGCCCGGC

AAGTTCGGCAACTGGCCCTCCTCCCTGTCCATCCCCTTVAACCCCAAGTCCAACCACAACGGCGGCATC

CAGGTGAAGGCCAACGCCTCCGCCCACCCCAAGGCCAACGGCTCCGCCGTGTCCCTGAAGGCCGGCTC

CCTGGAGACCCAGGAGGACACCTCCTCCCCCTCCCCCCCCCCCCGCACCTTCATCTCCCAGCTGCCCGA

CTGGTCCATGCTGGTGTCCGCCATCACCACCGTGTTCGTGGCCGCCGAGAAGCAGTGGACCATGCTGG

ACCGCAAGTCCAAGCGCCCCGACGTGCTGGTGGAGCCCTTCGTGCAGGACGGCGTGTCCTTCCGCCAG

TCCTTCTCCATCCGCTCCTACGAGATCGGCGTGGACCGCACCGCCTCCATCGAGACCCTGATGAACATC

TTCCAGGAGACCTCCCTGAACCACTGCAAGTCCCTGGGCCTGCTGAACGACGGCTTCGGCCGCACCCC

CGAGATGTGCAAGCGCGACCTGATCTGGGTGGTGACCAAGATGCAGATCGAGGTGAACCGCTACCCC

ACCTGGGGCGACACCATCGAGGTGACCACCTGGGTGTCCGAGTCCGGCAAGAACGGCATGTCCCGCG

ACTGGCTGATCTCCGACTGCCACTCCGGCGAGATCCTGATCCGCGCCACCTCCGTGTGGGCCATGATG

AACCAGAAGACCCGCCGCCTGTCCAAGATCCCCGACGAGGTGCGCCAGGAGATCGTGCCCTACTTCGT

GGACTCCGCCCCCGTGATCGAGGACGACCGCAAGCTGCACAAGCTGGACGTGAAGACCGGCGACTCC

ATCCGCAACGGCCTGACCCCCCGCTGGAACGACTTCGACGTGAACCAGCACGTGAACAACGTGAAGT

ACATCGCCTGGCTGCTGAAGTCCGTGCCCACCGAGGTGTTCGAGACCCAGGAGCTGTGCGGCCTGACC

CTGGAGTACCGCCGCGAGTGCCGCCGCGACTCCGTGCTGGAGTCCGTGACCGCCATGGACCCCTCCAA

GGAGGGCGACCGCTCCCTGTACCAGCACCTGCTGCGCCTGGAGAACGGCGCCGACATCGCCCTGGGCC

GCACCGAGTGGCGCCCCAAGAACGCCGGCGCCACCGGCGCCGTGTCCACCGGCAAGACCTCCAACGG

CAACTCCGTGTCCTGA

SEQ ID NO: 79
*Cuphea calcarata* (Ccalc) FATB1 amino acid sequence
MVAASASSAFFSVPTPGTSPKPGKFGNWPSSLSVPFKPRSNNSGGFQVKANASAHPKANGSAVSLKSGSLE

TQEDNSSSSRPPRTFIKQLPDWSMLLSAITTVFVAAEKQWTMFDRKSKRSDMLVDPFVVDRIVQDGVLFRQ

SFSFRSYEIGADRTASIETLIVINIFQETSLNECKSMGLLYEGFGRTPEMCKRDLIWVVTKIHIKVNRYPTWGD

TIEVITWVSESGKNGMGRDWLISDCHTGEILIRATSVWAMMNQTTRRLSKFPYELRQEIAPHFVDSDPVIED

NRRLLNFDVKTGDSIRKGLTPRWNDLDVNQHVNNVKYIGWILESVPTEVFDTRELCGLTLEYRQECGRGS

VLESVTAMDPSKEGDRSLYQHLLRLEDGTDIVKGRTEWRPKNAGINGPVSTRKTTNGSSVS

SEQ ID NO: 80
*Cuphea calcarata* (Ccalc) FATB1 coding DNA sequence
ATGGTGGCTGCTTCAGCAAGTTCTGCATTCTTCTCCGTCCCAACCCCGGGAACCTCTCCTAAACCCGGG

AAGTTCGGCAATTGGCCATCGAGCTTGAGCGTCCCATTCAAGCCCAGATCAAACAACAGTGGCGGCTT

TCAGGTTAAGGCAAACGCCAGTGCTCATCCTAAGGCTAACGGTTCTGCAGTAAGTCTAAAGTCTGGGA

GCCTCGAGACTCAGGAGGACAATTCGTCGTCGTCTCGTCCTCCTCGGACTTCATTAAACAGTTGCCGG

ACTGGAGTATGCTTCTTTCCGCGATCACAACCGTCTTCGTGGCGGCTGAGAAGCAGTGGACGATGTTT

-continued

GATCGGAAATCTAAGAGGTCTGACATGCTCGTGGACCCGTTTGTGGTTGACAGGATTGTTCAGGATGG

GGTTCTGTTCAGACAGAGTTTTTCGATTAGGTCTTACGAAATAGGCGCTGATCGAACAGCCTCTATTGA

GACGCTGATGAACATCTTCCAGGAAACATCTCTCAATCATTGTAAGAGTATGGGTCTTCTCTATGAAG

GCTTTGGTCGTACTCCTGAGATGTGTAAGAGGGACCTCATTTGGGTGGTTACGAAAATACATATCAAG

GTGAATCGCTATCCGACTTGGGGTGATACTATCGAGGTCACTACTTGGGTCTCCGAGTCGGGCAAAAA

CGGTATGGGTCGCGATTGGCTGATAAGTGATTGCCATACAGGAGAAATTCTTATAAGAGCAACGAGTG

TGTGGGCTATGATGAATCAAACGACGAGAAGATTGTCGAAATTTCCATATGAGCTTCGACAGGAGATA

GCGCCACATT'TTGTGGACTCGGATCCTGTCATTGAAGACAATCGAAGATTGCTCAACTTTGATGTGAA

GACGGGTGATTCCATTCGCAAGGGTCTAACTCCAAGGTGGAATGACTTGGATGTCAATCAGCACGTTA

ACAATGTGAAGTACATTGGGTGGATTCTCGAGAGTGTTCCAACAGAAGTTTTCGATACCCGGGAGCTA

TGCGGCCTCACCCTTGAGTATAGGCAGGAATGCGGAAGAGGAAGTGTGCTGGAGTCCGTGACCGCTAT

GGATCCCTCAAAAGAGGGAGACCGGTCTCTGTACCAGCACCTTCTTCGGCTTGAGGATGGGACTGATA

TCGTGAAGGGCAGAACCGAGTGGCGGCCAAAGAATGCAGGAACCAATGGGCCAGTATCAACAAGAA

AGACTACAAATGGAAGCTCAGTCTCTTAG

SEQ ID NO: 81
*Cuphea calcarata* (Ccalc) FATB1 coding DNA sequence codon optimized for *Prototheca moriformis*
ATGGTGGCCGCCTCCGCCTCCTCCGCCTTCTTCTCCGTGCCCACCCCCGGCACCTCCCCCAAGCCCGGC

AAGTTCGGCAACTGGCCCTCCTCCCTGTCCGTGCCCTTCAAGCCCCGCTCCAACAACTCCGGCGGCTTC

CAGGTGAAGGCCAACGCCTCCGCCCACCCCAAGGCCAACGGCTCCGCCGTGTCCCTGAAGTCCGGCTC

CCTGGAGACCCAGGAGGACAACTCCTCCTCCTCCCGCCCCCCCCGCACCTTCATCAAGCAGCTGCCCG

ACTGGTCCATGCTGCTGTCCGCCATCACCACCGTGTTCGTGGCCGCCGAGAAGCAGTGGACCATGTTC

GACCGCAAGTCCAAGCGCTCCGACATGCTGGTGGACCCCTTCGTGGTGGACCGCATCGTGCAGGACGG

CGTGCTGTTCCGCCAGTCCTTCTCCATCCGCTCCTACGAGATCGGCGCCGACCGCACCGCCTCCATCGA

GACCCTGATGAACATCTTCCAGGAGACCTCCCTGAACCACTGCAAGTCCATGGGCCTGCTGTACGAGG

GCTTCGGCCGCACCCCCGAGATGTGCAAGCGCGACCTGATCTGGGTGGTGACCAAGATCCACATCAAG

GTGAACCGCTACCCCACCTGGGGCGACACCATCGAGGTGACCACCTGGGTGTCCGAGTCCGGCAAGA

ACGGCATGGGCCGCGACTGGCTGATCTCCGACTGCCACACCGGCGAGATCCTGATCCGCGCCACCTCC

GTGTGGGCCATGATGAACCAGACCACCCGCCGCCTGTCCAAGTTCCCCTACGAGCTGCGCCAGGAGAT

CGCCCCCCACTTCGTGGACTCCGACCCCGTGATCGAGGACAACCGCCGCCTGCTGAACTTCGACGTGA

AGACCGGCGACTCCATCCGCAAGGGCCTGACCCCCCGCTGGAACGACCTGGACGTGAACCAGCACGT

GAACAACGTGAAGTACATCGGCTGGATCCTGGAGTCCGTGCCCACCGAGGTGTTCGACACCCGCGAGC

TGTGCGGCCTGACCCTGGAGTACCGCCAGGAGTGCGGCCGCGGCTCCGTGCTGGAGTCCGTGACCGCC

ATGGACCCCTCCAAGGAGGGCGACCGCTCCCTGTACCAGCACCTGCTGCGCCTGGAGGACGGCACCGA

CATCGTGAAGGGCCGCACCGAGTGGCGCCCCAAGAACGCCGGCACCAACGGCCCCGTGTCCACCCGC

AAGACCACCAACGGCTCCTCCGTGTCCTGA

SEQ ID NO: 82
*Cuphea painteri* (Cpai) FATB1 amino acid sequence
MVAAAATSAFFPVPAPGTSPNPRKFGSWPSSLSPSLPKSIPNGGFQVKANASAHPKANGSAVSLKSGSLNTQ

ENTSSSPPPRTFLHQLPDWSRLLTAITTVFVKSKRPDMHDRKSKRPDMLVDLFGLESSVQDALVFRQSFSIRS

YEIGTDRTASIETLMNHLQETSLNHCKSTGILLDGFGRTLEMCKRELIWVVIKMQIQVNRYPAWGDTVEINT

RFSRLGKIGMGRDWLISDCNTGEILIRATSEYAMMNQKTRRLSKLPYEVHQEIAPLFVDSPPVIEDNDLKVH

-continued

KFEVKTGDSIQKGLSPGWNDLDVNQHVSNVKYIGWILESMPTEVLETQELCSLALEYRRECGRDSVLESVT

AMDPSKVGGRSQYQHLLRLEDGTAIVNGITEWRPKNAGANGAISTGKTSNGNSVS

SEQ ID NO: 83
*Cuphea painteri* (Cpai) FATB1 coding DNA sequence
ATGGTGGCTGCTGCAGCAACTTCTGCATTCTTCCCTGTTCCAGCCCCGGGAACCTCCCCAAATCCCAGG

AAATTCGGAAGTTGGCCATCGAGCTTGAGCCCTTCCTTGCCCAAGTCAATCCCCAATGGCGGATTTCA

GGTAAAGGCAAATGCCAGTGCCCATCCGAAGGCTAACGGTTCTGCAGTTAGTCTAAAGTCTGGCAGCC

TCAACACTCAGGAGAACACTTCGTCGTCCCCTCCTCCTCGGACTTTCCrTCACCAGTTGCCTGATTGGA

GTAGGCTTCTGACTGCAATCACGACCGTGTTCGTGAAATCTAAGAGGCCTGACATGCATGATCGGAAA

TCTAAGAGGCCTGACATGCTGGTGGACTTGTTTGGGTTGGAAAGTAGTGTTCAGGATGCGCTCGTGTTC

AGACAGAGTTTTTCGATTAGGTCTTATGAAATAGGCACTGATCGAACAGCCTCTATAGAGACGCTGAT

GAACCACTTGCAGGAAACATCTCTCAATCATTGTAAAAGTACCGGTATTCTCCTTGACGGCTTCGGTCG

TACTCTTGAGATGTGTAAAAGGGAACTCATTTGGGTGGTAATAAAAATGCAAATTCAGGTGAATCGCT

ATCCAGCATGGGGCGATACTGTCGAGATCAATACCCGGTTCTCCCGGTTGGGGAAAATTGGTATGGGT

CGCGATTGGCTAATAAGTGATTGCAACACAGGAGAAATTCTAATAAGAGCAACGAGCGAGTATGCCA

TGATGAATCAAAAGACGAGAAGACTCTCAAAACTTCCATACGAGGTTCACCAGGAGATAGCGCCTCTT

TTTGTCGACTCTCCTCCTGTGATTGAAGACAATGATCTGAAAGTGCATAAATTTGAAGTGAAGACTGGT

GATTCCATTCAAAAGGGTCTATCCCCGGGGTGGAATGACTTGGATGTCAATCAGCACGTAAGCAACGT

GAAGTACATTGGGTGGATTCTCGAGAGTATGCCAACAGAAGTTTTGGAGACCCAGGAGCTATGCTCTC

TCGCCCTTGAATATAGGCGGGAATGCGGAAGGGACAGTGTGCTGGAGTCCGTGACCGCAATGGATCCC

TCAAAAGTTGGAGGCCGTTCTCAGTACCAGCACCTTCTGCGGCTTGAGGATGGGACTGCTATCGTGAA

CGGCATAACTGAGTGGCGGCCGAAGAATGCAGGAGCTAATGGGGCGATATCAACGGGAAAGACTTCA

AATGGAAACTCGGTCTCTTAG

SEQ ID NO: 84
*Cuphea painteri* (Cpai) FATB1 coding DNA sequence codon optimized for
*Prototheca moriformis*
ATGGTGGCCGCCGCCGCCACCTCCGCCTTCTTCCCCGTGCCCGCCCCCGGCACCTCCCCCAACCCCCGC

AAGTTCGGCTCCTGGCCCTCCTCCCTGTCCCCCTCCCTGCCCAAGTCCATCCCCAACGGCGGCTTCCAG

GTGAAGGCCAACGCCTCCGCCCACCCCAAGGCCAACGGCTCCGCCGTGTCCCTGAAGTCCGGCTCCCT

GAACACCCAGGAGAACACCTCCTCCTCCCCCCCCCCCCGCACCTTCCTGCACCAGCTGCCCGACTGGTC

CCGCCTGCTGACCGCCATCACCACCGTGTTCGTGAAGTCCAAGCGCCCCGACATGCACGACCGCAAGT

CCAAGCGCCCCGACATGCTGGTGGACCTGTTCGGCCTGGAGTCCTCCGTGCAGGACGCCCTGGTGTTC

CGCCAGTCCTTCTCCATCCGCTCCTACGAGATCGGCACCGACCGCACCGCCTCCATCGAGACCCTGATG

AACCACCTGCAGGAGACCTCCCTGAACCACTGCAAGTCCACCGGCATCCTGCTGGACGGCTTCGGCCG

CACCCTGGAGATGTGCAAGCGCGAGCTGATCTGGGTGGTGATCAAGATGCAGATCCAGGTGAACCGCT

ACCCCGCCTGGGGCGACACCGTGGAGATCAACACCCGCTTCTCCCGCCTGGGCAAGATCGGCATGGGC

CGCGACTGGCTGATCTCCGACTGCAACACCGGCGAGATCCTGATCCGCGCCACCTCCGAGTACGCCAT

GATGAACCAGAAGACCCGCCGCCTGTCCAAGCTGCCCTACGAGGTGCACCAGGAGATCGCCCCCCTGT

TCGTGGACTCCCCCCCCGTGATCGAGGACAACGACCTGAAGGTGCACAAGTTCGAGGTGAAGACCGG

CGACTCCATCCAGAAGGGCCTGTCCCCCGGCTGGAACGACCTGGACGTGAACCAGCACGTGTCCAACG

TGAAGTACATCGGCTGGATCCTGGAGTCCATGCCCACCGAGGTGCTGGAGACCCAGGAGCTGTGCTCC

CTGGCCCTGGAGTACCGCCGCGAGTGCGGCCGCGACTCCGTGCTGGAGTCCGTGACCGCCATGGACCC

CTCCAAGGTGGGCGGCCGCTCCCAGTACCAGCACCTGCTGCGCCTGGAGGACGGCACCGCCATCGTGA

-continued

ACGGCATCACCGAGTGGCGCCCCAAGAACGCCGGCGCCAACGGCGCCATCTCCACCGGCAAGACCTC

CAACGGCAACTCCGTGTCCTGA

SEQ ID NO: 85
*Cuphea hookeriana* (Chook) FATB4 amino acid sequence
MVAAAATSAFFPVPAPGTSPNPRKFGSWPSSLSPSLPNSIPNGGFQVKANASAHPKANGSAVSLKSGSLNTQ

ENTSSSPPPRTFLHQLPDWSRLLTAITTVFVKSKRPDMHDRKSKRPDMLVDLFGLESSVQDALVFRQRFSIR

SYEIGTDRTASMETLMNHLQETSLNHCKSTGILLDGFGRTLEMCKRELIWVVIKMQIQVNRYPAWGDTVEI

NTRFSRLGKIGMGRDWLISDCNTGEILIRATSEYAMMNQKTRRLSKLPYEVRQEIAPLFVDSPPVIEDNDLK

VHKFEVKTGDSIHKGLTPGWNDLDVNQHVNNVKYIGWILESTPPEVLETQELCSLTLEYRRECGRESVLES

LTAMDPSGGGYGSQFQFILLRLEDGGEIVKGRTEWRPKNGVINGVVPTGESSPGDYS

SEQ ID NO: 86
*Cuphea hookeriana* (Chook) FATB4 coding DNA sequence
ATGGTGGCTGCTGCAGCAACTTCTGCATTCTTCCCTGTTCCAGCCCCGGGAACCTCCCCTAATCCCAGG

AAATTCGGAAGTTGGCCATCGAGCTTGAGCCCTTCCTTGCCCAACTCAATCCCCAATGGCGGATTTCAG

GTAAAGGCAAATGCCAGTGCCCATCCGAAGGCTAACGGTTCTGCAGTTAGTCTAAAGTCTGGCAGCCT

CAACACTCAGGAGAACACTTCGTCGTCCCCTCCTCCTCGGACTTTCCTTCACCAGTTGCCTGATTGGAG

TAGGCTTCTGACTGCAATCACGACCGTGTTCGTGAAATCTAAGAGGCCTGACATGCATGATCGGAAAT

CTAAGAGGCCTGACATGCTGGTGGACTTGTTTGGGTTGGAGAGTAGTGTTCAGGATGCGCTCGTGTTC

AGACAGAGATTTTCGATTAGGTCTTATGAAATAGGCACTGATCGAACAGCCTCTATGGAGACGCTGAT

GAACCACTTGCAGGAAACATCTCTCAATCATTGTAAAAGTACCGGTATTCTCCTTGACGGCTTCGGTCG

TACTCTTGAGATGTGTAAAAGGGAACTCATTTGGGTGGTAATAAAAATGCAGATTCAGGTGAATCGCT

ATCCAGCATGGGGCGATACTGTCGAGATCAATACCCGGTTCTCCCGGTTGGGGAAAATTGGTATGGGT

CGCGATTGGCTAATAAGTGATTGCAACACAGGAGAAATTCTTATAAGAGCAACGAGCGAGTATGCCAT

GATGAATCAAAAGACGAGAAGACTCTCAAAACTTCCATACGAGGTTCGCCAGGAGATAGCGCCTCTTT

TTGTCGACTCTCCTCCTGTGATTGAAGACAATGATCTGAAAGTGCATAAATTTGAAGTGAAGACTGGT

GATTCCATTCACAAGGGTCTAACTCCGGGGTGGAATGACTTGGATGTCAATCAGCACGTCAACAACGT

GAAGTACATCGGGTGGATTCTTGAGAGTACTCCACCAGAAGTTCTGGAGACCCAGGAGTTATGTTCCC

TTACTCTGGAATACAGGCGGGAATGTGGAAGGGAGAGCGTGCTGGAGTCCCTCACTGCTATGGATCCC

TCTGGAGGGGGTTATGGGTCCCAGTTTCAGCACCTTCTGCGGCTTGAGGATGGAGGTGAGATCGTGAA

GGGGAGAACCGAGTGGCGACCCAAGAATGGTGTAATCAATGGGGTGGTACCAACCGGGGAGTCCTCA

CCTGGAGACTACTCTTAG

SEQ ID NO: 87
*Cuphea hookeriana* (Chook) FATB4 coding DNA sequence codon optimized for
*Prototheca moriformis*
ATGGTGGCCGCCGCCGCCACCTCCGCCTTCTTCCCCGTGCCCGCCCCCGGCACCTCCCCCAACCCCCGC

AAGTTCGGCTCCTGGCCCTCCTCCCTGTCCCCCTCCCTGCCCAACTCCATCCCCAACGGCGGCTTCCAG

GTGAAGGCCAACGCCTCCGCCCACCCCAAGGCCAACGGCTCCGCCGTGTCCCTGAAGTCCGGCTCCCT

GAACACCCAGGAGAACACCTCCTCCTCCCCCCCCCCCCGCACCTTCCTGCACCAGCTGCCCGACTGGTC

CCGCCTGCTGACCGCCATCACCACCGTGTTCGTGAAGTCCAAGCGCCCCGACATGCACGACCGCAAGT

CCAAGCGCCCCGACATGCTGGTGGACCTGTTCGGCCTGGAGTCCTCCGTGCAGGACGCCCTGGTGTTC

CGCCAGCGCTTCTCCATCCGCTCCTACGAGATCGGCACCGACCGCACCGCCTCCATGGAGACCCTGAT

GAACCACCTGCAGGAGACCTCCCTGAACCACTGCAAGTCCACCGGCATCCTGCTGGACGGCTTCGGCC

GCACCCTGGAGATGTGCAAGCGCGAGCTGATCTGGGTGGTGATCAAGATGCAGATCCAGGTGAACCG

CTACCCCGCCTGGGGCGACACCGTGGAGATCAACACCCGCTTCTCCCGCCTGGGCAAGATCGGCATGG

-continued

GCCGCGACTGGCTGATCTCCGACTGCAACACCGGCGAGATCCTGATCCGCGCCACCTCCGAGTACGCC

ATGATGAACCAGAAGACCCGCCGCCTGTCCAAGCTGCCCTACGAGGTGCGCCAGGAGATCGCCCCCCT

GTTCGTGGACTCCCCCCCCGTGATCGAGGACAACGACCTGAAGGTGCACAAGTTCGAGGTGAAGACCG

GCGACTCCATCCACAAGGGCCTGACCCCCGGCTGGAACGACCTGGACGTGAACCAGCACGTGAACAA

CGTGAAGTACATCGGCTGGATCCTGGAGTCCACCCCCCCCGAGGTGCTGGAGACCCAGGAGCTGTGCT

CCCTGACCCTGGAGTACCGCCGCGAGTGCGGCCGCGAGTCCGTGCTGGAGTCCCTGACCGCCATGGAC

CCCTCCGGCGGCGGCTACGGCTCCCAGTTCCAGCACCTGCTGCGCCTGGAGGACGGCGGCGAGATCGT

GAAGGGCCGCACCGAGTGGCGCCCCAAGAACGGCGTGATCAACGGCGTGGTGCCCACCGGCGAGTCC

TCCCCCGGCGACTACTCCTGA

SEQ ID NO: 88
Cuphea *avigera* var. *pulcherrima* (Ca) FATB1 amino acid sequence
MVAAAASSAFFSVPVPGTSPKPGKFRIWPSSLSPSFKPKPIPNGGLQVKANSRAHPKANGSAVSLKSGSLNT

QEDTSSSPPPRTFLHQLPDWSRLLTAITTVFVKSKRPDMHDRKSKRPDMLMDSFGLESIVQEGLEFRQSFSIR

SYEIGTDRTASIETLMNYLQETSLNHCKSTGILLDGFGRTPEMCKRDLIWVVIKMKIKVNRYPAWGDTVEI

NTWFSRLGKIGKGRDWLISDCNTGEILIRATSAYATMNQKTRRLSKLPYEVHQEIAPLFVDSPPVIEDNDLK

LHKFEVKTGDSIHKGLTPGWNDLDVNQHVSNVKYIGWILESMPTEVLETQELCSLALEYRRECGRDSVLES

VTAMDPTKVGGRSQYQHLLRLEDGTDIVKCRTEWRPKNPGANGAISTGKTSNGNSVS

SEQ ID NO: 89
*Cuphea avigera* var. *pulcherrima* (Ca) FATB1 coding DNA sequence
ATGGTGGCTGCTGCAGCAAGTTCTGCATTCTTCTCTGTTCCAGTCCCGGGAACCTCTCCTAAACCCGGG

AAGTTCAGAATTTGGCCATCGAGCTTGAGCCCTTCCTTCAAGCCCAAGCCGATCCCCAATGGTGGATT

GCAGGTTAAGGCAAATTCCAGGGCACATCCGAAGGCTAACGGTTCTGCAGTTAGTCTAAAGTCTGGCA

GCCTCAACACTCAGGAGGACACTTCGTCGTCCCCTCCTCCTCGGACTTTCCTTCACCAGTTGCCTGATT

GGAGTAGGCTTCTGACTGCAATCACGACCGTGTTCGTGAAATCTAAGAGGCCTGACATGCATGATCGG

AAATCTAAGAGGCCTGACATGCTGATGGACTCGTTTGGGTTGGAGAGTATTGTTCAAGAAGGGCTCGA

GTTCAGACAGAGTTTTTCGATTAGGTCTTATGAAATAGGCACTGATCGAACAGCCTCTATAGAGACGC

TGATGAACTACTTGCAGGAAACATCTCTCAATCATTGTAAGAGTACCGGTATTCTCCTTGACGGCTTTG

GTCGTACTCCTGAGATGTGTAAAAGGGACCTCATTTGGGTGGTAACAAAAATGAAGATCAAGGTGAAT

CGCTATCCAGCTTGGGGCGATACTGTCGAGATCAATACCTGGTTCTCCCGGTTGGGGAAAATCGGAAA

GGGTCGCGATTGGCTAATAAGTGATTGCAACACAGGAGAAATTCTTATAAGAGCAACGAGCGCGTAT

GCCACGATGAATCAAAAGACGAGAAGACTCTCAAAACTTCCATACGAGGTTCACCAGGAGATAGCGC

CTCTCTTTGTCGACTCTCCTCCTGTCATTGAAGACAATGATCTGAAATTGCATAAGTTTGAAGTGAAGA

CTGGTGATTCCATTCACAAGGGTCTAACTCCGGGGTGGAATGACTTGGATGTCAATCAGCACGTAAGC

AACGTGAAGTACATTGGGTGGATTCTCGAGAGTATGCCAACAGAAGTTTTGGAGACCCAGGAGCTATG

CTCTCTCGCCCTTGAATATAGGCGGGAATGCGGAAGGGACAGTGTGCTAGAGTCCGTGACAGCTATGG

ATCCCACAAAAGTTGGAGGCCGGTCTCAGTACCAGCACCTTCTGCGACTTGAGGATGGGACTGATATC

GTGAAGTGCAGAACTGAGTGGCGGCCGAAGAATCCAGGAGCTAATGGGGCAATATCAACGGGAAAGA

CTTCAAATGGAAACTCGGTCTCTTAG

SEQ ID NO: 90
*Cuphea avigera* var. *pulcherrima* (Ca) FATB1 coding DNA sequence codon optimized for *Prototheca moriformis*
ATGGTGGCCGCCGCCGCCTCCTCCGCCTTCTTCTCCGTGCCCGTGCCCGGCACCTCCCCCAAGCCCGGC

AAGTTCCGCATCTGGCCCTCCTCCCTGTCCCCCTCCTTCAAGCCCAAGCCCATCCCCAACGGCGGCCTG

CAGGTGAAGGCCAACTCCCGCGCCCACCCCAAGGCCAACGGCTCCGCCGTGTCCCTGAAGTCCGGCTC

-continued

CCTGAACACCCAGGAGGACACCTCCTCCTCCCCCCCCCCCCCGCACCTTCCTGCACCAGCTGCCCGACTG

GTCCCGCCTGCTGACCGCCATCACCACCGTGTTCGTGAAGTCCAAGCGCCCCGACATGCACGACCGCA

AGTCCAAGCGCCCCGACATGCTGATGGACTCCTTCGGCCTGGAGTCCATCGTGCAGGAGGGCCTGGAG

TTCCGCCAGTCCTTCTCCATCCGCTCCTACGAGATCGGCACCGACCGCACCGCCTCCATCGAGACCCTG

ATGAACTACCTGCAGGAGACCTCCCTGAACCACTGCAAGTCCACCGGCATCCTGCTGGACGGCTTCGG

CCGCACCCCCGAGATGTGCAAGCGCGACCTGATCTGGGTGGTGACCAAGATGAAGATCAAGGTGAAC

CGCTACCCCGCCTGGGGCGACACCGTGGAGATCAACACCTGGTTCTCCCGCCTGGGCAAGATCGGCAA

GGGCCGCGACTGGCTGATCTCCGACTGCAACACCGGCGAGATCCTGATCCGCGCCACCTCCGCCTACG

CCACCATGAACCAGAAGACCCGCCGCCTGTCCAAGCTGCCCTACGAGGTGCACCAGGAGATCGCCCCC

CTGTTCGTGGACTCCCCCCCCGTGATCGAGGACAACGACCTGAAGCTGCACAAGTTCGAGGTGAAGAC

CGGCGACTCCATCCACAAGGGCCTGACCCCCGGCTGGAACGACCTGGACGTGAACCAGCACGTGTCCA

ACGTGAAGTACATCGGCTGGATCCTGGAGTCCATGCCCACCGAGGTGCTGGAGACCCAGGAGCTGTGC

TCCCTGGCCCTGGAGTACCGCCGCGAGTGCGGCCGCGACTCCGTGCTGGAGTCCGTGACCGCCATGGA

CCCCACCAAGGTGGGCGGCCGCTCCCAGTACCAGCACCTGCTGCGCCTGGAGGACGGCACCGACATCG

TGAAGTGCCGCACCGAGTGGCGCCCCAAGAACCCCGGCGCCAACGGCGCCATCTCCACCGGCAAGAC

CTCCAACGGCAACTCCGTGTCC

SEQ ID NO: 91
*Cuphea paucipetala* (Cpau) FATB1 amino acid sequence
MVAAAASSAFFPVPAPGTSPKPGKSGNWPSSLSPSIKPMSIPNGGFQVKANASAHPKANGSAVNLKSGSLN

TQEDTSSSPPPRAFLNQLPDWSMLLTAITTVFVAAEKQWTMRDRKSKRPDMLVDSVGLKSVVLDGLVSRQ

IFSIRSYEIGADRTASIETLMNTILQETSINTICKSLGLLNDGFGRTPGMCKNDLIWVLIKMQ1MVNRYPTWGD

TVEINTWFSHSGKIGMASDWLITDCNTGEILIRATSVWAMMNQKTRRFSRLPYEVRQELTPHYVDSPHVIE

DNDRKLHKFDVKTGDSIRKGLTPRWNDLDVNQHVSNVKYIGWILESIVIPIEVLETQELCSLTVEYRRECGM

DSVLESVTAMDPSEDEGRSQYKHLLRLEDGTDIVKGRTEWRPKNAGTNGAISTAKPSNGNSVS

SEQ ID NO: 92
*Cuphea paucipetala* (Cpau) FATB1 coding DNA sequence
ATGGTGGCTGCTGCAGCAAGTTCTGCATTCTTCCCTGTTCCAGCCCCCGGAACCTCCCCTAAACCCGGG

AAGTCCGGCAACTGGCCATCAAGCTTGAGCCCTTCCATCAAGCCCATGTCAATCCCCAATGGCGGATT

TCAGGTTAAGGCAAATGCCAGTGCCCATCCTAAGGCTAACGGTTCTGCAGTAAATCTAAAGTCTGGCA

GCCTCAACACTCAGGAGGACACTTCGTCGTCCCCTCCTCCTCGGGCTTTCCTTAACCAGTTGCCTGATT

GGAGTATGCTTCTGACTGCAATCACGACCGTCTTCGTGGCGGCAGAGAAGCAGTGGACTATGCGTGAT

CGGAAATCTAAGAGGCCTGACATGCTCGTGGACTCGGTTGGGTTGAAGAGTGTTGTTCTGGATGGGCT

CGTGTCCAGACAGATTMTCGATTAGGTCTTATGAAATAGGCGCTGATCGAACTGCCTCTATAGAGAC

GCTGATGAACCACTTGCAGGAAACATCTATCAATCATTGTAAGAGTTTGGGTCTTCTCAATGACGGCTT

TGGTCGTACTCCTGGGATGTGTAAAAATGACCTCATTTGGGTGCTTACAAAAATGCAGATCATGGTGA

ATCGCTACCCAACTTGGGGCGATACTGTTGAGATCAATACCTGGTTCTCCCATTCGGGGAAAATTGGT

ATGGCTAGCGATTGGCTAATAACTGATTGCAACACAGGAGAAATTCTTATAAGAGCAACGAGCGTGTG

GGCCATGATGAATCAAAAGACGAGAAGATTCTCAAGACTTCCATACGAGGTTCGCCAGGAGTTAACG

CCTCATTATGTGGACTCTCCTCATGTCATTGAAGATAATGATCGGAAATTGCATAAGTTTGATGTGAAG

ACTGGTGATTCCATTCGTAAGGGTCTAACTCCGAGGTGGAATGACTTGGATGTCAATCAGCACGTAAG

CAACGTGAAGTACATTGGGTGGATTCTCGAGAGTATGCCAATAGAAGTTTTGGAGACCCAGGAGCTAT

GCTCTCTCACCGTTGAATATAGGCGGGAATGCGGAATGGACAGTGTGCTGGAGTCCGTGACTGCTATG

-continued

GATCCCTCAGAAGATGAAGGCCGGTCTCAGTACAAGCACCTTCTGCGGCTTGAGGATGGGACTGACAT

CGTGAAGGGCAGAACTGAGTGGCGACCGAAGAATGCAGGAACTAACGGGGCGATATCAACAGCAAA

GCCTTCAAATGGAAACTCGGTCTCTTAG

SEQ ID NO: 93
*Cuphea paucipetala* (Cpau) FATB1 coding DNA sequence codon optimized for *Prototheca moriformis*
ATGGTGGCCGCCGCCGCCTCCTCCGCCTTCTTCCCCGTGCCCGCCCCCGGCACCTCCCCCAAGCCCGGC

AAGTCCGGCAACTGGCCCTCCTCCCTGTCCCCCTCCATCAAGCCCATGTCCATCCCCAACGGCGGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGACCGCCATCACCACCGTGTTCGTGGCCGCCGAGAAGCAGTGGACCATGCGCGACC

GCAAGTCCAAGCGCCCCGACATGCTGGTGGACTCCGTGGGCCTGAAGTCCGTGGTGCTGGACGGCCTG

GTGTCCCGCCAGATCTTCTCCATCCGCTCCTACGAGATCGGCGCCGACCGCACCGCCTCCATCGAGACC

CTGATGAACCACCTGCAGGAGACCTCCATCAACCACTGCAAGTCCCTGC1C1CCTGCTGAACGACGGCTT

CGGCCGCACCCCCGGCATGTGCAAGAACGACCTGATCTGGGTGCTGACCAAGATGCAGATCATGGTGA

ACCGCTACCCCACCTGGGGCGACACCGTGGAGATCAACACCTGGTTCTCCCACTCCGGCAAGATCGGC

ATGGCCTCCGACTGGCTGATCACCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTACGTGGACTCCCCCCACGTGATCGAGGACAACGACCGCAAGCTGCACAAGTTCGACGTGAAG

ACCGGCGACTCCATCCGCAAGGGCCTGACCCCCCGCTGGAACGACCTGGACGTGAACCAGCACGTGTC

CAACGTGAAGTACATCGGCTGGATCCTGGAGTCCATGCCCATCGAGGTGCTGGAGACCCAGGAGCTGT

GCTCCCTGACCGTGGAGTACCGCCGCGAGTGCGGCATGGACTCCGTGCTGGAGTCCGTGACCGCCATG

GACCCCTCCGAGGACGAGGGCCGCTCCCAGTACAAGCACCTGCTGCGCCTGGAGGACGGCACCGACA

TCGTGAAGGGCCGCACCGAGTGGCGCCCCAAGAACGCCGGCACCAACGGCGCCATCTCCACCGCCAA

GCCCTCCAACGGCAACTCCGTGTCCTGA

SEQ ID NO: 94
*Cuphea procumbens* (Cproc) FATB1 amino acid sequence
MVAAAASSAFFPAPAPGSSPKPGKSGNWPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKNIVRDGLVSRQ

SFLIRSYEIGADRTASIETLMNHLQETSINHCKSLGLLNDGFGRTPGMCKNDLIWVLTKMQIMVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVSNVKYIGWILESMPIEVLEAQELCSLTVEYRRECGM

DSVLESVTAVDPSEDGGRSQYNHLLRLEDGTDVVKGRTEWRPKNAETNGAISPGNTSNGNSIS

SEQ ID NO: 95
*Cuphea procumbens* (Cproc) FATB1 coding DNA sequence
ATGGTGGCTGCTGCAGCAAGTTCTGCATTCTTCCCTGCTCCAGCCCCGGGATCCTCACCTAAACCCGGG

AAGTCCGGTAATTGGCCATCGAGCTTGAGCCCTTCCTTCAAGTCCAAGTCAATCCCCTATGGCCGATTT

CAGGTTAAGGCAAATGCCAGTGCCCATCCTAAGGCTAACGGTTCTGCAGTAAATCTAAAGTCTGGCAG

CCTCAACACTCAGGAGGACACTTCGTCGTCCCCTCCTCCTCGGGCTTTCCTTAACCAGTTGCCTGATTG

GAGTATGCTTCTGTCTGCAATCACGACTGTATTCGTGGCGGCAGAGAAGCAGTGGACTATGCTTGATC

GGAAATCTAAGAGGCCTGACATGCTTGTGGACTCGGTTGGGTTGAAGAATATTGTTCGGGATGGGCTC

GTGTCCAGACAGAGTTTTTTGATTAGATCTTATGAAATAGGCGCTGATCGAACAGCTTCTATAGAGAC

ACTGATGAACCACTTGCAGGAAACATCTATCAATCATTGTAAGAGTTTGGGTCTTCTCAATGACGGCTT

TGGTCGTACTCCTGGGATGTGTAAAAACGACCTCATTTGGGTGCTTACTAAAATGCAGATCATGGTGA

-continued

ATCGCTACCCAGCTTGGGGCGATACTGTTGAGATCAATACCTGGTTCTCCCAGTCGGGGAAAATCGGT

ATGGGTAGCGATTGGCTAATAAGTGATTGCAACACAGGAGAAATTCTTATAAGAGCAACGAGCGTGT

GGGCCATGATGAATCAAAAAACGAGAAGATTCTCAAGACTTCCATACGAGGTTCGCCAGGAGTTAAC

GCCTCATTTTGTGGACTCTCCTCATGTCATTGAAGACAATGATCGGAAATTGCATAAGTTCGATGTGAA

GACTGGTGATTCTATTCGCAAGGGTCTAACTCCGAGGTGGAATGACTTGGATGTCAATCAGCACGTGA

GCAACGTGAAGTACATTGGGTGGATTCTCGAGAGTATGCCAATAGAAGTTTTGGAGGCCCAGGAACTA

TGCTCTCTCACCGTTGAATATAGGCGGGAATGCGGAATGGACAGTGTGCTGGAGTCCGTGACTGCTGT

AGATCCCTCAGAAGATGGAGGCCGGTCTCAGTACAATCACCTTCTGCGGCTTGAGGATGGGACTGATG

TCGTGAAGGGCAGAACTGAGTGGCGACCGAAGAATGCAGAAACTAACGGGGCGATATCACCAGGAAA

CACTTCAAATGGAAACTCGATCTCCTAG

SEQ ID NO: 96
*Cuphea procumbens* (Cproc) FATB1 coding DNA sequence codon optimized for *Prototheca moriformis*
ATGGTGGCCGCCGCCGCCTCCTCCGCCTTCTTCCCCGCCCCCGCCCCCGGCTCCTCCCCCAAGCCCGGC

AAGTCCGGCAACTGGCCCTCCTCCCTGTCCCCCTCCTTCAAGTCCAAGTCCATCCCCTACGGCCGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGTCCGCCATCACCACCGTGTT'CGTGGCCGCCGAGAAGCAGTGGACCATGCTGGACC

GCAAGTCCAAGCGCCCCGACATGCTGGTGGACTCCGTGGGCCTGAAGAACATCGTGCGCGACGGCCTG

GTGTCCCGCCAGTCCTTCCTGATCCGCTCCTACGAGATCGGCGCCGACCGCACCGCCTCCATCGAGACC

CTGATGAACCACCTGCAGGAGACCTCCATCAACCACTGCAAGTCCCTGGGCCTGCTGAACGACGGCTT

CGGCCGCACCCCCGGCATGTGCAAGAACGACCTGATCTGGGTGCTGACCAAGATGCAGATCATGGTGA

ACCGCTACCCCGCCTGGGGCGACACCGTGGAGATCAACACCTGGTTCTCCCAGTCCGGCAAGATCGGC

ATGGGCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCGCAAGCTGCACAAGTTCGACGTGAAG

ACCGGCGACTCCATCCGCAAGGGCCTGACCCCCCGCTGGAACGACCTGGACGTGAACCAGCACGTGTC

CAACGTGAAGTACATCGGCTGGATCCTGGAGTCCATGCCCATCGAGGTGCTGGAGGCCCAGGAGCTGT

GCTCCCTGACCGTGGAGTACCGCCGCGAGTGCGGCATGGACTCCGTGCTGGAGTCCGTGACCGCCGTG

GACCCCTCCGAGGACGGCGGCCGCTCCCAGTACAACCACCTGCTGCGCCTGGAGGACGGCACCGACGT

GGTGAAGGGCCGCACCGAGTGGCGCCCCAAGAACGCCGAGACCAACGGCGCCATCTCCCCCGGCAAC

ACCTCCAACGGCAACTCCATCTCCTGA

SEQ ID NO: 97
*Cuphea procumbens* (Cproc) FATB2 amino acid sequence
MVAAAASSAFFPAPAPGSSPIPGKSGNWPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKNIVRDGLVSRQ

SFLIRSYEIGADRTASIETLMNELQETSINHICKSLGUNDGFGRTPGMCKNDLIWVLTKMQ1MVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVNNVKYIGWILESTPPEVLETQELCSLTLEYRQECGRE

SVLESLTAVDPSGKGFGSQFQHLLRLEDGGEIVKGRTEWRPKTAGINGAIASGETSPGDF

SEQ ID NO: 98
*Cuphea procumbens* (Cproc) FATB2 coding DNA sequence
ATGGTGGCTGCTGCAGCAAGTTCTGCATTCTTCCCTGCTCCAGCCCCGGGATCCTCACCTAAACCCGGG

AAGTCCGGTAATTGGCCATCGAGCTTGAGCCCTTCCTTCAAGTCCAAGTCAATCCCCTATGGCCGATTT

-continued

CAGGTTAAGGCAAATGCCAGTGCCCATCCTAAGGCTAACGGTTCTGCAGTAAATCTAAAGTCTGGCAG

CCTCAACACTCAGGAGGACACTTCGTCGTCCCCTCCTCCTCGGGCTTTCCTTAACCAGTTGCCTGATTG

GAGTATGCTTCTGTCTGCAATCACGACTGTATTCGTGGCGGCAGAGAAGCAGTGGACTATGCTTGATC

GGAAATCTAAGAGGCCTGACATGCTTGTGGACTCGGTTGGGTTGAAGAATATTGTTCGGGATGGGCTC

GTGTCCAGACAGAGTTTTTTGATTAGATCTTATGAAATAGGCGCTGATCGAACAGCTTCTATAGAGAC

ACTGATGAACCACTTGCAGGAAACATCTATCAATCATTGTAAGAGTTTGGGTCTTCTCAATGACGGCTT

TGGTCGTACTCCTGGGATGTGTAAAAACGACCTCATTTGGGTGC'TTACTAAAATGCAGATCATGGTGA

ATCGCTACCCAGCTTGGGGCGATACTGTTGAGATCAATACCTGGTTCTCCCAGTCGGGGAAAATCGGT

ATGGGTAGCGATTGGCTAATAAGTGATTGCAACACAGGAGAAATTCTTATAAGAGCAACGAGCGTGT

GGGCCATGATGAATCAAAAAACGAGAAGATTCTCAAGACTTCCATACGAGGTTCGCCAGGAGTTAAC

GCCTCATTTTGTGGACTCTCCTCATGTCATTGAAGACAATGATCGGAAATTGCATAAGTTCGATGTGAA

GACTGGTGATTCTATTCGCAAGGGTCTAACTCCGAGGTGGAATGACTTGGATGTCAATCAGCACGTCA

ACAACGTGAAGTACATCGGGTGGATTCTTGAGAGTACTCCACCAGAAGTTCTGGAGACCCAGGAGTTA

TGTTCCCTTACCCTGGAATACAGGCAGGAATGCGGAAGGGAGAGCGTGCTGGAGTCCCTCACTGCTGT

GGACCCCTCTGGAAAGGGCTTTGGGTCCCAGTTCCAACACCTTCTGAGGCTTGAGGATGGAGGTGAGA

TCGTGAAGGGGAGAACTGAGTGGCGACCCAAGACTGCAGGTATCAATGGGGCGATAGCATCCGGGGA

GACCTCACCTGGAGACTTTTAG

SEQ ID NO: 99
*Cuphea procumbens* (Cproc) FATB2 coding DNA sequence codon optimized for *Prototheca moriformis*
ATGGTGGCCGCCGCCGCCTCCTCCGCCTTCTTCCCCGCCCCCGCCCCCGGCTCCTCCCCCAAGCCCGGC

AAGTCCGGCAACTGGCCCTCCTCCCTGTCCCCCTCCTTCAAGTCCAAGTCCATCCCCTACGGCCGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGTCCGCCATCACCACCGTGTTCGTGGCCGCCGAGAAGCAGTGGACCATGCTGGACC

GCAAGTCCAAGCGCCCCGACATGCTGGTGGACTCCGTGGGCCTGAAGAACATCGTGCGCGACGGCCTG

GTGTCCCGCCAGTCCTTCCTGATCCGCTCCTACGAGATCGGCGCCGACCGCACCGCCTCCATCGAGACC

CTGATGAACCACCTGCAGGAGACCTCCATCAACCACTGCAAGTCCCTGGGCCTGCTGAACGACGGCTT

CGGCCGCACCCCCGGCATGTGCAAGAACGACCTGATCTGGGTGCTGACCAAGATGCAGATCATGGTGA

ACCGCTACCCCGCCTGGGGCGACACCGTGGAGATCAACACCTGGTTCTCCCAGTCCGGCAAGATCGGC

ATGGGCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCGCAAGCTGCACAAGTTCGACGTGAAG

ACCGGCGACTCCATCCGCAAGGGCCTGACCCCCCGCTGGAACGACCTGGACGTGAACCAGCACGTGA

ACAACGTGAAGTACATCGGCTGGATCCTGGAGTCCACCCCCCCCGAGGTGCTGGAGACCCAGGAGCTG

TGCTCCCTGACCCTGGAGTACCGCCAGGAGTGCGGCCGCGAGTCCGTGCTGGAGTCCCTGACCGCCGT

GGACCCCTCCGGCAAGGGCTTCGGCTCCCAGTTCCAGCACCTGCTGCGCCTGGAGGACGGCGGCGAGA

TCGTGAAGGGCCGCACCGAGTGGCGCCCCAAGACCGCCGGCATCAACGGCGCCATCGCCTCCGGCGA

GACCTCCCCCGGCGACTTCTGA

SEQ ID NO: 100
*Cuphea procumbens* (Cproc) FATB3 amino acid sequence
MVAAAASSAFFPAPAPGSSPKPGKSGNWPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKNIVRDGLVSRQ

-continued

SFLIRSYEIGADRTASIETLMNHLQETSINHCKSLGLLNDGFGRTPGMCKNDLIWVLIKMQIMVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVNNVKYIGWILESTPPEVLETQELCSLTLEYRRECGRE

SVLESLTAVDPSGEGGYGSQFQHLLRLEDGGEIVKGRTEWRPKNAGINGVLPTGE*

SEQ ID NO: 101
*Cuphea procumbens* (Cproc) FATB3 coding DNA sequence
ATGGTGGCTGCTGCAGCAAGTTCTGCATTCTTCCCTGCTCCAGCCCCGGGATCCTCACCTAAACCCGGG

AAGTCCGGTAATTGGCCATCGAGCTTGAGCCCTTCCTTCAAGTCCAAGTCAATCCCCTATGGCCGATTT

CAGGTTAAGGCAAATGCCAGTGCCCATCCTAAGGCTAACGGTTCTGCAGTAAATCTAAAGTCTGGCAG

CCTCAACACTCAGGAGGACACTTCGTCGTCCCCTCCTCCTCGGGCTTTCCTTAACCAGTTGCCTGATTG

GAGTATGCTTCTGTCTGCAATCACGACTGTATTCGTGGCGGCAGAGAAGCAGTGGACTATGCTTGATC

GGAAATCTAAGAGGCCTGACATGCTTGTGGACTCGGTTGGGTTGAAGAATATTGTTCGGGATGGGCTC

GTGTCCAGACAGAGTTTTTTGATTAGATCTTATGAAATAGGCGCTGATCGAACAGCTTCTATAGAGAC
ACTGATGAACCACTTGCAGGAAACATCTATCAATCATTGTAAGAGTTTGGGTCTTCTCAATGACGGCTT

TGGTCGTACTCCTGGGATGTGTAAAAACGACCTCATTTGGGTGCTTACTAAAATGCAGATCATGGTGA

ATCGCTACCCAGCTTGGGGCGATACTGTTGAGATCAATACCTGGTTCTCCCAGTCGGGGAAAATCGGT

ATGGGTAGCGATTGGCTAATAAGTGATTGCAACACAGGAGAAATTCTTATAAGAGCAACGAGCGTGT

GGGCCATGATGAATCAAAAAACGAGAAGATTCTCAAGACTTCCATACGAGGTTCGCCAGGAGTTAAC

GCCTCATTTTGTGGACTCTCCTCATGTCATTGAAGACAATGATCGGAAATTGCATAAGTTCGATGTGAA

GACTGGTGATTCTATTCGCAAGGGTCTAACTCCGAGGTGGAATGACTTGGATGTCAATCAGCACGTCA

ACAACGTGAAGTACATCGGGTGGATTCTTGAGAGTACTCCACCAGAAGTTCTGGAGACCCAGGAGTTA

TGTTCCCTTACCCTGGAATACAGGCGGGAATGTGGAAGGGAGAGCGTGCTGGAGTCCCTCACTGCTGT

GGACCCCTCTGGAGAGGGGGGCTATGGATCCCAGTTTCAGCACCTTCTGCGGCTTGAGGATGGAGGTG

AGATCGTGAAGGGGAGAACTGAGTGGCGACCCAAGAATGCTGGAATCAATGGGGTGTTACCAACCGG

GGAGTAG

SEQ ID NO: 102
*Cuphea procumbens* (Cproc) FATB3 coding DNA sequence codon optimized for
*Prototheca moriformis*
ATGGTGGCCGCCGCCGCCTCCTCCGCCTTCTTCCCCGCCCCCGCCCCCGGCTCCTCCCCCAAGCCCGGC

AAGTCCGGCAACTGGCCCTCCTCCCTGTCCCCCTCCTTCAAGTCCAAGTCCATCCCCTACGGCCGCTTC

CAGGTGAAGGCCAACGCCTCCGCCCACCCCAAGGCCAACGGCTCCGCCGTGAACCTGAAGTCCGGCTC

CCTGAACACCCAGGAGGACACCTCCTCCTCCCCCCCCCCCCGCGCCTTCCTGAACCAGCTGCCCGACTG

GTCCATGCTGCTGTCCGCCATCACCACCGTGTTCGTGGCCGCCGAGAAGCAGTGGACCATGCTGGACC

GCAAGTCCAAGCGCCCCGACATGCTGGTGGACTCCGTGGGCCTGAAGAACATCGTGCGCGACGGCCTG

GTGTCCCGCCAGTCCTTCCTGATCCGCTCCTACGAGATCGGCGCCGACCGCACCGCCTCCATCGAGACC

CTGATGAACCACCTGCAGGAGACCTCCATCAACCACTGCAAGTCCCTGGGCCTGCTGAACGACGGCTT

CGGCCGCACCCCCGGCATGTGCAAGAACGACCTGATCTGGGTGCTGACCAAGATGCAGATCATGGTGA

ACCGCTACCCCGCCTGGGGCGACACCGTGGAGATCAACACCTGGTTCTCCCAGTCCGGCAAGATCGGC

ATGGGCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCGCAAGCTGCACAAGTTCGACGTGAAG

ACCGGCGACTCCATCCGCAAGGGCCTGACCCCCCGCTGGAACGACCTGGACGTGAACCAGCACGTGA

ACAACGTGAAGTACATCGGCTGGATCCTGGAGTCCACCCCCCCCGAGGTGCTGGAGACCCAGGAGCTG

TGCTCCCTGACCCTGGAGTACCGCCGCGAGTGCGGCCGCGAGTCCGTGCTGGAGTCCCTGACCGCCGT

-continued

GGACCCCTCCGGCGAGGGCGGCTACGGCTCCCAGTTCCAGCACCTGCTGCGCCTGGAGGACGGCGGCG

AGATCGTGAAGGGCCGCACCGAGTGGCGCCCCAAGAACGCCGGCATCAACGGCGTGCTGCCCACCGG

CGAGTGA

SEQ ID NO: 103
*Cuphea ignea* (Cignea) FATB1 amino acid sequence
PGTSRKTGKFGNWPSSLSPSFKPKSIPNGGFQVKANARAHPKANGSAVSLKSVSLNTQEDTSLSPPPRAFLN

QLPDWRMLRTALTTVFVAAEKQWTMLDRKSKRPDMLVDSFGLESIVQEGLVFRQSFSIRSYEIGIDRTASIE

TLMNHLQETSLNQCKSAGILHDGFGRTLEMCKRDLIWVVIKMQIKVNRYPAWGDTVEISTRFSRLGKIGM

GRDWLICDCNTGEILIRATSAYAMMNQKTRRLSKLPNEVRQEIAPLFVDSDPVIEENDMKLHKFEVKTGDSI

CKGLTPRWSDLDVNQHVSNVKYIGWILESMPTEVLETQELCSLALEYRRECGRDSVLESVISMDPSKVGG

WSQYQHLLRLEDGADIVKGRTEWRPKNAGANGAISTGKT

SEQ ID NO: 104
*Cuphea ignea* (Cignea) FATB1 coding DNA sequence
CCGGGAACCTCACGTAAAACCGGGAAGTTCGGCAATTGGCCATCAAGCTTGAGCCCTTCCTTCAAGCC

CAAGTCAATCCCCAATGGCGGATTTCAGGTTAAGGCTAATGCCAGAGCCCATCCTAAGGCTAACGGTT

CTGCAGTAAGTCTAAAGTCTGTCAGCCTCAACACTCAGGAGGACACTTCGTTGTCCCCTCCTCCTCGTG

CTTTCCTTAACCAGTTGCCTGATTGGAGGATGCTTCGGACTGCACTCACGACCGTCTTTGTGGCGGCAG

AGAAGCAGTGGACTATGCTTGATCGGAAATCTAAGAGGCCTGACATGCTCGTGGACTCGTTTGGGTTG

GAGAGTATTGTTCAAGAAGGGCTCGTGTTCAGACAGAGCTTTTCGATTAGGTCTTATGAAATAGGCAT

TGATCGAACAGCCTCTATAGAGACGCTGATGAACCACTTCTCAGGAAACATCTCTCAATCAATGTAAGA

GTGCTGGTATTCTCCATGACGGCTTCGGTCGTACTCTTGAGATGTGTAAAAGGGACCTCATTTGGGTTG

TTACGAAAATGCAGATCAAGGTGAATCGCTATCCAGCTTGGGGCGATACTGTCGAGATCAGTACCCGG

TTCTCCCGGTTGGGGAAAATCGGTATGGGTCGCGATTGGCTAATATGTGATTGCAACACAGGAGAAAT

TCTTATAAGAGCAACGAGCGCGTATGCCATGATGAATCAAAAGACGAGAAGACTCTCAAAACTTCCA

AACGAGGTTCGCCAGGAGATAGCGCCTCTTTTTGTGGACTCTGATCCTGTCATTGAAGAAAATGATAT

GAAATTGCATAAGTTTGAAGTGAAGACTGGTGATTCCATTTGCAAGGGTCTAACTCCGAGGTGGAGTG

ACTTGGATGTCAATCAGCACGTAAGCAACGTGAAGTACATAGGGTGGATTCTCGAGAGTATGCCAACA

GAAGTTTTGGAGACACAGGAGCTATGCTCTCTCGCCCTTGAATATAGGCGGGAATGCGGAAGGGACA

GTGTGCTGGAGTCTGTGACCTCTATGGATCCCTCAAAAGTTGGAGGCTGGTCTCAGTACCAGCACCTTC

TGCGACTTGAGGATGGGGCGGATATCGTGAAGGGCAGAACTGAGTGGCGGCCGAAGAATGCAGGAGC

TAACGGGGCGATATCAACAGGAAAGACTTGA

SEQ ID NO: 105
*Cuphea ignea* (Cignea) FATB1 coding DNA sequence codon optimized for *Prototheca moriformis*
CCCGGCACCTCCCGCAAGACCGGCAAGTTCGGCAACTGGCCCTCCTCCCTGTCCCCCTCCTTCAAGCCC

AAGTCCATCCCCAACGGCGGCTTCCAGGTGAAGGCCAACGCCCGCGCCCACCCCAAGGCCAACGGCTC

CGCCGTGTCCCTGAAGTCCGTGTCCCTGAACACCCAGGAGGACACCTCCCTGTCCCCCCCCCCCCGCGC

CTTCCTGAACCAGCTGCCCGACTGGCGCATGCTGCGCACCGCCCTGACCACCGTGTTCGTGGCCGCCG

AGAAGCAGTGGACCATGCTGGACCGCAAGTCCAAGCGCCCCGACATGCTGGTGGACTCCTTCGGCCTG

GAGTCCATCGTGCAGGAGGGCCTGGTGTTCCGCCAGTCCTTCTCCATCCGCTCCTACGAGATCGGCATC

GACCGCACCGCCTCCATCGAGACCCTGATGAACCACCTGCAGGAGACCTCCCTGAACCAGTGCAAGTC

CGCCGGCATCCTGCACGACGGCTTCGGCCGCACCCTGGAGATGTGCAAGCGCGACCTGATCTGGGTGG

TGACCAAGATGCAGATCAAGGTGAACCGCTACCCCGCCTGGGGCGACACCGTGGAGATCTCCACCCGC

TTCTCCCGCCTGGGCAAGATCGGCATGGGCCGCGACTGGCTGATCTGCGACTGCAACACCGGCGAGAT

-continued

CCTGATCCGCGCCACCTCCGCCTACGCCATGATGAACCAGAAGACCCGCCGCCTGTCCAAGCTGCCCA

ACGAGGTGCGCCAGGAGATCGCCCCCCTGTTCGTGGACTCCGACCCCGTGATCGAGGAGAACGACATG

AAGCTGCACAAGTTCGAGGTGAAGACCGGCGACTCCATCTGCAAGGGCCTGACCCCCCGCTGGTCCGA

CCTGGACGTGAACCAGCACGTGTCCAACGTGAAGTACATCGGCTGGATCCTGGAGTCCATGCCCACCG

AGGTGCTGGAGACCCAGGAGCTGTGCTCCCTGGCCCTGGAGTACCGCCGCGAGTGCGGCCGCGACTCC

GTGCTGGAGTCCGTGACCTCCATGGACCCCTCCAAGGTGGGCGGCTGGTCCCAGTACCAGCACCTGCT

GCGCCTGGAGGACGGCGCCGACATCGTGAAGGGCCGCACCGAGTGGCGCCCCAAGAACGCCGGCGCC

AACGGCGCCATCTCCACCGGCAAGACCTGA

SEQ ID NO: 106
JcFatB1 consensus amino acid sequence
MVAAAASSAFFPVPAPGTSPKPGKSGNWPSSLSPSFKPKSEPNGGFQVKANASAHPKANGSAVNLKSGSLN

TQEDTSSSPPPRAFLNQLPDWSMLLTAITTVFVAAEKQWTMLDRKSKRPDMLVDSVGLKRIVQDGLVSRQ

SFSIRSYEIGADRIASIETLMNHLQETSINHCKSLGLLNDGFGRTPGMCKNDLIWVLTKMQIMVNRYPTWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVSNVKYIGWILESMPIEVLETQELCSLTVEYRRECGM

DSVLESVTAMDPSENGGRSQYKHLLRLEDGTDIVKGRTEWRPKNAGTNGAISTGKTSNGNSVS*

SEQ ID NO: 107
JcFatB1 consensus DNA sequence codon optimized for *Prototheca*
ATGGTGGCCGCCGCCGCCTCCTCCGCCTTCTTCCCCGTGCCCGCCCCCGGCACCTCCCCCAAGCCCGGC

AAGTCCGGCAACTGGCCCTCCTCCCTGTCCCCCTCCTTCAAGCCCAAGTCCATCCCCAACGGCGGCTTC

CAGGTGAAGGCCAACGCCTCCGCCCACCCCAAGGCCAACGGCTCCGCCGTGAACCTGAAGTCCGCTCTC

CCTGAACACCCAGGAGGACACCECCTCCTCCCCCCCCCCCCGCGCCTTCCTGAACCAGCTGCCCGACTG

GTCCATGCTGCTGACCGCCATCACCACCGTGTTCGTGGCCGCCGAGAAGCAGTGGACCATGCTGGACC

GCAAGTCCAAGCGCCCCGACATGCTGGTGGACTCCGTGGGCCTGAAGCGCATCGTGCAGGACGGCCTG

GTGTCCCGCCAGTCCTTCTCCATCCGCTCCTACGAGATCGGCGCCGACCGCACCGCCTCCATCGAGACC

CTGATGAACCACCTGCAGGAGACCTCCATCAACCACTGCAAGTCCCTGGGCCTGCTGAACGACGGCTT

CGGCCGCACCCCCGGCATGTGCAAGAACGACCTGATCTGGGTGCTGACCAAGATGCAGATCATGGTGA

ACCGCTACCCCACCTGGGGCGACACCGTGGAGATCAACACCTGGTTCTCCCAGTCCGGCAAGATCGGC

ATGGGCTCCGACTGGCTGATCTCCGACTGCAACACCGGCGAGATCCTGATCCGCGCCACCTCCGTGTG

GGCCATGATGAACCAGAAGACCCGCCGCTTCTCCCGCCTGCCCTACGAGGTGCGCCAGGAGCTGACCC

CCCACTTCGTGGACTCCCCCCACGTGATCGAGGACAACGACCGCAAGCTGCACAAGTTCGACGTGAAG

ACCGGCGACTCCATCCGCAAGGGCCTGACCCCCCGCTGGAACGACCTGGACGTGAACCAGCACGTGTC

CAACGTGAAGTACATCGGCTGGATCCTGGAGTCCATGCCCATCGAGGTGCTGGAGACCCAGGAGCTGT

GCTCCCTGACCGTGGAGTACCGCCGCGAGTGCGGCATGGACTCCGTGCTGGAGTCCGTGACCGCCATG

GACCCCTCCGAGAACGGCGGCCGCTCCCAGTACAAGCACCTGCTGCGCCTGGAGGACGGCACCGACA

TCGTGAAGGGCCGCACCGAGTGGCGCCCCAAGAACGCCGGCACCAACGGCGCCATCTCCACCGGCAA

GACCTCCAACGGCAACTCCGTGTCCTGA

SEQ ID NO: 108
JcFatB2 consensus amino acid sequence
MVATAASSAFFPVPSPDTSSRPGKLGNGSSSLSPLKPKSVANGGLQVKANASAPPKINGSSVGLKSGSLKTQ

EDTPSAPPPRTFINQLPDWSMLLAAITTVFLAAEKQWMMLDWKPKRPDMLVDPFGLGRIVQDGLVFRQNF

SIRSYEIGADRTASIETVMNHLQETALNHVKSAGLLNDGFGRTPEMYKRDLIWVVAKMQVMVNRYPTWG

DTVEVNTWVAKSGKNGMRRDWLISDCNTGEILTRASSVWVMMNQKTRRLSKIPDEVRHEIEPHFVDSAPV

-continued

IEDDDRKLPKLDEKTADSIRKGLTPKWNDLDVNQHVNNVKYIGWILESTPPEVLETQELCSLTLEYRRECG

RESVLESLTAVDPSGKGYGSQFQHLLRLEDGGEIVKGRTEWRPKTAGINGAIASGETSPGDSS*

SEQ ID NO: 109
JcFatB2 consensus DNA sequence codon optimized for *Prototheca*
ATGGTGGCCACCGCCGCCTCCTCCGCCTTCTTCCCCGTGCCCTCCCCCGACACCTCCTCCCGCCCCGGC

AAGCTGGGCAACGGCTCCTCCTCCCTGTCCCCCCTGAAGCCCAAGTCCGTGGCCAACGGCGGCCTGCA

GGTGAAGGCCAACGCCTCCGCCCCCCCCAAGATCAACGGCTCCTCCGTGGGCCTGAAGTCCGGCTCCC

TGAAGACCCAGGAGGACACCCCCTCCGCCCCCCCCCCCCGCACCTTCATCAACCAGCTGCCCGACTGG

TCCATGCTGCTGGCCGCCATCACCACCGTGTTCCTGGCCGCCGAGAAGCAGTGGATGATGCTGGACTG

GAAGCCCAAGCGCCCCGACATGCTGGTGGACCCCTTCGGCCTGGGCCGCATCGTGCAGGACGGCCTGG

TGTTCCGCCAGAACTTCTCCATCCGCTCCTACGAGATCGGCGCCGACCGCACCGCCTCCATCGAGACC

GTGATGAACCACCTGCAGGAGACCGCCCTGAACCACGTGAAGTCCGCCGGCCTGCTGAACGACGGCTT

CGGCCGCACCCCCGAGATGTACAAGCGCGACCTGATCTGGGTGGTGGCCAAGATGCAGGTGATGGTG

AACCGCTACCCCACCTGGGGCGACACCGTGGAGGTGAACACCTGGGTGGCCAAGTCCGGCAAGAACG

GCATGCGCCGCGACTGGCTGATCTCCGACTGCAACACCGGCGAGATCCTGACCCGCGCCTCCTCCGTG

TGGGTGATGATGAACCAGAAGACCCGCCGCCTGTCCAAGATCCCCGACGAGGTGCGCCACGAGATCG

AGCCCCACTTCGTGGACTCCGCCCCCGTGATCGAGGACGACGACCGCAAGCTGCCCAAGCTGGACGAG

AAGACCGCCGACTCCATCCGCAAGGGCCTGACCCCCAAGTGGAACGACCTGGACGTGAACCAGCACG

TGAACAACGTGAAGTACATCGGCTGGATCCTGGAGTCCACCCCCCCCGAGGTGCTGGAGACCCAGGA

GCTGTGCTCCCTGACCCTGGAGTACCGCCGCGAGTGCGGCCGCGAGTCCGTGCTGGAGTCCCTGACCG

CCGTGGACCCCTCCGGCAAGGGCTACGGCTCCCAGTTCCAGCACCTGCTGCGCCTGGAGGACGGCGGC

GAGATCGTGAAGGGCCGCACCGAGTGGCGCCCCAAGACCGCCGGCATCAACGGCGCCATCGCCTCCG

GCGAGACCTCCCCCGGCGACTCCTCCTGA

SEQ ID NO: 110
CuPSR23 FATB3 amino acid sequence
MVVAAATSAFFPVPAPGTSPKPGKSGNWPSSLSPTFKPKSIPNAGFQVKANASAHPKANGSAVNL

KSGSLNTQEDTSSSPPPRAFLNQLPDWSMLLTAITTVFVAAEKQWTMLDRKSKRPDMLVDSVGLKCIVRD

GLVSRQSFLIRSYEIGADRTASIETLMNHLQETSINHCKSLGLLNDGFGRTPGMCKNDLIWVLIKMQIMVNR

YPTWGDTVEINTWFSQSGKIGMASDWLISDCNTGEILIRATSVWAMMNQKTRRFSRLPYEVRQELTPHFVD

SPHVIEDNDQKLHKFDVKTGDSIRKGLTPRWNDLDVNQHVSNVKYIGWILESMPIEVLETQELCSLTVEYR

RECGMDSVLESVTAVDPSENGGRSQYKFILLRLEDGTDIVKSRTEWRPKNAGTNGAISTSTAKTSNGNSVS

SEQ ID NO: 111
CuPSR23 FATB3b amino acid sequence
MVVAAATSAFFPVPAPGTSPKPGKSGNWPSSLSPTFKPKSIPNAGFQVKANASAHPKANGSAVNL

KSGSLNTQEDTSSSPPPRAFLNQLPDWSMLLTAITTVFVAAEKQWTMLDRKSKRPDMLVDSVGLKSIVRDG

LVSRQSFLIRSYEIGADRTASIETLMNHLQETSINHCKSLGLLNDGFGRTPGMCKNDLIWVLTKMQIMVNRY

PTWGDTVEINTWFSQSGKIGMASDWLISDCNTGEILIRATSVWAMMNQKTRRFSRLPYEVRQELTPHFVDS

PHVIEDNDQKLHKFDVKTGDSIRKGLTPRWNDLDVNQHVSNVKYIGWILESMPIEVLETQELCSLTVEYRR

ECGMDSVLESVTAVDPSENGGRSQYKHLLRLEDGTDIVKSRTEWRPKNAGTNGAISTSTAKTSNGNSAS

SEQ ID NO: 112
CwFATB3 amino acid sequence:
MVVAAAASSAFFPVPAPRTTPKPGKFGNWPSSLSPPFKPKSNPNGRFQVKANVSPHPKANGSAVSL

KSGSLNTLEDPPSSPPPRTFLNQLPDWSRLRTAITTVFVAAEKQFTRLDRKSKRPDMLVDWFGSETIVQDGL

VFRERFSIRSYEIGADRTASIETLMNHLQDTSLNHCKSVGLLNDGFGRTSEMCTRDLIWVLTKMQIVVNRYP

TWGDTVEINSWFSQSGKIGMGRDWLISDCNTGEILVRATSAWAMMNQKTRRFSKLPCEVRQEIAPHFVDA

-continued

PPVIEDNDRKLHKFDVKTGDSICKGLTPGWNDLDVNQHVSNVKYIGWILESMPTEVLETQELCSLTLEYRR

ECGRESVVESVISMNPSKVGDRSQYQHLLRLEDGADIMKGRTEWRPKNAGTNRAIST

SEQ ID NO: 113
CwFATB3a amino acid sequence:
MVVAAAASSAFFPVPAPRTTPKPGKFGNWPSSLSPPFKPKSNPNGRFQVKANVSPHPKANGSAVSL

KSGSLNTLEDPPSSPPPRTFLNQLPDWSRLRTAITTVFVAAEKQFTRLDRKSKRPDMLVDWFGSETIVQDGL

VFRERFSIRSYEIGADRTASIETLMNHILQDTSLNHCKSVGLLNDGFGRTSEMCIRDLIWVLTKMQIVVNRYP

TWGDTVEINSWFSQSGKIGMGRDWLISDCNTGEILVRATSAWAMMNQKTRRFSKLPCEVRQEIAPHFVDA

PPVIEDNDRKLHKFDVKTGDSICKGLTPGWNDLDVNQHVSNVKYIGWILESMPTEVLETQELCSLTLEYRR

ECGRESVVESVISMNPSKVGDRSQYQHLLRLEDGADIMKGRTEWRPKNAGTNRAIST

SEQ ID NO: 114
CwFATB3b amino acid sequence
MVVAAAASSAFFPVPAPRTTPKPGKFGNWPSSLSPPFKPKSNPNGRFQVKANVSPHPKANGSAVSL

KSGSLNTLEDLPSSPPPRTFLNQLPDWSRLRTAITTVFVAAEKQFTRLDRKSKRPDMLVDWFGSETIVQDGL

VFRERFSIRSYEIGADRTASIETLMNHLQDTSLNHCKSVGLLNDGFGRTSEMCTRDLIWVLTKMQIVVNRYP

TWGDTVEINSWFSQSGKIGMGRDWLISDCNTGEILVRATSAWAMMNQKTRRFSKLPCEVRQEIAPHFVDA

PPVIEDNDRKLHKFDVKTGDSICKGLTPGWNDLDVNQHVSNVKYIGWILEKFWRPRSYALSPLNIGGNVEG

KVW

SEQ ID NO: 115
CwFATB3c amino acid sequence
MVVAAAASSAFFPVPAPRTIPKPGKFGNWPSSLSPPFKPKSNPNGRFQVKANVSPHPKANGSAVSL

KSGSLNTLEDLPSSPPPRTFLNQLPDWSRLRTAITTVFVATEKQFTRLDRKSKRPDMLVDWFGSETIVQDGL

VFRERFSIRSYEIGADRTASIETLMNHLQDTSLNHCKSVGLLNDGFGRTSEMCTRDLIWVLTKMQIVVNRYP

TWGDTVEINSWFSQSGKIGMGRDWLISDCNTGEILVRATSAWAMMNQKTRRFSKLPCEVRQEIAPHFVDA

PPVIEDNDRKLHKFDVKTGDSICKGLTPGWNDLDVNQHVSNVKYIGWILEKFWRPRSYALSPLNIGGNVEG

KVW

SEQ ID NO: 116
CwFATB4a amino acid sequence
MVATAASSAFFPVPSADTSSSRPGKLGSGPSSLSPLKPKSIPNGGLQVKANASAPPKINGSSVGLKS

GGFKTQEDSPSAPPPRTFINQLPDWSMLLAAITTVFLAAEKQWMMLDWKPKRPDMLVDPFGLGSIVQDGL

VFRQNFSIRSYEIGADRTASIETVMNHLQETALNHVKIAGLSNDGFGRTPEMYKRDLIWVVAKMQVMVNR

YPTWGDTVEVNTWVAKSGKNGMRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPPEVLETQELCSLTLE

YRRECGRESVLESLTAVDPSAEGYASRFQHLLRLEDGGEIVKARTEWRPKNAGINGVVPSEESSPGDFF

SEQ ID NO: 117
CwFATB4a.1 amino acid sequence
MVATAASSAFFPVPSADTSSSRPGKLGSGPSSLSPLKPKSIPNGGLQVKANASAPPKINGSSVGLKS

GGFKTQEDSPSAPPPRTFINQLPDWSMLLAAITTVFLAAEKQWMMLDWKPKRPDMLVDPFGLGSIVQDGL

VFRQNFSIRSYEIGADRTASIETVMNHLQETALNHVKIAGLSNDGFGRTPEMYKRDLIWVVAKMQVMVNR

YPTWGDTVEVNTWVAKSGKNG1VIRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPPEVLETQELCSLTLE

YRRECGRESVLESLTAVDPSAEGYASRFQHLLRLEDGGEIVKARTEWRPKNAGINWVVPSEESSPGDFF

SEQ ID NO: 118
CwFATB4a.2 amino acid sequence:
MVATAASSAFFPVPSADTSSSRPGKLGNGPSSLSPLKPKSIPNGGLQVKANASAPPKINGSSVGLKS

GSFKTQEDAPSAPPPRTFINQLPDWSMLLAAITTVFLAAEKQWMMLDWKPKRPDMLVDPFGLGSIVQDGL

-continued

VFRQNFSIRSYEIGADRTASIETVMNHLQETALNHVKIAGLSNDGFGRTPEMYKRDLIWVVAKMQVMVNR

YPTWGDTVEVNTWVAKSGKNGMRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPPEVLETQELCSLTLE

YRRECGRESVLESLTAVDPSAEGYASRFQHLLRLEDGGEIVKARTEWRPKNAGINGVVPSEESSPGDFF

SEQ ID NO: 119
CwFATB4a.3 amino acid sequence
MVATAASSAFFPVPSADTSSSRPGKLGSGPSSLSPLKPKSIPNGGLQVKANASAPPKINGSSVGLKS

GGFKTQEDSPSAPPPRTFINQLPDWSMLLAAITTVFLAAEKQWMMLDWKPKRPDMLVDPFGLGSIVQDGL

VFRQNFSIRSYEIGADRTASIETVMNHLQETALNHVKIAGLSNDGFGRTPEMYKRDLIWVVAKMQVMVNR

YPTWGDTVEVNTWVAKSGKNGMRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPPEVLETQELCSLTLE

YRRECGRESVLESLTAVDPSAEGYVSRFQHLLRLEDGGEIVKARTEWRPKNAGINGVVPSEESSPGDFF

SEQ ID NO: 120
CwFATB4b amino acid sequence
MVATAASSAFFPVPSADTSSSRPGKLGNGPSSLSPLKPKSIPNGGLQVKANASAPPKINGSSVGLKS

GSFKTQEDAPSAPPPRTFINQLPDWSMLLAAITTVFLAAEKQWMMLDWKPKRPDMLVDPFGLGSIVQDGL

VFRQNFSIRSYEIGADRTASIETVMNHLQETALNHVKIAGLSSDGFGRTPAMSKRDLIWVVAKMQVMVNR

YPAWGDTVEVNTWVAKSGKNGMRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPAEVLETQELCSLTLE

YRRECGRESVLESLTAVDPSGEGDGSKFQHLLRLEDGGEIVKARTEWRPKNAGINGVVPSEESSPGGDFF

SEQ ID NO: 121
CwFATB4b.1 amino acid sequence
MVATAASSAFFPVPSADTSSSRPGKLGSGPSSLSPLKPKSIPNGGLQVKANASAPPKINGSSVGLKS

GSFKTQEDAPSAPPPRTFINQLPDWSMLLAAITTVFLAAEKQWMMLDWKPKRPDMLVDPFGLGSIVQDGL

VFRQNFSIRSYEIGADRTASIETVMNELQETALNHVKIAGLSSDGFGRTPAMSKRDLIWVVAKMQVMVNR

YPAWGDTVEVNTWVAKSGKNGMRRDWLISDCNTGEILTRASSVWVMMNQKTRRLSKIPDEVRNEIEPHF

VDSAPVVEDDDRKLPKLDENTADSIRKGLTPRWNDLDVNQHVNNVKYIGWILESTPAEVLETQELCSLTLE

YRRECGRESVLESLTAVDPSGEGDGSKFQHLLRLEDGGEIVKARTEWRPKNAGINGVVPSEESSPGGDFF

SEQ ID NO: 122
CwFATB5 amino acid sequence
MVAAAASSAFFSVPTPGTPPKPGKFGNWPSSLSVPFKPDNGGFHVKANASAHPKANGSAVNLKSG

SLETPPRSFINQLPDLSVLLSKITTVFGAAEKQWKRPGMLVEPFGVDRIFQDGVFFRQSFSIRSYEIGVDRTAS

IETLMNIFQETSLNHCKSIGLLNDGFGRTPEMCKRDLIWVVTKIQVEVNRYPTWGDTIEVNTWVSESGKNG

MGRDWLISDCRTGEILIRATSVWAMMNQNTRRLSKFPYEVRQEIAPHFVDSAPVIEDDQKLQKLDVKTGDS

IRDGLTPRWNDLDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGRGWQPFRVVRLIF

SEQ ID NO: 123
CwFATB5a amino acid sequence
MVAAAASSAFFSVPTPGTPPKPGKFGNWPSSLSVPFKPDNGGFHVKANASAHPKANGSAVNLKSG

SLETPPRSFINQLPDLSVLLSKITTVFGAAEKQWKRPGMLVEPFGVDRIFQDGFFFRQSFSIRSYEIGVDRTAS

IETLMNIFQETSLNHCKSIGLLNDGFGRTPEMCKRDLIWVVTKIQVEVNRYPTWGDTIEVNTWVSESGKNG

MGRDWLISDCRTGEILIRATSVWAMMNQNTRRLSKFPYEVRQEIAPHFVDSAPVIEDDQKLQKLDVKTGDS

IRDGLTPRWNDLDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGRGWQPFRVVRLIF

-continued

SEQ ID NO: 124
CwFATB5b amino acid sequence
MVAAAASSAFFSVPTPGTPPKPGKFGNWPSSLSVPFKPDNGGFHVKANASAHPKANGSAVNLKSG

SLETPPRSFINQLPDLSVLLSKITTVFGAAEKQWKRPGMLVEPFGVDRIFQDGVFFRQSFSIRSYEIGVDRTAS

IETLMNIFQETSLNHCKSIGLLNDGFGRTPEMCKRDLIWVVTKIQVEVNRYPTWGDTIEVNTWVSESGKNG

MGRDWLISDCRTGEILIRATSVWAMMNQNTRRLSKFPYEVRQEIAPHFVDSAPVIEDDQKLQKLDVKTGDS

IRDGLTPRWNDLDVNQHVNNVKYIGWILKSVPIEVFETQELCGVTLEYRRECGRDSVLESVTAMDPAKEG

DRCVYQHLLWLEDGADITIGRTEWRPKNAGANGAMSSGKTSNGNCLIEGRGWQPFRVVRLIF

SEQ ID NO: 125
CwFATB5c amino acid sequence
MVAAAASSAFFSVPTPGTPPKPGKFGNWPSSLSVPFKPDNGGFHVKANASAHPKANGSAVNLKSG

SLETPPRSFINQLPDLSVLLSKITTVFGAAEKQWKRPGMLVEPFGVDRIFQDGVFFRQSFSIRSYEIGVDRTAS

IETLMNIFQETSLNHCKSIGLLNDGFGRTPEMCKRDLIWVVTKIQVEVNRYPIWGDTIEVNTWVSESGKNG

MGRDWLISDCRTGEILIRATSVWAMIVINQNTRRLSKFPYEVRQEIAPHFVDSAPVIEDDQKLQKLDVKTGDS

IRDGLTPRWNDLDVNQHVNNVKYIGWILKSVPIEVFETQELCGVTLEYRRECGRDSVLESVTAMDPAKEG

DRCVYQHLLRLEDGADITIGRTEWRPKNAGANGAMSSGKTSNGNCLIEGMGWQPFRVVRLIF

SEQ ID NO: 126
CwFATB5.1 amino acid sequence
MVAAAASSAFFSVPTPGTSPKPGKFRNWPSSLSVPFKPETNHNGGFHIKANASAHPKANGSALNLK

SGSLETQEDTSLSSPPRTFIKQLPDWSMLLSKITTVFGAAEKQLKRPGMLVEPFGVDRIFQDGVFFRQSFSIRS

YEIGADRTASIETLMNIFQETSLNIICKSIGLLNDGFGRTPEMCKRDLIWVVTKIQVEVNRYPTWGDTIEVNT

WVSESGKNGMGRDWLISDCRTGEILIRATSVWAMMNQNTRRLSKFPYEVRQEIAPHFVDSAPVIEDDRKL

YKLNVKTGDSIRDGLTPRWNDLDVNQHVNNVKFIGWILKSVPTKVFETQELCGVTLEYRRECGKDSVLES

VTAMDPAKEGDRSVYQHLLRLEDGADITIGRTEWRPKNAGANEAISSGKTSNGNSAS

SEQ ID NO: 127
CwFATB5.1a amino acid sequence
MVAAAASSAFFSVPTPGTSPKPGKFRNWPLSLSVPFKPETNHNGGFHIKANASAHPKANGSALNL

KSGSLETQEDTSLSSPPRTFIKQLPDWSMLLSKITTVFGAAEKQLKRPGMLVEPFGVDRIFQDGVFFRQSFSI

RSYEIGADRTASIETLMNIFQETSLNHCKSIGLLNDGFGRTPEMCKRDLIWVVTKIQVEVNRYPTWGDTIEV

NTWVSESGKNGMGRDWLISDCRTGEILIRATSVWAMMNQNTRRLSKFPYEVRQEIAPHFVDSAPVIEDDR

KLYKLNVKTGDSIRDGLTPRWNDLDVNQHVNNVKFIGWILKSVPTKVFETQELCGVTLEYRRECGKDSVL

ESVTAMDPAKEGDRSVYQHLLRLEDGADITIGRTEWRPKNAGANEAISSGKTSNGNSAS

SEQ ID NO: 128
CcFATB2b amino acid sequence
MVTTSLASAYFSMKAVMLAPDGRGIKPRSSGLQVRAGNERNSCKVINGTKVKDTEGLKGCSTLQ

GQSMLDDHFGLHGLVFRRTFAIRCYEVGPDRSTSIMAVMNHLQEAARNHAESLGLLGDGFGETLEMSKRD

LIWVVRRTHVAVERYPAWGDTVEVEAWVGASGNIGMRRDFLVRDCKTGHILTRCTSVSVMMNMRTRRL

SKIPQEVRAEIDPLFIEKVAVKEGEIKKLQKLNDSTADYIQGGWTPRWNDLDVNQHVNNIIYVGWIFKSVPD

SISENHHLSSITLEYRRECIRGNKLQSLTTVCGGSSEAGIICEHLLQLEDGSEVLRARTEWRPKHTDSFQGISE

RFPQQEPHIK

SEQ ID NO: 129
CcFATB3 amino acid sequence
MVATAAASAFFPVGAPATSSATSAKASMMPDNLDARGIKPKPASSSGLQVKANAHASPKINGSKV

STDTLKGEDTLTSSPAPRTFINQLPDWSMFLAAITTIFLAAEKQWTNLDWKPRRPDMLADPFGIGRFMQDG

LIFRQHFAIRSYEIGADRTASIETLMNHLQETALNHVRSAGLLGDGFGATPEMSRRDLIWVVTRMQVLVDR

YPAWGDIVEVETWVGASGKNGMRRDWLVRDSQTGEILTRATSVWVMMNKRTRRLSKLPEEVRGEIGPYF

-continued

IEDVAIIEEDNRKLQKLNENTADNVRRGLTPRWSDLDVNQHVNNVKYIGWILESAPGSILESHELSCMTLEY

RRECGKDSVLQSMTAVSGGGSAAGGSPESSVECDHLLQLESGPEVVRGRTEWRPKSANNSRSILEMPAESL

SEQ ID NO: 130
CcFATB3b amino acid sequence
MVATAAASAFFPVGAPATSSATSAKASMMPDNLDARGIKPKLASSSGLQVKANAHASPKINGSKV

STDTLKGEDTLTSSPAPRTFINQLPDWSMFLAAITTIFLAAEKQWTNLDWKPRRPDMLADPFGIGRFMQDG

LIFRQHFAIRSYEIGADRTASIETLIVINHLQETALNHVRSAGLLGDGFGATPEMSRRDLIWVVIRMQVLVDR

YPAWGDIVEVETWVGASGKNGMRRDWLVRDSQTGEILTRATSVWVMMNKRTRRLSKLPEEVRGEIGPYF

IEDVAIIEEDNRKLQKLNENTADNVRRGLTPRWSDLDVNQHVNNVKYIGWILESAPGSILESHELSCMTLEY

RRECGKDSVLQSMTAVSGGGSAAGGSPESSVECDHLLQLESGPEVVRGRTEWRPKSANNSRSILEMPAESL

SEQ ID NO: 131
CcFATB3c amino acid sequence
MVATAAASAFFPVGAPATSSATSAKASMMPDNLDARGIKPKPASSSGLQVKANAHASPKINGSKV

STDTLKGEDTLTSSPAPRTFINQLPDWSMFLAAITTIFLAAEKQWTNLDWKPRRPDMLADPFGIGRFMQDG

LIFRQHFAIRSYEIGADRTASIETLMNHLQETALNHVRSAGLLGDGFGATPEMSRRDLIWVVTRMQVLVDR

YPAWGDIVEVETWVGASGKNGMRRDWLVRDSQTGEILTRATSVWVMMNKRTRRLSKLPEEVRGEIGPYF

IEDVAIIEEDNRKLQKLNENTADNVRRGLTPRWSDLDVNQHVNNAKYIGWILESAPGSILESHELSCMTLEY

RRECGKDSVLQSMTAVSGGGSAAGGSPESSVECDHLLQLESGPEVVRGRTEWRPKSANNSRSILEMPAESL

SEQ ID NO: 132
ChtFATB1a amino acid sequence
MVAAAASSAFFSVPTPGTSTKPGNFGNWPSSLSVPFKPESNHNGGFRVKANASAHPKANGSAVNL

KSGSLETQEDTSSSSPPPRTFIKQLPDWGMLLSKITTVFGAAERQWKRPGMLVEPFGVDRIFQDGVFFRQSF

SIRSYEIGADRTASIETLMNIFQETSLNHCKSIGLLNDGFGRTPEMCKRDLIWVVTKIQVEVNRYPTWGDTIE

VNTWVSESGKNGMGRDWLISDCRTGEILIRATSVWAMMNRKTRRLSKFPVEVRQEIAPHFVDSAPVIEDD

KKLHKLDVKTGDSIRKGLTPRWNDLDVNQHVNNVKYIGWILKSVPAEVFETQELCGVTLEYRRECGRDSV

LESVTAMDTAKEGDRSLYQHLLRLEDGADITIGRTEWRPKNAGANGAISTGKTSNENSVS

SEQ ID NO: 133
ChtFATB1a.1 amino acid sequence
MVAAAASSAFFSVPTPGTSPKPGNFGNWPSSLSVPFKPESNHNGGFRVKANASAHPKANGSAVNL

KSGSLETQEDTSSSSPPPRTFIKQLPDWGMLLSKITTVFGAAERQWKRPGMLVEPFGVDRIFQDGVFFRHSF

SIRSYEIGADRTASIETLMNIFQETSLNHCKSIGLLNDGFGRTPEMCKRDLIWVVTKIQVEVNRYPTWGDTIE

VNTWVSESGKNGMGRDWLIGDCRTGEILIRATSVWAMMNRKTRRLSKFPYEVRQEIAPHFVDSAPVIEDD

KKLHKLDVKTGDSIRKGLTPRWNDLDVNQHVNNVKYIGWILKSVPAEVFETQELCGVTLEYRRECGRDSV

LESVTAMDTAKEGDRSLYQHLLRLEDGADITIGRTEWRPKNAGANGALSTGKTSNGNSVS

SEQ ID NO: 134
ChtFATB1a.2 amino acid sequence
MVAAAASSAFFSVPTPGTSPKPGNFGNWPSNLSVPFKPESNHNGGFRVKANASAHPKANGSAVNL

KSGSLETQEDTSSSSPPPRTFIKQLPDWGMLLSKITTVFGAAERQWKRPGMLVEPFGVDRIFQDGVFFRQSF

SIRSYEIGADRTASIETLMNIFQETSLNECKSIGLLNDGFGRTPEMCKRDLIWVVTKIQVEVNRYPTWGDTIE

VNTWVSESGKNGMGRDWLISDCRTGEILIRATSVWAMMNRKTRRLSKFPYEVRQEIAPHFVDSAPVIEDD

KKLHKLDVKTGDSIRKGLTPRWNDFDVNQHVNNVKYIGWILKSVPAEVFETQELCGVTLEYRRECGRDSV

LESVTAMDTAKEGDRSLYQHLLRLEDGADITIGRTEWRPKNAGANGAISTGKTSNENSVS

SEQ ID NO: 135
ChtFATB1a.3 amino acid sequence
MVAAAASSAFFSVPTPGTSPKPGNFGNWPSSLSVPFKPESNHNGGFRVKANASAHPKANGSAVNL

KSGSLETQEDTSSSSPPPRTFIKQLPDWGMLLSKITTVFGAAERQWKRPGMLVEPFGVDRIFQDGVFFRQSF

-continued

SIRSYEIGADRTASIETLMNIFQETSLNHCKSIGLLNDGFGRTPEMCKRDLIWVVTKIQVEVNRYPTWGDTIE

VNTWVSESGKNGMGRDWLISDCRTGEILIRATSVWAMMNRKTRRLSKFPYEVRQEIAPHFVDSAPVIEDD

KKLHKLDVKTGDSIRKGLTPRWNDFDVNQHVNNVKYIGWILKSVPAEVFETQELCGVTLEYRRECGRDSV

LESVTAMDTAKEGDRSLYQHLLRLEDGADITIGRTEWRPKNAGVNGAISTGKTSNENSVS

SEQ ID NO: 136
ChtFATB1a.4 amino acid sequence
MVAAAASSAFFSVPTPGTSPKPGNFGNWPSSLSVPFKPESNHNGGFRVKANASAHPKANGSAVNL

KSGSLETQEDTSSSSPPPRTFIKQLPDWSMLLSKITTVFGAAERQWKRPGMLVEPFGVDRIFQDGVFFRQSFS

IRSYEIGADRTASIETLMNIFQETSLNECKSIGLLNDGFGRTPEMCKRDLIWVVTKIQVEVNRYPTWGDTIEV

NTWVSESGKNGMGRDWLISDCRTGEILIRATSVWAMMNRKTRRLSKFPYEVRQEIAPHFVDSAPVIEDDK

KLHKLDVKTGDSIRKGLTPRWNDFDVNQHVNNVKYIGWILKSVPAEVFETQELCGVTLEYRRECGRDSVL

ESVTAMDTAKEGDRSLYQHLLRLEDGADITIGRTEWRPKNAGANGAISTGKTSNENSVS

SEQ ID NO: 137
ChtFATB1b amino acid sequence
MVAAAASSAFFSVPTSGTSPKPGNFGNVVPSSLSVPFKPESSHNGGFQVKANASAHPKANGSAVNL

KSGSLETQEDTSSSSPPPRTFIKQLPDWSMLLSKITTVFWAAERQWKRPGMLVEPFGVDRIFQDGVFFRQSF

SIRSYEIGADRTASIETLMNIFQETSLNHCKSIGLLNDGFGRTPEMCKRDLIWVVTKIQVEVNRYPTWGDTIE

VNTWVSESGKNGMGRDWLISDCRTGEILIRATSVWAMMNRKTRRLSKFPYEVRQEIAPHFVDSAPVIEDD

KKLHKLDVKTGDFIRKGLTPRWNDFDVNQHVNNVKYIGWILKSVPAEVFETQELCGVTLEYRRECGRDSV

LESVTAMDTAKEGDRSLYQHLLRLEDGADITIGRTEWRPKNAGANGAISTGKTSNENSVS

SEQ ID NO: 138
ChtFATB2b amino acid sequence
MVVAAAASSAFFPVPASGTSPKPGIUGTWLSSSSPSYKPKSNPSGGFQVKANASAHPKANGSAVS

LKSGSLNIQEGTSSSPPPRTFLNQLPDWSRLRTAITTVFVAAEKQLTMLQRKSKKPDMIFIVDWFGLEIIVQD

GLVFRESFSIRSYEIGADRTASIETLMNHLQDTSLNHCKSVGLLNDGFGRTPEMCKRDLIWVLIKMQIMVN

RYPTWGDTVEINSWFSQSGKIGMGRNWLISDCNTGEILIRATSIWAMMNQKTRRFSKLPNEVRQEIAPHFV

DAPPVIEDNDRKLHKFDVKTGDSICKGLTPEWNDLDVNQHVSNVKYIGWILESMPKEVLDTQELCSLTLEY

RRECGRDSVLESVTAMDPSKVGDRSQYQHLLRLEDGTDIMKGRTEWRPKNAGTNGAISTGKTSNGNSVS

SEQ ID NO: 139
ChtFATB2a amino acid sequence
MVVAAAASSAFFPVPAPGTTSKPGKFGNWPSSLSPSFKPKSNPNGGFQVKANASAHPKANGSAVS

LKSGSLNTKEDTPSSPPPRTFLNQLPDWSRLRTAITTVFVAAEKQLTMLDRKSKKPDMHVDWFGLEIIVQD

WLVFRESFSIRSYEIGADRTASIETLMNHLQDTSLNHCKSVGLLNDGFGRTPEMCKRDLIWVLTKMQIMVN

RYPTWGDTVEINSWFSQSGKIGMGRNWLISDCNTGEILIRATSIWAMMNQKTRRFSKLPNEVRQEIAPHFV

DAPPLIEDNDRKLHKFDVKTGDSICKGLTPEWNDLDVNQHVSNVKYIGWILESMPKEVLDTQELCSLTLEY

RRECGRDSVLESVTAMDPSKVGDRSQYQHLLRLEDGTDIMKGRTEWRPKNAGTNGAISTGKTSNGNSVS

SEQ ID NO: 140
ChtFATB2c amino acid sequence
MVVAAAASSAFFPVPASGTSPKPGKFGTWLSSSSPSYKPKSNPSGGFQVKANASAHPKANGSAVS

LKSGSLNTKEDTPSSPPPRTFLNQLPDWNRLRTAITTVFVAAEKQLTMLDRKSKKPDMHVDWFGLEIIVQD

GLVFRESFSIRSYEIGADRTASIETLMNHLQDTSLNHCKSVGLLNDGFGRTPEMCKRDLIWVLTKMQIMVN

RYPTWGDTVEINSWFSQSGKIGMGRNWLISDCNTGEILIRATSIWAMMNQKTRRFSKLPNEVRQEIAPHFV

DAPPVIEDNDRKLHKFDVKTGDSICKGLIPEWNDLDVNQHVSNVKYIGWILESMPKEVLDTQELCSLTLEY

RRECGRDSVLESVTAMDPSKVGDRSQYQHLLRLEDGTDIMKGRTEWRPKNAGINGAISTGKTSNGNSVS

-continued

SEQ ID NO: 141
ChtFATB2d amino acid sequence
MVVAAAASSAFFPVPAPGTTSKPGKFGNWPSSLSPSFKPKSNPNGGFQVKANASAHPKANGSAVS

LKSGSLNTQEDTSSSPPPRTFLNQLPDWSRLLTAISTVFVAAEKQLTMLDRKSKRPDMLVDLFGLESIVQDG

LVFRESYSIRSYEIGADRTASIETLMNHLQDTSLNHCKSVGLLNDGFGRTPEMCKRDLIWVLTKMQIMVNR

YPTWGDTVEINSWFSQSGKIGMGRNWLISDCNTGEILIRATSIWAMMNQNTRRFSKLPNEVRQEIAPHFVD

APPVIEDNDRKLHKFDVKTGDSIRKGLTPGWNDLDVNQHVSNVKYIGWILESMPTEVLETQELCSLTLEYR

RECGRESVLESVTAMNPSKVGDRSQYQHLLRLEDGADIMKGRTEWRPKNAGTNGAISTGKTSNGNSVS

SEQ ID NO: 142
ChtFATB2e amino acid sequence
MVVAAAASSAFFPVPASGTSPKPGKFGTWLSSSSPSYKPKSNPSGGFQVKANASAHPKANGSAVS

LKSGSLNIQEDTSSSPPPQTFLNQLPDWSRLLTAISTVFVAAEKQLTMLDRKSKRPDMLVDWFGLESIVQD

GLVFRESYSIRSYEISADRTASIETVMNLLQETSLINITICKSMGILNDGFGRTPEMCKRDLIWVLIKMQILV

NRYPNWGDTVEINSWFSQSGKIGMGRNWLISDCNTGEILIRATSIWAMMNQNTRRFSKLPNEVRQEIAPHFVD

APPVIEDNDRKLHKFDVKTGDSIRKGLTPGWNDLDVNQHVSNVKYIGWILESMPTEVLETQELCSLTLEYR

RECGRDSVLESVTAMNPSKVGDRSQYQHLLRLEDGADIMKGRTEWRPKNAGINGAISTGKTSNGNSVS

SEQ ID NO: 143
ChtFATB2f amino acid sequence
MVVAAAASSAFFPVPASGTSPKPGKFGTWLSSSSPSYKPKSNPSGGFQVKANASAHPKANGSAVS

LKSGSLNTQEGTSSSPPPRTFLNQLPDWSRLLTAISTVFVAAEKQLTMLDRKSKRPDMLVDWFGLESIVQD

GLVFRESYSIRSYEISADRTASIETVMNLLQETSLNHCKSMGILNDGFGRTPEMCKRDLIWVLTKMQILVNR

YPNWGDTVEINSWFSQSGKIGMGRNWLISDCNTGEILIRATSIWAMMNQKTRRFSKLPNEVRQEIAPHFVD

APPVIEDNDRKLHKFDVKTGDSICKGLTPEWNDLDVNQHVSNVKYIGWILESMPKEVLDTQELCSLTLEYR

RECGRDSVLESVTAMDPSKVGDRSQYQHLLRLEDGTDIMKGRTEWRPKNAGINGAISTGKTSNGNSVS

SEQ ID NO: 144
ChtFATB2g amino acid sequence
MVVAATASSAFFPVPVPGTSPKPGKFGTWLSSSSPSYKPKSNPSGGFQVKANASAHPKANGSAVSL

KSGSLNTQEDTSSSPPPRTFLNQLPDWSRLLTAISTVFVAAEKQLTMLDRKSKRPDMLVDWFGLESIVQDG

LVFREIYSIRSYEISADRTTSIETVMNLLQETSLNHCKSMGILNDGFGRTPEMCKRDLIWVLTKMQILVNRYP

NWGDTVEINSWFSQSGKIGMGRNWLISDCNTGEILIRATSIWAMMNQKTRRFSKLPNEVRQEIAPHFVDAP

PVIEDNDRKLHKFDVKTGDSICKGLTPEWNDLDVNQHVSNVKYIGWILESMPKEVLDTQELCSLTLEYRRE

CGRDSVLESVTAMDPSKVGDRSQYQHLLRLEDGTDIMKGRTEWRPKNAGTNGAISTGKTSNANSVS

SEQ ID NO: 145
ChtFATB2h amino acid sequence
MVVAAAASSAFFPVPASGTSPKPGKFGTWLSSSSPSYKPKSNPSGGFQVKANASAHPKANGSAVS

LKSGSLNTQEGTSSSPPPRTFLNQLPDWSRLLTAISTVFVAAEKQLTMLDRKSKRPDMLVDWFGLESIVQD

GLVFRESYSIRSYEISADRTASIETVMNLLQETSLNHCKSMGILNDGFGRTPEMCKRDLIWVLTKMQILVNR

YPNWGDTVEINSWFSQSGKIGMGRNWLISDCNTGEILIRATSIWAMMNQNTRRFSKLPNEVRQEIAPHFVD

APPVIEDNDRKLHKFDVKTGDSIRKGLTPGWNDLDVNQHVSNVKYIGWILESIPTEVLETQELCSLTLEYRR

ECGRESVLESVTAMNPSKVGDRSQYQUILLRLEDGADIMKGRTEWRPKNAGTNGAISTGKTSNGNSVS

SEQ ID NO: 146
ChtFATB3a amino acid sequence
MVATAASSAFFPVPSPDTSSRPGKLGNGSSSLRPLKPKFVANAGLQVKANASAPPKINGSSVSLKS

CSLKTHEDTPSAPPPRTFINQLPDWSMLLAAITTVFLAAEKQWMMLDWKPKRPDMLVDPFGLGRIVQDGL

VFRQNFSIRSYEIGADRTASIETVMNHLQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHETEPHF

-continued

VDSAPVIEDDDWKLPKLDEKTADSIRKGLTPKWNDLDVNQHVNNVKYIGWILESTPPEVLETQELCSLTLE

YRRECGRESVLESLTAVDPSGKGFGPQFQHLLRLEDGGEIVKGRTEWRPKTAGINGTIASGETSPGNS

SEQ ID NO: 147
ChtFATB3b amino acid sequence
MVATAASSAFFPVPSPDTSSRPGKLGNGSSSLRPLKPKFVANAGLQVKANASAPPKINGSSVSLKS

GSLKTQEDTPSAPPPRTFINQLPDWSMLLAAITTVFLAAEKQWMMLDWKPKRPDMLVDPFGFGRIVQDGL

VFRQNFSIRSYEIGADRTASIETVMNHLQETALNHVKSAGLLIEGFGRTPEMYKRDLIWVVAKMQVMVNR

YPTWGDTVEVNTWVAKSGKNGMRRDWLISDCNTGEILTRASSVWVIVIMNQKTRKLSKIPDEVRHEIEPHF

VDSAPVIEDDDWKLPKLDEKTADSIRKGLTPKWNDLDVNQHVNNVKYIGWILESTPPEVLETQELCSLTLE

YRRECGRESVLESLTAVDPSGKGFGPQFQHLLRLEDGGEIVKGRTEWRPKTAGINGTIASGETSPGNS

SEQ ID NO: 148
ChtFATB3c amino acid sequence
MVATAASSAFFPVPSPDTSSRPGKLGNGSSSLRPLKPKFVANAGLQVKANASAPPKINGSSVSLKS

CSLKTHEDTPSAPPPRTFINQLPDWSMLLAAITTVFLAAEKQWMMLDWKPKRPDMLVDPFGLGRIVQDGL

VFRQNFSIRSYEIGADRTASIETVMNFILQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHELEPHF

VDSAPVIEDDDRKLPKLDEKTADSIRKGLTPKWNDLDVNQHVNNVKYIGWILESTPPEVLETQELCSLTLE

YRRECGRESVLESLTAVDPSEKGFGPQFQHLLRLEDGGEIVKGRTEWRPKTAGINGAIAFGETSPGDS

SEQ ID NO: 149
ChtFATB3d amino acid sequence
MVATAASSAFFPVPSPDTSSRPCiKLGNGSSSLRPLKPKFVANAGLQVKANASAPPKINGSSVSLKS

CSLKTHEDTPSAPPPRTFINQLPDWSMLLAAITTVFLAAEKQWMMLDWKPKRPDMLVDPFGLGRIVQDGL

VFRQNFSIRSYEIGADRTASIKTVMNHLQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHEIEPHF

VDSAPVIEDDDWKLPKLDEKTADSIRKGLTPKWNDLDVNQHVNNVKYIGWILESTPPEVLETQELCSLTLE

YRRECGRESVLESLTAVDPSGKGFGPQFQHLLRLEDGGEIVKGRTEWRPKTAGINGTIASGETSPGNS

SEQ ID NO: 150
ChtFATB3e amino acid sequence
MVATAASSAFFPVPSPDTSSRPGKLGNGSSSLRPLKPKFVANAGLQVKANASAPPKINGSSVSLKS

GSLKTHEDTPSAPPPRTFINQLPDWSMLLAAITTVFLAAEKQWMMLDWKPKRPDWILVDPFGLGRIVQDGL

VFRQNFSIRSYEIGADRTASIETVMNHLQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHEIEPHF

VDSAPVIEDDDWKLPKLDEKTADSIRKGLTPKWNDLDVNQHVNNVKYIGWILESTPPEVLETQELCSLTLE

YRRECGRESVLESLTAVDPSGKGFGPQFQHLLRLEDGGEIVKGRTEWRPKTAGINGTIASGETSPGNS

SEQ ID NO: 151
ChtFATB3f amino acid sequence
MVATAASSAFFPVPSPDTSSRLGKLGNGSSSLRPLKPKFVANAGLQVKANASAPPKINGSSVSLKS

GSLKTQEDTPSAPPPRTFINQLPDWSMLLAAITTVFLAAEKQWMMLDWKPKRPDMPVDPFGLGRIVQDGL

VFRQNFSIRSYEIGADRTASIETVMNFILQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHEIEPHF

VDSAPVIEDDDWKLPKLDEKTADSIRKGLTPKWNDLDVNQHVNNVKYIGWILESTPPEVLETQELCSLTLE

YRRECGRESVLESLTAVDPSEKGFGPQFQHLLRLEDGGEIVKGRTEWRPKTAGINGTIASGETSPGNS

SEQ ID NO: 152
ChtFATB3g amino acid sequence
MVATAASSAFFPVPSPDTSSRAGKLGNGSSSLRPLKPKFVANAGLQVKANASAPPKINGSSVSLKS

GSLKTQEDTPSAPPPRTFINQLPDWSMLLAAITTVFLAAEKQWMMLDWKPKRPDMLVDPFGLGRIVQDGL

-continued

VFRQNFSIRSYEIGADRTASIETVMNHLQETALNHVKSAGLLNEGFGRTPEMYKRDLIWVVAKMQVMVNR

YPTWGDTVEVNTWVAKSGKNGMRRDWLISDCNTGEILTRASSVWVMMNQKTRKLSKIPDEVRHEIEPHF

VDSAPVIEDDDWKLPKLDEKTADSIRKGLTPKWNDLDVNQHVNNVKYIGWILESTPPEVLETQELCSLTLE

YRRECGUSVLESLTAVDPSGKGFGPQFQHLLRLEDGGEIVKGRTEWRPKTAGINGTIASGETSPGNS

SEQ ID NO: 153
ChsFATB1 amino acid sequence
MVATNAAAFSAYTFFLTSPTHGYSSKRLADTQNGYPGTSLKSKSTPPPAAAAARNGALPLLASICK

CPKKADGSMQLDSSLVFGFQFYIRSYEVGADQTVSIQTVLNYLQEAAINHVQSAGYFGDSFGATPEMTKRN

LIWVITKMQVLVDRYPAWGDVVQVDTWTCSSGKNSMQRDWFVRDLKTGDIITRASSVWVLMNRLTRKL

SKIPEAVLEEAKLFVMNTAPTVDDNRKLPKIDGSSADYVLSGLTPRWSDLDMNQHVNNVKYIAWILESVP

QSIPETHKLSAITVEYRRECGKNSVLQSLTNVSGDGITCGNSIIECHFILLQLETGPEILLARTEWISKEPGF

RGAPIQAEKVYNNK

SEQ ID NO: 154
ChsFATB2 amino acid sequence
MVATAASSAFFPVPSPDASSRPGKLGNGSSSLSPLKPKLMANGGLQVKANASAPPKINGSSVGLKS

GSLKTQEDTPSAPPPRTFINQLPDWSMLLAAITTVFLAAEKQWMMLDWKPKRPDMLVDPFGLGRIVQDGL

VFRQNFSIRSYEIGADRTASIETVMNHLQETALNHVKSAGLLNDGEGRTLEMYKRDLIWVVAKMQVMVN

RYPTWGDTVEVNTWVAKSGKNGMRRDWLISDCNTGEILTRASSVWVMMNQKTRRLSKIPDEVRHEIEPH

FVDSAPVIEDDDRKLPKLDEKTADSIRKGLTPKWNDLDVNQHVNNVKYIGWILESTPPEVLETQELCSLTLE

YRRECGRESVLESLTAVDPSGKGSGSQFQHLLRLEDGGEIVKGRTEWRPKTAGINGPIASGETSPGDSS

SEQ ID NO: 155
ChsFatB2b amino acid sequence
MVATAASSAFFPVPSPDASSRPGKLGNGSSSLSPLKPKLMANGGLQVKANASAPPKINGSSVGLKS

GSLKTQEDTPSAPPPRTFINQLPDWSMLLAAITTVFLAAEKQWMMLDWKPKRPDMLVDPFGLGRIVQDGL

VFRQNFSIRSYEIGADRTASIETVMNHLQETALNHVKSAGLLNDGFGRTLEMYKRDLIWVVAKMQVMVN

RYPTWGDTVEVNTWVAKSGKNGMRRDWLISDCNTGEILTRASSKSQIMLPLHYCSVWVMNINQKTRRLS

KIPDEVRHEFEPHFVDSAPVIEDDDRKLPKLDEKTADSIRKGLTPKWNDLDVNQHVNNVKYIGWILESTPPE

VLETQELCSLTLEYRRECGRESVLESLTAVDPSGKGSGSQFQHLLRLEDGGEIVKGRTEWRPKTAGINGPIA

SGETSPGDSS

SEQ ID NO: 156
ChsFatB2c amino acid sequence
MVATAASSAFFPVPSPDASSRPGKLGNGSSSLSPLKPKLMANGGLQVKANASAPPKINGSSVGLKS

GSLKTQEDTPSAPPPRTFINQLPDWSMLLAAITTVFLAAEKQWMMLDWKPKRPDMIVDPFGLGRIVQDGL

VFRQNFSIRSYEIGADRTASIETVMNHLQETALNHVKSAGLLNDGFGRTLEMYKRDLIWVVAKMQVMVN

RYPTWGDTVEVNTWVAKSGKNGMRRDWLISDCNTGEILTRASSVWVMMNQKTRRLSKIPDEVRHEIEPH

FVDSAPVIEDDDRKLPKLDEKTADSIRKGLTPKWNDLDVNQHVNNVKYIGWILESTPPEVLETQELCSLTLE

YRRECGRESVLESLTAVDPSGKGSGSQFQHLMRLEDGGEIVKGRTEWRPKTAGINGPIASGETSPGDSS

SEQ ID NO: 157
ChsFatB2d amino acid sequence
MVATAASSAFFPVPSPDASSRPGKLGNGSSSLSPLKPKLMANGGLQVKANASAPPK1NGSSVGLKS

GSLKTQEDTPSAPPPRTFINQLPDWSMLLAAITTVFLAAEKQWMMLDWKPKRPDMLVDPFGLGRIVQDGL

VFRQNFSIRSYEIGADRTASIETVMNHLQETALNHVKSAGLLNDGFGRTPEMYKRDLIWVVAKMQVMVNR

YPTWGDTVEVNTWVAKSGKNGMRRDWLISDCNTGEILTRASSVWVMMNQKTRRLSKIPDEVRHEIEPHF

VDSAPVIEDDDRKLPKLDEKTADSIRKGLTPKWNDLDVNQHVNNVKYIGWILESTPPEVLETQELCSLTLE

YRRECGRESVLESLTAVDPSGKGSGSQFQHLLRLEDGGEIVKGRTEWRPKTAGINGPIASGETSPGDSS

-continued

SEQ ID NO: 158
Chs FATB3 amino acid sequence
MVAAEASSALFSVRTPGTSPKPGKFGNWPTSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMHVEVN

RYPTWGDTIEVNTWVSESGKTGMGRDWLISDCHTGEILIRATSMCAMMNQKTRRFSKFPYEVRQELAPHF

VDSAPVIEDYQKLHKLDVKTGDSICNGLTPRWNDLDVNQHVNNVKYIGWILESVPTEVFETQELCGLTLEY

RRECGRDSVLESVTAMDPSKEGDRSLYQHLLRLEDGADIAKGRTKWRPKNAGTNGAISTGKTSNGNSIS

SEQ ID NO: 159
ChsFatb3b amino acid sequence
MVAAEASSALFSVRTPGTSPKPGKFGNWPTSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMHIEVNR

YPTWGDTIEVNTWVSESGKTGMGRDWLISDFHTGDILIRATSVCAMMNQKTRRFSKFPYEVRQELAPHFV

DSAPVIEDYQKLHKLDVKTGDSICNGLTPRWNDLDVNQHVNNVKYIGWILESVPTEVFETQELCGLTLEYR

RECGRDSVLESVTAMDPSKEGDRSLYQHLLRLEDGADIAKGRTKWRPKNAGINGAISTGKTSNGNSIS

SEQ ID NO: 160
ChsFatB3c amino acid sequence
MVAAEASSALFSVRTPUTSPKPGKFGNWPTSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMHVEVN

RYPTWGDTIEVNTWVSESGKTGMGRDWLISDCHTGEILIRATSMCAMMNQKTRRFSKFPYEVRQELAPHF

VDSAPVIEDYQKLHKLDVKTGDSICNCLEMWNDLDVNQHVNNVKYIGWILESVPTEVFETQELCGLTLEY

RQECGRDSVLESVTAMDPSKEGDRSLYQHLLRLEDGTDIAKGRTKWRPKNAGKTSNGNSIS

SEQ ID NO: 161
ChsFATB3d amino acid sequence
MVAAEASSALFSVRTPGTSPKPGKFGNWPSSLSVPFKSKSNHNGGFQVKANASARPKANGSAVSL

KSGSLDTQEDASSSSSPPRTFINQLPDWSMLLSAITTVFVAAEKQWTMLDRKSKRSDMLMDPFGVDRVVQ

DGAVFRQSFSIRSYEIGADRTASIETLMNIFQETSLNHCKSIGLLNDGFGRTPEMCKRDLIWVVIKMHVEVN

RYPTWGDTIEVNTWVSESGKTGMGRDWLISDCHTGEILIRATSMCAMMNQKTRRFSKFPYEVRQELAPHF

VDSAPVIEDYQKLFIKLDVKTGDSICNGLTPRWNDLDVNQHVNNVKYIGWILESVPTEVFETQELCGLTLEY

RRECGRDSVLESVTAMDPSKEGDRSLYQHLLRLEDGADIAKGRTKWRPKNAGTNGAISTGKTSNGNSIS

SEQ ID NO: 162
ChsFATB3e amino acid sequence
MVAAEASSALFSVRTPGTSPKPGKFGNWPSSLSVPFKSKSNHNGGFQVKANASARPKANGSAVSL

KSGSLDTQEDASSSSSPPRTFINQLPDWSMLLSAITTVFVAAEKQWTMLDRKSKRSDMLMDPFGVDRVVQ

DGVVFRQSFSIRSYEIGADRTASIETLMNIFQETSLNHCKSIGLLNDGFGRTPEMCKRDLIWVVIKMHVEVN

RYPTWGDTIEVNTWVSESGKTGMGRDWLISDCHTGEILIRATSMCAMMNQKTRRFSKFPYEVRQELAPHF

VDSAPVIEDYQKLIEKLDVKTGDSICNGLTPRWNDLDVNQHVNNVKYIGWILESVPTEVFETQELCGLTLEY

RRECGRDSVLESVTAMDPSKEGDRSLYQHLLRLEDGADIAKGRTKWRPKNAGINGAISTGKTSNGNSIS

SEQ ID NO: 163
ChsFATB3f amino acid sequence
MVAAEASSALFSVRTPGTSPKPGKFGNWPSSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMTIVEVN

RYPTWGDTIEVNTWVSESGKTGMGRDWLISDCHTGEILIRATSMCAMMNQKTRRFSKFPYEVRQELAPHF

-continued

VDSAPVIEDYQKLHKLDVKTGDSICNGLTPRWNDLDVNQHVNNVKYIGWILESVPTEVFETQELCGLTLEY

RRECGRDSVLESVTAMDPSKEGDRSLYQHLLRLEDGADIAKGRTKWRPKNAGTNGAISTGKTSNGNSIS

SEQ ID NO: 164
ChsFATB3g amino acid sequence
MVAAEASSALFSVRTPGTSPKPGKFGNWPTSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMHIEVNR

YPTWGDTIEVNTWVSESGKTGMGRDWLISDFHTGDILIRATSVCAMMNQKTRRFSKFPYEVRQELAPHFV

DSAPVIEDYQKLHKLDVKTGDSICNGLTPRWNDLDVNQHVNNVKYIGWILESVPTEVFETQELCGLTLEYR

QECGRDSVLESVTAMDPSKEGDRSLYQHLLRLEDGTDIAKGRTKWRPKNAGKTSNGNSIS

SEQ ID NO: 165
ChsFATB3h amino acid sequence
MVAAEASSALFSVRTPGTSPKPGKFGNWPSSLSVPFKSKSNHNGGFQVKANASARPKANGSAVSL

KSGSLDTQEDASSSSSPPRTFINQLPDWSMLLSAITTVFVAAEKQWTMLDRKSKRSDMLMDPFGVDRVVQ

DGVVFRQSFSIRSYEIGADRTASIETLMNIFQETSLNHCKSIGLLNDGFGRTPEMCKRDLIWVVIKMHIEVNR

YPTWGDTIEVNTWVSESGKTGMGRDWLISDFHTGDILIRATSVCAMMNQKTRRFSKFPYEVRQELAPHFV

DSAPVIEDYQKLHKLDVKTGDSICNGLTPRWNDLDVNQHVNNVKYIGWILESVPTEVFETQELCGLTLEYR

QECGRDSVLESVTAMDPSKEGDRSLYQHLLRLEDGTDIAKGRTKWRPKNAGKTSNGNSIS

SEQ ID NO: 166
ChsFATB3i amino acid sequence
MVAAEASSALFSVRTPGTSPKPGKFGNWPTSLSVPFKSKSNHNGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMTIVEVN

RYPTWGDTIEVNTWVSESGKTGMGRDWLISDCHTGEILIRATSMCAMMNQKTRRFSKFPYEVRQELAPHF

VDSAPVIEDYQKLHKLDVKTGDSICNGLTPRWNDLDVNQHVNNVKYIGWILESVPTEVFETQELCGLTLEY

RRECGGDSVLESVTAMDPSKEGDRSLYQHLLRLEDGADIAKGRTKWRPKNAGTNGAISTGKTSNGNSIS

SEQ ID NO: 167
ChsFATB3j amino acid sequence
MVAAEASSALFSVRTPGTSPKPGKFGNWPTSLSVPFKSKSNIINGGFQVKANASARPKANGSAVSL

KSGSLDTQEDTSSSSSPPRTFINQLPDWSMLLSAITTVFVAAEKQWTMLDRKSKRPDMLMDPFGVDRVVQ

DGAVFRQSFSIRSYEIGADRTASIETLMNIFQETSLNHCKSIGLLNDGFGRTPEMCKRDLIWVVTKMHIEVNR

YPTWGDTIEVNTWVSESGKTGMGRDWLISDFHTGDILIRATSVCAMMNQKTRRFSKFPYEVRQELAPHFV

DSAPVIEDYQKLHKLDVKTGDSICNGLTPRWNDLDVNQHVNNVKYIGWILESVPTEVFETQELCGLTLEYR

QECGRDSVLESVTAMDPSKEGDRSLYQHLLRLEDGTDIAKGRTKWRPKNAGKTSNGNSIS

SEQ ID NO: 168
CcalcFATB1 (*Cuphea calcarata* FATB1)
MVAAAATSAFFPVPAPGTSPNPRKFGSWPSSLSPSLPKSIPNGGFQVKANASAFIPKANGSAVSLKSGSLNTQ

ENTSSSPPPRTFLHQLPDWSRLLTAITTVFVKSKRPDMHDRKSKRPDMLVDLFGLESSVQDALVFRQSFSIRS

YEIGTDRTASIETLMNHLQETSLNECKSTGILLDGFGRTLEMCKRELIWVVIKMQIQVNRYPAWGDTVEINT

RFSRLGKIGMGRDWLISDCNTGEILIRATSEYAMMNQKTRRLSKLPYEVHQEIAPLFVDSPPVIEDNDLKVH

KFEVKTGDSIQKGLSPGWNDLDVNQHVSNVKYIGWILESMPTEVLETQELCSLALEYRRECGRDSVLESVT

AMDPSKVGGRSQYQHLLRLEDGTAIVNGITEWRPKNAGANGAISTGKTSNGNSVS

SEQ ID NO: 169
ChookFATB4 (*Cuphea hookeriana* FATB4)
MVAAAATSAFFPVPAPGTSPNPRKFGSWPSSLSPSLPNSIPNGGFQVKANASAHPKANGSAVSLKSGSLNTQ

ENTSSSPPPRTFLHQLPDWSRLLTAITTVFVKSKRPDMHDRKSKRPDMLVDLFGLESSVQDALVFRQRFSIR

-continued

SYEIGTDRTASMETLMNHLQETSLNHCKSTGILLDGFGRTLEMCKRELIWVVIKMQIQVNRYPAWGDTVEI

NTRFSRLGKIGMGRDWLISDCNTGEILIRATSEYAMMNQKTRRLSKLPYEVRQEIAPLFVDSPPVIEDNDLK

VHICFEVKTGDSIHKGLTPGWNDLDVNQHVNNVKYIGWILESTPPEVLETQELCSLTLEYRRECGRESVLES

LTAMDPSGGGYGSQFQHLLRLEDGGEIVKGRTEWRPKNGVINGVVPTGESSPGDYS

SEQ ID NO: 170
CaFATB1 (*Cuphea avigera* var. *pulcherrima* FATB1)
MVAAAASSAFFSVPVPGTSPKPGKFRIWPSSLSPSFKPKPIPNGGLQVKANSRAHPKANGSAVSLKSGSLNT

QEDTSSSPPPRTFLHQLPDWSRLLTAITTVFVKSKRPDMHDRKSKRPDMLMDSFGLESIVQEGLEFRQSFSIR

SYEIGTDRTASIETLMNYLQETSLNHCKSTGILLDGFGRTPEMCKRDLIWVVTKMKIKVNRYPAWGDTVEI

NTWFSRLGKIGKGRDWLISDCNTGEILIRATSAYATMNQKTRRLSKLPYEVHQEIAPLFVDSPPVIEDNDLK

LHICFEVKTGDSIHKGLTPGWNDLDVNQHVSNVKYIGWILESMPTEVLETQELCSLALEYRRECGRDSVLES

VTAMDPTKVGGRSQYQHLLRLEDGTDIVKCRTEWRPKNPGANGAISTGKTSNGNSVS

SEQ ID NO: 171
CpauFATB1 (*Cuphea paucipetala* FATB1)
MVAAAASSAFFPVPAPGTSPKPGKSGNWPSSLSPSIKPMSIPNGGFQVKANASAHPKANGSAVNLKSGSLN

TQEDTSSSPPPRAFLNQLPDWSMLLTAITTVFVAAEKQWTMRDRKSKRPDMLVDSVGLKSVVLDGLVSRQ

IFSIRSYEIGADRTASIETLMNHLQETSINHCKSLGLLNDGFGRTPGMCKNDLIWVLTKMQIMVNRYPTWGD

TVEINTWFSHSGKIGMASDWLITDCNTGEILIRATSVWAMMNQKTRRFSRLPYEVRQELTPHYVDSPHVIE

DNDRKLHKFDVKTGDSIRKGLTPRWNDLDVNQHVSNVKYIGWILESMPIEVLETQELCSLTVEYRRECGM

DSVLESVTAMDPSEDEGRSQYKHLLRLEDGTDIVKGRTEWRPKNAGTNGAISTAKPSNGNSVS

SEQ ID NO: 172
CprocFATB1 (*Cuphea procumbens* FATB1)
MVAAAASSAFFPAPAPGSSPKPGKSGNWPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKNIVRDGLVSRQ

SFLIRSYEIGADRTASIETLMNHLQETSINHCKSLGLLNDGEGRTPGMCKNDLIWVLTKMQIMVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVSNVKYIGWILESMPIEVLEAQELCSLTVEYRRECGM

DSVLESVTAVDPSEDGGRSQYNHLLRLEDGTDVVKGRTEWRPKNAETNGAISPGNTSNGNSIS

SEQ ID NO: 173
CprocFATB2 (*Cuphea procumbens* FATB2)
MVAAAASSAFFPAPAPGSSPKPGKSGNWPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKNIVRDGLVSRQ

SFLIRSYEIGADRTASIETLMNHLQETSINHCKSLGLLNDGFGRTPGMCKNDLIWVLTKMQLMVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVNNVKYIGWILESTPPEVLETQELCSLTLEYRQECGRE

SVLESLTAVDPSGKGFGSQFQHLLRLEDGGEIVKGRTEWRPKTAGINGAIASGETSPGDF

SEQ ID NO: 174
CprocFATB3 (*Cuphea procumbens* FATB3)
MVAAAASSAFFPAPAPGSSPKPGKSGNVVPSSLSPSFKSKSIPYGRFQVKANASAHPKANGSAVNLKSGSLN

TQEDTSSSPPPRAFLNQLPDWSMLLSAITTVFVAAEKQWTMLDRKSKRPDMLVDSVGLKN1VRDGLVSRQ

SFLIRSYEIGADRTASIETLMNHLQETSINHCKSLGLLNDGFGRTPGMCKNDLIWVLTKMQ1MVNRYPAWG

DTVEINTWFSQSGKIGMGSDWLISDCNTGEILIRATSVWAMMNQKTRRFSRLPYEVRQELTPHFVDSPHVIE

DNDRKLHKFDVKTGDSIRKGLTPRWNDLDVNQHVNNVKYIGWILESTPPEVLETQELCSLTLEYRRECGRE

SVLESLTAVDPSGEGGYGSQFQHLLRLEDGGEIVKGRTEWRPKNAGINGVLPTGE

-continued

SEQ ID NO: 175
CigneaFATB1 (*Cuphea ignea* FATB1)
PGTSRKTGKFGNWPSSLSPSFKPKSIPNGGFQVKANARAHPKANGSAVSLKSVSLNTQEDTSLSPPPRAFLN

QLPDWRMLRTALTTVFVAAEKQWTMLDRKSKRPDMLVDSFGLESIVQEGLVFRQSFSIRSYEIGIDRTASIE

TLMNHLQETSLNQCKSAGILHDGFGRTLEMCKRDLIWVVTKMQ1KVNRYPAWGDTVEISTRFSRLGKIGM

GRDWLICDCNTGEILIRATSAYAMMNQKTRRLSKLPNEVRQEIAPLFVDSDPVIEENDMKLHKFEVKTGDSI

CKGLTPRWSDLDVNQHVSNVKYIGWILESMPTEVLETQELCSLALEYRRECGRDSVLESVTSMDPSKVGG

WSQYQHLLRLEDGADIVKGRTEWRPKNAGANGAISTGKT

SEQ ID NO: 176
CcalcFATB1 (*Cuphea calcarata* FATB1)
MATASTFSAFNARCGDLRRSAGSGPRRPARPLPVRAAINASAHPKANGSAVSLKSGSLETQEDNSSSSRPPR

TFIKQLPDWSIMLLSAITTVFVAAEKQWTMFDRKSKRSDMLVDPFVVDRIVQDGVLFRQSFSIRSYEIGADR

TASIETLMNIFQETSLNHCKSMGLLYEGFGRTPEMCKRDLIWVVTKIHIKVNRYPTWGDTIEVTTWVSESG

KNGMGRDWLISDCHTGEILIRATSVWAMMNQTTRRLSKFPYELRQEIAPHFVDSDPVIEDNRRLLNFDVKT

GDSIRKGLTPRWNDLDVNQHVNNVKYIGWILESVPTEVFDTRELCGLTLEYRQECGRGSVLESVTAMDPS

KEGDRSLYQFILLRLEDGTDIVKGRTEWRPKNAGTNGPVSTRKTINGSSVS

SEQ ID NO: 177
ChookFATB4 (*Cuphea hookeriana* FATB4)
MATASTFSAFNARCGDLRRSAGSGPRRPARPLPVRAAINASAHPKANGSAVSLKSGSLNTQENTSSSPPPRT

FLHQLPDWSRLLTAITTVFVKSKRPDMHDRKSKRPDMLVDLFGLESSVQDALVFRQRFSIRSYEIGTDRTAS

METLMNHLQETSLNHCKSTGILLDGFGRTLEMCKRELIWVVIKMQIQVNRYPAWGDTVEINTRFSRLGKIG

MGRDWLISDCNTGEILIRATSEYAMMNQKTRRLSKLPYEVRQEIAPLFVDSPPVIEDNDLKVHKFEVKTGD

SIHKGLTPGWNDLDVNQHVNNVKYIGWILESTPPEVLETQELCSLTLEYRRECGRESVLESLTAMDPSGGG

YGSQFQHLLRLEDGGEIVKGRTEWRPKNGVINGVVPTGESSPGDYS

SEQ ID NO: 178
CaFATB1 (*Cuphea avigera* var. *pulcherrima* FATB1)
MATASTFSAFNARCGDLRRSAGSGPRRPARPLPVRAAINSRAHPKANGSAVSLKSGSLNTQEDTSSSPPPRT

FLHQLPDWSRLLTAITTVFVKSKRPDMHDRKSKRPDMLMDSFGLESIVQEGLEFRQSFSIRSYEIGTDRTASI

ETLMNYLQETSLNHCKSTGILLDGFGRTPEMCKRDLIWVVTKMKIKVNRYPAWGDTVEINTWFSRLGKIG

KGRDWLISDCNTGEILIRATSAYATMNQKTRRLSKLPYEVHQEIAPLFVDSPPVIEDNDLKLHKFEVKTGDSI

HKGLTPGWNDLDVNQHVSNVKYIGWILESMPTEVLETQELCSLALEYRRECGRDSVLESVTAMDPTKVGG

RSQYQHLLRLEDGTDIVKCRTEWRPKNPGANGAISTGKTSNGNSVS

SEQ ID NO: 179
CpauFATB1 (*Cuphea paucipetala* FATB1)
MATASTFSAFNARCGDLRRSAGSGPRRPARPLPVRAAINASAHPKANGSAVNLKSGSLNTQEDTSSSPPPR

AFLNQLPDWSMLLTAITTVFVAAEKQWTMRDRKSKRPDMLVDSVGLKSVVLDGLVSRQIFSIRSYEIGADR

TASIETLMNHLQETSINHCKSLGLLNDGFGRTPGMCKNDLIWVLIKMQIMVNRYPTWGDTVEINTWFSHS

GKIGMASDWLITDCNTGEILIRATSVWAMMNQKTRRFSRLPYEVRQELTPHYVDSPHVIEDNDRKLHKFD

VKTGDSIRKGLTPRWNDLDVNQHVSNVKYIGWILESMPIEVLETQELCSLTVEYRRECGMDSVLESVTAM

DPSEDEGRSQYKHLLRLEDGTDIVKGRTEWRPKNAGINGAISTAKPSNGNSVS

SEQ ID NO: 180
CprocFATB1 (*Cuphea procumbens* FATB1)
MATASTFSAFNARCGDLRRSAGSGPRRPARPLPVRAAINASAHPKANGSAVNLKSGSLNTQEDTSSSPPPR

AFLNQLPDWSMLLSAITTVFVAAEKQWTMLDRKSKRPDMLVDSVGLKNIVRDGLVSRQSFLIRSYEIGADR

TASIETLMNHLQETSINHCKSLGLLNDGFGRTPGMCKNDLIWVLIKMQIMVNRYPAWGDTVEINTWFSQS

GKIGMGSDWLISDCNTGEILIRATSVWAMMNQKTRRFSRLPYEVRQELTPHFVDSPHVIEDNDRKLHKFDV

-continued

KTGDSIRKGLTPRWNDLDVNQHVSNVKYIGWILESMPIEVLEAQELCSLTVEYRRECGMDSVLESVTAVDP

SEDGGRSQYNHLLRLEDGTDVVKGRTEWRPKNAETNGAISPGNTSNGNSIS

SEQ ID NO: 181
CprocFATB2 (*Cuphea procumbens* FATB2)
MATASTFSAFNARCGDLRRSAGSGPRRPARPLPVRAAINASAHPKANGSAVNLKSGSLNTQEDTSSSPPPR

AFLNQLPDWSMLLSAITTVFVAAEKQWTMLDRKSKRPDMLVDSVGLKNIVRDGLVSRQSFLIRSYEIGADR

TASIETLMNHLQETSINHCKSLGLLNDGFGRTPGMCKNDLIWVLTKMQIMVNRYPAWGDTVEINTWFSQS

GKIGMGSDWLISDCNTGEILIRATSVWAMMNQKTRRFSRLPYEVRQELTPHFVDSPHVIEDNDRKLHKFDV

KTGDSIRKGLTPRWNDLDVNQHVNNVKYIGWILESTPPEVLETQELCSLTLEYRQECGRESVLESLTAVDPS

GKGFGSQFQHLLRLEDGGEIVKGRTEWRPKTAGINGAIASGETSPGDF

SEQ ID NO: 182
CprocFATB3 (*Cuphea procumbens* FATB3)
MATASTFSAFNARCGDLRRSAGSGPRRPARPLPVRAAINASAHPKANGSAVNLKSGSLNTQEDTSSSPPPR

AFLNQLPDWSMLLSAITTVFVAAEKQWTMLDRKSKRPDMLVDSVGLKNIVRDGLVSRQSFLIRSYEIGADR

TASIETLMNHLQETSINHCKSLGLLNDGFGRTPGMCKNDLIWVLTKMQIMVNRYPAWGDTVEINTWFSQS

GKIGMGSDWLISDCNTGEILIRATSVWAMMNQKTRRFSRLPYEVRQELTPHFVDSPHVIEDNDRKLHKFDV

KTGDSIRKGLTPRWNDLDVNQHVNNVKYIGWILESTPPEVLETQELCSLTLEYRRECGRESVLESLTAVDPS

GEGGYGSQFQHLLRLEDGGEIVKGRTEWRPKNAGINGVLPTGE

SEQ ID NO: 183
CigneaFATB1 (*Cuphea ignea* FATB1)
MATASTFSAFNARCGDLRRSAGSGPRRPARPLPVRAAINARAHPKANGSAVSLKSVSLNTQEDTSLSPPPR

AFLNQLPDWRMLRTALTTVFVAAEKQWTMLDRKSKRPDMLVDSFGLESIVQEGLVFRQSFSIRSYEIGIDR

TASIETLMNIALQETSLNQCKSAGILHDGFGRTLEMCKRDLIWVVIKMQIKVNRYPAWGDTVEISTRFSRLG

KIGMGRDWLICDCNTGEILIRATSAYAMMNQKTRRLSKLPNEVRQEIAPLFVDSDPVIEENDMKLHKFEVK

TGDSICKGLTPRWSDLDVNQHVSNVKYIGWILESMPTEVLETQELCSLALEYRRECGRDSVLESVTSMDPS

KVGGWSQYQHLLRLEDGADIVKGRTEWRPKNAGANGAISTGKT

SEQ ID NO: 184
CgFATB1 (*Cuphea glossostoma* FATB1)_
MVAAAASSAFFPSPAPGSSPKPGNRPSSLSPSFKPKSIPNGAFQVKANASAHPKANGSAVNLKSGSLNTQED

SSSSPSPRAFLNQLPDWSVLLTAITTVFVAAEKQWTMLDRKSKRPDVLVDSVGLKSIVQDGLVSRQSFSIRS

YEIGADRTASIETLMNHLQETSINHCKSLGLLNDGFGRTPGMCKNDLIWVLTKMQIMVNRYPAWGDTVEI

NTWFSQSGKIGMGSDWLISDCNTGEILIRATSVWAMMNQKTRRFSRLPYEVRQELTPHFVDSPHVIEDNDR

KLHKFDVKTGDSIRKGLTPRWNDLDVNQHVSNVKYIGWILESMPIEVLETQELCSLTVEYRRECGMDSVL

ESVTAMDPSEDGGRSQYNHLLRLEDGTDVVKGRTEWRPKNAGTNGAISTTKTSNGNSVS

SEQ ID NO: 185
CgFATB1b (*Cuphea glossostoma* FATB1 C170F, M198T, T374S variant)
MVAAAASSAFFPSPAPGSSPKPGNRPSSLSPSFKPKSIPNGAFQVKANASAHPKANGSAVNLKSGSLNIQED

SSSSPSPRAFLNQLPDWSVLLTAITTVFVAAEKQWTMLDRKSKRPDVLVDSVGLKSIVQDGLVSRQSFSIRS

YEIGADRTASIETLMNHLQETSINHFKSLGLLNDGFGRTPGMCKNDLIWVLIKTQIMVNRYPAWGDTVEIN

TWFSQSGKIGMGSDWLISDCNTGEILIRATSVWAMMNQKTRRFSRLPYEVRQELTPHFVDSPHVIEDNDRK

LHKFDVKTGDSIRKGLTPRWNDLDVNQHVSNVKYIGWILESMPIEVLETQELCSLTVEYRRECGMDSVLES

VSAMDPSEDGGRSQYNHLLRLEDGTDVVKGRTEWRPKNAGTNGAISTTKTSNGNSVS

SEQ ID NO: 186
*Umbellularia californica* UcFATB3 amino acid sequence
MVATAAASAFFPVGSPATSSATSAKASIVIMPDNLDARGIKPKPASSSGLQVKANAHASPKINGSKVSTDTLK

GEDTLTSSPAPRTFINQLPDWSMFLAAITTIFLAAEKQWTNLDWKPRRPDMLADPFGIGRFMQDGLIFRQHF

AIRSYEIGADRTASIETLMNHLQETALNHVRSAGLLGDGFGATPEMSRRDLIWVVTRMQVLVDRYPAWGD

-continued

IVEVETWVGASGKNGMRRDWLVRDSQTGEILTRATSVWVMMNKRTRRLSKIPEEVRGEIGPYFMENVAII

EEDSRKLQKLNENIIEEDSRKLQKLNENTADNVRRGLTPRWSDLDVNQHVNNVKYIGWILESAPGSILESHE

LSCMTLEYRRECGKDSVLQSMTVVSGGGSAAGGSPESSVECDHLLQLESGPEVVKARTEWRPKSANNPRSI

LEMPAESS*

SEQ ID NO: 187
*Cuphea carthagenensis* CCrFATB2c (V138L variant of FATB2)
MVAAAASSAFFPVTTPGTSRKPGKFGNWLSSLSPPFRPKSIPSGGFQVKANASAHPKANGSAVSLKSGSLNT

QEDTSSSPPPRAFINQLPDWSMLLTAITTVFVAAEKQWTMLDRKSKRSDMLVDSFGMERIVQDGLLFRQSF

SIRSYEIGADRRASIETLMNHLQETSLNHCKSIRLLNEGFGRTPEMCKRDLIWVVIRMHIMVNRYPTWGDT

VEINTWVSQSGKNGMGRDWLISDCNTGEILIRATSAWAMMNQKTRRLSKLPYEVSQEIAPHFVDSPPVIED

GDRKLHKFDVKTGDSIRKGLTPRWNDLDVNQHVNNVKYIGWILESMPTEVLETHELCFLTLEYRRECGRD

SVLESVTAMDPSNEGGRSHYQHLLRLEDGTDIVKGRTEWRPKNARNIGAISTGKTSNGNPAS*

SEQ ID NO: 188
*Cuphea carthagenensis* CCrFATB2
MVAAAASSAFFPVTTPGTSRKPGIUGNWLSSLSPPFRPKSIPSGGFQVKANASAHPKANGSAVSLKSGSLNT

QEDTSSSPPPRAFINQLPDWSMLLTAITTVFVAAEKQWTMLDRKSKRSDMLVDSFGMERIVQDGLVFRQSF

SIRSYEIGADRRASIETLMNHLQETSLNHCKSIRLLNEGFGRTPEMCKRDLIWVVTRMHIMVNRYPTWGDT

VEINTWVSQSGKNGMGRDWLISDCNTGEILIRATSAWAMMNQKTRRLSKLPYEVSQEIAPHFVDSPPVIED

GDRKLHKFDVKTGDSIRKGLTPRWNDLDVNQHVNNVKYIGWILESMPTEVLETHELCFLTLEYRRECGRD

SVLESVTAMDPSNEGGRSHYQHLLRLEDGTDIVKGRTEWRPKNARNIGAISTGKTSNGNPAS*

SEQ ID NO: 189
CcrFATB2b
MVAAAASSAFFPVTTPGTSRKPGKFGNWLSSLSPPFRPKSIPSGGFQVKANASAHPKANGSAVSLKSGSLNT

QEDTSSSPPPRAFINQLPDWSMLLTAITTVFVAAEKQWTMLDRKSKRSDMLVDSFGMERIVQDGLVFRQSF

SIRSYEIGADRRASIETLMNHLQETSLNHCKSIRLLNEGFGRTPEMCKRDLIWVFTRMHIMVNRYPTWGDT

VEINTWVSQSGKNGMGRDWLISDCNTGEILIRATSAWAMMNQKTRRLSKLPYEVSQEIAPHFVDSPPVIED

GDRKLHKFDVKTGDSIRKGLTPRWNDLDVNQHVNNVKYIGWILESMPTEVLETHELCFLTLEYRRECGRD

SVLESVTAMDPSNEGGRSHYQHLLRLEDGTDIVKGRTEWRPKNARNIGAIPTGKTSNGNPAS*

SEQ ID NO: 190
CcrFATB1
MVATAASSAFFPVPSPDSSSRPGKLGNGPSSLSPLKPKSTPNGGLQVKANASAPPKINGSSVGLKSSSLKTQD

DTPSAPPPRTFINQLPDWSMLLAAITTVFLAAEKQWMMLDWKPKRPDMLTDPFGLGRIVQDGLVFRQNFSI

RSYEIGADRTASIETVMNHLQETALNHVKSAGLLNDGFGRTPEMYKRDLIWVVAKMQVMVNRYPTWGD

TVEVNTWVAKSGKNGMRRDWLISDCNTGEILTRASSVWVMMNQKTRRLSKIPDEVRHEIEPHFVDSAPVI

EDDDRKLPKLDEKTADSIRKGLTPKWNDLDVNQHVNNVKYIGWILESTPPEVLETQELCSLTLEYRRECGK

ESVLESLTAVDPSGKGWGSHFQHLLRLEDGGEIVKGRTEWRPKNAGINGAVAFEETSPGDS*

SEQ ID NO: 191
CcrFATB1b
MVATAASSAFFPVPSPDSSSRPGKLGNGPSSLSPLKPKSTPNGGLQVKANASAPPKINGSSVGLKSSSLKTQD

DTPSAPPPRTFINQLPDWSMLLAAITTVFLAAEKQWMMLDWKPKRPDMLTDPFGLGRIAQDGLVFRQNFSI

RSYEIGADRTASIETVMNHLQETALNHVKSAGLLNDGFGRTPEMYKRDLIWVVAKMQVMVNRYPTWGD

TVEVNTWVAKSGKNGMRRDWLISDCNTGEILTRASSVWVMMNQKTRRLSKIPDEVRHEIEPHFVDSAPVI

EDDDRKLPKLDEKTADSIRKGLTPKWNDLDVNQHVNNVKYIGWILESTPPEVLETQELCSLTLEYRRECGK

ESVLESLTAVDPSGKGWGSHFQHLLRLEDGGEIVKGRTEWRPKNAGINGAVAFEETSPGDS*

-continued

SEQ ID NO: 192
CCrFATB1c
MVATAASSAFFPVPSPDSSSRPGKLGNGPSSLSPLKPKSTPNGGLQVKANASAPPKINGSSVGLKSSSLKTQD

DTPSAPPPRTFINQLPDWSMLLAAITTVFLAAEKQWMMLDWKPKRPDMLTDPFGLGRIVQDGLVFRQNFSI

RSYEIGADRTASIETVMNHLQETALNHVKSAGLLNDGFGRTPEMYKRDLIWVVAKMQVMVNRYPTWGD

TVEVNTWVAKSGKNGMRRDWLISDCNTGEILTRASSVWVMMNQKTRRLSKIPDEVRHEIEPHFVDSAPVI

EDDDRKLPKLDEKTADSIRKGLTPKWNDLDVNQHVNNVKYIGWILESTPPEVLETQELCSLTLEYRRECGK

ESVLESLTAVDPSGKGWGSHFQHLLRLEDGGEIVKGRTEWRPKNA*.

---

What is claimed is:

1. A recombinant nucleic acid construct comprising a regulatory element and a FatB gene expressing an active acyl-ACP thioesterase operable to produce an altered fatty acid profile in an oil produced by a cell expressing the nucleic acid construct, wherein the FatB gene expresses a protein having at least 94.6%, 95%, 96%, 97%, 98%, or 99% sequence identity with SEQ ID NOs: 82 or 178, and optionally wherein the fatty acid of the oil is enriched in C8 and C10 fatty acids.

2. An isolated nucleic acid or recombinant DNA construct comprising a nucleic acid, wherein the nucleic acid has at least 95%, 96%, 97%, 98%, or 99% sequence identity to any of SEQ ID NOS: 83, 84, 90, or any equivalent sequences by virtue of the degeneracy of the genetic code, wherein the isolated nucleic acid or recombinant DNA construct encodes an active acyl-ACP thiostearase operable to produce an altered fatty acid profile in an oil produced by a cell expressing said isolated nucleic acid or recombinant DNA construct.

3. An isolated nucleic acid sequence encoding a protein or a host cell expressing a protein having at least 95%, 96%, 97%, 98%, or 99% sequence identity to any of SEQ ID NOS: 82, 178 or a fragment thereof, said isolated nucleic acid sequence encoding a protein having acyl-ACP thioesterase activity.

4. The isolated nucleic acid of claim 3, wherein, the protein has acyl-ACP thioesterase activity operable to alter the fatty acid profile of an oil produced by a recombinant cell comprising that sequence.

5. A method of producing a recombinant cell that produces an altered fatty acid profile, the method comprising transforming the cell with a nucleic acid construct according to claim 1.

6. A host cell produced by the method of claim 5.

7. The host cell of claim 6, wherein the host cell is selected from a plant cell, a microbial cell, and a microalgal cell.

8. A method for producing an oil or oil-derived product, the method comprising cultivating a host cell of claim 6, and extracting oil produced thereby, optionally wherein the cultivation is heterotrophic growth on sugar.

9. The method of claim 8, further comprising producing a fatty acid, fuel, chemical, or other oil-derived product from the oil.

* * * * *